(12) United States Patent
Bacac et al.

(10) Patent No.: US 11,718,680 B2
(45) Date of Patent: Aug. 8, 2023

(54) COMBINATION THERAPY OF ANTI-CD20/ANTI-CD3 BISPECIFIC ANTIBODIES AND 4-1BB (CD137) AGONISTS

(71) Applicant: Hoffmann-La Roche Inc., Little Falls, NJ (US)

(72) Inventors: Marina Bacac, Schlieren (CH); Claudia Ferrara Koller, Schlieren (CH); Christian Klein, Schlieren (CH); Mario Perro, Schlieren (CH); Johannes Sam, Schlieren (CH); Pablo Umaña, Schlieren (CH); Wei Xu, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 214 days.

(21) Appl. No.: 16/820,504

(22) Filed: Mar. 16, 2020

(65) Prior Publication Data

US 2020/0325238 A1 Oct. 15, 2020

Related U.S. Application Data

(63) Continuation of application No. 16/446,478, filed on Jun. 19, 2019, now abandoned, which is a continuation of application No. PCT/EP2017/083222, filed on Dec. 18, 2017.

(30) Foreign Application Priority Data

Dec. 20, 2016 (EP) .................................. 16205493

(51) Int. Cl.
| | |
|---|---|
| C07K 16/28 | (2006.01) |
| A61P 35/00 | (2006.01) |
| C07K 14/705 | (2006.01) |
| C07K 16/46 | (2006.01) |
| A61K 39/00 | (2006.01) |
| A61K 9/00 | (2006.01) |

(52) U.S. Cl.
CPC .. C07K 16/2887 (2013.01); A61K 39/001112 (2018.08); A61K 39/001117 (2018.08); A61K 39/001129 (2018.08); A61P 35/00 (2018.01); C07K 14/70532 (2013.01); C07K 14/70575 (2013.01); C07K 16/2809 (2013.01); C07K 16/2818 (2013.01); C07K 16/2827 (2013.01); C07K 16/2878 (2013.01); C07K 16/468 (2013.01); A61K 9/0019 (2013.01); A61K 2039/505 (2013.01); A61K 2039/545 (2013.01); C07K 2317/31 (2013.01); C07K 2317/52 (2013.01); C07K 2317/565 (2013.01); C07K 2317/71 (2013.01); C07K 2319/00 (2013.01)

(58) Field of Classification Search
None
See application file for complete search history.

(56) References Cited

U.S. PATENT DOCUMENTS

| | | | |
|---|---|---|---|
| 9,011,847 B2 | 4/2015 | Bacac et al. | |
| 9,173,961 B2 | 11/2015 | Deckert et al. | |
| 10,253,110 B2 | 4/2019 | Bacac et al. | |
| 10,392,445 B2 | 8/2019 | Amann et al. | |
| 10,464,981 B2 | 11/2019 | Amann et al. | |
| 10,526,413 B2 | 1/2020 | Amann et al. | |
| 10,577,429 B2 | 3/2020 | Bacac et al. | |
| 11,149,083 B2 | 10/2021 | Amann et al. | |
| 11,267,903 B2 | 3/2022 | Amann et al. | |
| 11,306,154 B2 | 4/2022 | Amann et al. | |
| 2006/0235201 A1 | 10/2006 | Kischel | |
| 2009/0155275 A1 | 6/2009 | Wu et al. | |
| 2016/0075785 A1* | 3/2016 | Ast | C07K 16/32 |
| | | | 435/254.2 |
| 2017/0174786 A1 | 6/2017 | Bacac et al. | |
| 2017/0209573 A1* | 7/2017 | Bacac | A61P 35/00 |
| 2017/0247467 A1 | 8/2017 | Amann et al. | |
| 2018/0230215 A1 | 8/2018 | Hofer et al. | |
| 2018/0282409 A1 | 10/2018 | Koller et al. | |
| 2018/0340030 A1 | 11/2018 | Bruenker et al. | |
| 2019/0016771 A1 | 1/2019 | Amann et al. | |
| 2019/0185566 A1 | 6/2019 | Koller et al. | |
| 2019/0194291 A1 | 6/2019 | Bruenker et al. | |
| 2019/0211113 A1 | 7/2019 | Amann et al. | |
| 2019/0382507 A1 | 12/2019 | Amann et al. | |
| 2020/0071411 A1 | 3/2020 | Amann et al. | |
| 2020/0079873 A1 | 3/2020 | Bacac et al. | |
| 2020/0190206 A1 | 6/2020 | Koller et al. | |
| 2020/0190207 A1 | 6/2020 | Bruenker | |
| 2020/0199234 A1 | 6/2020 | Georges et al. | |

(Continued)

FOREIGN PATENT DOCUMENTS

| | | |
|---|---|---|
| CN | 106279434 A | 1/2017 |
| EP | 2995626 A1 | 3/2016 |

(Continued)

OTHER PUBLICATIONS

Malia et al, Proteins 2016; 84;427-434.*
De Genst et al, Developmental and Comparative Immunology, 2006, 30:187-98.*
Ward et al (Nature, 1989, 341:544-546).*
Barthelemy et al (Journal of Biological Chemistry, 2008, 283:3639-3654).*

(Continued)

*Primary Examiner* — Brad Duffy
(74) *Attorney, Agent, or Firm* — Lawrence S. Graham

(57) ABSTRACT

The present invention relates to combination therapies employing anti-CD20/anti-CD3 bispecific antibodies and 4-1BB (CD137) agonists, in particular 4-1BBL trimer containing antigen binding molecules, the use of these combination therapies for the treatment of cancer and methods of using the combination therapies.

32 Claims, 13 Drawing Sheets

Specification includes a Sequence Listing.

(56) References Cited

U.S. PATENT DOCUMENTS

| | | |
|---|---|---|
| 2020/0231691 A1 | 7/2020 | Grau-Richards et al. |
| 2020/0247904 A1 | 8/2020 | Amann et al. |
| 2020/0270321 A1 | 8/2020 | Amann et al. |
| 2020/0277392 A1 | 9/2020 | Amann et al. |
| 2020/0317774 A1 | 10/2020 | Hofer et al. |
| 2020/0325225 A1 | 10/2020 | Bacac et al. |
| 2020/0347115 A1 | 11/2020 | Duerr et al. |
| 2020/0392237 A1 | 12/2020 | Bacac et al. |
| 2021/0009656 A1 | 1/2021 | Bruenker et al. |
| 2021/0024610 A1 | 1/2021 | Koller et al. |
| 2021/0070882 A1 | 3/2021 | Bacac et al. |
| 2021/0095002 A1 | 4/2021 | Claus et al. |
| 2021/0163617 A1 | 6/2021 | Ferrara et al. |
| 2021/0188992 A1 | 6/2021 | Bruenker et al. |
| 2021/0253724 A1 | 8/2021 | Claus et al. |
| 2021/0292426 A1 | 9/2021 | Duerr et al. |
| 2021/0324108 A1 | 10/2021 | Amann et al. |
| 2022/0025069 A1 | 1/2022 | Claus et al. |
| 2022/0073646 A1 | 3/2022 | Amann et al. |

FOREIGN PATENT DOCUMENTS

| | | |
|---|---|---|
| EP | 3559034 B1 | 12/2020 |
| WO | 2004/035607 A2 | 4/2004 |
| WO | 2004/056312 A2 | 7/2004 |
| WO | 2005/044859 A2 | 5/2005 |
| WO | 2005/103081 A2 | 11/2005 |
| WO | 2007/031875 A2 | 3/2007 |
| WO | 2010/10051 A1 | 1/2010 |
| WO | 2012/130831 A1 | 10/2012 |
| WO | 2015/006749 A2 | 1/2015 |
| WO | 2015/095392 A1 | 6/2015 |
| WO | 2016/016859 A1 | 2/2016 |
| WO | 2016/020309 A1 | 2/2016 |
| WO | 2016/075278 A1 | 5/2016 |
| WO | 2016/110576 A1 | 7/2016 |
| WO | 2020/208049 A1 | 10/2020 |
| WO | 2020/260329 A1 | 12/2020 |
| WO | 2021/140130 A1 | 7/2021 |
| WO | 2021/198335 A1 | 10/2021 |

OTHER PUBLICATIONS

Choi et al, 2011, Molecular BioSystems, 2011, 7:3327-3334.*
Griffiths et al (The EMBO Journal, 1993, 12:725-734).*
Klimka et al, British Journal of Cancer, 2000, 83:252-260.*
Beiboer et al (Journal of Molecular Biology, 2000, 296:833-849).*
Markman (Drugs, 76:1227-1232, 2016).*
Lloyd et al (Protein Engineering, Design & Selection, 22:159-168, 2009).*
Edwards et al (J Mol Biol, 14;334(1):103-118, 2003).*
Tame (J. Comput. Aided Mol. Des. Mar. 1999; 13 (2): 99-108).*
Lensink et al. (Proteins. 2007; 69: 704-718.*
Bartkowiak, T., et al., "4-1BB Agonists: Multi-Potent Potentiators of Tumor Immunity" Front Oncol 5(117):1-16 (Jun. 8, 2015).
Buhmann, R. et al., "Immunotherapy with FBTA05 (Bi20), a trifunctional bispecific anti-CD3 X anti-CD20 antibody and donor lymphocyte infusion (DLI) in relapsed or refractory B-cell lymphoma after allogeneic stem cell transplantation: study protocol of an investigator-driven, open-label, non-randomized" J Transl Med 11(1):160 (Jul. 2, 2013).
Cragg, M., et al., "Antibody Specificity Controls in Vivo Effector Mechanisms of Anti-CD20 Regents" Blood 103(7):2738-2743 (Apr. 1, 2004).
Cragg, M., et al., "Complement-mediated lysis by anti-CD20 mAb correlates with segregation into lipid rafts" Blood 101(3):1045-1052 (Feb. 1, 2003).
Dai, M., et al., "Curing Mice with Large Tumors by Locally Delivering Combinations of Immunomodulatory Antibodies" Clin Cancer Res 21(5):1127-1138 (Mar. 1, 2015).
Diehl, L., et al., "In Vivo Triggering Through 4-1BB Enables Th-Independent Priming of CTL in the Presence of an Intact CD28 Costimulatory Pathway" J Immunol 168(8):3755-3762 (Apr. 15, 2002).
Dubrot, J., et al., "Treatment with anti-CD137 mAbs causes intense accumulations of liver T cells without selective antitumor immunotherapeutic effects in this organ" Cancer Immunol Immun 59(8):1223-1233 (Aug. 1, 2010)
Goodwin, R., et al., "Molecular cloning of a ligand for the inducible T cell gene 4-1BB: a member of an emerging family of cytokines with homology to tumor necrosis factor" Eur J Immunol 23(10):2631-2641 (Oct. 1, 1993).
Hornig, N., et al., "Combination of a Bispecific Antibody and Costimulatory Antibody-Ligand Fusion Proteins for Targeted Cancer Immunotherapy" J Immunother 35(5):418-429 (Jun. 1, 2012).
Ingle, G., et al., "High CD21 expression inhibits inteinalization of anti-CD19 antibodies and cytotoxicity of an anti-CD19-drug conjugate" Br J Haematol 140(1):46-58 (Jan. 1, 2008).
"International Preliminary Report on Patentability—PCT/EP2017/083222":pp. 1-11 (dated Jul. 4, 2019).
"International Search Report—PCT/EP2017/083222":pp. 1-8 (dated Mar. 14, 2018).
Klein, C. et al., "Epitope interactions of monoclonal antibodies targeting CD20 and their relationship to functional properties" MABS 5(1):22-33 (Jan. 31, 2013).
Kwon, B., et al., "cDNA sequences of two inducible T-eell genes" PNAS USA 86(6):1963-1967 (Mar. 1, 1989).
Li, F., et al., "Inhibitory Fcγ Receptor Engagement Drives Adjuvant and Anti-Tumor Activities of Agonistie CD40 Antibodies" Science 333(6045):1030-1034 (Aug. 19, 2011).
Liu, R., et al., "Efficient Inhibition of Human B-cell Lymphoma in SCID Mice by Synergistic Antitumor Effect of Human 4-1BB Ligand/Anti-CD20 Fusion Proteins and Anti-CD3/Anti-CD20 Diabodies" J Immunother 33(5):500-509 (Jun. 1, 2010).
Lum, L., et al., "CD20-Targeted T Cells after Stem Cell Transplantation for High Risk and Refractory Non-Hodgkin's Lymphoma" Biol Bone Marrow Transpl 19(6):925-933 (Mar. 22, 2013).
Lum, L., et al., "Targeting CD138-/CD20+ Clonogenic Myelorna Precursor Cells Decreases These Cells and Induces Transferable Antimyelorna Immunity" Biol Bone Marrow Transpl 22(5):869-878 (Jan. 28, 2016).
Melero, I. et al., "Monoclonal Antibodies Against the 4-1BB T-cell Activation Molecule Eradicate Established Tumors" Nat Med 3(6):682-685 (Jun. 1, 1997).
Mueller, D. et al., "A Novel Antibody—4-1BBL Fusion Protein for Targeted Costimulation in Cancer Immunotherapy" J Immunother 31(8):714-722 (Oct. 1, 2008).
Poppema, S., et al., "Preparation and Application of Monoclonal Antibodies: B Cell Panel and Paraffin Tissue Reactive Panel." Biotest Bulletin 3:131-139 ( 1987).
Shao, Z., et al., "Mini-Review: CD137 ligand, a member of the tumor necrosis factor family, regulates immune responses via reverse signal transduction" J Leukocyte Biol 89(1):21-29 (Jan. 1, 2011).
Simeone, E. et al., "Immunomodulating antibodies in the treatment of metastatic melanoma: The experience with anti-CTLA-4, anti-CD137, and anti-PD1" J Immunotoxcity 9(3):241-247 (Jul. 1, 2012).
Snell, L., et al., "T-Cell intrinsic effects of GITR and 4-1BB during viral infection and cancer immunotherapy" Immunol Rev 244(1):197-217 (Nov. 1, 2011).
Sun, L., et al., "Anti-CD20/CD3 T cell-dependent bispecific antibody for the treatment of B cell malignancies" Sci Trans Med 7(287 SUPPL 287ra70):1-10 (May 13, 2015).
Suntharalingam, G., et al., "Cytokine storm in a phase 1 trial of the anti-CD28 monoclonal antibody TGN1412" New Engl J Med 355(10):1018-1028 (Sep. 7, 2006).
Us Nih et al., "Clinical Trials Identifier—NCT00309023—Urelumab" Study of BMS-663513 in Patients With Advanced Cancer:1-6 (Oct. 12, 2015).
Us Nih, "Clinical Trials Identifier—NCT00612664—Urelumab" Phase II, 2nd Line Melanoma—RAND Monotherapy:1-6 (Oct. 12, 2015).
Vinay, D. et al., "4-1BB signaling beyond T cells" Cell Mol Immunol 8(4):281-284 (Jul. 1, 2011).
WHO Drug Information, 2008, vol. 22, No. 2, pp. 123-124, pp. 2.

(56) References Cited

OTHER PUBLICATIONS

World Health Organization et al., "International Nonproprietary Names for Pharmaceutical Substances (INN)—obinutuzumab" WHO Drug Information 25(1):75-76 (Mar. 1, 2011).

World Health Organization et al., "Proposed International Nonproprietary Names—obinutuzumabum" WHO Drug Information 26(4):453 (Jan. 10, 2013).

Zhang, N., et al., "Targeted and untargeted CD137L fusion proteins for the immunotherapy of experimental solid tumors" Clin Cancer Res 13(9):2758-2767 (May 1, 2007).

Zhang, X., et al., "CD137 Promotes Proliferation and Survival of Human B Cells" J Immunol 184(2):787-795 (Jan. 15, 2010).

Claus, C., et al., "Tumor-targeted 4-1BB agonists for combination with T cell bispecific antibodies as off-the-shelf therapy" Sci Transl Med 11(496):eaav5989 (1-13) (Jun. 12, 2019).

Hutchings et al., "Phase 1 Study of CD19 Targeted 4-1BBL Costimulatory Agonist to Enhance T Cell (Glofitamab Combination) or NK Cell Effector Function (Obinutuzumab Combination) in Relapsed/Refractory B Cell Lymphoma" Blood 136( SUPPL 1):16-17 (2020).

Liu et al., "Efficient inhibition of human B-cell lymphoma in SCID mice by synergistic antitumor effect of human 4-1BB ligand/anti-CD20 fusion proteins and anti-CD3/anti-CD20 diabodies" J Immunother 33(5):500-509 (2010).

U.S. Appl. No. 16/522,391, filed Jul. 25, 2019, Granted, U.S. Pat. No. 11,306,154.

U.S. Appl. No. 16/522,412, filed Jul. 25, 2019, Granted, U.S. Pat. No. 11,267,903.

U.S. Appl. No. 17/580,970, filed Jan. 21, 2022, UnPublished.

U.S. Appl. No. 17/580,980, filed Jan. 21, 2022, UnPublished.

U.S. Appl. No. 17/347,257, filed Jun. 14, 2021, Published, US 2022/0073646 A1.

U.S. Appl. No. 16/721,272, filed Dec. 19, 2019, Published, US 2020/0199234 A1.

U.S. Appl. No. 17/498,515, filed Oct. 11, 2021, Published, US 2022/0025069 A1.

\* cited by examiner

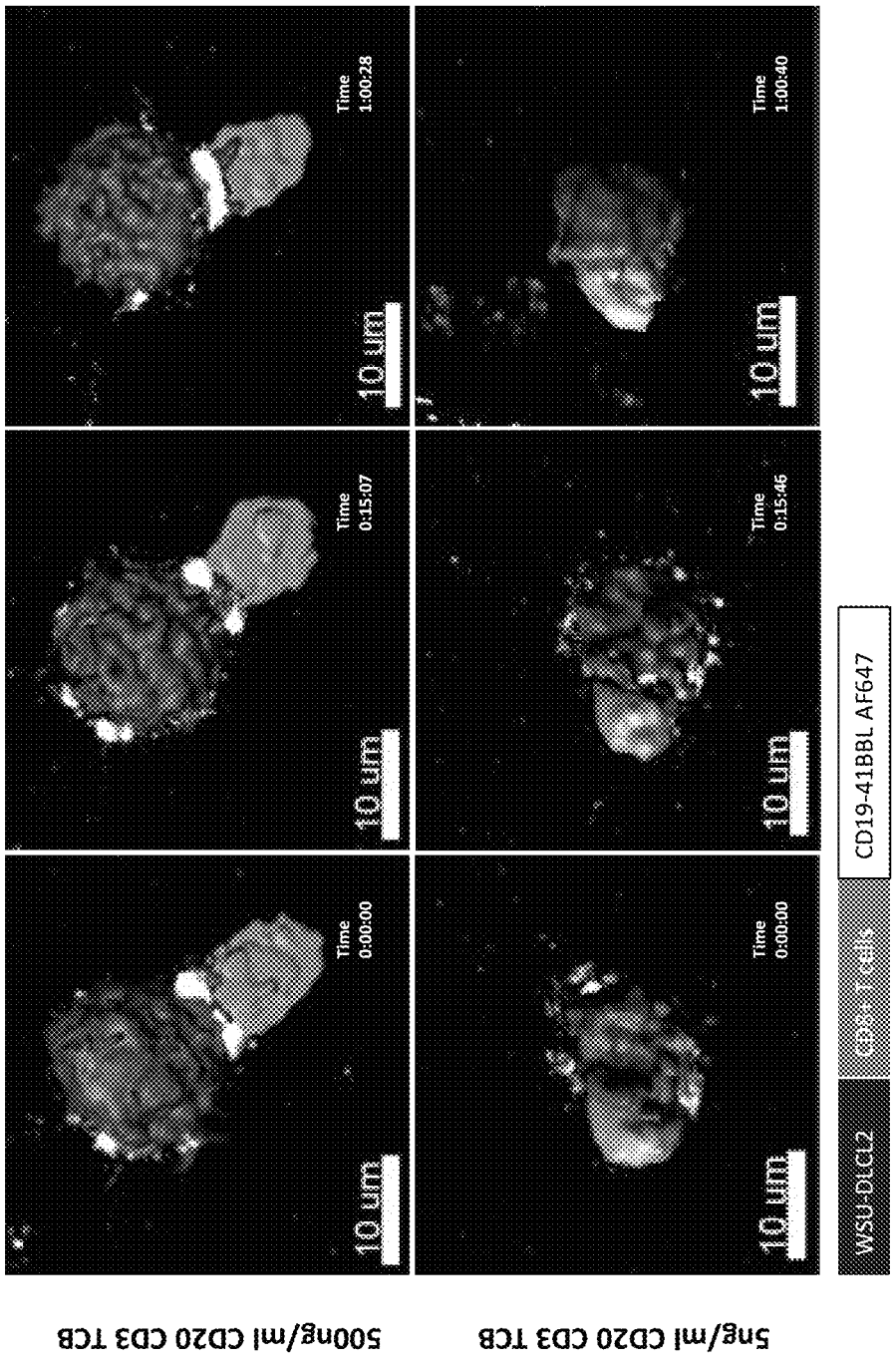

FIG. 8

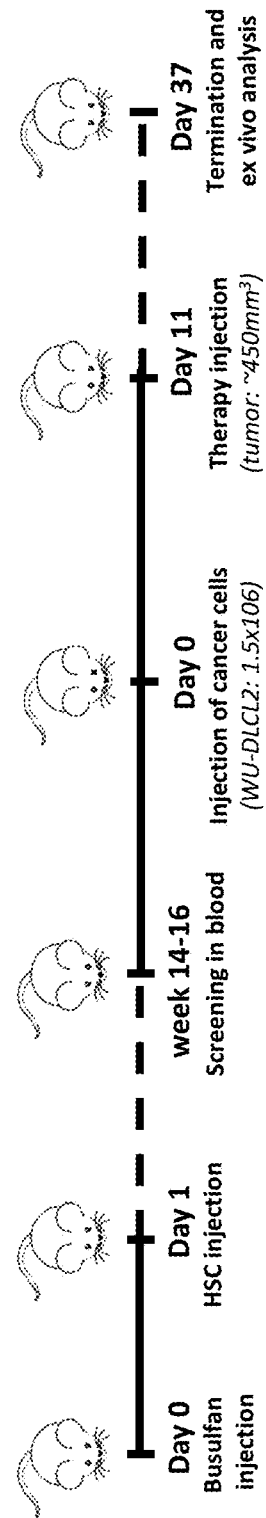

| Day 0 | Day 1 | week 14-16 | Day 0 | Day 11 | Day 37 |
|---|---|---|---|---|---|
| Busulfan injection | HSC injection | Screening in blood | Injection of cancer cells (WU-DLCL2: 1.5x106) | Therapy injection (tumor:~450mm³) | Termination and ex vivo analysis |

| Group | No. of animals | Compound | Dose (mg/kg) | Route of administration (therapy) | No. of treatments |
|---|---|---|---|---|---|
| A | 10 | Vehicle | --- | i.v. | 4 (once weekly) |
| B | 10 | CD20 TCB | 0.15 | i.v. | 4 (once weekly) |
| C | 10 | mono CD19 (018)-4-1BBL | 10 | i.v. | 4 (once weekly) |
| D | 10 | bi CD19 (018)-4-1BBL | 10 | i.v. | 4 (once weekly) |
| E | 10 | CD20 TCB + mono CD19 (018)-4-1BBL | 0.15 / 10 | i.v. | 4 (once weekly) |
| F | 10 | CD20 TCB + mono CD19 (018)-4-1BBL | 0.15 / 3 | i.v. | 4 (once weekly) |
| G | 10 | CD20 TCB + bi CD19 (018)-4-1BBL | 0.15 / 10 | i.v. | 4 (once weekly) |
| H | 10 | CD20 TCB + bi CD19 (018)-4-1BBL | 0.15 / 3 | i.v. | 4 (once weekly) |
| I | 10 | CD20 TCB + mono untarg.-4-1BBL | 0.15 / 10 | i.v. | 4 (once weekly) |

COMBINATION THERAPY OF ANTI-CD20/ANTI-CD3 BISPECIFIC ANTIBODIES AND 4-1BB (CD137) AGONISTS

CROSS REFERENCE TO RELATED APPLICATIONS

This application is a Continuation Application of U.S. application Ser. No. 16/446,478, filed Jun. 19, 2019 (abandoned), which is a Continuation Application of International Application No. PCT/EP2017/083222, filed Dec. 18, 2017, which claims the benefit of priority to EP 16205493.6, filed Dec. 20, 2016, each of which is incorporated herein by reference in its entirety.

SEQUENCE LISTING

This application contains a Sequence Listing which has been submitted electronically in ASCII format and is hereby incorporated by reference in its entirety. Said ASCII copy, created on Mar. 16, 2020, is named "P33995-US-1_Sequence_Listing" and is 249,157 bytes in size.

FIELD OF THE INVENTION

The present invention relates to combination therapies employing anti-CD20/anti-CD3 bispecific antibodies and 4-1BB (CD137) agonists, in particular 4-1BBL trimer containing antigen binding molecules, the use of these combination therapies for the treatment of cancer and methods of using the combination therapies.

BACKGROUND

B-cell proliferative disorders describe a heterogeneous group of malignancies that includes both leukemias and lymphomas. Lymphomas develop from lymphatic cells and include two main categories: Hodgkin lymphomas (HL) and the non-Hodgkin lymphomas (NHL). In the United States, lymphomas of B cell origin constitute approximately 80-85% of all non-Hodgkin lymphoma cases, and there is considerable heterogeneity within the B-cell subset, based upon genotypic and phenotypic expression patterns in the B-cell of origin. For example, B cell lymphoma subsets include the slow-growing indolent and incurable diseases, such as Follicular lymphoma (FL) or chronic lymphocytic leukemia (CLL), as well as the more aggressive subtypes, mantle cell lymphoma (MCL) and diffuse large B cell lymphoma (DLBCL). Despite the availability of various agents for the treatment of B-cell proliferative disorders, there is an ongoing need for development of safe and effective therapies to prolong remission and improve cure rates in patients.

An anti-CD20/anti-CD3 bispecific antibody is a molecule that targets CD20 expressed on B cells and CD3 epsilon chain (CD3ε) present on T cells. Simultaneous binding leads to T-cell activation and T-cell mediated killing of B cells. In the presence of CD20+ B cells, whether circulating or tissue resident, pharmacologically active doses of anti-CD20/anti-CD3 bispecific antibody will trigger T-cell activation and associated cytokine release. Parallel to B cell depletion in the peripheral blood, anti-CD20/anti-CD3 bispecific antibody leads to a transient decrease of T cells in the peripheral blood within 24 hours after the first administration and to a peak in cytokine release, followed by rapid T-cell recovery and return of cytokine levels to baseline within 72 hours. Thus, in order to achieve complete elimination of tumor cells, there is a need of an additional agent that conserves T-cell activation and delivers durable immune response to cancer cells.

4-1BB (CD137), a member of the TNF receptor superfamily, was first identified as an inducible molecule expressed by activated by T cells (Kwon and Weissman, 1989). Subsequent studies demonstrated that many other immune cells also express 4-1BB, including NK cells, B cells, NKT cells, monocytes, neutrophils, mast cells, dendritic cells (DCs) and cells of non-hematopoietic origin such as endothelial and smooth muscle cells (Vinay and Kwon, 2011). Expression of 4-1BB in different cell types is mostly inducible and driven by various stimulatory signals, such as T-cell receptor (TCR) or B-cell receptor triggering, as well as signaling induced through co-stimulatory molecules or receptors of pro-inflammatory cytokines (Diehl et al., 2002; Zhang et al., 2010).

4-1BB ligand (4-1BBL or CD137L) was identified in 1993 (Goodwin et al., 1993). It has been shown that expression of 4-1BBL was restricted on professional antigen presenting cells (APC) such as B-cells, DCs and macrophages. Inducible expression of 4-1BBL is characteristic for T-cells, including both αβ and γδ T-cell subsets, and endothelial cells (Shao and Schwarz, 2011).

Co-stimulation through the 4-1BB receptor (for example by 4-1BBL ligation) activates multiple signaling cascades within the T cell (both $CD4^+$ and $CD8^+$ subsets), powerfully augmenting T cell activation (Bartkowiak and Curran, 2015). In combination with TCR triggering, agonistic 4-1BB-specific antibodies enhance proliferation of T-cells, stimulate lymphokine secretion and decrease sensitivity of T-lymphocytes to activation-induced cells death (Snell et al., 2011). This mechanism was further advanced as the first proof of concept in cancer immunotherapy. In a preclinical model administration of an agonistic antibody against 4-1BB in tumor bearing mice led to potent anti-tumor effect (Melero et al., 1997). Later, accumulating evidence indicated that 4-1BB usually exhibits its potency as an anti-tumor agent only when administered in combination with other immunomodulatory compounds, chemotherapeutic reagents, tumor-specific vaccination or radiotherapy (Bartkowiak and Curran, 2015).

Signaling of the TNFR-superfamily needs cross-linking of the trimerized ligands to engage with the receptors, so does the 4-1BB agonistic antibodies which require wild type Fc-binding (Li and Ravetch, 2011). However, systemic administration of 4-1BB-specific agonistic antibodies with the functionally active Fc domain resulted in influx of $CD8^+$ T-cells associated with liver toxicity (Dubrot et al., 2010) that is diminished or significantly ameliorated in the absence of functional Fc-receptors in mice. In the clinic, an Fc-competent 4-1BB agonistic Ab (BMS-663513) (NCT00612664) caused a grade 4 hepatitis leading to termination of the trial (Simeone and Ascierto, 2012). Therefore, there is a need for effective and safer 4-1BB agonists.

Fusion proteins composed of one extracellular domain of a 4-1BB ligand and a single chain antibody fragment (Hornig et al., 2012; Müller et al., 2008) or a single 4-1BB ligand fused to the C-terminus of a heavy chain (Zhang et al., 2007) have been made. WO 2010/010051 discloses the generation of fusion proteins that consist of three TNF ligand ectodomains linked to each other and fused to an antibody part. In the present invention, antigen binding molecules composed of a trimeric and thus biologically active 4-1BB ligand and an antigen binding domain specific for the tumor antigen CD19 and an Fc inactive domain, are shown particularly stable and robust (herein named as CD19-4-1BBL). These constructs are disclosed in WO 2016/075278 and replace unspecific FcγR-mediated crosslinking responsible for Fc-mediated toxicity, by CD19-targeted B cell specific crosslinking.

CD19 is an ideal target for immunotherapy of B-cell malignancies as it is expressed on the surface of B-cells and is almost specific to these cells. CD19 is more broadly expressed than CD20 on B cells during the B cell development, so typically a CD20 positive cell will also expressed CD19. During differentiation of B cells towards plasma cells (antibody-secreting cells), B cells down-regulates CD20 expression. Sometimes, B cell lymhomas also down-regulate CD20 expression, but remain positive for CD19. Therefore, targeting both CD19 and CD20 would cover broadly the diseased B cells in lymphomas, which might also deviate the selection pressure from CD20 to both CD19 and CD20. Though it is not known if CD19 contributes directly to B cell carcinogenesis, its expression is highly conserved on most B cell tumors such as acute lymphoblastic leukemias (ALL), chronic lymphocytic leukemias (CLL) and B cell lymphomas. In acute leukemias CD19 is steadily and continuously expressed on almost all subtypes while only a small number of leukemias express CD20.

It has been found that a maximum anti-tumor effect of 4-1BB agonism is achieved when the CD19-targeted 4-1BBL antigen binding molecule is combined with an anti-CD20/anti-CD3 bispecific antibody, i.e. a CD20 T cell bispecific antibody. The T-cell bispecific antibody provides the initial TCR activating signalling to T cells, and then the combination with CD19-4-1BBL leads to a further boost of anti-tumor T cell immunity. Thus, we herein describe a novel combination therapy for cancer with B cell malignancy.

SUMMARY OF THE INVENTION

The present invention relates to anti-CD20/anti-CD3 bispecific antibodies and their use in combination with 4-1BB (CD137) agonists, in particular 4-1BB (CD137) agonists comprising at least one antigen binding domain capable of specific binding to CD19, particularly 4-1BBL trimer containing antigen binding molecules, in a method for treating or delaying progression of cancer, more particularly for treating or delaying progression of B-cell proliferative disorders. It has been found that the combination therapy described herein is more effective in inhibiting tumor growth and eliminating tumor cells than treatment with the anti-CD20/anti-CD3 bispecific antibodies alone.

In one aspect, the invention provides an anti-CD20/anti-CD3 bispecific antibody for use in a method for treating or delaying progression of cancer, wherein the anti-CD20/anti-CD3 bispecific antibody is used in combination with a 4-1BB (CD137) agonist comprising at least one antigen binding domain capable of specific binding to CD19, in particular a 4-1BB agonist comprising three ectodomains of 4-1BBL or fragments thereof and at least one antigen binding domain capable of specific binding to CD19.

In particular, the 4-1BB agonist is an antigen binding molecule comprising at least one antigen binding domain capable of specific binding to CD19. In one aspect, the 4-1BB agonist is an antigen binding molecule comprising a Fc domain. In a particular aspect, the -1BB agonist is an antigen binding molecule comprising a Fc domain with modifications reducing or preferably eliminating Fcγ receptor binding and/or effector function.

In a further aspect, provided is an anti-CD20/anti-CD3 bispecific antibody for use in a method for treating or delaying progression of cancer, wherein the anti-CD20/anti-CD3 bispecific antibody and the 4-1BB agonist comprising at least one antigen binding domain capable of specific binding to CD19 are administered together in a single composition or administered separately in two or more different compositions.

In another aspect, provided is an anti-CD20/anti-CD3 bispecific antibody for use in a method for treating or delaying progression of cancer, wherein the anti-CD20/anti-CD3 bispecific antibody is administered concurrently with, prior to, or subsequently to the 4-1BB agonist comprising at least one antigen binding domain capable of specific binding to CD19.

In one aspect, the invention provides an anti-CD20/anti-CD3 bispecific antibody for use in a method for treating or delaying progression of cancer, wherein the 4-1BB agonist comprises three ectodomains of 4-1BBL or fragments thereof. In a further aspect, provided is an anti-CD20/anti-CD3 bispecific antibody for use in a method for treating or delaying progression of cancer, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5. More particularly, the ectodomains of 4-1BBL comprise an amino acid sequence of SEQ ID NO:5.

In a further aspect, provided is an anti-CD20/anti-CD3 bispecific antibody for use in a method for treating or delaying progression of cancer, wherein the 4-1BB agonist is an antigen binding molecule comprising three ectodomains of 4-1BBL or fragments thereof and at least one antigen binding domain capable of specific binding to CD19. In one aspect, the antigen binding molecule comprising three ectodomains of 4-1BBL or fragments thereof and at least one antigen binding domain capable of specific binding to CD19 will not be internalized by CD19-expressing B cells. In another aspect, provided is an anti-CD20/anti-CD3 bispecific antibody for use in a method for treating or delaying progression of cancer, wherein the 4-1BB agonist is an antigen binding molecule comprising three ectodomains of 4-1BBL or fragments thereof and at least one moiety capable of specific binding to CD19, wherein the antigen binding domain capable of specific binding to CD19 comprises (a) a heavy chain variable region ($V_H$CD19) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$CD19) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region ($V_H$CD19) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region ($V_L$CD19) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In a particular aspect, provided is an anti-CD20/anti-CD3 bispecific antibody for use in a method for treating or delaying progression of cancer, wherein the 4-1BB agonist is an antigen binding molecule comprising three ectodomains of 4-1BBL or fragments thereof and at least one antigen binding domain capable of specific binding to CD19, wherein the antigen binding domain capable of specific binding to CD19 comprises a heavy chain variable region ($V_H$CD19) comprising an amino acid sequence of SEQ ID NO:21 and a light chain variable region ($V_L$CD19) comprising an amino acid sequence of SEQ ID NO:22 or wherein the antigen binding domain capable of specific binding to CD19 comprises a heavy chain variable region ($V_H$CD19) comprising an amino acid sequence of SEQ ID NO:23 and a light chain variable region ($V_L$CD19) comprising an amino acid sequence of SEQ ID NO:24. In a particular aspect, the antigen binding domain capable of specific binding to CD19 comprises a heavy chain variable region ($V_H$CD19) comprising an amino acid sequence of SEQ ID NO:23 and a light chain variable region ($V_L$CD19) comprising an amino acid sequence of SEQ ID NO:24.

In one aspect, provided is an anti-CD20/anti-CD3 bispecific antibody for use in a method for treating or delaying progression of cancer, wherein the 4-1BB agonist comprising at least one antigen binding domain capable of specific binding to CD19 is an antigen binding molecule further comprising a Fc domain composed of a first and a second subunit capable of stable association. In particular, the 4-1BB agonist is an antigen binding molecule comprising an IgG Fc domain, specifically an IgG1 Fc domain or an IgG4 Fc domain. More particularly, the 4-1BB agonist is an antigen binding molecule comprising a Fc domain that comprises one or more amino acid substitution that reduces binding to an Fc receptor and/or effector function. In a particular aspect, the 4-1BB agonist comprises an IgG1 Fc domain comprising the amino acid substitutions L234A, L235A and P329G.

In another aspect of the invention, provided is an anti-CD20/anti-CD3 bispecific antibody for use in a method for treating or delaying progression of cancer, wherein the 4-1BB agonist is an antigen binding molecule comprising
(a) at least one antigen binding domain capable of specific binding to CD19,
(b) a first and a second polypeptide that are linked to each other by a disulfide bond,
wherein the first polypeptide comprises two ectodomains of 4-1BBL or fragments thereof that are connected to each other by a peptide linker and wherein the second polypeptide comprises one ectodomain of 4-1BBL or a fragment thereof.

In another aspect, the invention provides an anti-CD20/anti-CD3 bispecific antibody for use in a method for treating or delaying progression of cancer, wherein the 4-1BB agonist is an antigen binding molecule comprising
(a) at least one Fab domain capable of specific binding to CD19, and
(b) a first and a second polypeptide that are linked to each other by a disulfide bond,
wherein the antigen binding molecule is characterized in that
  (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or
  (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
  (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

In one aspect, provided is an anti-CD20/anti-CD3 bispecific antibody for use in a method for treating or delaying progression of cancer, wherein the 4-1BB agonist is an antigen binding molecule comprising
(a) at least one Fab domain capable of specific binding to CD19 comprising a heavy chain variable region ($V_H$CD19) comprising the amino acid sequence of SEQ ID NO:21 and a light chain variable region ($V_L$CD19) comprising the amino acid sequence of SEQ ID NO:22 or a heavy chain variable region ($V_H$CD19) comprising the amino acid sequence of SEQ ID NO:23 and a light chain variable region ($V_L$CD19) comprising the amino acid sequence of SEQ ID NO:24, and
(b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In a particular aspect, provided is an anti-CD20/anti-CD3 bispecific antibody for use in a method for treating or delaying progression of cancer, wherein the 4-1BB agonist is an antigen binding molecule selected from the group consisting of
a) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:35 and a second light chain comprising the amino acid sequence of SEQ ID NO:36;
b) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:37 and a second light chain comprising the amino acid sequence of SEQ ID NO:38;
c) a molecule comprising two light chains comprising the amino acid sequence of SEQ ID NO:34, a first heavy chain comprising the amino acid sequence of SEQ ID NO:39 and a second heavy chain comprising the amino acid sequence of SEQ ID NO:40;

d) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:41 and a second light chain comprising the amino acid sequence of SEQ ID NO:42;

e) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:43 and a second light chain comprising the amino acid sequence of SEQ ID NO:44;

f) a molecule comprising two light chains comprising the amino acid sequence of SEQ ID NO:34, a first heavy chain comprising the amino acid sequence of SEQ ID NO:45 and a second heavy chain comprising the amino acid sequence of SEQ ID NO:46;

g) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:35 and a second light chain comprising the amino acid sequence of SEQ ID NO:36;

h) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:37 and a second light chain comprising the amino acid sequence of SEQ ID NO:38;

i) a molecule comprising two light chains comprising the amino acid sequence of SEQ ID NO:48, a first heavy chain comprising the amino acid sequence of SEQ ID NO:49 and a second heavy chain comprising the amino acid sequence of SEQ ID NO:50;

j) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:41 and a second light chain comprising the amino acid sequence of SEQ ID NO:42;

k) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:43 and a second light chain comprising the amino acid sequence of SEQ ID NO:44; and l) a molecule comprising two light chains comprising the amino acid sequence of SEQ ID NO:48, a first heavy chain comprising the amino acid sequence of SEQ ID NO:51 and a second heavy chain comprising the amino acid sequence of SEQ ID NO:52.

In another aspect, the invention provides an anti-CD20/anti-CD3 bispecific antibody for use in a method for treating or delaying progression of cancer, wherein the 4-1BB agonist is an antigen binding molecule comprising
(a) at least one antigen binding domain capable of specific binding to CD19,
(b) a polypeptide comprising three ectodomains of 4-1BBL or fragments thereof that are connected to each other by peptide linkers.

In one aspect, provided is an anti-CD20/anti-CD3 bispecific antibody for use in a method for treating or delaying progression of cancer, wherein the 4-1BB agonist is an antigen binding molecule comprising
(a) at least one antigen binding domain capable of specific binding to CD19,
(b) a polypeptide comprising three ectodomains of 4-1BBL or fragments thereof that are connected to each other by peptide linkers, and
(c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

In a particular aspect, provided is an anti-CD20/anti-CD3 bispecific antibody for use in a method for treating or delaying progression of cancer, wherein the 4-1BB agonist is an antigen binding molecule selected from the group consisting of
(a) a molecule comprising a heavy chain variable region ($V_H$CD19) comprising the amino acid sequence of SEQ ID NO:33, a light chain variable region ($V_L$CD19) comprising the amino acid sequence of SEQ ID NO:34, and a fusion protein comprising the amino acid sequence of SEQ ID NO:53,
(b) a molecule comprising a heavy chain variable region ($V_H$CD19) comprising the amino acid sequence of SEQ ID NO:47, a light chain variable region ($V_L$CD19) comprising the amino acid sequence of SEQ ID NO:48 and a fusion protein comprising the amino acid sequence of SEQ ID NO:53;
(c) a molecule comprising a heavy chain variable region ($V_H$CD19) comprising the amino acid sequence of SEQ ID NO:33, a light chain variable region ($V_L$CD19) comprising the amino acid sequence of SEQ ID NO:34, and a fusion protein comprising the amino acid sequence of SEQ ID NO:54, and
(d) a molecule comprising a heavy chain variable region ($V_H$CD19) comprising the amino acid sequence of SEQ ID NO:47, a light chain variable region ($V_L$CD19) comprising the amino acid sequence of SEQ ID NO:48, and a fusion protein comprising the amino acid sequence of SEQ ID NO:55.

In another aspect, the invention provides an anti-CD20/anti-CD3 bispecific antibody for use in a method for treating or delaying progression of cancer, wherein the 4-1BB agonist is an anti-CD19/anti-4-1BB bispecific antibody.

In all these aspects, the invention further provides an anti-CD20/anti-CD3 bispecific antibody for use in a method for treating or delaying progression of cancer, wherein the anti-CD20/anti-CD3 bispecific antibody comprises a first antigen binding domain that binds to CD3, and a second antigen binding domain that binds to CD20. In particular, the anti-CD20/anti-CD3 bispecific antibody comprises a first antigen binding domain comprising a heavy chain variable region ($V_H$CD3) and a light chain variable region ($V_L$CD3), and a second antigen binding domain comprising a heavy chain variable region ($V_H$CD20) and a light chain variable region ($V_L$CD20). In one aspect, the first antigen binding domain comprises a heavy chain variable region ($V_H$CD3) comprising CDR-H1 sequence of SEQ ID NO:56, CDR-H2 sequence of SEQ ID NO:57, and CDR-H3 sequence of SEQ ID NO:58; and/or a light chain variable region ($V_L$CD3) comprising CDR-L1 sequence of SEQ ID NO:59, CDR-L2 sequence of SEQ ID NO:60, and CDR-L3 sequence of SEQ ID NO:61. More particularly, the first antigen binding domain comprises a heavy chain variable region ($V_H$CD3) comprising the amino acid sequence of SEQ ID NO:62 and/or a light chain variable region ($V_L$CD3) comprising the amino acid sequence of SEQ ID NO:63. In another aspect, the second antigen binding domain comprises a heavy chain variable region (V$_H$CD20) comprising CDR-H1 sequence of SEQ ID NO:64, CDR-H2 sequence of SEQ ID NO:65, and CDR-H3 sequence of SEQ ID NO:66, and/or a light chain variable region (V$_L$CD20) comprising CDR-L1 sequence of SEQ ID NO:67, CDR-L2 sequence of SEQ ID NO:68, and CDR-L3 sequence of SEQ ID NO:69. More particularly, the second antigen binding domain comprises a heavy chain variable region (V$_H$CD20) comprising the amino acid sequence of SEQ ID NO:70 and/or a light chain variable region (V$_L$CD20) comprising the amino acid sequence of SEQ ID NO:71.

In another aspect, the invention further provides an anti-CD20/anti-CD3 bispecific antibody for use in a method for treating or delaying progression of cancer, wherein the anti-CD20/anti-CD3 bispecific antibody further comprises a third antigen binding domain that binds to CD20. In particular, the third antigen binding domain comprises a heavy chain variable region (V$_H$CD20) comprising CDR-H1 sequence of SEQ ID NO:64, CDR-H2 sequence of SEQ ID NO:65, and CDR-H3 sequence of SEQ ID NO:66; and/or a light chain variable region (V$_L$CD20) comprising CDR-L1 sequence of SEQ ID NO:67, CDR-L2 sequence of SEQ ID NO:68, and CDR-L3 sequence of SEQ ID NO:69. More particularly, the third antigen binding domain comprises a heavy chain variable region (V$_H$CD20) comprising the amino acid sequence of SEQ ID NO:70 and/or a light chain variable region (V$_L$CD20) comprising the amino acid sequence of SEQ ID NO:71.

In a further aspect, provided is an anti-CD20/anti-CD3 bispecific antibody for use in a method for treating or delaying progression of cancer, wherein the first antigen binding domain is a cross-Fab molecule wherein the variable domains or the constant domains of the Fab heavy and light chain are exchanged, and the second and third, if present, antigen binding domain is a conventional Fab molecule.

In a further aspect, provided is an anti-CD20/anti-CD3 bispecific antibody for use in a method for treating or delaying progression of cancer, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

In a further aspect, the invention provides an anti-CD20/anti-CD3 bispecific antibody for use in a method for treating or delaying progression of cancer, wherein the anti-CD20/anti-CD3 bispecific antibody comprises an Fc domain comprising one or more amino acid substitutions that reduce binding to an Fc receptor and/or effector function. More particularly, the anti-CD20/anti-CD3 bispecific antibody comprises an IgG1 Fc domain comprising the amino acid substitutions L234A, L235A and P329G.

In another aspect, provided is an anti-CD20/anti-CD3 bispecific antibody for use in a method for treating or delaying progression of cancer, wherein the anti-CD20/anti-CD3 bispecific antibody is used in combination with a 4-1BB (CD137) agonist comprising at least one antigen binding domain capable of specific binding to CD19 and wherein the combination is administered at intervals from about one week to three weeks.

In another aspect, provided is an anti-CD20/anti-CD3 bispecific antibody for use in a method for treating or delaying progression of cancer, wherein the anti-CD20/anti-CD3 bispecific antibody is used in combination with a 4-1BB (CD137) agonist comprising at least one antigen binding domain capable of specific binding to CD19 and wherein a pretreatment with an Type II anti-CD20 antibody, preferably obinutuzumab, is performed prior to the combination treatment, wherein the period of time between the pretreatment and the combination treatment is sufficient for the reduction of B-cells in the individual in response to the Type II anti-CD20 antibody, preferably obinutuzumab.

In another aspect, provided is an anti-CD20/anti-CD3 bispecific antibody for use in a method for treating or delaying progression of cancer, wherein the anti-CD20/anti-CD3 bispecific antibody is used in combination with a 4-1BB (CD137) agonist comprising at least one antigen binding domain capable of specific binding to CD19 and wherein furthermore a PD1 or PD-L1 antibody, preferably atezolizumab, is administered.

In a further aspect, the invention provides a pharmaceutical product comprising (A) a first composition comprising as active ingredient an anti-CD20/anti-CD3 bispecific antibody and a pharmaceutically acceptable carrier; and (B) a second composition comprising as active ingredient a 4-1BB agonist comprising at least one antigen binding domain capable of specific binding to CD19 and a pharmaceutically acceptable carrier, for use in the combined, sequential or simultaneous treatment of a disease, in particular for the treatment of cancer.

In another aspect, provided is a pharmaceutical composition comprising an anti-CD20/anti-CD3 bispecific antibody and a 4-1BB agonist comprising at least one antigen binding domain capable of specific binding to CD19. In particular, the pharmaceutical composition is for use in in the treatment of B-cell proliferative disorders, in particular a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

In an additional aspect, the invention provides a kit for treating or delaying progression of cancer in a subject, comprising a package comprising (A) a first composition comprising as active ingredient an anti-CD20/anti-CD3 bispecific antibody and a pharmaceutically acceptable carrier; (B) a second composition comprising as active ingredient a 4-1BB agonist comprising at least one antigen binding domain capable of specific binding to CD19 and a pharmaceutically acceptable carrier, and (C) instructions for using the compositions in a combination therapy.

In a further aspect, the invention relates to the use of a combination of an anti-CD20/anti-CD3 bispecific antibody and a 4-1BB agonist comprising at least one antigen binding domain capable of specific binding to CD19 in the manufacture of a medicament for treating or delaying progression of a proliferative disease, in particular cancer.

In particular, provided is the use of a combination of an anti-CD20/anti-CD3 bispecific antibody and a 4-1BB agonist comprising at least one antigen binding domain capable of specific binding to CD19 in the manufacture of a medicament for treating a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

In another aspect, the invention provides a method for treating or delaying progression of cancer in a subject comprising administering to the subject an effective amount of an anti-CD20/anti-CD3 antibody and a 4-1BB agonist comprising at least one antigen binding domain capable of specific binding to CD19. In particular, the invention relates to a method for treating or delaying progression of cancer in a subject, wherein the 4-1BB agonist is an antigen binding molecule comprising at least one antigen binding domain capable of specific binding to CD19. In one aspect, the 4-1BB agonist is an antigen binding molecule comprising a Fc domain. In a particular aspect, the -1BB agonist is an antigen binding molecule comprising a Fc domain with modifications reducing Fcγ receptor binding and/or effector function. In a particular aspect, the 4-1BB agonist comprising at least one antigen binding domain capable of specific binding to CD19 is an antigen binding molecule comprising three ectodomains of 4-1BBL or fragments thereof. More particularly, the 4-1BB agonist is an antigen binding molecule comprising three ectodomains of 4-1BBL or fragments thereof and an antigen binding domain capable of specific binding to CD19.

In a further aspect, the invention provides a method for treating or delaying progression of cancer in a subject comprising administering to the subject an effective amount of the anti-CD20/anti-CD3 antibody and the 4-1BB agonist comprising at least one antigen binding domain capable of specific binding to CD19, wherein the anti-CD20/anti-CD3 bispecific antibody and the 4-1BB agonist comprising at least one antigen binding domain capable of specific binding to CD19 are administered together in a single composition or administered separately in two or more different compositions. In particular, the anti-CD20/anti-CD3 bispecific antibody and the 4-1BB (CD137) agonist comprising at least one antigen binding domain capable of specific binding to CD19 are administered intravenously or subcutaneously. In a further aspect, the anti-CD20/anti-CD3 bispecific antibody is administered concurrently with, prior to, or subsequently to the 4-1BB agonist comprising at least one antigen binding domain capable of specific binding to CD19.

BRIEF DESCRIPTION OF THE DRAWINGS

FIG. 1A shows a monovalent CD19 4-1BBL-trimer containing antigen binding molecule with modifications in the CH1 and CL domain adjacent to the 4-1BBL dimer and 4-1BBL monomer. As it comprised the CD19 binder 8B8-018, it was named mono CD19(018)-4-1BBL herein. The construct shown in FIG. 1B differs from FIG. 1A in that it comprises the CD19 binder 8B8-2B11 and was thus termed mono CD19(2B11)-4-1BBL. FIG. 1C shows the bivalent construct with binder CD19(018), termed bi CD19(018)-4-1BBL. In FIG. 1D an exemplary bispecific anti-CD20/anti-CD3 antibody in 2+1 format is shown (named CD20 TCB). FIGS. 1E and 1F show untargeted control molecules (the CD19 binder has been replaced by a non-binding DP47 Fab).

FIGS. 5A and 5B show a visualization of dynamic antibody localization by Fluorescence Confocal Microscopy. An analysis over time showed that the CD19-41BBL molecule (shown in white) polarizes towards T cell/tumor cell site of interaction in the presence of 500 ng/ml CD20 CD3 TCB and not when 5 ng/ml CD20 CD3 TCB was used, as seen in snapshots of T cells in contact with tumor cells at three different time points (FIG. 5A). The labelled CD19-41BBL was quantified over time (FIG. 5B), showing a stable localization of CD19-41BBL at the site of interaction in a dose-dependent manner.

FIG. 8 shows the protocol of the in vivo efficacy study of mono vs. bi CD19 (018)-4-1BBL constructs in combination with CD20 TCB in WSU-DLCL2-bearing fully humanized NOG mice. In the table below the subgroups of mice receiving different combinations and doses are defined. The experiment is described in Example 5b and the results are shown in FIGS. 9A and 9B. The combination of mono CD19 (018)-4-1BBL in combination with CD20 TCB did not only induce stronger and faster tumor growth inhibition as compared to monotherapy with CD20 TCB, but was also superior to the combination of bi CD19 (018)-4-1BBL or mono untargeted 4-1BBL and CD20 TCB in all doses tested.

Figure 12A:
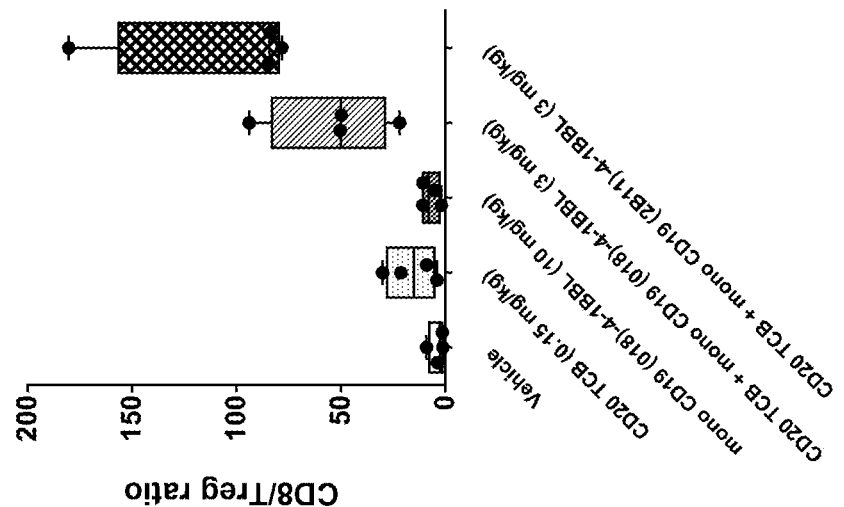
Figure 12B:
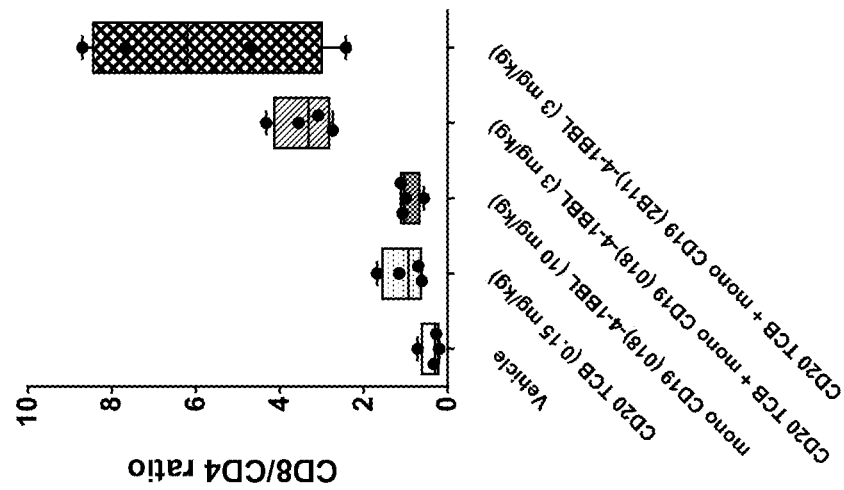
Figure 12C:
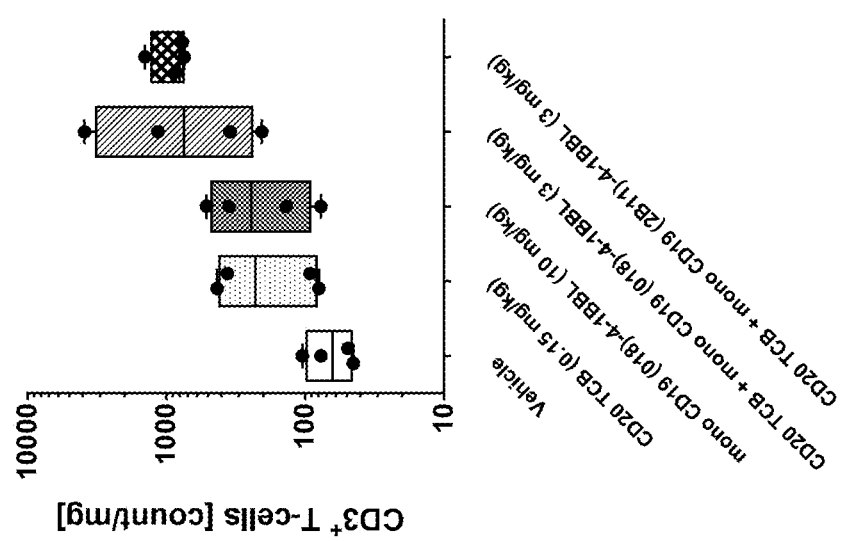

The Immuno-pharmacodynamics (PD) data of tumors from animals (scouts) sacrificed at study day 20 are shown in FIGS. 12A, 12B and 12C. The data revealed an enhanced intra-tumoral human T-cell infiltration (FIG. 12A), shift of CD8/CD4 ratios (FIG. 12B) and CD8/Treg ratios (FIG. 12C) towards CD8 cells in both combination groups as compared to CD20 TCB alone or vehicle tumors. However, no differences were observed between the two groups for the combination of CD20 TCB with either mono CD19 (018)-4-1BBL or mono CD19 (2B11)-4-1BBL.

DETAILED DESCRIPTION OF THE INVENTION

Definitions

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869, 046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134

(2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments in which the cysteine residue(s) of the constant domains bear a free thiol group. Pepsin treatment yields an F(ab')2 fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the VH with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin).

Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633.

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

A single-domain antibody is an antibody fragment consisting of a single monomeric variable antibody domain. The first single domains were derived from the variable domain of the antibody heavy chain from camelids (nanobodies or VHH fragments). Furthermore, the term single-domain antibody includes an autonomous human heavy chain variable domain (aVH) or $V_{NAR}$ fragments derived from sharks.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

A "B-cell antigen" as used herein refers to an antigenic determinant presented on the surface of a B lymphocyte, particularly a malignant B lymphocyte (in that case the antigen also being referred to as "malignant B-cell antigen").

The term "CD19" refers to B-lymphocyte antigen CD19, also known as B-lymphocyte surface antigen B4 or T-cell surface antigen Leu-12 and includes any native CD19 from any vertebrate source, including mammals such as primates (e.g. humans) non-human primates (e.g. cynomolgus monkeys) and rodents (e.g. mice and rats), unless otherwise indicated. The amino acid sequence of human CD19 is shown in Uniprot accession no. P15391 (version 160, SEQ ID NO:80). The term encompasses "full-length" unprocessed human CD19 as well as any form of human CD19 that results from processing in the cell as long as the antibody as reported herein binds thereto. CD19 is a structurally distinct cell surface receptor expressed on the surface of human B cells, including, but not limited to, pre-B cells, B cells in early development {i.e., immature B cells), mature B cells through terminal differentiation into plasma cells, and malignant B cells. CD19 is expressed by most pre-B acute lymphoblastic leukemias (ALL), non-Hodgkin's lymphomas, B cell chronic lymphocytic leukemias (CLL), pro-lymphocytic leukemias, hairy cell leukemias, common acute lymphocytic leukemias, and some Null-acute lymphoblastic leukemias. The expression of CD19 on plasma cells further suggests it may be expressed on differentiated B cell tumors such as multiple myeloma. Therefore, the CD19 antigen is a target for immunotherapy in the treatment of non-Hodgkin's lymphoma, chronic lymphocytic leukemia and/or acute lymphoblastic leukemia.

"CD20" refers to B-lymphocyte antigen CD20, also known as B-lymphocyte surface antigen B1 or Leukocyte surface antigen Leu-16, and includes any native CD20 from any vertebrate source, including mammals such as primates (e.g. humans) non-human primates (e.g. cynomolgus monkeys) and rodents (e.g. mice and rats), unless otherwise indicated. The amino acid sequence of human CD20 is shown in Uniprot accession no. P11836 (version 149, SEQ ID NO:81). CD20 is a hydrophobic transmembrane protein with a molecular weight of approximately 35 kD expressed on pre-B and mature B lymphocytes. The corresponding human gene is membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein. The term "CD20" encompasses "full-length," unprocessed CD20 as well as any form of CD20 that results from processing in the cell. The term also encompasses naturally occurring variants of CD20, e.g., splice variants or allelic variants.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-CD20 antibody binds to an epitope of CD20 that is conserved among CD20 from different species.

By "Type II anti-CD20 antibody" is meant an anti-CD20 antibody having binding properties and biological activities of Type II anti-CD20 antibodies as described in Cragg et al., Blood 103 (2004) 2738-2743; Cragg et al., Blood 101 (2003) 1045-1052, Klein et al., mAbs 5 (2013), 22-33, and summarized in Table 1 below.

TABLE A

Properties of type I and type II anti-CD20 antibodies

| type I anti-CD20 antibodies | type II anti-CD20 antibodies |
|---|---|
| Bind class I CD20 epitope | Bind class II CD20 epitope |
| Localize CD20 to lipid rafts | Do not localize CD20 to lipid rafts |
| High CDC * | Low CDC * |
| ADCC activity * | ADCC activity * |
| Full binding capacity to B cells | Approx. half binding capacity to B cells |
| Weak homotypic aggregation | Homotypic aggregation |
| Low cell death induction | Strong cell death induction |

* if IgG$_1$ isotype

Examples of type II anti-CD20 antibodies include e.g. obinutuzumab (GA101), tositumumab (B1), humanized B-Ly1 antibody IgG1 (a chimeric humanized IgG1 antibody as disclosed in WO 2005/044859), 11B8 IgG1 (as disclosed in WO 2004/035607) and AT80 IgG1.

In one aspect, the Type II anti-CD20 antibody comprises the heavy chain variable region sequence (V$_H$CD20) of SEQ ID NO: 70 and the light chain variable region sequence (V$_L$CD20) of SEQ ID NO: 71. In another aspect, the Type II anti-CD20 antibody is engineered to have an increased proportion of non-fucosylated oligosaccharides in the Fc region as compared to a non-engineered antibody. In one aspect, at least about 40% of the N-linked oligosaccharides in the Fc region of the Type II anti-CD20 antibody are non-fucosylated.

In a particular aspect, the Type II anti-CD20 antibody is obinutuzumab (recommended INN, WHO Drug Information, Vol. 26, No. 4, 2012, p. 453). As used herein, obinutuzumab is synonymous for GA101. The tradename is GAZYVA® or GAZYVARO®. This replaces all previous versions (e.g. Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124). In one embodiment, the Type II anti-CD20 antibody comprises the heavy chain variable region sequence of SEQ ID NO: 10 and the light chain variable region sequence of SEQ ID NO: 11. In one aspect, the Type II anti-CD20 antibody is tositumomab.

Examples of type I anti-CD20 antibodies include e.g. rituximab, ofatumumab, veltuzumab, ocaratuzumab, ocrelizumab, PRO131921, ublituximab, HI47 IgG3 (ECACC, hybridoma), 2C6 IgG1 (as disclosed in WO 2005/103081), 2F2 IgG1 (as disclosed in WO 2004/035607 and WO 2005/103081) and 2H7 IgG1 (as disclosed in WO 2004/056312).

The term "humanized B-Ly1 antibody" refers to humanized B-Ly1 antibody as disclosed in WO 2005/044859 and WO 2007/031875, which were obtained from the murine monoclonal anti-CD20 antibody B-Ly1 (variable region of the murine heavy chain (VH): SEQ ID NO:82; variable region of the murine light chain (VL): SEQ ID NO:83 (see Poppema, S. and Visser, L., Biotest Bulletin 3 (1987) 131-139) by chimerization with a human constant domain from IgG1 and following humanization (see WO 2005/044859 and WO 2007/031875). These "humanized B-Ly1 antibodies" are disclosed in detail in WO 2005/044859 and WO 2007/031875.

The term "reduction" (and grammatical variations thereof such as "reduce" or "reducing"), for example reduction of the number of B cells or cytokine release, refers to a decrease in the respective quantity, as measured by appropriate methods known in the art. For clarity the term includes also reduction to zero (or below the detection limit of the analytical method), i.e. complete abolishment or elimination. Conversely, "increased" refers to an increase in the respective quantity.

A "T-cell antigen" as used herein refers to an antigenic determinant presented on the surface of a T lymphocyte, particularly a cytotoxic T lymphocyte.

A "T cell activating therapeutic agent" as used herein refers to a therapeutic agent capable of inducing T cell activation in a subject, particularly a therapeutic agent designed for inducing T-cell activation in a subject. Examples of T cell activating therapeutic agents include bispecific antibodies that specifically bind an activating T cell antigen, such as CD3, and a target cell antigen, such as CD20 or CD19. Further examples include chimeric antigen receptors (CARs) which comprise a T cell activating domain and an antigen binding moiety that specifically binds to a target cell antigen, such as CD20 or CD19.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3.

The term "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3ε). The amino acid sequence of human CD3ε is shown in UniProt (www.uniprot.org) accession no. P07766 (version 144), or NCBI (www.ncbi.nlm.nih.gov/) RefSeq NP_000724.1. See also SEQ ID NO: 84. The amino acid sequence of cynomolgus [*Macaca fascicularis*] CD3ε is shown in NCBI GenBank no. BAB71849.1. See also SEQ ID NO: 85.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table B as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE B

| CDR Definitions[1] | | | |
| --- | --- | --- | --- |
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

As used herein, the term "effector cells" refers to a population of lymphocytes that display effector moiety receptors, e.g. cytokine receptors, and/or Fc receptors on their surface through which they bind an effector moiety, e.g. a cytokine, and/or an Fc region of an antibody and contribute to the destruction of target cells, e.g. tumor cells. Effector cells may for example mediate cytotoxic or phagocytic effects. Effector cells include, but are not limited to, effector T cells such as CD8$^+$cytotoxic T cells, CD4$^+$ helper T cells, γδ T cells, NK cells, lymphokine-activated killer (LAK) cells and macrophages/monocytes.

An "ectodomain" is the domain of a membrane protein that extends into the extracellular space (i.e. the space outside the target cell). Ectodomains are usually the parts of proteins that initiate contact with surfaces, which leads to signal transduction. The ectodomain of 4-1BBL as defined herein thus refers to the part of the 4-1BBL that extends into the extracellular space (the extracellular domain), but also includes shorter parts or fragments thereof that are responsible for the trimerization and for the binding to the corresponding receptor 4-1BB. The term "ectodomain of 4-1BBL or a fragment thereof" thus refers to the extracellular domain of 4-1BBL that forms the extracellular domain or to parts thereof that are still able to bind to the receptor (receptor binding domain).

"4-1BBL" or "4-1BB ligand" or "CD137L" is a costimulatory TNF ligand family member, which is able to costimulate proliferation and cytokine production of T-cells. Costimulatory TNF family ligands can costimulate TCR signals upon interaction with their corresponding TNF receptors and the interaction with their receptors leads to recruitment of TNFR-associated factors (TRAF), which initiate signalling cascades that result in T-cell activation. 4-1BBL is a type II transmembrane protein. Complete or full length 4-1BBL having the amino acid sequence of SEQ ID NO:86 has been described to form trimers on the surface of cells. The formation of trimers is enabled by specific motives of the ectodomain of 4-1BBL. Said motives are designated herein as "trimerization region". The amino acids 50-254 of the human 4-1BBL sequence (SEQ ID NO:87) form the extracellular domain of 4-1BBL, but even fragments thereof are able to form the trimers. In specific embodiments of the invention, the term "ectodomain of 4-1BBL or a fragment thereof" refers to a polypeptide having an amino acid sequence selected from SEQ ID NO:4 (amino acids 52-254 of human 4-1BBL), SEQ ID NO:1 (amino acids 71-254 of human 4-1BBL), SEQ ID NO:3 (amino acids 80-254 of human 4-1BBL), SEQ ID NO:2 (amino acids 85-254 of human 4-1BBL), SEQ ID NO:5 (amino acids 71-248 of human 4-1BBL), SEQ ID NO:6 (amino acids 85-248 of human 4-1BBL), SEQ ID NO:7 (amino acids 80-248 of human 4-1BBL) and SEQ ID NO:8 (amino acids 52-248 of human 4-1BBL), but also other fragments of the ectodomain capable of trimerization are included herein.

The term "4-1BB" or "CD137", as used herein, refers to any native 4-1BB from any vertebrate source, including mammals such as primates (e.g. humans) and rodents (e.g., mice and rats), unless otherwise indicated. The term encompasses "full-length," unprocessed 4-1BB as well as any form of 4-1BB that results from processing in the cell. The term also encompasses naturally occurring variants of 4-1BB, e.g., splice variants or allelic variants. The amino acid sequence of an exemplary human 4-1BB is shown in SEQ ID NO: 88 (Uniprot accession no. Q07011), the amino acid sequence of an exemplary murine 4-1BB is shown in SEQ ID NO: 89 (Uniprot accession no. P20334) and the amino acid sequence of an exemplary cynomolgous 4-1BB (from Macaca mulatta) is shown in SEQ ID NO:90 (Uniprot accession no. F6W5G6).

The terms "anti-4-1BB antibody", "anti-4-1BB", "4-1BB antibody and "an antibody that specifically binds to 4-1BB" refer to an antibody that is capable of binding 4-1BB with sufficient affinity such that the antibody is useful as a diagnostic and/or therapeutic agent in targeting 4-1BB. In one embodiment, the extent of binding of an anti-4-1BB antibody to an unrelated, non-4-1BB protein is less than about 10% of the binding of the antibody to 4-1BB as measured, e.g., by a radioimmunoassay (RIA) or flow cytometry (FACS). In certain embodiments, an antibody that binds to 4-1BB has a dissociation constant ($K_D$) of ≤1 µM, ≤100 nM, ≤10 nM, ≤1 nM, ≤0.1 nM, ≤0.01 nM, or ≤0.001 nM (e.g. $10^{-6}$ M or less, e.g. from $10^{-68}$ M to $10^{-13}$ M, e.g., from $10^{-8}$ M to $10^{-10}$ M).

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 2 and 4, in particular 2, i.e. the peptides selected from the group consisting of GGGGS (SEQ ID NO: 91) GGGGSGGGGS (SEQ ID NO:92), SGGGGSGGGG (SEQ ID NO:93) and GGGGSGGGGSGGGG (SEQ ID NO:94), but also include the sequences GSPGSSSSGS (SEQ ID NO:95), (G4S)$_3$ (SEQ ID NO:96), (G4S)$_4$ (SEQ ID NO:97), GSGSGSGS (SEQ ID NO:98), GSGSGNGS (SEQ ID NO:99), GGSGSGSG (SEQ ID NO:100), GGSGSG (SEQ ID NO:101), GGSG (SEQ ID NO:102), GGSGNGSG (SEQ ID NO:103), GGNGSGSG (SEQ ID NO:104) and GGNGSG (SEQ ID NO:105). Peptide linkers of particular interest are (G4S) (SEQ ID NO:91), (G4S)$_2$ and GGGGSGGGGS (SEQ ID NO:92).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a polypeptide and an ectodomain of 4-1BBL) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the antigen binding molecules provided herein are contemplated. For example, it may be desirable to improve the binding affinity and/or other biological properties of the antigen binding molecules. Amino acid sequence variants of the antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table C under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE C

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more CDR residues are mutated and the variant antigen binding molecules displayed on phage and screened for a particular biological activity (e.g. binding affinity). In certain embodiments, substitutions, insertions, or deletions may occur within one or more CDRs so long as such alterations do not substantially reduce the ability of the antigen binding molecule to bind antigen. For example, conservative alterations (e.g., conservative substitutions as provided herein) that do not substantially reduce binding affinity may be made in CDRs. A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antigen binding molecules with an N-terminal methionyl residue. Other insertional variants of the molecule include the fusion to the N- or C-terminus to a polypeptide which increases the serum half-life of the antigen binding molecules.

In certain embodiments, the antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antigen binding molecules may be made in order to create variants with certain improved properties. In one aspect, variants of antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

Engineering", particularly with the prefix "glyco-", as well as the term "glycosylation engineering" includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity. Glycosylation engineering can be used to obtain a "host cell having increased GnTIII activity" (e.g. a host cell that has been manipulated to express increased levels of one or more polypeptides having β(1,4)-N-acetylglucosaminyltransferase III (GnTIII) activity), a "host cell having increased ManII activity" (e.g. a host cell that has been manipulated to express increased levels of one or more polypeptides having a-mannosidase II (ManII) activity), or a "host cell having decreased α(1,6) fucosyltransferase activity" (e.g. a host cell that has been manipulated to express decreased levels of α(1,6) fucosyltransferase).

As used herein, the term "polypeptide having GnTIII activity" refers to polypeptides that are able to catalyze the addition of a N-acetylglucosamine (GlcNAc) residue in β-1,4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependency in a given activity as compared to the GnTIII (i.e. the candidate polypeptide will exhibit greater activity or not more than about 25-fold less and, preferably, not more than about ten-fold less activity, and most preferably, not more than about three-fold less activity relative to the GnTIII).

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g. to express the glycosyltransferase, GnTIII, or other glycosyltransferases) by the methods described herein, is relative to the ADCC mediated by the same antibody produced by the same type of non-engineered host cells.

In certain aspects, the invention contemplates an antibody variant that possesses some but not all effector functions, which make it a desirable candidate for applications in which the half life of the antibody in vivo is important yet certain effector functions (such as complement-dependent cytotoxicity (CDC) and antibody-dependent cell-mediated cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166: 1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). Clq binding assays may also be carried out to confirm that the antibody is unable to bind Clq and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006); WO 2013/120929 A1).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).) In certain embodiments, an antibody variant comprises an Fc region with one or more amino acid substitutions which improve ADCC, e.g., substitutions at positions 298, 333, and/or 334 of the Fc region (EU numbering of residues).

In certain aspects, an antibody variant comprises an Fc region with one or more amino acid substitutions which diminish FcγR binding, e.g., substitutions at positions 234 and 235 of the Fc region (EU numbering of residues). In one aspect, the substitutions are L234A and L235A (LALA). In certain aspects, the antibody variant further comprises D265A and/or P329G in an Fc region derived from a human IgG1 Fc region. In one aspect, the substitutions are L234A, L235A and P329G (LALA-PG) in an Fc region derived from a human IgG1 Fc region. (See, e.g., WO 2012/130831). In another aspect, the substitutions are L234A, L235A and D265A (LALA-DA) in an Fc region derived from a human IgG1 Fc region.

In some embodiments, alterations are made in the Fc region that result in altered (i.e., either improved or diminished) Clq binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (See, e.g., U.S. Pat. No. 7,371,826; Dall'Acqua, W. F., et al. J. Biol. Chem. 281 (2006) 23514-23524).

In certain aspects, an antibody variant comprises an Fc region with one or more amino acid substitutions, which reduce FcRn binding, e.g., substitutions at positions 253, and/or 310, and/or 435 of the Fc-region (EU numbering of residues). In certain aspects, the antibody variant comprises an Fc region with the amino acid substitutions at positions 253, 310 and 435. In one aspect, the substitutions are I253A, H310A and H435A in an Fc region derived from a human IgG1 Fc-region. See e.g., Grevys, A., et al., J. Immunol. 194 (2015) 5497-5508.

In another aspect, an antibody variant comprises an Fc region with one or more amino acid substitutions, which reduce FcRn binding, e.g., substitutions at positions 310, and/or 433, and/or 436 of the Fc region (EU numbering of residues). In certain aspects, the antibody variant comprises an Fc region with the amino acid substitutions at positions 310, 433 and 436. In one aspect, the substitutions are H310A, H433A and Y436A in an Fc region derived from a human IgG1 Fc-region. (See, e.g., WO 2014/177460 A1).

In certain aspects, an antibody variant comprises an Fc region with one or more amino acid substitutions which increase FcRn binding, e.g., substitutions at positions 252, and/or 254, and/or 256 of the Fc region (EU numbering of residues). In certain embodiments, the antibody variant comprises an Fc region with amino acid substitutions at positions 252, 254, and 256. In one embodiment the substitutions are M252Y, S254T and T256E in an Fc region derived from a human IgG1 Fc-region (see also Duncan & Winter, Nature 322:738-40 (1988); U.S. Pat. Nos. 5,648,260; 5,624,821; and WO 94/29351 concerning other examples of Fc region variants.

In certain embodiments, it may be desirable to create cysteine engineered variants of the antigen binding molecules of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed. In another aspect, immunoconjugates of the 4-1BBL-containing antigen binding molecules provided herein maybe obtained. An "immunoconjugate" is an antibody conjugated to one or more heterologous molecule(s), including but not limited to a cytotoxic agent.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas or lymphocytic leukemias, or melanoma.

By "B cell proliferative disorder" is meant a disease wherein the number of B cells in a patient is increased as compared to the number of B cells in a healthy subject, and particularly wherein the increase in the number of B cells is the cause or hallmark of the disease. A "CD20-positive B cell proliferative disorder" is a B cell proliferative disorder wherein B-cells, particularly malignant B-cells (in addition to normal B-cells), express CD20. Exemplary B cell proliferation disorders include Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), as well as some types of Multiple myeloma (MM) and Hodgkin lymphoma (HL).

Exemplary Anti-CD20/Anti-CD3 Bispecific Antibodies for Use in the Invention

The present invention relates to anti-CD20/anti-CD3 bispecific antibodies and their use in combination with 4-1BB (CD137) agonists, in particular to their use use in a method for treating or delaying progression of cancer, more particularly for treating or delaying progression of B-cell proliferative disorders. The anti-CD20/anti-CD3 bispecific antibodies as used herein are bispecific antibodies comprising a first antigen binding domain that binds to CD3, and a second antigen binding domain that binds to CD20.

Thus, the anti-CD20/anti-CD3 bispecific antibody as used herein comprises a first antigen binding domain comprising a heavy chain variable region ($V_H$CD3) and a light chain variable region ($V_L$CD3), and a second antigen binding domain comprising a heavy chain variable region ($V_H$CD20) and a light chain variable region ($V_L$CD20).

In a particular aspect, the anti-CD20/anti-CD3 bispecific antibody for use in the combination comprises a first antigen binding domain comprising a heavy chain variable region ($V_H$CD3) comprising CDR-H1 sequence of SEQ ID NO:56, CDR-H2 sequence of SEQ ID NO:57, and CDR-H3 sequence of SEQ ID NO:58; and/or a light chain variable region ($V_L$CD3) comprising CDR-L1 sequence of SEQ ID NO:59, CDR-L2 sequence of SEQ ID NO:60, and CDR-L3 sequence of SEQ ID NO:61. More particularly, the anti-CD20/anti-CD3 bispecific comprises a first antigen binding domain comprising a heavy chain variable region ($V_H$CD3) that is at least 90%, 95%, 96%, 97%, 98%, or 99% identical to the amino acid sequence of SEQ ID NO:62 and/or a light chain variable region ($V_L$CD3) that is at least 90%, 95%, 96%, 97%, 98%, or 99% identical to the amino acid sequence of SEQ ID NO:63. In a further aspect, the anti-CD20/anti-CD3 bispecific antibody comprises a heavy chain variable region ($V_H$CD3) comprising the amino acid sequence of SEQ ID NO:62 and/or a light chain variable region ($V_L$CD3) comprising the amino acid sequence of SEQ ID NO:63.

In one aspect, the antibody that specifically binds to CD3 is a full-length antibody. In one aspect, the antibody that specifically binds to CD3 is an antibody of the human IgG class, particularly an antibody of the human IgG$_1$ class. In one aspect, the antibody that specifically binds to CD3 is an antibody fragment, particularly a Fab molecule or a scFv molecule, more particularly a Fab molecule. In a particular aspect, the antibody that specifically binds to CD3 is a crossover Fab molecule wherein the variable domains or the constant domains of the Fab heavy and light chain are exchanged (i.e. replaced by each other). In one aspect, the antibody that specifically binds to CD3 is a humanized antibody.

In another aspect, the anti-CD20/anti-CD3 bispecific antibody comprises a second antigen binding domain comprising a heavy chain variable region ($V_H$CD20) comprising CDR-H1 sequence of SEQ ID NO:64, CDR-H2 sequence of SEQ ID NO:65, and CDR-H3 sequence of SEQ ID NO:66, and/or a light chain variable region ($V_L$CD20) comprising CDR-L1 sequence of SEQ ID NO:67, CDR-L2 sequence of SEQ ID NO:68, and CDR-L3 sequence of SEQ ID NO:69.

More particularly, the anti-CD20/anti-CD3 bispecific comprises a second antigen binding domain comprising a heavy chain variable region ($V_H$CD20) that is at least 90%, 95%, 96%, 97%, 98%, or 99% identical to the amino acid sequence of SEQ ID NO:70 and/or a light chain variable region ($V_L$CD20) that is at least 90%, 95%, 96%, 97%, 98%, or 99% identical to the amino acid sequence of SEQ ID NO:71. In a further aspect, the anti-CD20/anti-CD3 bispecific comprises a second antigen binding domain comprising a heavy chain variable region ($V_H$CD20) comprising the amino acid sequence of SEQ ID NO:70 and/or a light chain variable region ($V_L$CD20) comprising the amino acid sequence of SEQ ID NO:71.

In another particular aspect, the anti-CD20/anti-CD3 bispecific antibody comprises a third antigen binding domain that binds to CD20. In particular, the anti-CD20/anti-CD3 bispecific antibody comprises a third antigen binding domain comprising a heavy chain variable region ($V_H$CD20) comprising CDR-H1 sequence of SEQ ID NO:64, CDR-H2 sequence of SEQ ID NO:65, and CDR-H3 sequence of SEQ ID NO:66; and/or a light chain variable region ($V_L$CD20) comprising CDR-L1 sequence of SEQ ID NO:67, CDR-L2 sequence of SEQ ID NO:68, and CDR-L3 sequence of SEQ ID NO:69. More particularly, the anti-CD20/anti-CD3 bispecific comprises a third antigen binding domain comprising a heavy chain variable region ($V_H$CD20) that is at least 90%, 95%, 96%, 97%, 98%, or 99% identical to the amino acid sequence of SEQ ID NO:70 and/or a light chain variable region ($V_L$CD20) that is at least 90%, 95%, 96%, 97%, 98%, or 99% identical to the amino acid sequence of SEQ ID NO:71. In a further aspect, the anti-CD20/anti-CD3 bispecific comprises a third antigen binding domain comprising a heavy chain variable region ($V_H$CD20) comprising the amino acid sequence of SEQ ID NO:70 and/or a light chain variable region ($V_L$CD20) comprising the amino acid sequence of SEQ ID NO:71.

In a further aspect, the anti-CD20/anti-CD3 bispecific antibody is bispecific antibody, wherein the first antigen binding domain is a cross-Fab molecule wherein the variable domains or the constant domains of the Fab heavy and light chain are exchanged, and the second and third, if present, antigen binding domain is a conventional Fab molecule.

In another aspect, the anti-CD20/anti-CD3 bispecific antibody is bispecific antibody, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

The Fab molecules may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one embodiment said peptide linker has a length of at least 5 amino acids, in one embodiment a length of 5 to 100, in a further embodiment of 10 to 50 amino acids. In one embodiment said peptide linker is $(GxS)_n$ or $(GxS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one embodiment x=4 and n=2 or 3, in a further embodiment x=4 and n=2. In one embodiment said peptide linker is $(G_4S)_2$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence (D)-$(G_4S)_2$. Another suitable such linker comprises the sequence $(G_4S)_4$. Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

In a further aspect, the anti-CD20/anti-CD3 bispecific antibody comprises an Fc domain comprising one or more amino acid substitutions that reduce binding to an Fc receptor and/or effector function. In particular, the anti-CD20/anti-CD3 bispecific antibody comprises an IgG1 Fc domain comprising the amino acid substitutions L234A, L235A and P329G.

In a particular aspect, the anti-CD20/anti-CD3 bispecific antibody comprises a polypeptide that is at least 95%, 96%, 97%, 98%, or 99% identical to the sequence of SEQ ID NO: 76, a polypeptide that is at least 95%, 96%, 97%, 98%, or 99% identical to the sequence of SEQ ID NO: 77, a polypeptide that is at least 95%, 96%, 97%, 98%, or 99% identical to the sequence of SEQ ID NO: 78, and a polypeptide that is at least 95%, 96%, 97%, 98%, or 99% identical to the sequence of SEQ ID NO: 79. In a further particular embodiment, the bispecific antibody comprises a polypeptide sequence of SEQ ID NO: 76, a polypeptide sequence of SEQ ID NO: 77, a polypeptide sequence of SEQ ID NO: 78 and a polypeptide sequence of SEQ ID NO: 79 (CD20 TCB).

Particular bispecific antibodies are described in PCT publication no. WO 2016/020309 A1 or in WO 2015/095392 A1.

In a further aspect, the anti-CD20/anti-CD3 bispecific antibody may also comprise a bispecific T cell engager (BiTE®). In a further aspect, the anti-CD20/anti-CD3 bispecific antibody is XmAb® 13676. In another aspect, the bispecific antibody is REGN1979. In another aspect, the bispecific antibody is FBTA05 (*Lymphomun*).

Exemplary 4-1BB Agonists for Use in the Invention

In particular, the 4-1BB agonists comprising at least one antigen binding domain capable of specific binding to CD19 as used in combination with the anti-CD20/anti-CD3 bispecific antibody are molecules comprising 4-1BBL. In particular, the 4-1BB agonist used in the invention comprises three ectodomains of 4-1BBL or fragments thereof.

In a particular aspect, the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

It has been shown herein, that the 4-1BB agonist is especially useful if it comprises an antigen binding domain that is specific for a tumor target, in particular for a target on B cells. Thus, in another aspect, the 4-1BB agonist is an antigen binding molecule comprising three ectodomains of 4-1BBL or fragments thereof and at least one antigen binding domain capable of specific binding to CD19.

It has been further shown herein, that a 4-1BB agonist comprising at least one antigen binding domain capable of specific binding to CD19 was not internalized by CD19 into B cells and thus did not loss its ability to interact with the tumor microenvironment. In a further aspect, provided is a 4-1BB agonist that will not be internalized in B cells, thereby maintaining its activity.

In another aspect, the 4-1BB agonist is an antigen binding molecule comprising three ectodomains of 4-1BBL or fragments thereof and at least one moiety capable of specific binding to CD19, wherein the antigen binding domain capable of specific binding to CD19 is cyno-cross-reactive, i.e. the antigen binding domain capable of specific binding to CD19 specifically binds to human and to cynomolgus CD19.

In a further aspect, the 4-1BB agonist is an antigen binding molecule comprising three ectodomains of 4-1BBL or fragments thereof and at least one moiety capable of specific binding to CD19, wherein the antigen binding domain capable of specific binding to CD19 comprises
(a) a heavy chain variable region ($V_H$CD19) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$CD19) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
(b) a VH domain comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a VL domain comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In a particular aspect, the antigen binding domain capable of specific binding to CD19 comprises a VH domain comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a VL domain comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In a further aspect, the 4-1BB agonist is an antigen binding molecule comprising three ectodomains of 4-1BBL or fragments thereof and at least one antigen binding domain capable of specific binding to CD19, wherein the antigen binding domain capable of specific binding to CD19 comprises a heavy chain variable region ($V_H$CD19) comprising an amino acid sequence of SEQ ID NO:21 and a light chain variable region ($V_L$CD19) comprising an amino acid sequence of SEQ ID NO:22 or wherein the antigen binding domain capable of specific binding to CD19 comprises a heavy chain variable region ($V_H$CD19) comprising an amino acid sequence of SEQ ID NO:23 and a light chain variable region ($V_L$CD19) comprising an amino acid sequence of SEQ ID NO:24. More particularly, the antigen binding domain capable of specific binding to CD19 comprises a heavy chain variable region ($V_H$CD19) comprising an amino acid sequence of SEQ ID NO:23 and a light chain variable region ($V_L$CD19) comprising an amino acid sequence of SEQ ID NO:24.

In another aspect, the 4-1BB agonist is an antigen binding molecule further comprising a Fc domain composed of a first and a second subunit capable of stable association. In one aspect, the 4-1BB agonist is an antigen binding molecule comprising an IgG Fc domain, specifically an IgG1 Fc domain or an IgG4 Fc domain. Particularly, the 4-1BB agonist is an antigen binding molecule comprising a Fc domain that comprises one or more amino acid substitution that reduces binding to an Fc receptor and/or effector function. In a particular aspect, the 4-1BB agonist is an antigen binding molecule comprising an IgG1 Fc domain comprising the amino acid substitutions L234A, L235A and P329G.

In one aspect, the 4-1BB agonist is an antigen binding molecule comprising
(a) at least one antigen binding domain capable of specific binding to CD19,
(b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

In a particular aspect, the 4-1BB agonist is an antigen binding molecule comprising
(a) at least one Fab domain capable of specific binding to CD19, and
(b) a first and a second polypeptide that are linked to each other by a disulfide bond, wherein the antigen binding molecule is characterized in that
 (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment therof connected via a peptide linker to the CL or CH1 domain of said polypeptide, or
 (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
 (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

In another aspect, the 4-1BB agonist is an antigen binding molecule comprising
(a) at least one Fab domain capable of specific binding to CD19 comprising a heavy chain variable region ($V_H$CD19) comprising the amino acid sequence of SEQ ID NO:21 and a light chain variable region ($V_L$CD19) comprising the amino acid sequence of SEQ ID NO:22 or a heavy chain variable region ($V_H$CD19) comprising the amino acid sequence of SEQ ID NO:23 and a light chain variable region ($V_L$CD19) comprising the amino acid sequence of SEQ ID NO:24, and
(b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In a particular aspect, the 4-1BB agonist is an antigen binding molecule selected from the group consisting of
a) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:35 and a second light chain comprising the amino acid sequence of SEQ ID NO:36;
b) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:37 and a second light chain comprising the amino acid sequence of SEQ ID NO:38;
c) a molecule comprising two light chains comprising the amino acid sequence of SEQ ID NO:34, a first heavy chain comprising the amino acid sequence of SEQ ID NO:39 and a second heavy chain comprising the amino acid sequence of SEQ ID NO:40;
d) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:41 and a second light chain comprising the amino acid sequence of SEQ ID NO:42;
e) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:43 and a second light chain comprising the amino acid sequence of SEQ ID NO:44;
f) a molecule comprising two light chains comprising the amino acid sequence of SEQ ID NO:34, a first heavy chain comprising the amino acid sequence of SEQ ID NO:45 and a second heavy chain comprising the amino acid sequence of SEQ ID NO:46;
g) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:35 and a second light chain comprising the amino acid sequence of SEQ ID NO:36;
h) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:37 and a second light chain comprising the amino acid sequence of SEQ ID NO:38;
i) a molecule comprising two light chains comprising the amino acid sequence of SEQ ID NO:48, a first heavy chain comprising the amino acid sequence of SEQ ID NO:49 and a second heavy chain comprising the amino acid sequence of SEQ ID NO:50;
j) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:41 and a second light chain comprising the amino acid sequence of SEQ ID NO:42;
k) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:43 and a second light chain comprising the amino acid sequence of SEQ ID NO:44; and
l) a molecule comprising two light chains comprising the amino acid sequence of SEQ ID NO:48, a first heavy chain comprising the amino acid sequence of SEQ ID NO:51 and a second heavy chain comprising the amino acid sequence of SEQ ID NO:52.

In another aspect, the 4-1BB agonist is an antigen binding molecule comprising
(a) at least one antigen binding domain capable of specific binding to CD19,
(b) a polypeptide comprising three ectodomains of 4-1BBL or fragments thereof that are connected to each other by peptide linkers.

In one aspect, the 4-1BB agonist is an antigen binding molecule comprising
(a) at least one antigen binding domain capable of specific binding to CD19,
(b) a polypeptide comprising three ectodomains of 4-1BBL or fragments thereof that are connected to each other by peptide linkers, and
(c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

In a particular aspect, the 4-1BB agonist is an antigen binding molecule selected from the group consisting of
(a) a molecule comprising a heavy chain variable region ($V_H$CD19) comprising the amino acid sequence of SEQ ID NO:33, a light chain variable region ($V_L$CD19) comprising the amino acid sequence of SEQ ID NO:34, and a fusion protein comprising the amino acid sequence of SEQ ID NO:53,
(b) a molecule comprising a heavy chain variable region ($V_H$CD19) comprising the amino acid sequence of SEQ ID NO:47, a light chain variable region ($V_L$CD19) comprising the amino acid sequence of SEQ ID NO:48 and a fusion protein comprising the amino acid sequence of SEQ ID NO:53;
(c) a molecule comprising a heavy chain variable region ($V_H$CD19) comprising the amino acid sequence of SEQ ID NO:33, a light chain variable region ($V_L$CD19) comprising the amino acid sequence of SEQ ID NO:34, and a fusion protein comprising the amino acid sequence of SEQ ID NO:54, and (d) a molecule comprising a heavy chain variable region (V$_H$CD19) comprising the amino acid sequence of SEQ ID NO:47, a light chain variable region (V$_L$CD19) comprising the amino acid sequence of SEQ ID NO:48, and a fusion protein comprising the amino acid sequence of SEQ ID NO:55.

In a further aspect, the 4-1BB agonist is an anti-CD19/ anti-4-1BB bispecific antibody.

Preparation of Bispecific Antibodies for Use in the Invention

In certain aspects, the therapeutic agents used in the combination comprise multispecific antibodies, e.g. bispecific antibodies. Multispecific antibodies are monoclonal antibodies that have binding specificities for at least two different sites. In certain aspects, the binding specificities are for different antigens. In certain aspects, the binding specificities are for different epitopes on the same antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking of two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibodies or fragmentsa herein also include a "Dual Acting FAb" or "DAF" comprising an antigen binding site that binds to two different antigens (see, US 2008/0069820, for example). "Crossmab" antibodies are also included herein (see e.g. WO 2009/080251, WO 2009/080252, WO2009/080253, or WO2009/080254).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain (VH) and a variable light chain (VL) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell.

As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species. In one aspect, the bispecific bispecific antibodies used in the invention are composed of a single polypeptide chain comprising two single chain FV fragments (scFV) fused to each other by a peptide linker.

Fc Domain Modifications Reducing Fc Receptor Binding and/or Effector Function

The Fc domain of the antigen binding molecules of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

The Fc domain confers favorable pharmacokinetic properties to the antigen binding molecules of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular aspects, the Fc domain of the antigen binding molecules of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region)

comprising an amino acid modification (e.g. a substitution) at one or more amino acid positions.

In a particular aspect, the invention provides an antibody, wherein the Fc domain comprises one or more amino acid substitution that reduces binding to an Fc receptor, in particular towards Fcγ receptor.

In one aspect, the Fc domain of the antibody of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is an antibody according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or cell activating antibodies comprising an Fc domain for Fc receptors may be evaluated using cell lines known to express particular Fc receptors, such as human NK cells expressing FcγIIIa receptor.

Effector function of an Fc domain, or antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some aspects, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antigen binding molecule of the invention is able to bind C1q and hence has CDC activity (see e.g., C1q and C3c binding ELISA in WO 2006/029879 and WO 2005/100402). To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Fc Domain Modifications Promoting Heterodimerization

The bispecific antigen binding molecules of the invention comprise different antigen-binding sites, fused to one or the other of the two subunits of the Fc domain, thus the two subunits of the Fc domain may be comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc domain of the bispecific antigen binding molecules of the invention a modification promoting the association of the desired polypeptides.

Accordingly, in particular aspects the invention relates to the bispecific antigen binding molecule comprising (a) at least one moiety capable of specific binding to CD19, (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof, and (c) a Fc domain composed of a first and a second subunit capable of stable association, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect said modification is a so-called "knob-into-hole" modification, comprising a "knob" modification in one of the two subunits of the Fc domain and a "hole" modification in the other one of the two subunits of the Fc domain. Thus, the invention relates to an antigen binding molecule comprising (a) at least one moiety capable of specific binding to CD19, (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof, and (c) a Fc domain composed of a first and a second subunit capable of stable association, wherein the first subunit of the Fc domain comprises knobs and the second subunit of the Fc domain comprises holes according to the knobs into holes method. In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc domain of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A).

In yet a further aspect, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in the formation of a disulfide bridge between the two subunits of the Fc domain that further stabilizes the dimer (Carter (2001), J Immunol Methods 248, 7-15). In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

The C-terminus of the heavy chain of the bispecific antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, a bispecific antibody comprising a heavy chain including a C-terminal CH3 domain as specified herein, comprises the C-terminal glycine-lysine dipeptide (G446 and K447, numbering according to Kabat EU index). In one embodiment of all aspects as reported herein, a bispecific antibody comprising a heavy chain including a C-terminal CH3 domain, as specified herein, comprises a C-terminal glycine residue (G446, numbering according to Kabat EU index).

Modifications in the Fab Domains

In one aspect, the invention relates to a 4-1BBL-containing antigen binding molecule, comprising (a) a Fab fragment capable of specific binding to CD19, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and (c) a Fc domain composed of a first and a second subunit capable of stable association, wherein in one of the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In one aspect, the invention relates to a bispecific antigen binding molecule comprising (a) a first Fab fragment capable of specific binding to CD19, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and wherein each of them is linked to a CH1 or CL domain, and (c) a Fc domain composed of a first and a second subunit capable of stable association, wherein the constant domains CL and CH1 adjacent to 4-1BBL are replaced by each other so that the CH1 domain is part of the light chain and the CL domain is part of the heavy chain.

In another aspect, the invention relates to a bispecific antigen binding molecule, comprising (a) two light chains and two heavy chains of an antibody comprising two Fab fragments capable of specific binding to a costimulatory TNF receptor family member and the Fc domain, and (b) two additional Fab fragments capable of specific binding to a target cell antigen, wherein said additional Fab fragments are each connected via a peptide linker to the C-terminus of the heavy chains of (a). In a particular aspect, the additional Fab fragments are Fab fragments, wherein the variable domains VL and VH are replaced by each other so that the VH domain is part of the light chain and the VL domain is part of the heavy chain.

In another aspect, and to further improve correct pairing, the bispecific antigen binding molecule comprising (a) a first Fab fragment capable of specific binding to CD19, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and wherein each of them is linked to a CH1 or CL domain, and (c) a Fc domain composed of a first and a second subunit capable of stable association, can contain different charged amino acid substitutions (so-called "charged residues"). These modifications are introduced in the crossed or non-crossed CH1 and CL domains. In a particular aspect, the invention relates to a bispecific antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E).

More particularly, the invention relates to a bispecific antigen binding molecule comprising a Fab, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E).

Polynucleotides

The invention further provides isolated polynucleotides encoding a bispecific antibody as described herein or a fragment thereof.

The isolated polynucleotides encoding the antibodies of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated polynucleotide encodes the entire antibody according to the invention as described herein. In other embodiments, the isolated polynucleotide encodes a polypeptide comprised in the antibody according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Bispecific antibodies as used in the invention may be obtained, for example, by solid-state peptide synthesis (e.g. Merrifield solid phase synthesis) or recombinant production. For recombinant production one or more polynucleotide encoding the antibody or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the antibody (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the antibody or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody or polypeptide fragments thereof is desired, DNA encoding a signal sequence may be placed upstream of the nucleic acid an antibody of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding an antibody of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) an antibody of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040, 498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr-CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing an antibody of the invention or polypeptide fragments thereof is provided, wherein the method comprises culturing a host cell comprising polynucleotides encoding the antibody of the invention or polypeptide fragments thereof, as provided herein, under conditions suitable for expression of the antibody of the invention or polypeptide fragments thereof, and recovering the antibody of the invention or polypeptide fragments thereof from the host cell (or host cell culture medium).

In certain embodiments the moieties capable of specific binding to a target cell antigen (e.g. Fab fragments) forming part of the antigen binding molecule comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the antibodies are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, N.J.). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch. 14 (Cold Spring Harbor Laboratory, Cold Spring Harbor, N.Y.).

Antibodies of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the antigen binding molecule or fragments thereof can be determined by any of a variety of well-known analytical methods including gel electrophoresis, high pressure liquid chromatography, and the like. For example, the 4-1BBL-containing antigen binding molecules expressed as described in the Examples were shown to be intact and properly assembled as demonstrated by reducing and non-reducing SDS-PAGE.

Assays

The antigen binding molecules provided herein may be identified, screened for, or characterized for their physical/chemical properties and/or biological activities by various assays known in the art.

1. Affinity Assays

The affinity of the bispecific antigen binding molecules provided herein for the corresponding receptor can be determined in accordance with the methods set forth in the Examples by surface plasmon resonance (SPR), using standard instrumentation such as a BIAcore instrument (GE Healthcare), and receptors or target proteins such as may be obtained by recombinant expression. The affinity of the bispecific antigen binding molecule for the target cell antigen can also be determined by surface plasmon resonance (SPR), using standard instrumentation such as a BIAcore instrument (GE Healthcare), and receptors or target proteins such as may be obtained by recombinant expression. For the CD19-4-1BBL antigen binding molecules the methods have been described in more detail in International Patent Appl. Publ. No. WO 2016/075278 A1. According to one aspect, $K_D$ is measured by surface plasmon resonance using a BIACORE® T100 machine (GE Healthcare) at 25° C.

2. Binding Assays and Other Assays

In one aspect, the CD19-4-1BBL antigen binding molecules as reported herein are tested for its antigen binding activity as described in more detail in Example 3a.

3. Activity Assays

In one aspect, assays are provided for identifying the biological activity of CD19-4-1BBL antigen binding molecules. Biological activity may include, e.g., inhibition of B-cell proliferation or killing of B-cells. Antibodies having such biological activity in vivo and/or in vitro are also provided.

In certain embodiments, an antibody as reported herein is tested for such biological activity.

Pharmaceutical Compositions, Formulations and Routes of Administration

In a further aspect, the invention provides pharmaceutical compositions comprising the anti-CD20/anti-CD3 antibodies and 4-1BB agonists provided herein, e.g., for use in any of the below therapeutic methods. In one embodiment, a pharmaceutical composition comprises an antibody provided herein and at least one pharmaceutically acceptable excipient. In another embodiment, a pharmaceutical composition comprises an antibody provided herein and at least one additional therapeutic agent, e.g., as described below.

Pharmaceutical compositions of the present invention comprise a therapeutically effective amount of one or more bispecific antibodies dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one antibody and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the bispecific antibodies may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The bispecific antibody of the invention may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

In one aspect, there is provided a pharmaceutical composition comprising an anti-CD20/anti-CD3 bispecific antibody and a pharmaceutically acceptable carrier, and a second medicament comprising a 4-1BB agonist comprising at least one antigen binding domain capable of specific binding to CD19 as described herein. In a particular aspect, the pharmaceutical composition is for use in the treatment of B-cell proliferative disorders, in particular a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

The formulations to be used for in vivo administration are generally sterile. Sterility may be readily accomplished, e.g., by filtration through sterile filtration membranes.

Administration of the Anti-CD20/Anti-CD3 Bispecific Antibody and the 4-1BB Agonist Both the anti-CD20/anti-CD3 bispecific antibody and the 4-1BB agonist (both called substance herein) can be administered by any suitable means, including parenteral, intrapulmonary, and intranasal, and, if desired for local treatment, intralesional administration. The methods of the present invention are particularly useful, however, in relation to therapeutic agents administered by parenteral, particularly intravenous, infusion.

Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein. In one embodiment, the therapeutic agent is administered parenterally, particularly intravenously. In a particular embodiment, the substance is administered by intravenous infusion. In another aspect, the substance is administered subcutaneously.

Both the anti-CD20/anti-CD3 bispecific antibody and the 4-1BB agonist would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. Both the anti-CD20/anti-CD3 bispecific antibody and the 4-1BB agonist need not be, but are optionally formulated with one or more agents currently used to prevent or treat the disorder in question. The effective amount of such other agents depends on the amount of therapeutic agent present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of the anti-CD20/anti-CD3 bispecific antibody and the 4-1BB agonist (when used in their combination or with one or more other additional therapeutic agents) will depend on the type of disease to be treated, the type of 4-1BB agent, the severity and course of the disease, whether both agents are administered for preventive or therapeutic purposes, previous therapy, the patient's clinical history and response to the therapeutic agent, and the discretion of the attending physician. Each substance is suitably administered to the patient at one time or over a series of treatments. Depending on the type and severity of the disease, about 1 µg/kg to 15 mg/kg (e.g. 0.1 mg/kg-10 mg/kg) of the substance can be an initial candidate dosage for administration to the subject, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of each substance would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the subject. Such doses may be administered intermittently, e.g. every week, every two weeks, or every three weeks (e.g. such that the subject receives from about two to about twenty, or e.g. about six doses of the therapeutic agent). An initial higher loading dose, followed by one or more lower doses, or an initial lower dose, followed by one or more higher doses may be administered. An exemplary dosing regimen comprises administering an initial dose of about 10 mg, followed by a bi-weekly dose of about 20 mg of the therapeutic agent. However, other dosage regimens may be useful. The progress of this therapy is easily monitored by conventional techniques and assays.

In one aspect, the administration of both the anti-CD20/anti-CD3 bispecific antibody and the 4-1BB agonist is a single administration. In certain aspects, the administration of the therapeutic agent is two or more administrations. In one such aspect, the substances are administered every week, every two weeks, or every three weeks, particularly every two weeks. In one aspect, the substance is administered in a therapeutically effective amount. In one aspect the substance is administered at a dose of about 50 µg/kg, about 100 µg/kg, about 200 µg/kg, about 300 µg/kg, about 400 µg/kg, about 500 µg/kg, about 600 µg/kg, about 700 µg/kg, about 800 µg/kg, about 900 µg/kg or about 1000 µg/kg. In one embodiment, the anti-CD20/anti-CD3 bispecific antibody is administered at a dose which is higher than the dose of the anti-CD20/anti-CD3 bispecific antibody in a corresponding treatment regimen without the administration of the 4-1BB agonist. In one aspect, the administration of the anti-CD20/anti-CD3 bispecific antibody comprises an initial administration of a first dose of the anti-CD20/anti-CD3 bispecific antibody, and one or more subsequent administrations of a second dose of the anti-CD20/anti-CD3 bispecific antibody, wherein the second dose is higher than the first dose. In one aspect, the administration of the anti-CD20/anti-CD3 bispecific antibody comprises an initial administration of a first dose of the anti-CD20/anti-CD3 bispecific antibody, and one or more subsequent administrations of a second dose of the anti-CD20/anti-CD3 bispecific antibody, wherein the first dose is not lower than the second dose.

In one aspect, the administration of the anti-CD20/anti-CD3 bispecific antibody in the treatment regimen according to the invention is the first administration of the anti-CD20/anti-CD3 bispecific antibody to the subject (at least within the same course of treatment). In one aspect, no administration of the 4-1BB agonist is made to the subject prior to the administration of the anti-CD20/anti-CD3 bispecific antibody. In another aspect, the 4-1BB agonist is administered prior to the administration of the anti-CD20/anti-CD3 bispecific antibody.

In another aspect, the anti-CD20/anti-CD3 bispecific antibody is for use in combination with a 4-1BB (CD137) agonist comprising at least one antigen binding domain capable of specific binding to CD19, wherein a pretreatment with an Type II anti-CD20 antibody, preferably obinutuzumab, is performed prior to the combination treatment, wherein the period of time between the pretreatment and the combination treatment is sufficient for the reduction of B-cells in the individual in response to the Type II anti-CD20 antibody, preferably obinutuzumab.

Activation of T cells can lead to severe cytokine release syndrome (CRS). In a phase 1 study conducted by TeGenero (Suntharalingam et al., N Engl J Med (2006) 355, 1018-1028), all 6 healthy volunteers experienced near fatal, severe cytokine release syndrome (CRS) rapidly post-infusion of an inappropriately-dosed, T-cell stimulating super-agonist anti-CD28 monoclonal antibody. The cytokine release associated with administration of a T-cell activating therapeutic agent, such as the anti-CD20/anti-CD3 bispecific antibody, to a subject can be significantly reduced by pre-treatment of said subject with a Type II anti-CD20 antibody, such as obinutuzumab. the use of GAZYVA® pre-treatment (Gpt) should aid in the rapid depletion of B cells, both in the peripheral blood and in secondary lymphoid organs, such that the risk of highly relevant adverse events (AEs) from strong systemic T cell activation by T-cell activating therapeutic agents (e.g. CRS) is reduced, while supporting exposure levels of T-cell activating therapeutic agents that are high enough from the start of dosing to mediate tumour cell elimination. To date, the safety profile of obinutuzumab (including cytokine release) has been assessed and managed in hundreds of patients in ongoing obinutuzumab clinical trials. Finally, in addition to supporting the safety profile of T-cell activating therapeutic agents such as the anti-CD20/anti-CD3 bispecific antibody, Gpt should also help prevent the formation of anti-drug antibodies (ADAs) to these unique molecules.

In the present invention, the combination of the anti-CD20/anti-CD3 bispecific antibody and the 4-1BB agonist can be used in combination with one or more further agents in a therapy. For instance, at least one additional therapeutic agent may be co-administered. In certain aspects, an additional therapeutic agent is an immunotherapeutic agent.

In one aspect of the invention, the anti-CD20/anti-CD3 bispecific antibody is for use in a method for treating or delaying progression of cancer, wherein the anti-CD20/anti-CD3 bispecific antibody is used in combination with a 4-1BB (CD137) agonist comprising at least one antigen binding domain capable of specific binding to CD19, and additionally they are combined with an agent blocking PD-L1/PD-1 interaction. An agent blocking PD-L1/PD-1 interaction is a PD-L1 binding antagonist or a PD-1 binding antagonist. In particular, the agent blocking PD-L1/PD-1 interaction is an anti-PD-L1 antibody or an anti-PD-1 antibody.

In one aspect, the agent blocking PD-L1/PD-1 interaction is an anti-PD-L1 antibody. The term "PD-L1", also known as CD274 or B7-H1, refers to any native PD-L1 from any vertebrate source, including mammals such as primates (e.g. humans) non-human primates (e.g. cynomolgus monkeys) and rodents (e.g. mice and rats), in particular to "human PD-L1". The amino acid sequence of complete human PD-L1 is shown in UniProt (www.uniprot.org) accession no. Q9NZQ7 (SEQ ID NO:106). The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In particular, a PD-L1 binding antagonist is an anti-PD-L1 antibody. The term "anti-PD-L1 antibody" or "antibody binding to human PD-L1" or "antibody that specifically binds to human PD-L1" or "antagonistic anti-PD-L1" refers to an antibody specifically binding to the human PD-L1 antigen with a binding affinity of KD-value of $1.0 \times 10^{-8}$ mol/l or lower, in one aspect of a KD-value of $1.0 \times 10^{-9}$ mol/l or lower. The binding affinity is determined with a standard binding assay, such as surface plasmon resonance technique (BIAcore®, GE-Healthcare Uppsala, Sweden).

In a specific aspect, the anti-PD-L1 antibody is selected from the group consisting of atezolizumab (MPDL3280A, RG7446), durvalumab (MEDI4736), avelumab (MSB0010718C) and MDX-1105. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MEDI4736 (durvalumab). In yet a further aspect, an anti-PD-L1 antibody is MSB0010718C (avelumab). More particularly, the agent blocking PD-L1/PD-1 interaction is atezolizumab (MPDL3280A). In another aspect, the agent blocking PD-L1/PD-1 interaction is an anti-PD-L1 antibody comprising a heavy chain variable domain VH(PDL-1) of SEQ ID NO:108 and a light chain variable domain VL(PDL-1) of SEQ ID NO:109. In another aspect, the agent blocking PD-L1/PD-1 interaction is an anti-PD-L1 antibody comprising a heavy chain variable domain VH(PDL-1) of SEQ ID NO:110 and a light chain variable domain VL(PDL-1) of SEQ ID NO:111.

The term "PD-1", also known as CD279, PD1 or programmed cell death protein 1, refers to any native PD-L1 from any vertebrate source, including mammals such as primates (e.g. humans) non-human primates (e.g. cynomolgus monkeys) and rodents (e.g. mice and rats), in particular to the human protein PD-1 with the amino acid sequence as shown in UniProt (www.uniprot.org) accession no. Q15116 (SEQ ID NO:107). The term "PD-1 binding antagonist" refers to a molecule that inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In particular, a PD-L1 binding antagonist is an anti-PD-L1 antibody. The term "anti-PD-1 antibody" or "antibody binding to human PD-1" or "antibody that specifically binds to human PD-1" or "antagonistic anti-PD-1" refers to an antibody specifically binding to the human PD1 antigen with a binding affinity of KD-value of $1.0 \times 10^{-8}$ mol/l or lower, in one aspect of a KD-value of $1.0 \times 10^{-9}$ mol/l or lower. The binding affinity is determined with a standard binding assay, such as surface plasmon resonance technique (BIAcore®, GE-Healthcare Uppsala, Sweden).

In one aspect, the agent blocking PD-L1/PD-1 interaction is an anti-PD-1 antibody. In a specific aspect, the anti-PD-1 antibody is selected from the group consisting of MDX 1106 (nivolumab), MK-3475 (pembrolizumab), CT-011 (pidilizumab), MEDI-0680 (AMP-514), PDR001, REGN2810, and BGB-108, in particular from pembrolizumab and nivolumab. In another aspect, the agent blocking PD-L1/PD-1 interaction is an anti-PD-1 antibody comprising a heavy chain variable domain VH(PD-1) of SEQ ID NO:112 and a light chain variable domain VL(PD-1) of SEQ ID NO:113. In another aspect, the agent blocking PD-L1/PD-1 interaction is an anti-PD-1 antibody comprising a heavy chain variable domain VH(PD-1) of SEQ ID NO:114 and a light chain variable domain VL(PD-1) of SEQ ID NO:115.

Such combination therapies noted above encompass combined administration (where two or more therapeutic agents are included in the same or separate formulations), and separate administration, in which case, administration of the therapeutic agent can occur prior to, simultaneously, and/or following, administration of an additional therapeutic agent or agents. In one embodiment, administration of the therapeutic agent and administration of an additional therapeutic agent occur within about one month, or within about one, two or three weeks, or within about one, two, three, four, five, or six days, of each other.

Therapeutic Methods and Compositions

CD20 and CD19 are expressed on most B-cells (pan-B-cell marker) with the exception of stem cells and plasma cells, and are frequently expressed on most human B-cell malignancies (tumor associated antigen), such as lymphoma and leukemias except for multiple myeloma, e.g. in non-Hodgkin lymphoma and acute lymphoblastic leukemia.

Bispecific antibodies recognizing two cell surface proteins on different cell populations hold the promise to redirect cytotoxic immune cells for destruction of pathogenic target cells.

In one aspect, there is provided a method for treating or delaying progression of cancer in a subject comprising administering to the subject an effective amount of an anti-CD20/anti-CD3 antibody and a 4-1BB agonist comprising at least one antigen binding domain capable of specific binding to CD19.

In one such aspect, the method further comprises administering to the subject an effective amount of at least one additional therapeutic agent. In further embodiments, herein is provided a method for depleting B-cells comprising administering to the subject an effective amount of an anti-CD20/anti-CD3 antibody and a 4-1BB agonist comprising at least one antigen binding domain capable of specific binding to CD19. An "individual" or a "subject" according to any of the above aspects is preferably a human.

In further aspects, a composition for use in cancer immunotherapy is provided comprising an anti-CD20/anti-CD3 antibody and a 4-1BB agonist comprising at least one antigen binding domain capable of specific binding to CD19. In certain embodiments, a composition comprising an anti-CD20/anti-CD3 antibody and a 4-1BB agonist comprising at least one antigen binding domain capable of specific binding to CD19 for use in a method of cancer immunotherapy is provided.

In a further aspect, herein is provided the use of a composition comprising an anti-CD20/anti-CD3 antibody and a 4-1BB agonist comprising at least one antigen binding domain capable of specific binding to CD19 in the manufacture or preparation of a medicament. In one embodiment, the medicament is for treatment of a B-cell proliferative disorder. In a further embodiment, the medicament is for use in a method of treating a B-cell proliferative disorder comprising administering to an individual having a B-cell proliferative disorder an effective amount of the medicament. In one such embodiment, the method further comprises administering to the individual an effective amount of at least one additional therapeutic agent. In a further embodiment, the medicament is for depleting B-cells. B-cell proliferative disorders are selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL). In one particular aspect, the B-cell cancer is non-Hodgkin lymphoma or acute lymphoblastic leukemia.

In a further aspect, herein is provided a method for treating a B-cell cancer. In one embodiment, the method comprises administering to an individual having such B-cell cancer an effective amount of an anti-human CD19 antibody. In one such embodiment, the method further comprises administering to the individual an effective amount of at least one additional therapeutic agent, as described below. An "individual" according to any of the above embodiments may be a human. The B-cell cancer is in one embodiment a B-cell lymphoma or a B-cell leukemia. In one embodiment the B-cell cancer is non-Hodgkin lymphoma or acute lymphoblastic leukemia.

The combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one embodiment, administration of the anti-human CD19 antibody and administration of an additional therapeutic agent occur within about one month, or within about one, two or three weeks, or within about one, two, three, four, five, or six days, of each other.

Both the anti-CD20/anti-CD3 bispecific antibody and the 4-1BB agonist as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Both the anti-CD20/anti-CD3 bispecific antibody and the 4-1BB agonist as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibodies need not be, but are optionally formulated with one or more agents currently used to prevent or treat the disorder in question. The effective amount of such other agents depends on the amount of antibodies present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

Other Agents and Treatments

The antigen binding molecules of the invention may be administered in combination with one or more other agents in therapy. For instance, a fusion protein of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of fusion protein used, the type of disorder or treatment, and other factors discussed above. The antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antigen binding molecules of the invention can occur prior to, simultaneously, and/or following, administration of the additional therapeutic agent and/or adjuvant.

Articles of Manufacture (Kits)

In another aspect of the invention, a kit containing materials useful for the treatment, prevention and/or diagnosis of the disorders described above is provided. The kit comprises at least one container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least two active agents in the kit are an anti-CD20/anti-CD3 bispecific antibody and a 4-1BB agonist comprising at least one antigen binding domain capable of specific binding to CD19 of the invention.

In a particular aspect, provided is a kit for treating or delaying progression of cancer in a subject, comprising a package comprising (A) a first composition comprising as active ingredient an anti-CD20/anti-CD3 bispecific antibody and a pharmaceutically acceptable carrier; (B) a second composition comprising as active ingredient a 4-1BB agonist comprising at least one antigen binding domain capable of specific binding to CD19 and a pharmaceutically acceptable carrier, and (C) instructions for using the compositions in a combination therapy.

The label or package insert indicates how the composition is used for treating the condition of choice and provides the instructions for using the compositions in a combination therapy. Moreover, the kit may comprise (a) a first container with a composition contained therein, wherein the composition comprises an anti-CD20/anti-CD3 bispecific antibody of the invention; and (b) a second container with a composition contained therein, wherein the composition comprises a 4-1BB agonist comprising at least one antigen binding domain capable of specific binding to CD19 of the invention. In addition, the kit may comprise one or more further containers comprising further active ingredients that can be used in combination. The article of manufacture in this embodiment of the invention may further comprise a package insert indicating that the compositions can be used to treat a particular condition.

Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE D (Sequences):

| SEQ ID NO: | Name | Sequence |
|---|---|---|
| 1 | Human (hu) 4-1BBL (71-254) | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSE |
| 2 | hu 4-1BBL (85-254) | LDLRQGMFAQLVAQNVLLIDGPLSWYSDPGLAGVSL TGGLSYKEDTKELVVAKAGVYYVFFQLELRRVVAG EGSGSVSLALHLQPLRSAAGAAALALTVDLPPASSEA RNSAFGFQGRLLHLSAGQRLGVHLHTEARARHAWQ LTQGATVLGLFRVTPEIPAGLPSPRSE |
| 3 | hu 4-1BBL (80-254) | DPAGLLDLRQGMFAQLVAQNVLLIDGPLSWYSDPGL AGVSLTGGLSYKEDTKELVVAKAGVYYVFFQLELRR VVAGEGSGSVSLALHLQPLRSAAGAAALALTVDLPP ASSEARNSAFGFQGRLLHLSAGQRLGVHLHTEARAR HAWQLTQGATVLGLFRVTPEIPAGLPSPRSE |
| 4 | hu 4-1BBL (52-254) | PWAVSGARASPGSAASPRLREGPELSPDDPAGLLDLR QGMFAQLVAQNVLLIDGPLSWYSDPGLAGVSLTGGL SYKEDTKELVVAKAGVYYVFFQLELRRVVAGEGSG SVSLALHLQPLRSAAGAAALALTVDLPPASSEARNSA FGFQGRLLHLSAGQRLGVHLHTEARARHAWQLTQG ATVLGLFRVTPEIPAGLPSPRSE |

TABLE D-continued (Sequences):

| SEQ ID NO: | Name | Sequence |
|---|---|---|
| 5 | Human (hu) 4-1BBL (71-248) | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGL |
| 6 | hu 4-1BBL (85-248) | LDLRQGMFAQLVAQNVLLIDGPLSWYSDPGLAGVSL TGGLSYKEDTKELVVAKAGVYYVFFQLELRRVVAG EGSGSVSLALHLQPLRSAAGAAALALTVDLPPASSEA RNSAFGFQGRLLHLSAGQRLGVHLHTEARARHAWQ LTQGATVLGLFRVTPEIPAGL |
| 7 | hu 4-1BBL (80-248) | DPAGLLDLRQGMFAQLVAQNVLLIDGPLSWYSDPGL AGVSLTGGLSYKEDTKELVVAKAGVYYVFFQLELRR VVAGEGSGSVSLALHLQPLRSAAGAAALALTVDLPP ASSEARNSAFGFQGRLLHLSAGQRLGVHLHTEARAR HAWQLTQGATVLGLFRVTPEIPAGL |
| 8 | hu 4-1BBL (52-248) | PWAVSGARASPGSAASPRLREGPELSPDDPAGLLDLR QGMFAQLVAQNVLLIDGPLSWYSDPGLAGVSLTGGL SYKEDTKELVVAKAGVYYVFFQLELRRVVAGEGSG SVSLALHLQPLRSAAGAAALALTVDLPPASSEARNSA FGFQGRLLHLSAGQRLGVHLHTEARARHAWQLTQG ATVLGLFRVTPEIPAGL |
| 9 | CD19 (8B8-018) CDR-H1 | DYIMH |
| 10 | CD19 (8B8-018) CDR-H2 | YINPYNDGSKYTEKFQG |
| 11 | CD19 (8B8-018) CDR-H3 | GTYYYGSALFDY |
| 12 | CD19 (8B8-018) CDR-L1 | KSSQSLENPNGNTYLN |
| 13 | CD19 (8B8-018) CDR-L2 | RVSKRFS |
| 14 | CD19 (8B8-018) CDR-L3 | LQLTHVPYT |
| 15 | CD19 (8B8-2B11) CDR-H1 | DYIMH |
| 16 | CD19 (8B8-2B11) CDR-H2 | YINPYNDGSKYTEKFQG |
| 17 | CD19 (8B8-2B11) CDR-H3 | GTYYYGPQLFDY |
| 18 | CD19 (8B8-2B11) CDR-L1 | KSSQSLETSTGTTYLN |
| 19 | CD19 (8B8-2B11) CDR-L2 | RVSKRFS |
| 20 | CD19 (8B8-2B11) CDR-L3 | LQLLEDPYT |
| 21 | CD19 (8B8-018) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSS |
| 22 | CD19 (8B8-018) VL | DIVMTQTPLSLSVTPGQPASISCKSSQSLENPNGNTYL NWYLQKPGQSPQLLIYRVSKRFSGVPDRFSGSGSGTD FTLKISRVEAEDVGVYYCLQLTHVPYTFGQGTKLEIK |
| 23 | CD19 (8B8-2B11) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSS |
| 24 | CD19 (8B8-2B11) VL | DIVMTQTPLSLSVTPGQPASISCKSSQSLETSTGTTYL NWYLQKPGQSPQLLIYRVSKRFSGVPDRFSGSGSGTD FTLKISRVEAEDVGVYYCLQLLEDPYTFGQGTKLEIK |
| 25 | dimeric hu 4-1BBL (71-254) connected by (G4S)$_2$ linker | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSEGGGGSGGGGSREGPELSPDDPAGLLDLRQGM FAQLVAQNVLLIDGPLSWYSDPGLAGVSLTGGLSYK |

TABLE D-continued (Sequences):

| SEQ ID NO: | Name | Sequence |
|---|---|---|
| | | EDTKELVVAKAGVYYVFFQLELRRVVAGEGSGSVSL ALHLQPLRSAAGAAALALTVDLPPASSEARNSAFGF QGRLLHLSAGQRLGVHLHTEARARHAWQLTQGATV LGLFRVTPEIPAGLPSPRSE |
| 26 | dimeric hu 4-1BBL (85-254) connected by (G4S)₂ linker | LDLRQGMFAQLVAQNVLLIDGPLSWYSDPGLAGVSL TGGLSYKEDTKELVVAKAGVYYVFFQLELRRVVAG EGSGSVSLALHLQPLRSAAGAAALALTVDLPPASSEA RNSAFGFQGRLLHLSAGQRLGVHLHTEARARHAWQ LTQGATVLGLFRVTPEIPAGLPSPRSEGGGGSGGGGS LDLRQGMFAQLVAQNVLLIDGPLSWYSDPGLAGVSL TGGLSYKEDTKELVVAKAGVYYVFFQLELRRVVAG EGSGSVSLALHLQPLRSAAGAAALALTVDLPPASSEA RNSAFGFQGRLLHLSAGQRLGVHLHTEARARHAWQ LTQGATVLGLFRVTPEIPAGLPSPRSE |
| 27 | dimeric hu 4-1BBL (80-254) connected by (G4S)₂ linker | DPAGLLDLRQGMFAQLVAQNVLLIDGPLSWYSDPGL AGVSLTGGLSYKEDTKELVVAKAGVYYVFFQLELRR VVAGEGSGSVSLALHLQPLRSAAGAAALALTVDLPP ASSEARNSAFGFQGRLLHLSAGQRLGVHLHTEARAR HAWQLTQGATVLGLFRVTPEIPAGLPSPRSEGGGGSG GGGSDPAGLLDLRQGMFAQLVAQNVLLIDGPLSWY SDPGLAGVSLTGGLSYKEDTKELVVAKAGVYYVFFQ LELRRVVAGEGSGSVSLALHLQPLRSAAGAAALALT VDLPPASSEARNSAFGFQGRLLHLSAGQRLGVHLHT EARARHAWQLTQGATVLGLFRVTPEIPAGLPSPRSE |
| 28 | dimeric hu 4-1BBL (52-254) connected by (G4S)₂ linker | PWAVSGARASPGSAASPRLREGPELSPDDPAGLLDLR QGMFAQLVAQNVLLIDGPLSWYSDPGLAGVSLTGGL SYKEDTKELVVAKAGVYYVFFQLELRRVVAGEGSG SVSLALHLQPLRSAAGAAALALTVDLPPASSEARNSA FGFQGRLLHLSAGQRLGVHLHTEARARHAWQLTQG ATVLGLFRVTPEIPAGLPSPRSEGGGGSGGGGSPWAV SGARASPGSAASPRLREGPELSPDDPAGLLDLRQGMF AQLVAQNVLLIDGPLSWYSDPGLAGVSLTGGLSYKE DTKELVVAKAGVYYVFFQLELRRVVAGEGSGSVSL ALHLQPLRSAAGAAALALTVDLPPASSEARNSAFGF QGRLLHLSAGQRLGVHLHTEARARHAWQLTQGATV LGLFRVTPEIPAGLPSPRSE |
| 29 | dimeric hu 4-1BBL (71-248) connected by (G4S)2 linker | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLG GGGSGGGGSREGPELSPDDPAGLLDLRQGMFAQLVA QNVLLIDGPLSWYSDPGLAGVSLTGGLSYKEDTKEL VVAKAGVYYVFFQLELRRVVAGEGSGSVSLALHLQP LRSAAGAAALALTVDLPPASSEARNSAFGFQGRLLH LSAGQRLGVHLHTEARARHAWQLTQGATVLGLFRV TPEIPAGL |
| 30 | dimeric hu 4-1BBL (85-248) connected by (G4S)2 linker | LDLRQGMFAQLVAQNVLLIDGPLSWYSDPGLAGVSL TGGLSYKEDTKELVVAKAGVYYVFFQLELRRVVAG EGSGSVSLALHLQPLRSAAGAAALALTVDLPPASSEA RNSAFGFQGRLLHLSAGQRLGVHLHTEARARHAWQ LTQGATVLGLFRVTPEIPAGLGGGGSGGGGSLDLRQ GMFAQLVAQNVLLIDGPLSWYSDPGLAGVSLTGGLS YKEDTKELVVAKAGVYYVFFQLELRRVVAGEGSGS VSLALHLQPLRSAAGAAALALTVDLPPASSEARNSAF GFQGRLLHLSAGQRLGVHLHTEARARHAWQLTQGA TVLGLFRVTPEIPAGL |

TABLE D-continued (Sequences):

| SEQ ID NO: | Name | Sequence |
|---|---|---|
| 31 | dimeric hu 4-1BBL (80-248) connected by (G4S)2 linker | DPAGLLDLRQGMFAQLVAQNVLLIDGPLSWYSDPGL AGVSLTGGLSYKEDTKELVVAKAGVYYVFFQLELRR VVAGEGSGSVSLALHLQPLRSAAGAAALALTVDLPP ASSEARNSAFGFQGRLLHLSAGQRLGVHLHTEARAR HAWQLTQGATVLGLFRVTPEIPAGLGGGGSGGGGSD PAGLLDLRQGMFAQLVAQNVLLIDGPLSWYSDPGLA GVSLTGGLSYKEDTKELVVAKAGVYYVFFQLELRRV VAGEGSGSVSLALHLQPLRSAAGAAALALTVDLPPA SSEARNSAFGFQGRLLHLSAGQRLGVHLHTEARARH AWQLTQGATVLGLFRVTPEIPAGL |
| 32 | dimeric hu 4-1BBL (52-248) connected by (G4S)2 linker | PWAVSGARASPGSAASPRLREGPELSPDDPAGLLDLR QGMFAQLVAQNVLLIDGPLSWYSDPGLAGVSLTGGL SYKEDTKELVVAKAGVYYVFFQLELRRVVAGEGSG SVSLALHLQPLRSAAGAAALALTVDLPPASSEARNSA FGFQGRLLHLSAGQRLGVHLHTEARARHAWQLTQG ATVLGLFRVTPEIPAGLGGGGSGGGGSPWAVSGARA SPGSAASPRLREGPELSPDDPAGLLDLRQGMFAQLV AQNVLLIDGPLSWYSDPGLAGVSLTGGLSYKEDTKE LVVAKAGVYYVFFQLELRRVVAGEGSGSVSLALHL QPLRSAAGAAALALTVDLPPASSEARNSAFGFQGRL LHLSAGQRLGVHLHTEARARHAWQLTQGATVLGLF RVTPEIPAGL |
| 33 | anti-CD19(8B8-018) Fc hole chain | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVCTLPPSR DELTKNQVSLSCAVKGFYPSDIAVEWESNGQPENNY KTTPPVLDSDGSFFLVSKLTVDKSRWQQGNVFSCSV MHEALHNHYTQKSLSLSPGK |
| 34 | anti-CD19(8B8-018) light chain | DIVMTQTPLSLSVTPGQPASISCKSSQSLENPNGNTYL NWYLQKPGQSPQLLIYRVSKRFSGVPDRFSGSGSGTD FTLKISRVEAEDVGVYYCLQLTHVPYTFGQGTKLEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |
| 35 | dimeric hu 4-1 BBL (71-254)-CL* Fc knob chain | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSEGGGGSGGGGSREGPELSPDDPAGLLDLRQGM FAQLVAQNVLLIDGPLSWYSDPGLAGVSLTGGLSYK EDTKELVVAKAGVYYVFFQLELRRVVAGEGSGSVSL ALHLQPLRSAAGAAALALTVDLPPASSEARNSAFGF QGRLLHLSAGQRLGVHLHTEARARHAWQLTQGATV LGLFRVTPEIPAGLPSPRSEGGGGSGGGGSRTVAAPS VFIFPPSDRKLKSGTASVVCLLNNFYPREAKVQWKV DNALQSGNSQESVTEQDSKDSTYSLSSTLTLSKADYE KHKVYACEVTHQGLSSPVTKSFNRGECDKTHTCPPC PAPEAAGGPSVFLFPPKPKDTLMISRTPEVTCVVVDV SHEDPEVKFNWYVDGVEVHNAKTKPREEQYNSTYR VVSVLTVLHQDWLNGKEYKCKVSNKALGAPIEKTIS KAKGQPREPQVYTLPPCRDELTKNQVSLWCLVKGFY PSDIAVEWESNGQPENNYKTTPPVLDSDGSFFLYSKL TVDKSRWQQGNVFSCSVMHEALHNHYTQKSLSLSP GK |
| 36 | monomeric hu 4-1BBL (71-254)-CH1* | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSEGGGGSGGGGSASTKGPSVFPLAPSSKSTSGGT AALGCLVEDYFPEPVTVSWNSGALTSGVHTFPAVLQ |

TABLE D-continued (Sequences):

| SEQ ID NO: | Name | Sequence |
|---|---|---|
| | | SSGLYSLSSVVTVPSSSLGTQTYICNVNHKPSNTKVD EKVEPKSC |
| 37 | dimeric hu 4-1BBL (71-254)-CL Fc knob chain | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSEGGGGSGGGGSREGPELSPDDPAGLLDLRQGM FAQLVAQNVLLIDGPLSWYSDPGLAGVSLTGGLSYK EDTKELVVAKAGVYYVFFQLELRRVVAGEGSGSVSL ALHLQPLRSAAGAAALALTVDLPPASSEARNSAFGF QGRLLHLSAGQRLGVHLHTEARARHAWQLTQGATV LGLFRVTPEIPAGLPSPRSEGGGGSGGGGSRTVAAPS VFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGECDKTHTCPPC PAPEAAGGPSVFLFPPKPKDTLMISRTPEVTCVVVDV SHEDPEVKFNWYVDGVEVHNAKTKPREEQYNSTYR VVSVLTVLHQDWLNGKEYKCKVSNKALGAPIEKTIS KAKGQPREPQVYTLPPCRDELTKNQVSLWCLVKGFY PSDIAVEWESNGQPENNYKTTPPVLDSDGSFFLYSKL TVDKSRWQQGNVFSCSVMHEALHNHYTQKSLSLSP GK |
| 38 | monomeric hu 4-1BBL (71-254)-CH1 | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSEGGGGSGGGGSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KKVEPKSC |
| 39 | anti-CD19(8B8-018) Fc hole dimeric ligand chain | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVCTLPPSR DELTKNQVSLSCAVKGFYPSDIAVEWESNGQPENNY KTTPPVLDSDGSFFLVSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLPSPRSEGGG GSGGGGSREGPELSPDDPAGLLDLRQGMFAQLVAQN VLLIDGPLSWYSDPGLAGVSLTGGLSYKEDTKELVV AKAGVYYVFFQLELRRVVAGEGSGSVSLALHLQPLR SAAGAAALALTVDLPPASSEARNSAFGFQGRLLHLS AGQRLGVHLHTEARARHAWQLTQGATVLGLFRVTP EIPAGLPSPRSE |
| 40 | anti-CD19(8B8-018) Fc knob monomeric ligand | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVYTLPPCR DELTKNQVSLWCLVKGFYPSDIAVEWESNGQPENNY KTTPPVLDSDGSFFLYSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL |

TABLE D-continued (Sequences):

| SEQ ID NO: | Name | Sequence |
|---|---|---|
| | | RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLPSPRSE |
| 41 | dimeric hu 4-1BBL (71-248)-CL* Fc knob chain | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLG GGGSGGGGSREGPELSPDDPAGLLDLRQGMFAQLVA QNVLLIDGPLSWYSDPGLAGVSLTGGLSYKEDTKEL VVAKAGVYYVFFQLELRRVVAGEGSGSVSLALHLQP LRSAAGAAALALTVDLPPASSEARNSAFGFQGRLLH LSAGQRLGVHLHTEARARHAWQLTQGATVLGLFRV TPEIPAGLGGGGSGGGGSRTVAAPSVFIFPPSDRKLKS GTASVVCLLNNFYPREAKVQWKVDNALQSGNSQES VTEQDSKDSTYSLSSTLTLSKADYEKHKVYACEVTH QGLSSPVTKSFNRGECDKTHTCPPCPAPEAAGGPSVF LFPPKPKDTLMISRTPEVTCVVVDVSHEDPEVKFNW YVDGVEVHNAKTKPREEQYNSTYRVVSVLTVLHQD WLNGKEYKCKVSNKALGAPIEKTISKAKGQPREPQV YTLPPCRDELTKNQVSLWCLVKGFYPSDIAVEWESN GQPENNYKTTPPVLDSDGSFFLYSKLTVDKSRWQQG NVFSCSVMHEALHNHYTQKSLSLSPGK |
| 42 | monomeric hu 4-1BBL (71-248)-CH1* | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLG GGGSGGGGSASTKGPSVFPLAPSSKSTSGGTAALGCL VEDYFPEPVTVSWNSGALTSGVHTFPAVLQSSGLYSL SSVVTVPSSSLGTQTYICNVNHKPSNTKVDEKVEPKS C |
| 43 | Dimeric hu 4-1BBL (71-248) - CL Fc knob chain | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLG GGGSGGGGSREGPELSPDDPAGLLDLRQGMFAQLVA QNVLLIDGPLSWYSDPGLAGVSLTGGLSYKEDTKEL VVAKAGVYYVFFQLELRRVVAGEGSGSVSLALHLQP LRSAAGAAALALTVDLPPASSEARNSAFGFQGRLLH LSAGQRLGVHLHTEARARHAWQLTQGATVLGLFRV TPEIPAGLGGGGSGGGGSRTVAAPSVFIFPPSDEQLKS GTASVVCLLNNFYPREAKVQWKVDNALQSGNSQES VTEQDSKDSTYSLSSTLTLSKADYEKHKVYACEVTH QGLSSPVTKSFNRGECDKTHTCPPCPAPEAAGGPSVF LFPPKPKDTLMISRTPEVTCVVVDVSHEDPEVKFNW YVDGVEVHNAKTKPREEQYNSTYRVVSVLTVLHQD WLNGKEYKCKVSNKALGAPIEKTISKAKGQPREPQV YTLPPCRDELTKNQVSLWCLVKGFYPSDIAVEWESN GQPENNYKTTPPVLDSDGSFFLYSKLTVDKSRWQQG NVFSCSVMHEALHNHYTQKSLSLSPGK |
| 44 | Monomeric hu 4-1BBL (71-248) - CH1 | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLG GGGSGGGGSASTKGPSVFPLAPSSKSTSGGTAALGCL VKDYFPEPVTVSWNSGALTSGVHTFPAVLQSSGLYS LSSVVTVPSSSLGTQTYICNVNHKPSNTKVDKKVEPK SC |
| 45 | anti-CD19(8B8-018) Fc hole dimeric ligand (71-248) chain | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE |

TABLE D-continued (Sequences):

| SEQ ID NO: | Name | Sequence |
|---|---|---|
| | | YKCKVSNKALGAPIEKTISKAKGQPREPQVCTLPPSR DELTKNQVSLSCAVKGFYPSDIAVEWESNGQPENNY KTTPPVLDSDGSFFLVSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLGGGGSGGG GSREGPELSPDDPAGLLDLRQGMFAQLVAQNVLLID GPLSWYSDPGLAGVSLTGGLSYKEDTKELVVAKAG VYYVFFQLELRRVVAGEGSGSVSLALHLQPLRSAAG AAALALTVDLPPASSEARNSAFGFQGRLLHLSAGQR LGVHLHTEARARHAWQLTQGATVLGLFRVTPEIPAG L |
| 46 | anti-CD19(8B8-018) Fc knob monomeric (71-248) ligand | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVYTLPPCR DELTKNQVSLWCLVKGFYPSDIAVEWESNGQPENNY KTTPPVLDSDGSFFLYSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGL |
| 47 | anti-CD19(8B8-2B11) Fc hole chain | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVCTLPPSR DELTKNQVSLSCAVKGFYPSDIAVEWESNGQPENNY KTTPPVLDSDGSFFLVSKLTVDKSRWQQGNVFSCSV MHEALHNHYTQKSLSLSPGK |
| 48 | CD19 (8B8-2B11) light chain | DIVMTQTPLSLSVTPGQPASISCKSSQSLETSTGTTYL NWYLQKPGQSPQLLIYRVSKRFSGVPDRFSGSGSGTD FTLKISRVEAEDVGVYYCLQLLEDPYTFGQGTKLEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |
| 49 | anti-CD 19(8B 8-2B11) Fc hole dimeric ligand (71-254) chain | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVCTLPPSR DELTKNQVSLSCAVKGFYPSDIAVEWESNGQPENNY KTTPPVLDSDGSFFLVSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLPSPRSEGGG GSGGGGSREGPELSPDDPAGLLDLRQGMFAQLVAQN |

TABLE D-continued (Sequences):

| SEQ ID NO: | Name | Sequence |
|---|---|---|
| | | VLLIDGPLSWYSDPGLAGVSLTGGLSYKEDTKELVV AKAGVYYVFFQLELRRVVAGEGSGSVSLALHLQPLR SAAGAAALALTVDLPPASSEARNSAFGFQGRLLHLS AGQRLGVHLHTEARARHAWQLTQGATVLGLFRVTP EIPAGLPSPRSE |
| 50 | anti-CD19(8B8-2B11) Fc knob monomeric (71-254) ligand | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVYTLPPCR DELTKNQVSLWCLVKGFYPSDIAVEWESNGQPENNY KTTPPVLDSDGSFFLYSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLPSPRSE |
| 51 | anti-CD19(8B8-2B11) Fc hole dimeric ligand (71-248) chain | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVCTLPPSR DELTKNQVSLSCAVKGFYPSDIAVEWESNGQPENNY KTTPPVLDSDGSFFLVSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLGGGGSGGG GSREGPELSPDDPAGLLDLRQGMFAQLVAQNVLLID GPLSWYSDPGLAGVSLTGGLSYKEDTKELVVAKAG VYYVFFQLELRRVVAGEGSGSVSLALHLQPLRSAAG AAALALTVDLPPASSEARNSAFGFQGRLLHLSAGQR LGVHLHTEARARHAWQLTQGATVLGLFRVTPEIPAG L |
| 52 | anti-CD19(8B8-2B11) Fc knob monomeric (71-248) ligand | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVYTLPPCR DELTKNQVSLWCLVKGFYPSDIAVEWESNGQPENNY KTTPPVLDSDGSFFLYSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGL |
| 53 | trimeric hu 4-1BBL (71-254) Fc knob chain | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSEGGGGSGGGGSREGPELSPDDPAGLLDLRQGM |

TABLE D-continued (Sequences):

| SEQ ID NO: Name | Sequence |
|---|---|
| | FAQLVAQNVLLIDGPLSWYSDPGLAGVSLTGGLSYK EDTKELVVAKAGVYYVFFQLELRRVVAGEGSGSVSL ALHLQPLRSAAGAAALALTVDLPPASSEARNSAFGF QGRLLHLSAGQRLGVHLHTEARARHAWQLTQGATV LGLFRVTPEIPAGLPSPRSEGGGGSGGGGSREGPELSP DDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLPSPRSEGSPG SSSSGSDKTHTCPPCPAPEAAGGPSVFLFPPKPKDTL MISRTPEVTCVVVDVSHEDPEVKFNWYVDGVEVHN AKTKPREEQYNSTYRVVSVLTVLHQDWLNGKEYKC KVSNKALGAPIEKTISKAKGQPREPQVYTLPPCRDEL TKNQVSLWCLVKGFYPSDIAVEWESNGQPENNYKTT PPVLDSDGSFFLYSKLTVDKSRWQQGNVFSCSVMHE ALHNHYTQKSLSLSPGK |
| 54 anti-CD19(8B8-018) Fc knob chain fused to trimeric hu 4-1BBL (71-254) | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVYTLPPCR DELTKNQVSLWCLVKGFYPSDIAVEWESNGQPENNY KTTPPVLDSDGSFFLYSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLPSPRSEGGG GSGGGGSREGPELSPDDPAGLLDLRQGMFAQLVAQN VLLIDGPLSWYSDPGLAGVSLTGGLSYKEDTKELVV AKAGVYYVFFQLELRRVVAGEGSGSVSLALHLQPLR SAAGAAALALTVDLPPASSEARNSAFGFQGRLLHLS AGQRLGVHLHTEARARHAWQLTQGATVLGLFRVTP EIPAGLPSPRSEGGGGSGGGGSREGPELSPDDPAGLL DLRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSEAR NSAFGFQGRLLHLSAGQRLGVHLHTEARARHAWQL TQGATVLGLFRVTPEIPAGLPSPRSE |
| 55 anti-CD19(8B8-2B11) Fc knob chain fused to trimeric hu 4-1BBL (71-254) | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAAGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALGAPIEKTISKAKGQPREPQVYTLPPCR DELTKNQVSLWCLVKGFYPSDIAVEWESNGQPENNY KTTPPVLDSDGSFFLYSKLTVDKSRWQQGNVFSCSV MHEALHNHYTQKSLSLSPGGGGSGGGGSREGPELS PDDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLPSPRSEGGG GSGGGGSREGPELSPDDPAGLLDLRQGMFAQLVAQN VLLIDGPLSWYSDPGLAGVSLTGGLSYKEDTKELVV AKAGVYYVFFQLELRRVVAGEGSGSVSLALHLQPLR SAAGAAALALTVDLPPASSEARNSAFGFQGRLLHLS AGQRLGVHLHTEARARHAWQLTQGATVLGLFRVTP EIPAGLPSPRSEGGGGSGGGGSREGPELSPDDPAGLL DLRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSEAR |

TABLE D-continued (Sequences):

| SEQ ID NO: | Name | Sequence |
|---|---|---|
| | | NSAFGFQGRLLHLSAGQRLGVHLHTEARARHAWQL TQGATVLGLFRVTPEIPAGLPSPRSE |
| 56 | CD3-HCDR1 | TYAMN |
| 57 | CD3-HCDR2 | RIRSKYNNYATYYADSVKG |
| 58 | CD3-HCDR3 | HGNFGNSYVSWFAY |
| 59 | CD3-LCDR1 | GSSTGAVTTSNYAN |
| 60 | CD3-LCDR2 | GTNKRAP |
| 61 | CD3-LCDR3 | ALWYSNLWV |
| 62 | CD3 VH | EVQLLESGGGLVQPGGSLRLSCAASGFTFSTYAMNW VRQAPGKGLEWVSRIRSKYNNYATYYADSVKGRFTI SRDDSKNTLYLQMNSLRAEDTAVYYCVRHGNFGNS YVSWFAYWGQGTLVTVSS |
| 63 | CD3 VL | QAVVTQEPSLTVSPGGTVTLTCGSSTGAVTTSNYAN WVQEKPGQAFRGLIGGTNKRAPGTPARFSGSLLGGK AALTLSGAQPEDEAEYYCALWYSNLWVFGGGTKLT VL |
| 64 | CD20-HCDR1 | YSWIN |
| 65 | CD20-HCDR2 | RIFPGDGDTDYNGKFK |
| 66 | CD20-HCDR3 | NVFDGYWLVY |
| 67 | CD20-LCDR1 | RSSKSLLHSNGITYLY |
| 68 | CD20-LCDR2 | QMSNLVS |
| 69 | CD20-LCDR3 | AQNLELPYT |
| 70 | CD20 VH | QVQLVQSGAEVKKPGSSVKVSCKASGYAFSYSWIN WVRQAPGQGLEWMGRIFPGDGDTDYNGKFKGRVTI TADKSTSTAYMELSSLRSEDTAVYYCARNVFDGYW LVYWGQGTLVTVSS |
| 71 | CD20 VL | DIVMTQTPLSLPVTPGEPASISCRSSKSLLHSNGITYLY WYLQKPGQSPQLLIYQMSNLVSGVPDRFSGSGSGTD FTLKISRVEAEDVGVYYCAQNLELPYTFGGGTKVEIK RTV |
| 72 | DP47 Fc hole chain | EVQLLESGGGLVQPGGSLRLSCAASGFTFSSYAMSW VRQAPGKGLEWVSAISGSGGSTYYADSVKGRFTIS RDNSKNTLYLQMNSLRAEDTAVYYCAKGSGFDYWG QGTLVTVSSASTKGPSVFPLAPSSKSTSGGTAALGCL VKDYFPEPVTVSWNSGALTSGVHTFPAVLQSSGLYS LSSVVTVPSSSLGTQTYICNVNHKPSNTKVDKKVEPK SCDKTHTCPPCPAPEAAGGPSVFLFPPKPKDTLMISRT PEVTCVVVDVSHEDPEVKFNWYVDGVEVHNAKTKP REEQYNSTYRVVSVLTVLHQDWLNGKEYKCKVSNK ALGAPIEKTISKAKGQPREPQVCTLPPSRDELTKNQV SLSCAVKGFYPSDIAVEWESNGQPENNYKTTPPVLDS DGSFFLVSKLTVDKSRWQQGNVFSCSVMHEALHNH YTQKSLSLSPGK |
| 73 | DP47 light chain | EIVLTQSPGTLSLSPGERATLSCRASQSVSSSYLAWY QQKPGQAPRLLIYGASSRATGIPDRFSGSGSGTDFTLT ISRLEPEDFAVYYCQQYGSSPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 74 | DP47 Fc hole chain fused to dimeric hu 4-1BBL (71-254) | EVQLLESGGGLVQPGGSLRLSCAASGFTFSSYAMSW VRQAPGKGLEWVSAIIGSGASTYYADSVKGRFTISRD NSKNTLYLQMNSLRAEDTAVYYCAKGWFGGFNYW GQGTLVTVSSASTKGPSVFPLAPSSKSTSGGTAALGC LVKDYFPEPVTVSWNSGALTSGVHTFPAVLQSSGLY SLSSVVTVPSSSLGTQTYICNVNHKPSNTKVDKKVEP KSCDKTHTCPPCPAPEAAGGPSVFLFPPKPKDTLMIS |

TABLE D-continued (Sequences):

| SEQ ID NO: Name | Sequence |
|---|---|
| | RTPEVTCVVVDVSHEDPEVKFNWYVDGVEVHNAKT KPREEQYNSTYRVVSVLTVLHQDWLNGKEYKCKVS NKALGAPIEKTISKAKGQPREPQVCTLPPSRDELTKN QVSLSCAVKGFYPSDIAVEWESNGQPENNYKTTPPV LDSDGSFFLVSKLTVDKSRWQQGNVFSCSVMHEALH NHYTQKSLSLSPGGGGSGGGGSREGPELSPDDPAG LLDLRQGMFAQLVAQNVLLIDGPLSWYSDPGLAGVS LTGGLSYKEDTKELVVAKAGVYYVFFQLELRRVVA GEGSGSVSLALHLQPLRSAAGAAALALTVDLPPASSE ARNSAFGFQGRLLHLSAGQRLGVHLHTEARARHAW QLTQGATVLGLFRVTPEIPAGLPSPRSEGGGGSGGGG SREGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAGA AALALTVDLPPASSEARNSAFGFQGRLLHLSAGQRL GVHLHTEARARHAWQLTQGATVLGLFRVTPEIPAGL PSPRSE |
| 75  DP47 Fc knob chain fused to monomeric hu 4-1BBL (71-254) | EVQLLESGGGLVQPGGSLRLSCAASGFTFSSYAMSW VRQAPGKGLEWVSAIIGSGASTYYADSVKGRFTISRD NSKNTLYLQMNSLRAEDTAVYYCAKGWFGGFNYW GQGTLVTVSSASTKGPSVFPLAPSSKSTSGGTAALGC LVKDYFPEPVTVSWNSGALTSGVHTFPAVLQSSGLY SLSSVVTVPSSSLGTQTYICNVNHKPSNTKVDKKVEP KSCDKTHTCPPCPAPEAAGGPSVFLFPPKPKDTLMIS RTPEVTCVVVDVSHEDPEVKFNWYVDGVEVHNAKT KPREEQYNSTYRVVSVLTVLHQDWLNGKEYKCKVS NKALGAPIEKTISKAKGQPREPQVYTLPPCRDELTKN QVSLWCLVKGFYPSDIAVEWESNGQPENNYKTTPPV LDSDGSFFLYSKLTVDKSRWQQGNVFSCSVMHEALH NHYTQKSLSLSPGGGGSGGGGSREGPELSPDDPAG LLDLRQGMFAQLVAQNVLLIDGPLSWYSDPGLAGVS LTGGLSYKEDTKELVVAKAGVYYVFFQLELRRVVA GEGSGSVSLALHLQPLRSAAGAAALALTVDLPPASSE ARNSAFGFQGRLLHLSAGQRLGVHLHTEARARHAW QLTQGATVLGLFRVTPEIPAGLPSPRSE |
| 76  CD20 VH-CH1(EE)-CD3 VL-CH1-Fc (knob, P329G LALA) | QVQLVQSGAEVKKPGSSVKVSCKASGYAFSYSWIN WVRQAPGQGLEWMGRIFPGDGDTDYNGKFKGRVTI TADKSTSTAYMELSSLRSEDTAVYYCARNVFDGYW LVYWGQGTLVTVSSASTKGPSVFPLAPSSKSTSGGTA ALGCLVEDYFPEPVTVSWNSGALTSGVHTFPAVLQS SGLYSLSSVVTVPSSSLGTQTYICNVNHKPSNTKVDE KVEPKSCDGGGGSGGGGSQAVVTQEPSLTVSPGGTV TLTCGSSTGAVTTSNYANWVQEKPGQAFRGLIGGTN KRAPGTPARFSGSLLGGKAALTLSGAQPEDEAEYYC ALWYSNLWVFGGGTKLTVLSSASTKGPSVFPLAPSS KSTSGGTAALGCLVKDYFPEPVTVSWNSGALTSGVH TFPAVLQSSGLYSLSSVVTVPSSSLGTQTYICNVNHKP SNTKVDKKVEPKSCDKTHTCPPCPAPEAAGGPSVFLF PPKPKDTLMISRTPEVTCVVVDVSHEDPEVKFNWYV DGVEVHNAKTKPREEQYNSTYRVVSVLTVLHQDWL NGKEYKCKVSNKALGAPIEKTISKAKGQPREPQVYT LPPCRDELTKNQVSLWCLVKGFYPSDIAVEWESNGQ PENNYKTTPPVLDSDGSFFLYSKLTVDKSRWQQGNV FSCSVMHEALHNHYTQKSLSLSP |
| 77  CD20 VH-CH1(EE)-Fc (hole, P329G LALA) | QVQLVQSGAEVKKPGSSVKVSCKASGYAFSYSWIN WVRQAPGQGLEWMGRIFPGDGDTDYNGKFKGRVTI TADKSTSTAYMELSSLRSEDTAVYYCARNVFDGYW LVYWGQGTLVTVSSASTKGPSVFPLAPSSKSTSGGTA ALGCLVEDYFPEPVTVSWNSGALTSGVHTFPAVLQS SGLYSLSSVVTVPSSSLGTQTYICNVNHKPSNTKVDE KVEPKSCDKTHTCPPCPAPEAAGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALGAPIEKTISKAKGQPREPQVCTLPPSRDE LTKNQVSLSCAVKGFYPSDIAVEWESNGQPENNYKT TPPVLDSDGSFFLVSKLTVDKSRWQQGNVFSCSVMH EALHNHYTQKSLSLSP |
| 78  CD20 VL-CL(RK) | DIVMTQTPLSLPVTPGEPASISCRSSKSLLHSNGITYLY WYLQKPGQSPQLLIYQMSNLVSGVPDRFSGSGSGTD FTLKISRVEAEDVGVYYCAQNLELPYTFGGGTKVEIK RTVAAPSVFIFPPSDRKLKSGTASVVCLLNNFYPREA |

TABLE D-continued (Sequences):

| SEQ ID NO: | Name | Sequence |
|---|---|---|
| | | KVQWKVDNALQSGNSQESVTEQDSKDSTYSLSSTLT LSKADYEKHKVYACEVTHQGLSSPVTKSFNRGEC |
| 79 | CD3 VH-CL | EVQLLESGGGLVQPGGSLRLSCAASGFTFSTYAMNW VRQAPGKGLEWVSRIRSKYNNYATYYADSVKGRFTI SRDDSKNTLYLQMNSLRAEDTAVYYCVRHGNFGNS YVSWFAYWGQGTLVTVSSASVAAPSVFIFPPSDEQL KSGTASVVCLLNNFYPREAKVQWKVDNALQSGNSQ ESVTEQDSKDSTYSLSSTLTLSKADYEKHKVYACEV THQGLSSPVTKSFNRGEC |
| 80 | CD19 | UniProt accession No. P15391 |
| 81 | CD20 | UniProt accession No. P11836 |
| 82 | murine anti-CD20 B-Ly1 VH | GPELVKPGASVKISCKASGYAFSYSWMNWVKLRPG QGLEWIGRIFPGDGDTDYNGKFKGKATLTADKSSNT AYMQLTSLTSVDSAVYLCARNVFDGYWLVYWGQG TLVTVSA |
| 83 | murine anti-CD20 B-Ly1 VL | NPVTLGTSASISCRSSKSLLHSNGITYLYWYLQKPGQ SPQLLIYQMSNLVSGVPDRFSSSGSGTDFTLRISRVEA EDVGVYYCAQNLELPYTFGGGTKLEIKR |
| 84 | human CD3ε | UniProt accession no. P07766 |
| 85 | cynomolgus CD3ε | NCBI GenBank no. BAB71849.1 |
| 86 | full length 4-1BBL | UniProt No. P41273 |
| 87 | 4-1BBL (50-254) | ACPWAVSGARASPGSAASPRLREGPELSPDDPAGLL DLRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSEAR NSAFGFQGRLLHLSAGQRLGVHLHTEARARHAWQL TQGATVLGLFRVTPEIPAGLPSPRSE |
| 88 | human 4-1BB | UniProt accession No. Q07011 |
| 89 | murine 4-1BB | UniProt accession No. P20334 |
| 90 | cynomolgus 4-1BB | Uniprot accession No. F6W5G6 |
| 91 | G4S peptide linker | GGGGS |
| 92 | (G4S)2 | GGGGSGGGGS |
| 93 | (SG4)2 | SGGGGSGGGG |
| 94 | peptide linker | GGGGSGGGGSGGGG |
| 95 | peptide linker | GSPGSSSSGS |
| 96 | (G4S)3 peptide linker | GGGGSGGGGSGGGGS$_3$ |
| 97 | (G4S)4 peptide linker | GGGGSGGGGSGGGGSGGGGS |
| 98 | peptide linker | GSGSGSGS |
| 99 | peptide linker | GSGSGNGS |
| 100 | peptide linker | GGSGSGSG |
| 101 | peptide linker | GGSGSG |
| 102 | peptide linker | GGSG |
| 103 | peptide linker | GGSGNGSG |
| 104 | peptide linker | GGNGSGSG |
| 105 | peptide linker | GGNGSG |

TABLE D-continued (Sequences):

| SEQ ID NO: | Name | Sequence |
|---|---|---|
| 106 | human PD-L1 (Uniprot Q9NZQ7) | MRIFAVFIFMTYWHLLNAFTVTVPKDLYVVEYGSNM TIECKFPVEKQLDLAALIVYWEMEDKNIIQFVHGEED LKVQHSSYRQRARLLKDQLSLGNAALQITDVKLQDA GVYRCMISYGGADYKRITVKVNAPYNKINQRILVVD PVTSEHELTCQAEGYPKAEVIWTSSDHQVLSGKTTTT NSKREEKLFNVTSTLRINTTTNEIFYCTFRRLDPEENH TAELVIPELPLAHPPNERTHLVILGAILLCLGVALTFIF RLRKGRMMDVKKCGIQDTNSKKQSDTHLEET |
| 107 | human PD-1 (Uniprot Q15116) | MQIPQAPWPVVWAVLQLGWRPGWFLDSPDRPWNPP TFSPALLVVTEGDNATFTCSFSNTSESFVLNWYRMSP SNQTDKLAAFPEDRSQPGQDCRFRVTQLPNGRDFHM SVVRARRNDSGTYLCGAISLAPKAQIKESLRAELRVT ERRAEVPTAHPSPSPRPAGQFQTLVVGVVGGLLGSL VLLVWVLAVICSRAARGTIGARRTGQPLKEDPSAVP VFSVDYGELDFQWREKTPEPPVPCVPEQTEYATIVFP SGMGTSSPARRGSADGPRSAQPLRPEDGHCSWPL |
| 108 | VH (PD-L1) | EVQLVESGGGLVQPGGSLRLSCAASGFTFSDSWIHW VRQAPGKGLEWVAWISPYGGSTYYADSVKGRFTISA DTSKNTAYLQMNSLRAEDTAVYYCARRHWPGGFDY WGQGTLVTVSS |
| 109 | VL (PD-L1) | DIQMTQSPSSLSASVGDRVTITCRASQDVSTAVAWY QQKPGKAPKLLIYSASFLYSGVPSRFSGSGSGTDFTLT ISSLQPEDFATYYCQQYLYHPATFGQGTKVEIK |
| 110 | VH (PD-L1) | EVQLVESGGGLVQPGGSLRLSCAASGFTFSRYWMS WVRQAPGKGLEWVANIKQDGSEKYYVDSVKGRFTI SRDNAKNSLYLQMNSLRAEDTAVYYCAREGGWFGE LAFDYWGQGTLVTVSS |
| 111 | VL (PD-L1) | EIVLTQSPGTLSLSPGERATLSCRASQRVSSSYLAWY QQKPGQAPRLLIYDASSRATGIPDRFSGSGSGTDFTLT ISRLEPEDFAVYYCQQYGSLPWTFGQGTKVEIK |
| 112 | VH (PD-1) | QVQLVQSGVEVKKPGASVKVSCKASGYTFTNYYMY WVRQAPGQGLEWMGGINPSNGGTNFNEKFKNRVTL TTDSSTTTAYMELKSLQFDDTAVYYCARRDYRFDM GFDYWGQGTTVTVSS |
| 113 | VL (PD-1) | EIVLTQSPATLSLSPGERATLSCRASKGVSTSGYSYLH WYQQKPGQAPRLLIYLASYLESGVPARFSGSGSGTDF TLTISSLEPEDFAVYYCQHSRDLPLTFGGGTKVEIK |
| 114 | VH (PD-1) | QVQLVESGGGVVQPGRSLRLDCKASGITFSNSGMHW VRQAPGKGLEWVAVIWYDGSKRYYADSVKGRFTIS RDNSKNTLFLQMNSLRAEDTAVYYCATNDDYWGQ GTLVTVSS |
| 115 | VL (PD-1) | EIVLTQSPATLSLSPGERATLSCRASQSVSSYLAWYQ QKPGQAPRLLIYDASNRATGIPARFSGSGSGTDFTLTI SSLEPEDFAVYYCQQSSNWPRTFGQGTKVEIK |

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to the numbering systems according to Kabat (Kabat, E. A., et al., Sequences of Proteins of Immunological Interest, 5th ed., Public Health Service, National Institutes of Health, Bethesda, Md. (1991)) as defined above.

Aspects of the Invention

In the following, some of the aspects of the invention are listed.

1. An anti-CD20/anti-CD3 bispecific antibody for use in a method for treating or delaying progression of cancer, wherein the anti-CD20/anti-CD3 bispecific antibody is used in combination with a 4-1BB (CD137) agonist.

2. The anti-CD20/anti-CD3 bispecific antibody for use in a method of aspect 1, wherein the anti-CD20/anti-CD3 bispecific antibody and the 4-1BB agonist are administered together in a single composition or administered separately in two or more different compositions.

3. The anti-CD20/anti-CD3 bispecific antibody for use in a method of the preceding aspects, wherein the anti-CD20/anti-CD3 bispecific antibody is administered concurrently with, prior to, or subsequently to the 4-1BB agonist.

4. The anti-CD20/anti-CD3 bispecific antibody for use in a method of any one of the preceding aspects, wherein the 4-1BB agonist comprises three ectodomains of 4-1BBL or fragments thereof.

5. The anti-CD20/anti-CD3 bispecific antibody for use in a method of any one of the preceding aspects, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

6. The anti-CD20/anti-CD3 bispecific antibody for use in a method of any one of the preceding aspects, wherein the 4-1BB agonist is an antigen binding molecule comprising three ectodomains of 4-1BBL or fragments thereof and at least one antigen binding domain capable of specific binding to CD19.

7. The anti-CD20/anti-CD3 bispecific antibody for use in a method of any one of the preceding aspects, wherein the antigen binding molecule comprising three ectodomains of 4-1BBL or fragments thereof and at least one antigen binding domain capable of specific binding to CD19 will not be internalized by CD19-expressing B cells.

8. The anti-CD20/anti-CD3 bispecific antibody for use in a method of any one of the preceding aspects, wherein the 4-1BB agonist is an antigen binding molecule comprising three ectodomains of 4-1BBL or fragments thereof and at least one moiety capable of specific binding to CD19, wherein the antigen binding domain capable of specific binding to CD19 comprises
(a) a heavy chain variable region ($V_H$CD19) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$CD19) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
(b) a VH domain comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a VL domain comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

9. The anti-CD20/anti-CD3 bispecific antibody for use in a method of any one of the preceding aspects, wherein the 4-1BB agonist is an antigen binding molecule comprising three ectodomains of 4-1BBL or fragments thereof and at least one antigen binding domain capable of specific binding to CD19, wherein the antigen binding domain capable of specific binding to CD19 comprises a heavy chain variable region ($V_H$CD19) comprising an amino acid sequence of SEQ ID NO:21 and a light chain variable region ($V_L$CD19) comprising an amino acid sequence of SEQ ID NO:22 or wherein the antigen binding domain capable of specific binding to CD19 comprises a heavy chain variable region ($V_H$CD19) comprising an amino acid sequence of SEQ ID NO:23 and a light chain variable region ($V_L$CD19) comprising an amino acid sequence of SEQ ID NO:24.

10. The anti-CD20/anti-CD3 bispecific antibody for use in a method of any one of the preceding aspects, wherein the 4-1BB agonist is an antigen binding molecule further comprising a Fc domain composed of a first and a second subunit capable of stable association.

11. The anti-CD20/anti-CD3 bispecific antibody for use in a method of any one of the preceding aspects, wherein the 4-1BB agonist is an antigen binding molecule comprising an IgG Fc domain, specifically an IgG1 Fc domain or an IgG4 Fc domain.

12. The anti-CD20/anti-CD3 bispecific antibody for use in a method of any one of the preceding aspects, wherein the 4-1BB agonist is an antigen binding molecule comprising a Fc domain that comprises one or more amino acid substitution that reduces or eliminates binding to an Fc receptor and/or effector function.

13. The anti-CD20/anti-CD3 bispecific antibody for use in a method of any one of of the preceding aspects, wherein the 4-1BB agonist is an antigen binding molecule comprising an IgG1 Fc domain comprising the amino acid substitutions L234A, L235A and P329G.

14. The anti-CD20/anti-CD3 bispecific antibody for use in a method of any one of the preceding aspects, wherein the 4-1BB agonist is an antigen binding molecule comprising
(a) at least one antigen binding domain capable of specific binding to CD19,
(b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

15. The anti-CD20/anti-CD3 bispecific antibody for use in a method of any one of the preceding aspects, wherein the 4-1BB agonist is an antigen binding molecule comprising
(a) at least one Fab domain capable of specific binding to CD19, and
(b) a first and a second polypeptide that are linked to each other by a disulfide bond, wherein the antigen binding molecule is characterized in that
  (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment therof connected via a peptide linker to the CL or CH1 domain of said polypeptide, or
  (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

16. The anti-CD20/anti-CD3 bispecific antibody for use in a method of any one of the preceding aspects, wherein the 4-1BB agonist is an antigen binding molecule comprising
(a) at least one Fab domain capable of specific binding to CD19 comprising a heavy chain variable region ($V_H$CD19) comprising the amino acid sequence of SEQ ID NO:21 and a light chain variable region ($V_L$CD19) comprising the amino acid sequence of SEQ ID NO:22 or a heavy chain variable region ($V_H$CD19) comprising the amino acid sequence of SEQ ID NO:23 and a light chain variable region ($V_L$CD19) comprising the amino acid sequence of SEQ ID NO:24, and
(b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

17. The anti-CD20/anti-CD3 bispecific antibody for use in a method of any one of the preceding aspects, wherein the 4-1BB agonist is an antigen binding molecule selected from the group consisting of
a) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:35 and a second light chain comprising the amino acid sequence of SEQ ID NO:36;
b) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:37 and a second light chain comprising the amino acid sequence of SEQ ID NO:38;
c) a molecule comprising two light chains comprising the amino acid sequence of SEQ ID NO:34, a first heavy chain comprising the amino acid sequence of SEQ ID NO:39 and a second heavy chain comprising the amino acid sequence of SEQ ID NO:40;
d) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:41 and a second light chain comprising the amino acid sequence of SEQ ID NO:42;
e) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:43 and a second light chain comprising the amino acid sequence of SEQ ID NO:44;
f) a molecule comprising two light chains comprising the amino acid sequence of SEQ ID NO:34, a first heavy chain comprising the amino acid sequence of SEQ ID NO:45 and a second heavy chain comprising the amino acid sequence of SEQ ID NO:46;
g) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:35 and a second light chain comprising the amino acid sequence of SEQ ID NO:36;
h) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:37 and a second light chain comprising the amino acid sequence of SEQ ID NO:38;
i) a molecule comprising two light chains comprising the amino acid sequence of SEQ ID NO:48, a first heavy chain comprising the amino acid sequence of SEQ ID NO:49 and a second heavy chain comprising the amino acid sequence of SEQ ID NO:50;
j) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:41 and a second light chain comprising the amino acid sequence of SEQ ID NO:42;
k) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:43 and a second light chain comprising the amino acid sequence of SEQ ID NO:44; and
l) a molecule comprising two light chains comprising the amino acid sequence of SEQ ID NO:48, a first heavy chain comprising the amino acid sequence of SEQ ID NO:51 and a second heavy chain comprising the amino acid sequence of SEQ ID NO:52.

18. The anti-CD20/anti-CD3 bispecific antibody for use in a method of any one of aspects 1 to 13, wherein the 4-1BB agonist is an antigen binding molecule comprising
(a) at least one antigen binding domain capable of specific binding to CD19,
(b) a polypeptide comprising three ectodomains of 4-1BBL or fragments thereof that are connected to each other by peptide linkers.

19. The anti-CD20/anti-CD3 bispecific antibody for use in a method of any one of aspects 1 to 13 or 18, wherein the 4-1BB agonist is an antigen binding molecule comprising
(a) at least one antigen binding domain capable of specific binding to CD19,
(b) a polypeptide comprising three ectodomains of 4-1BBL or fragments thereof that are connected to each other by peptide linkers, and
(c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

20. The anti-CD20/anti-CD3 bispecific antibody for use in a method of any one of aspects 1 to 13 or 18 or 19, wherein the 4-1BB agonist is an antigen binding molecule selected from the group consisting of
(a) a molecule comprising a heavy chain variable region (V$_H$CD19) comprising the amino acid sequence of SEQ ID NO:33, a light chain variable region (V$_L$CD19) comprising the amino acid sequence of SEQ ID NO:34, and a fusion protein comprising the amino acid sequence of SEQ ID NO:53,
(b) a molecule comprising a heavy chain variable region (V$_H$CD19) comprising the amino acid sequence of SEQ ID NO:47, a light chain variable region (V$_L$CD19) comprising the amino acid sequence of SEQ ID NO:48 and a fusion protein comprising the amino acid sequence of SEQ ID NO:53;
(c) a molecule comprising a heavy chain variable region (V$_H$CD19) comprising the amino acid sequence of SEQ ID NO:33, a light chain variable region (V$_L$CD19) comprising the amino acid sequence of SEQ ID NO:34, and a fusion protein comprising the amino acid sequence of SEQ ID NO:54, and
(d) a molecule comprising a heavy chain variable region (V$_H$CD19) comprising the amino acid sequence of SEQ ID NO:47, a light chain variable region (V$_L$CD19) comprising the amino acid sequence of SEQ ID NO:48, and a fusion protein comprising the amino acid sequence of SEQ ID NO:55.

21. The anti-CD20/anti-CD3 bispecific antibody for use in a method of any one of aspects 1 to 3, wherein the 4-1BB agonist is an anti-CD19/anti-4-1BB bispecific antibody.

22. The anti-CD20/anti-CD3 bispecific antibody for use in a method of any one of the preceding aspects, wherein the anti-CD20/anti-CD3 bispecific antibody comprises a first antigen binding domain that binds to CD3, and a second antigen binding domain that binds to CD20.

23. The anti-CD20/anti-CD3 bispecific antibody for use in a method of any one of the preceding aspects, wherein the anti-CD20/anti-CD3 bispecific antibody comprises a first antigen binding domain comprising a heavy chain variable region (V$_H$CD3) and a light chain variable region (V$_L$CD3), and a second antigen binding domain comprising a heavy chain variable region (V$_H$CD20) and a light chain variable region (V$_L$CD20).

24. The anti-CD20/anti-CD3 bispecific antibody for use in a method of any one of the preceding aspects, wherein the first antigen binding domain comprises a heavy chain variable region (V$_H$CD3) comprising CDR-H1 sequence of SEQ ID NO:56, CDR-H2 sequence of SEQ ID NO:57, and CDR-H3 sequence of SEQ ID NO:58; and/or a light chain variable region (V$_L$CD3) comprising CDR-L1 sequence of SEQ ID NO:59, CDR-L2 sequence of SEQ ID NO:60, and CDR-L3 sequence of SEQ ID NO:61.

25. The anti-CD20/anti-CD3 bispecific antibody for use in a method of any one of the preceding aspects, wherein the first antigen binding domain comprises a heavy chain variable region (V$_H$CD3) comprising the amino acid sequence of SEQ ID NO:62 and/or a light chain variable region (V$_L$CD3) comprising the amino acid sequence of SEQ ID NO:63.

26. The anti-CD20/anti-CD3 bispecific antibody for use in a method of any one of the preceding aspects, wherein the second antigen binding domain comprises a heavy chain variable region (V$_H$CD20) comprising CDR-H1 sequence of SEQ ID NO:64, CDR-H2 sequence of SEQ ID NO:65, and CDR-H3 sequence of SEQ ID NO:66; and/or a light chain variable region (V$_L$CD20) comprising CDR-L1 sequence of SEQ ID NO:67, CDR-L2 sequence of SEQ ID NO:68, and CDR-L3 sequence of SEQ ID NO:69.

27. The anti-CD20/anti-CD3 bispecific antibody for use in a method of any one of the preceding aspects, wherein the second antigen binding domain comprises a heavy chain variable region (V$_H$CD20) comprising the amino acid sequence of SEQ ID NO:70 and/or a light chain variable region (V$_L$CD20) comprising the amino acid sequence of SEQ ID NO:71.

28. The anti-CD20/anti-CD3 bispecific antibody for use in a method of any one of the preceding aspects, wherein the anti-CD20/anti-CD3 bispecific antibody comprises a third antigen binding domain that binds to CD20.

29. The anti-CD20/anti-CD3 bispecific antibody for use in a method of any one of the preceding aspects, wherein the third antigen binding domain comprises a heavy chain variable region (V$_H$CD20) comprising CDR-H1 sequence of SEQ ID NO:64, CDR-H2 sequence of SEQ ID NO:65, and CDR-H3 sequence of SEQ ID NO:66; and/or a light chain variable region (V$_L$CD20) comprising CDR-L1 sequence of SEQ ID NO:67, CDR-L2 sequence of SEQ ID NO:68, and CDR-L3 sequence of SEQ ID NO:69.

30. The anti-CD20/anti-CD3 bispecific antibody for use in a method of any one of the preceding aspects, wherein the third antigen binding domain comprises a heavy chain variable region (V$_H$CD20) comprising the amino acid sequence of SEQ ID NO:70 and/or a light chain variable region (V$_L$CD20) comprising the amino acid sequence of SEQ ID NO:71.

31. The anti-CD20/anti-CD3 bispecific antibody for use in a method of any one of the preceding aspects, wherein the first antigen binding domain is a cross-Fab molecule wherein the variable domains or the constant domains of the Fab heavy and light chain are exchanged, and the second and third, if present, antigen binding domain is a conventional Fab molecule.

32. The anti-CD20/anti-CD3 bispecific antibody for use in a method of any one of of the preceding aspects, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

33. The anti-CD20/anti-CD3 bispecific antibody for use in a method of any one of the preceding aspects, wherein the anti-CD20/anti-CD3 bispecific antibody comprises an Fc domain comprising one or more amino acid substitutions that reduce binding to an Fc receptor and/or effector function.

34. The anti-CD20/anti-CD3 bispecific antibody for use in a method of any one of the preceding aspects, wherein the anti-CD20/anti-CD3 bispecific antibody comprises an IgG1 Fc domain comprising the amino acid substitutions L234A, L235A and P329G.

35. An anti-CD20/anti-CD3 bispecific antibody for use in a method of any one of the preceding aspects, wherein the anti-CD20/anti-CD3 bispecific antibody is used in combination with a 4-1BB (CD137) agonist and wherein the combination is administered at intervals from about one week to three weeks.

36. A pharmaceutical product comprising (A) a first composition comprising as active ingredient an anti-CD20/anti-CD3 bispecific antibody and a pharmaceutically acceptable carrier; and (B) a second composition comprising as active ingredient a 4-1BB agonist and a pharmaceutically acceptable carrier, for use in the combined, sequential or simultaneous, treatment of a disease, in particular cancer.

37. The pharmaceutical product of aspect 36 for use in the treatment of B-cell proliferative disorders, in particular a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

37. A pharmaceutical composition comprising an anti-CD20/anti-CD3 bispecific antibody and a 4-1BB agonist.

38. The pharmaceutical composition of aspect 37, wherein the anti-CD20/anti-CD3 bispecific antibody and the 4-1BB agonist are administered together in a single composition or administered separately in two or more different compositions.

39. The pharmaceutical composition of aspect 37 or 38, wherein the anti-CD20/anti-CD3 bispecific antibody is administered concurrently with, prior to, or subsequently to the 4-1BB agonist.

40. The pharmaceutical composition of any one of aspects 37 to 39, wherein the 4-1BB agonist comprises three ectodomains of 4-1BBL or fragments thereof.

41. The pharmaceutical composition of any one of aspects 37 to 40, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

42. The pharmaceutical composition of any one of aspects 37 to 41, wherein the 4-1BB agonist is an antigen binding molecule comprising three ectodomains of 4-1BBL or fragments thereof and at least one antigen binding domain capable of specific binding to CD19.

43. The pharmaceutical composition of any one of aspects 37 to 42, wherein the 4-1BB agonist will not be internalized in B cells.

44. The pharmaceutical composition of any one of aspects 37 to 43, wherein the 4-1BB agonist is an antigen binding molecule comprising three ectodomains of 4-1BBL or fragments thereof and at least one moiety capable of specific binding to CD19, wherein the antigen binding domain capable of specific binding to CD19 comprises
(a) a heavy chain variable region ($V_H$CD19) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$CD19) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
(b) a VH domain comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a VL domain comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

45. The pharmaceutical composition of any one of aspects 37 to 44, wherein the 4-1BB agonist is an antigen binding molecule comprising three ectodomains of 4-1BBL or fragments thereof and at least one antigen binding domain capable of specific binding to CD19, wherein the antigen binding domain capable of specific binding to CD19 comprises a heavy chain variable region ($V_H$CD19) comprising an amino acid sequence of SEQ ID NO:21 and a light chain variable region ($V_L$CD19) comprising an amino acid sequence of SEQ ID NO:22 or wherein the antigen binding domain capable of specific binding to CD19 comprises a heavy chain variable region ($V_H$CD19) comprising an amino acid sequence of SEQ ID NO:23 and a light chain variable region ($V_L$CD19) comprising an amino acid sequence of SEQ ID NO:24.

46. The pharmaceutical composition of any one of aspects 37 to 45, wherein the 4-1BB agonist is an antigen binding molecule further comprising a Fc domain composed of a first and a second subunit capable of stable association.

47. The pharmaceutical composition of any one of aspects 37 to 45, wherein the 4-1BB agonist is an antigen binding molecule comprising an IgG Fc domain, specifically an IgG1 Fc domain or an IgG4 Fc domain.

48. The pharmaceutical composition of any one of aspects 37 to 47, wherein the 4-1BB agonist is an antigen binding molecule comprising a Fc domain that comprises one or more amino acid substitution that reduces binding to an Fc receptor and/or effector function.

49. The pharmaceutical composition of any one of aspects 37 to 48, wherein the 4-1BB agonist is an antigen binding molecule comprising an IgG1 Fc domain comprising the amino acid substitutions L234A, L235A and P329G.

50. The pharmaceutical composition of any one of aspects 37 to 49, wherein the 4-1BB agonist is an antigen binding molecule comprising
(a) at least one antigen binding domain capable of specific binding to CD19,
(b) a first and a second polypeptide that are linked to each other by a disulfide bond,
wherein the first polypeptide comprises two ectodomains of 4-1BBL or fragments thereof that are connected to each other by a peptide linker and in that the second polypeptide comprises one ectodomain of 4-1BBL or a fragment thereof.

51. The pharmaceutical composition of any one of aspects 37 to 50, wherein the 4-1BB agonist is an antigen binding molecule comprising
(a) at least one Fab domain capable of specific binding to CD19, and
(b) a first and a second polypeptide that are linked to each other by a disulfide bond,
wherein the antigen binding molecule is characterized in that
(i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment therof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

52. The pharmaceutical composition of any one of aspects 37 to 51, wherein the 4-1BB agonist is an antigen binding molecule comprising
(a) at least one Fab domain capable of specific binding to CD19 comprising a heavy chain variable region ($V_H$CD19) comprising the amino acid sequence of SEQ ID NO:21 and a light chain variable region ($V_L$CD19) comprising the amino acid sequence of SEQ ID NO:22 or a heavy chain variable region ($V_H$CD19) comprising the amino acid sequence of SEQ ID NO:23 and a light chain variable region ($V_L$CD19) comprising the amino acid sequence of SEQ ID NO:24, and
(b) a first and a second polypeptide that are linked to each other by a disulfide bond,
wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

53. The pharmaceutical composition of any one of aspects 37 to 52, wherein the 4-1BB agonist is an antigen binding molecule selected from the group consisting of a) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:35 and a second light chain comprising the amino acid sequence of SEQ ID NO:36;

b) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:37 and a second light chain comprising the amino acid sequence of SEQ ID NO:38;

c) a molecule comprising two light chains comprising the amino acid sequence of SEQ ID NO:34, a first heavy chain comprising the amino acid sequence of SEQ ID NO:39 and a second heavy chain comprising the amino acid sequence of SEQ ID NO:40;

d) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:41 and a second light chain comprising the amino acid sequence of SEQ ID NO:42;

e) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:43 and a second light chain comprising the amino acid sequence of SEQ ID NO:44;

f) a molecule comprising two light chains comprising the amino acid sequence of SEQ ID NO:34, a first heavy chain comprising the amino acid sequence of SEQ ID NO:45 and a second heavy chain comprising the amino acid sequence of SEQ ID NO:46;

g) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:35 and a second light chain comprising the amino acid sequence of SEQ ID NO:36;

h) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:37 and a second light chain comprising the amino acid sequence of SEQ ID NO:38;

i) a molecule comprising two light chains comprising the amino acid sequence of SEQ ID NO:48, a first heavy chain comprising the amino acid sequence of SEQ ID NO:49 and a second heavy chain comprising the amino acid sequence of SEQ ID NO:50;

j) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:41 and a second light chain comprising the amino acid sequence of SEQ ID NO:42;

k) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:43 and a second light chain comprising the amino acid sequence of SEQ ID NO:44; and l) a molecule comprising two light chains comprising the amino acid sequence of SEQ ID NO:48, a first heavy chain comprising the amino acid sequence of SEQ ID NO:51 and a second heavy chain comprising the amino acid sequence of SEQ ID NO:52.

54. The pharmaceutical composition of any one of aspects 37 to 49, wherein the 4-1BB agonist is an antigen binding molecule comprising
(a) at least one antigen binding domain capable of specific binding to CD19,
(b) a polypeptide comprising ectodomains of 4-1BBL or fragments thereof that are connected to each other by peptide linkers.

55. The pharmaceutical composition of any one of aspects 37 to 49 or 54, wherein the 4-1BB agonist is an antigen binding molecule comprising
(a) at least one antigen binding domain capable of specific binding to CD19,
(b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

56. The pharmaceutical composition of any one of aspects 37 to 49 or 54 or 55, wherein the 4-1BB agonist is an antigen binding molecule selected from the group consisting of
(a) a molecule comprising a heavy chain variable region ($V_H$CD19) comprising the amino acid sequence of SEQ ID NO:33, a light chain variable region ($V_L$CD19) comprising the amino acid sequence of SEQ ID NO:34, and a fusion protein comprising the amino acid sequence of SEQ ID NO:53,
(b) a molecule comprising a heavy chain variable region ($V_H$CD19) comprising the amino acid sequence of SEQ ID NO:47, a light chain variable region ($V_L$CD19) comprising the amino acid sequence of SEQ ID NO:48 and a fusion protein comprising the amino acid sequence of SEQ ID NO:53;
(c) a molecule comprising a heavy chain variable region ($V_H$CD19) comprising the amino acid sequence of SEQ ID NO:33, a light chain variable region ($V_L$CD19) comprising the amino acid sequence of SEQ ID NO:34, and a fusion protein comprising the amino acid sequence of SEQ ID NO:54, and
(d) a molecule comprising a heavy chain variable region ($V_H$CD19) comprising the amino acid sequence of SEQ ID NO:47, a light chain variable region ($V_L$CD19) comprising the amino acid sequence of SEQ ID NO:48, and a fusion protein comprising the amino acid sequence of SEQ ID NO:55.

57. The pharmaceutical composition of any one of aspects 37 to 39, wherein the 4-1BB agonist is an anti-CD19/anti-4-1BB bispecific antibody.

58. The pharmaceutical composition of any one of aspects 37 to 57, wherein the anti-CD20/anti-CD3 bispecific antibody comprises a first antigen binding domain that binds to CD3, and a second antigen binding domain that binds to CD20.

59. The pharmaceutical composition of any one of aspects 37 to 58, wherein the anti-CD20/anti-CD3 bispecific antibody comprises a first antigen binding domain comprising a heavy chain variable region ($V_H$CD3) and a light chain variable region ($V_L$CD3), and a second antigen binding domain comprising a heavy chain variable region ($V_H$CD20) and a light chain variable region ($V_L$CD20).

60. The pharmaceutical composition of any one of aspects 37 to 59, wherein the first antigen binding domain comprises a heavy chain variable region ($V_H$CD3) comprising CDR-H1 sequence of SEQ ID NO:56, CDR-H2 sequence of SEQ ID NO:57, and CDR-H3 sequence of SEQ ID NO:58; and/or a light chain variable region ($V_L$CD3) comprising CDR-L1 sequence of SEQ ID NO:59, CDR-L2 sequence of SEQ ID NO:60, and CDR-L3 sequence of SEQ ID NO:61.

61. The pharmaceutical composition of any one of aspects 37 to 60, wherein the first antigen binding domain comprises a heavy chain variable region ($V_H$CD3) comprising the amino acid sequence of SEQ ID NO:62 and/or a light chain variable region ($V_L$CD3) comprising the amino acid sequence of SEQ ID NO:63.

62. The pharmaceutical composition of any one of aspects 37 to 61, wherein the second antigen binding domain comprises a heavy chain variable region ($V_H$CD20) comprising CDR-H1 sequence of SEQ ID NO:64, CDR-H2 sequence of SEQ ID NO:65, and CDR-H3 sequence of SEQ ID NO:66, and/or a light chain variable region ($V_L$CD20) comprising CDR-L1 sequence of SEQ ID NO:67, CDR-L2 sequence of SEQ ID NO:68, and CDR-L3 sequence of SEQ ID NO:69.

63. The pharmaceutical composition of any one of aspects 37 to 62, wherein the second antigen binding domain comprises a heavy chain variable region ($V_H$CD20) comprising the amino acid sequence of SEQ ID NO:70 and/or a light chain variable region ($V_L$CD20) comprising the amino acid sequence of SEQ ID NO:71.

64. The pharmaceutical composition of any one of aspects 37 to 63, wherein the anti-CD20/anti-CD3 bispecific antibody comprises a third antigen binding domain that binds to CD20.

65. The pharmaceutical composition of any one of aspects 37 to 64, wherein the third antigen binding domain comprises a heavy chain variable region ($V_H$CD20) comprising CDR-H1 sequence of SEQ ID NO:64, CDR-H2 sequence of SEQ ID NO:65, and CDR-H3 sequence of SEQ ID NO:66; and/or a light chain variable region ($V_L$CD20) comprising CDR-L1 sequence of SEQ ID NO:67, CDR-L2 sequence of SEQ ID NO:68, and CDR-L3 sequence of SEQ ID NO:69.

66. The pharmaceutical composition of any one of aspects 37 to 65, wherein the third antigen binding domain comprises a heavy chain variable region ($V_H$CD20) comprising the amino acid sequence of SEQ ID NO:70 and/or a light chain variable region ($V_L$CD20) comprising the amino acid sequence of SEQ ID NO:71.

67. The pharmaceutical composition of any one of aspects 37 to 66, wherein the first antigen binding domain is a cross-Fab molecule wherein the variable domains or the constant domains of the Fab heavy and light chain are exchanged, and the second and third, if present, antigen binding domain is a conventional Fab molecule.

68. The pharmaceutical composition of any one of aspects 37 to 67, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

69. The pharmaceutical composition of any one of aspects 37 to 68, wherein the anti-CD20/anti-CD3 bispecific antibody comprises an Fc domain comprising one or more amino acid substitutions that reduce binding to an Fc receptor and/or effector function.

70. The pharmaceutical composition of any one of aspects 37 to 68, wherein the anti-CD20/anti-CD3 bispecific antibody comprises an IgG1 Fc domain comprising the amino aciod substitutions L234A, L235A and P329G.

71. The pharmaceutical composition of any one of aspects 37 to 70, wherein the anti-CD20/anti-CD3 bispecific antibody is used in combination with a 4-1BB (CD137) agonist and wherein the combination is administered at intervals from about about one week to three weeks.

72. The pharmaceutical composition of any one of aspects 37 to 71 for use in treating or delaying progression of a proliferative disease, in particular cancer.

73. The pharmaceutical composition of any one of aspects 37 to 712 for use in the treatment of B-cell proliferative disorders, in particular a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

74. A kit for treating or delaying progression of cancer in a subject, comprising a package comprising (A) a first composition comprising as active ingredient an anti-CD20/anti-CD3 bispecific antibody and a pharmaceutically acceptable carrier; (B) a second composition comprising as active ingredient a 4-1BB agonist and a pharmaceutically acceptable carrier, and (C) instructions for using the compositions in a combination therapy.

75. Use of a combination of an anti-CD20/anti-CD3 bispecific antibody and a 4-1BB agonist in the manufacture of a medicament for treating or delaying progression of a proliferative disease, in particular cancer.

76. Use of a combination of an anti-CD20/anti-CD3 bispecific antibody and a 4-1BB agonist in the manufacture of a medicament, wherein the medicament is for the treatment of B-cell proliferative disorders, in particular a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

77. A method for treating or delaying progression of cancer in a subject comprising administering to the subject an effective amount of an anti-CD20/anti-CD3 antibody and a 4-1BB agonist.

78. A method for treating or delaying progression of cancer in a subject comprising administering to the subject an effective amount of an anti-CD20/anti-CD3 antibody and a 4-1BB agonist, wherein the 4-1BB agonist is an antigen binding molecule.

79. The method of aspects 77 or 78, wherein the 4-1BB agonist is an antigen binding molecule comprising a Fc domain.

80. The method of any one of aspects 77 to 79, wherein the 4-1BB agonist is an antigen binding molecule comprising a Fc domain with modifications reducing Fcγ receptor binding and/or effector function.

81. The method of any one of aspects 77 to 80, wherein the 4-1BB agonist is an antigen binding molecule comprising three ectodomains of 4-1BBL or fragments thereof.

82. The method of any one of aspects 77 to 81, wherein the -1BB agonist is an antigen binding molecule comprising three ectodomains of 4-1BBL or fragments thereof and an antigen binding domain capable of specific binding to CD19.

83. The method of any one of aspects 77 to 82, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

84. The method of any one of aspects 77 to 83, wherein the 4-1BB agonist will not be internalized in B cells.

85. The method of any one of aspects 77 to 84, wherein the 4-1BB agonist is an antigen binding molecule comprising three ectodomains of 4-1BBL or fragments thereof and at least one moiety capable of specific binding to CD19, wherein the antigen binding domain capable of specific binding to CD19 comprises
(a) a heavy chain variable region ($V_H$CD19) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$CD19) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
(b) a VH domain comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a VL domain comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

86. The method of any one of aspects 77 to 85, wherein the 4-1BB agonist is an antigen binding molecule comprising three ectodomains of 4-1BBL or fragments thereof and at least one antigen binding domain capable of specific binding to CD19, wherein the antigen binding domain capable of specific binding to CD19 comprises a heavy chain variable region ($V_H$CD19) comprising an amino acid sequence of SEQ ID NO:21 and a light chain variable region ($V_L$CD19) comprising an amino acid sequence of SEQ ID NO:22 or wherein the antigen binding domain capable of specific binding to CD19 comprises a heavy chain variable region ($V_H$CD19) comprising an amino acid sequence of SEQ ID NO:23 and a light chain variable region ($V_L$CD19) comprising an amino acid sequence of SEQ ID NO:24.

87. The method of any one of aspects 77 to 86, wherein the 4-1BB agonist is an antigen binding molecule further comprising a Fc domain composed of a first and a second subunit capable of stable association.

88. The method of any one of aspects 77 to 87, wherein the 4-1BB agonist is an antigen binding molecule comprising an IgG Fc domain, specifically an IgG1 Fc domain or an IgG4 Fc domain.

89. The method of any one of aspects 77 to 88, wherein the 4-1BB agonist is an antigen binding molecule comprising a Fc domain that comprises one or more amino acid substitution that reduces binding to an Fc receptor and/or effector function.

90. The method of any one of aspects 77 to 89, wherein the 4-1BB agonist is an antigen binding molecule comprising an IgG1 Fc domain comprising the amino acid substitutions L234A, L235A and P329G.

91. The method of any one of aspects 77 to 90, wherein the 4-1BB agonist is an antigen binding molecule comprising
(a) at least one antigen binding domain capable of specific binding to CD19,
(b) a first and a second polypeptide that are linked to each other by a disulfide bond,
wherein the first polypeptide comprises two ectodomains of 4-1BBL or fragments thereof that are connected to each other by a peptide linker and in that the second polypeptide comprises one ectodomain of 4-1BBL or a fragment thereof.

92. The method of any one of aspects 77 to 91, wherein the 4-1BB agonist is an antigen binding molecule comprising
(a) at least one Fab domain capable of specific binding to CD19, and
(b) a first and a second polypeptide that are linked to each other by a disulfide bond,
wherein the antigen binding molecule is characterized in that
  (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment therof connected via a peptide linker to the CL or CH1 domain of said polypeptide, or
  (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
  (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

93. The method of any one of aspects 77 to 92, wherein the 4-1BB agonist is an antigen binding molecule comprising
(a) at least one Fab domain capable of specific binding to CD19 comprising a heavy chain variable region ($V_H$CD19) comprising the amino acid sequence of SEQ ID NO:21 and a light chain variable region ($V_L$CD19) comprising the amino acid sequence of SEQ ID NO:22 or a heavy chain variable region ($V_H$CD19) comprising the amino acid sequence of SEQ ID NO:23 and a light chain variable region ($V_L$CD19) comprising the amino acid sequence of SEQ ID NO:24, and
(b) a first and a second polypeptide that are linked to each other by a disulfide bond,
wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

94. The method of any one of aspects 77 to 93, wherein the 4-1BB agonist is an antigen binding molecule selected from the group consisting of
  a) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:35 and a second light chain comprising the amino acid sequence of SEQ ID NO:36;
  b) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:37 and a second light chain comprising the amino acid sequence of SEQ ID NO:38;
  c) a molecule comprising two light chains comprising the amino acid sequence of SEQ ID NO:34, a first heavy chain comprising the amino acid sequence of SEQ ID NO:39 and a second heavy chain comprising the amino acid sequence of SEQ ID NO:40;
  d) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:41 and a second light chain comprising the amino acid sequence of SEQ ID NO:42;
  e) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:43 and a second light chain comprising the amino acid sequence of SEQ ID NO:44;
  f) a molecule comprising two light chains comprising the amino acid sequence of SEQ ID NO:34, a first heavy chain comprising the amino acid sequence of SEQ ID NO:45 and a second heavy chain comprising the amino acid sequence of SEQ ID NO:46;
  g) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:35 and a second light chain comprising the amino acid sequence of SEQ ID NO:36;
  h) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:37 and a second light chain comprising the amino acid sequence of SEQ ID NO:38;
  i) a molecule comprising two light chains comprising the amino acid sequence of SEQ ID NO:48, a first heavy chain comprising the amino acid sequence of SEQ ID NO:49 and a second heavy chain comprising the amino acid sequence of SEQ ID NO:50;
  j) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:41 and a second light chain comprising the amino acid sequence of SEQ ID NO:42;
  k) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:43 and a second light chain comprising the amino acid sequence of SEQ ID NO:44; and l) a molecule comprising two light chains comprising the amino acid sequence of SEQ ID NO:48, a first heavy chain comprising the amino acid sequence of SEQ ID NO:51 and a second heavy chain comprising the amino acid sequence of SEQ ID NO:52.

95. The method of any one of aspects 77 to 90, wherein the 4-1BB agonist is an antigen binding molecule comprising
(a) at least one antigen binding domain capable of specific binding to CD19,
(b) a polypeptide comprising three ectodomains of 4-1BBL or fragments thereof that are connected to each other by peptide linkers.

96. The method of any one of aspects 77 to 90 or 95, wherein the 4-1BB agonist is an antigen binding molecule comprising
(a) at least one antigen binding domain capable of specific binding to CD19,
(b) a polypeptide comprising three ectodomains of 4-1BBL or fragments thereof that are connected to each other by peptide linkers, and
(c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

97. The method of any one of aspects 77 to 90 or 95 or 96, wherein the 4-1BB agonist is an antigen binding molecule selected from the group consisting of
(a) a molecule comprising a heavy chain variable region ($V_H$CD19) comprising the amino acid sequence of SEQ ID NO:33, a light chain variable region ($V_L$CD19) comprising the amino acid sequence of SEQ ID NO:34, and a fusion protein comprising the amino acid sequence of SEQ ID NO:53,
(b) a molecule comprising a heavy chain variable region ($V_H$CD19) comprising the amino acid sequence of SEQ ID NO:47, a light chain variable region ($V_L$CD19) comprising the amino acid sequence of SEQ ID NO:48 and a fusion protein comprising the amino acid sequence of SEQ ID NO:53;
(c) a molecule comprising a heavy chain variable region ($V_H$CD19) comprising the amino acid sequence of SEQ ID NO:33, a light chain variable region ($V_L$CD19) comprising the amino acid sequence of SEQ ID NO:34, and a fusion protein comprising the amino acid sequence of SEQ ID NO:54, and
(d) a molecule comprising a heavy chain variable region ($V_H$CD19) comprising the amino acid sequence of SEQ ID NO:47, a light chain variable region ($V_L$CD19) comprising the amino acid sequence of SEQ ID NO:48, and a fusion protein comprising the amino acid sequence of SEQ ID NO:55.

98. The method of any one of aspects 77 to 80, wherein the 4-1BB agonist is an anti-CD19/anti-4-1BB bispecific antibody.

99. The method of any one of aspects 77 to 98, wherein the anti-CD20/anti-CD3 bispecific antibody comprises a first antigen binding domain that binds to CD3, and a second antigen binding domain that binds to CD20.

100. The method of any one of aspects 77 to 99, wherein the anti-CD20/anti-CD3 bispecific antibody comprises a first antigen binding domain comprising a heavy chain variable region ($V_H$CD3) and a light chain variable region ($V_L$CD3), and a second antigen binding domain comprising a heavy chain variable region ($V_H$CD20) and a light chain variable region ($V_L$CD20).

101. The method of any one of aspects 77 to 100, wherein the first antigen binding domain comprises a heavy chain variable region ($V_H$CD3) comprising CDR-H1 sequence of SEQ ID NO:56, CDR-H2 sequence of SEQ ID NO:57, and CDR-H3 sequence of SEQ ID NO:58; and/or a light chain variable region ($V_L$CD3) comprising CDR-L1 sequence of SEQ ID NO:59, CDR-L2 sequence of SEQ ID NO:60, and CDR-L3 sequence of SEQ ID NO:61.

102. The method of any one of aspects 77 to 101, wherein the first antigen binding domain comprises a heavy chain variable region ($V_H$CD3) comprising the amino acid sequence of SEQ ID NO:62 and/or a light chain variable region ($V_L$CD3) comprising the amino acid sequence of SEQ ID NO:63.

103. The method of any one of aspects 77 to 102, wherein the second antigen binding domain comprises a heavy chain variable region ($V_H$CD20) comprising CDR-H1 sequence of SEQ ID NO:64, CDR-H2 sequence of SEQ ID NO:65, and CDR-H3 sequence of SEQ ID NO:66, and/or a light chain variable region ($V_L$CD20) comprising CDR-L1 sequence of SEQ ID NO:67, CDR-L2 sequence of SEQ ID NO:68, and CDR-L3 sequence of SEQ ID NO:69.

104. The method of any one of aspects 77 to 103, wherein the second antigen binding domain comprises a heavy chain variable region ($V_H$CD20) comprising the amino acid sequence of SEQ ID NO:70 and/or a light chain variable region ($V_L$CD20) comprising the amino acid sequence of SEQ ID NO:71.

105. The method of any one of aspects 77 to 104, wherein the anti-CD20/anti-CD3 bispecific antibody comprises a third antigen binding domain that binds to CD20.

106. The method of any one of aspects 77 to 105, wherein the third antigen binding domain comprises a heavy chain variable region ($V_H$CD20) comprising CDR-H1 sequence of SEQ ID NO:64, CDR-H2 sequence of SEQ ID NO:65, and CDR-H3 sequence of SEQ ID NO:66; and/or a light chain variable region ($V_L$CD20) comprising CDR-L1 sequence of SEQ ID NO:67, CDR-L2 sequence of SEQ ID NO:68, and CDR-L3 sequence of SEQ ID NO:69.

107. The method of any one of aspects 77 to 106, wherein the third antigen binding domain comprises a heavy chain variable region ($V_H$CD20) comprising the amino acid sequence of SEQ ID NO:70 and/or a light chain variable region ($V_L$CD20) comprising the amino acid sequence of SEQ ID NO:71.

108. The method of any one of aspects 77 to 107, wherein the first antigen binding domain is a cross-Fab molecule wherein the variable domains or the constant domains of the Fab heavy and light chain are exchanged, and the second and third, if present, antigen binding domain is a conventional Fab molecule.

109. The method of any one of aspects 77 to 108, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

110. The method of any one of aspects 77 to 109, wherein the anti-CD20/anti-CD3 bispecific antibody comprises an Fc domain comprising one or more amino acid substitutions that reduce binding to an Fc receptor and/or effector function.

111. The method of any one of aspects 77 to 110, wherein the anti-CD20/anti-CD3 bispecific antibody comprises an IgG1 Fc domain comprising the amino acid substitutions L234A, L235A and P329G.

112. The method of any one of aspects 77 to 111, wherein the anti-CD20/anti-CD3 bispecific antibody is used in combination with a 4-1BB (CD137) agonist and wherein the combination is administered at intervals from about one week to three weeks.

113. The method of any one of aspects 77 to 112, wherein the anti-CD20/anti-CD3 bispecific antibody and the 4-1BB agonist are administered together in a single composition or administered separately in two or more different compositions.

114. The method of any one of aspects 77 to 113, wherein the the anti-CD20/anti-CD3 bispecific antibody and the 4-1BB (CD137) agonist are administered intravenously or subcutaneously.

115. The method of any one of aspects 77 to 114, wherein the anti-CD20/anti-CD3 bispecific antibody is administered concurrently with, prior to, or subsequently to the 4-1BB agonist.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

This section describes the characterization of the multispecific antibodies with VH/VL exchange (VH/VL CrossMabs) with emphasis on their correct assembly. The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 µg deglycosylated VH/VL CrossMabs in a Tris buffer pH 8 at room temperature for 120 hours and at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Determination of Binding and Binding Affinity of Multi-specific Antibodies to the Respective Antigens Using Surface Plasmon Resonance (SPR) (BIACORE)

Binding of the generated antibodies to the respective antigens is investigated by surface plasmon resonance using a BIACORE instrument (GE Healthcare Biosciences AB, Uppsala, Sweden). Briefly, for affinity measurements Goat-Anti-Human IgG, MR 109-005-098 antibodies are immobilized on a CM5 chip via amine coupling for presentation of the antibodies against the respective antigen. Binding is measured in HBS buffer (HBS-P (10 mM HEPES, 150 mM NaCl, 0.005% Tween 20, ph 7.4), 25° C. (or alternatively at 37° C.). Antigen (R&D Systems or in house purified) was added in various concentrations in solution. Association was measured by an antigen injection of 80 seconds to 3 minutes; dissociation was measured by washing the chip surface with HBS buffer for 3-10 minutes and a KD value was estimated using a 1:1 Langmuir binding model. Negative control data (e.g. buffer curves) are subtracted from sample curves for correction of system intrinsic baseline drift and for noise signal reduction. The respective Biacore Evaluation Software is used for analysis of sensorgrams and for calculation of affinity data.

Further details of the invention are illustrated by the following non-limiting Examples. The disclosures of all citations in the specification are expressly incorporated herein by reference.

Example 1

Preparation, Purification and Characterization of CD19-41BBL Antigen Binding Molecules CD19-targeted 4-1BB ligand trimer-containing Fc fusion antigen binding molecules were prepared as described in International Patent Appl. Publ. No. WO 2016/075278 A1.

In particular, the following molecules were made:

a) Monovalent CD19-targeted and untargeted 4-1BB ligand trimer-containing Fc fusion antigen binding molecules A polypeptide encoding a dimeric 4-1BB ligand fused to human CL domain was subcloned in frame with the human IgG1 heavy chain CH2 and CH3 domains on the knob (Merchant, Zhu et al. 1998). A polypeptide containing one ectodomain of the 4-1BB ligand was fused to the human IgG1-CH1 domain. In Construct 3.4, in order to improve correct pairing the following mutations were additionally introduced in the crossed CH-CL (charged variant). In the dimeric 4-1BB ligand fused to human CL, E123R and Q124K, in the monomeric 4-1BB ligand fused to human CH1, K147E and K213E.

Figure 1A:
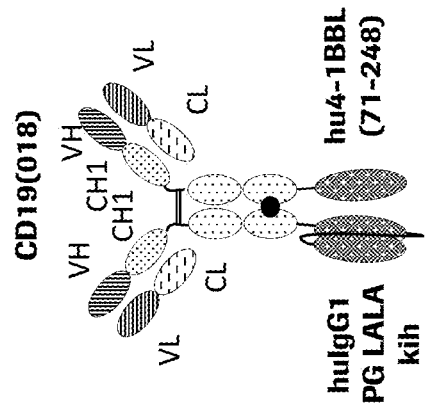
FIGS. 1A-1F show particular CD19-4-1BBL antigen binding molecules and a particular anti-CD20/anti-CD3 bispecific antibody as used in the Examples. These molecules are described in more detail in Examples 1 and 2, respectively. The thick black point stands for the knob-into-hole modification. * symbolizes amino acid modifications in the CH1 and CL domain (so-called charged residues).
Figure 1B:
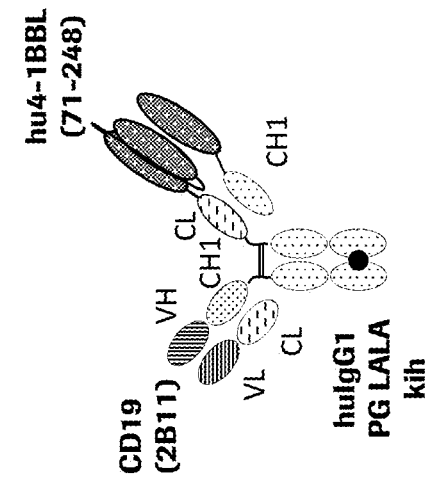
Figure 1C:
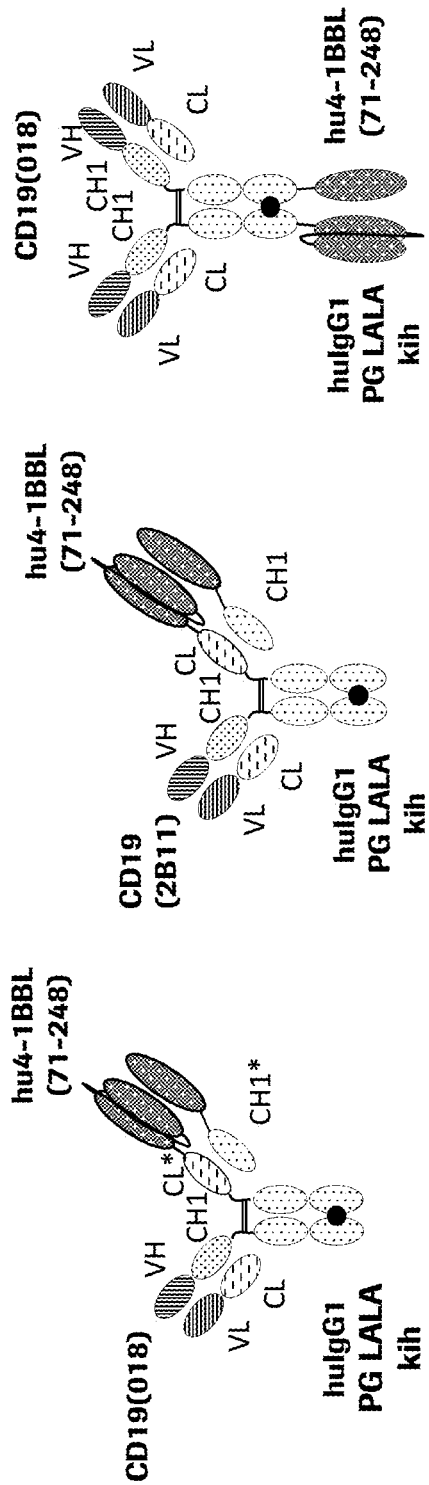
Figure 1D:
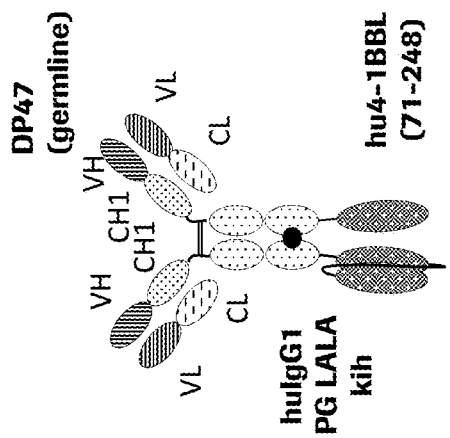
Figure 1E:
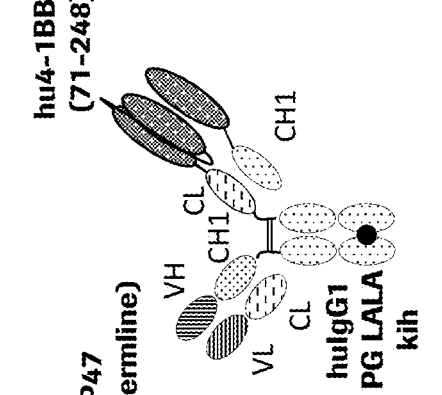

The variable region of heavy and light chain DNA sequences encoding a binder specific for CD19, clone 8B8-018 or clone 8B8-2B11, were subcloned in frame with either the constant heavy chain of the hole or the constant light chain of human IgG1. The Pro329Gly, Leu234Ala and Leu235Ala mutations have been introduced in the constant region of the knob and hole heavy chains to abrogate binding to Fc gamma receptors according to the method described in WO 2012/130831. Combination of the dimeric ligand-Fc knob chain containing the S354C/T366W mutations, the monomeric CH1 fusion, the targeted anti-CD19-Fc hole chain containing the Y349C/T366S/L368A/Y407V mutations and the anti-CD19 light chain allows generation of a heterodimer, which includes an assembled trimeric 4-1BB ligand and a CD19 binding Fab (FIGS. 1A and 1B). An untargeted version has been prepared accordingly by replacing the CD19 binder by germline DP47 (FIG. 1E).

TABLE 1

Monovalent Constructs used in the experiments

Figure 1F:
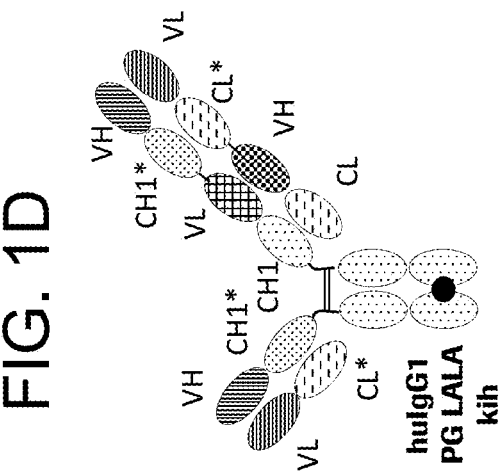

| | Example in WO 2016/075278 | composed of |
|---|---|---|
| mono CD19(018)-4-1BBL (Charged variant) | Example 7.1.6 (Construct 3.4) | SEQ ID NO: 33, SEQ ID NO: 34 SEQ ID NO: 41 and SEQ ID NO: 42 |
| mono CD19(2B11)-4-1BBL | Example 7.2.7 (Construct 4.5) | SEQ ID NO: 47, SEQ ID NO: 48 SEQ ID NO: 43 and SEQ ID NO: 44 |
| mono untargeted DP47-4-1BBL | Example 7.3.12 (Control D) | SEQ ID NO: 68, SEQ ID NO: 69 SEQ ID NO: 43 and SEQ ID NO: 44 | a) Bivalent CD19-Targeted and Untargeted 4-1BB Ligand Trimer-Containing Fc Fusion Antigen Binding Molecules The DNA sequences encoding the heavy and light chain variable regions of heavy and light chain specific a binder specific for CD19, clone 8B8-018 or clone 8B8-2B11, were subcloned in frame with either the constant heavy chain of the hole, the knob or the constant light chain of human IgG1. The Pro329Gly, Leu234Ala and Leu235Ala mutations were introduced in the constant region of the knob and hole heavy chains to abrogate binding to Fc gamma receptors according to the method described in WO 2012/130831. Furthermore, a polypeptide comprising two ectodomains of 4-1BB ligand was fused to the C-terminus of human IgG1 Fc hole chain and a polypeptide comprising one ectodomain of 4-1BB ligand was fused to the C-terminus of human IgG1 Fc knob chain. Combination of the anti-CD19 huIgG1 hole dimeric ligand heavy chain containing the Y349C/T366S/L368A/Y407V mutations, the anti-CD19 huIgG1 knob monomeric ligand heavy chain containing the S354C/T366W mutations and the anti-CD19 light chains allowed generation of a heterodimer, which included an assembled trimeric 4-1BB ligand and two CD19 binding Fabs (FIG. 1C). An untargeted version has been prepared accordingly by replacing the CD19 binder by germline DP47 (FIG. 1F).

TABLE 2

Bivalent Constructs used in the experiments

| | Example in WO 2016/075278 | composed of |
|---|---|---|
| bi CD19(018)-4-1BBL | Example 7.1.8 (Construct 3.6) | 2 x SEQ ID NO: 34, SEQ ID NO: 45 and SEQ ID NO: 46 |
| bi CD19(2B11)-4-1BBL | Example 7.2.8 (Construct 4.6) | 2 x SEQ ID NO: 48 SEQ ID NO: 51 and SEQ ID NO: 52 |
| bi untargeted DP47-4-1BBL | Example 7.3.12 (Control C) | 2 x SEQ ID NO: 69 SEQ ID NO: 74 and SEQ ID NO: 75 |

The production and characterization of the CD19-targeted and untargeted 4-1BB ligand trimer-containing Fc fusion antigen binding molecules is described in detail in WO 2016/075278, Example 7.4 and Examples 8 to 11, respectively.

Example 2

Preparation, Purification and Characterization of T-Cell Bispecific (TCB) Antibodies TCB molecules have been prepared according to the methods described in WO 2016/020309 A1.

The anti-CD20/anti-CD3 bispecific antibody (CD20 CD3 TCB or CD20 TCB) used in the experiments corresponds to molecule B as described in Example 1 of WO 2016/020309 A1. Molecule B is a "2+1 IgG CrossFab" antibody and is comprised of two different heavy chains and two different light chains. Point mutations in the CH3 domain ("knobs into holes") were introduced to promote the assembly of the two different heavy chains. Exchange of the VH and VL domains in the CD3 binding Fab and point mutations in the CH and CL domains in the CD20 binding Fab were made in order to promote the correct assembly of the two different light chains. 2+1 means that the molecule has two antigen binding domains specific for CD20 and one antigen binding domain specific for CD3.

CD20 TCB comprises the amino acid sequences of SEQ ID NO:76, SEQ ID NO:77, SEQ ID NO:78 and SEQ ID NO:79. A schematic scheme of the bispecific antibody in 2+1 format is shown in FIG. 1D.

The molecule is further characterized in Example 1 of WO 2016/020309 A1.

Example 3

Properties of CD19-4-1BBL Antigen Binding Molecules (Constructs)

a) CD19-4-1BBL Binds to CD19

The ability of CD19-4-1BBL to bind to CD19 was measured on primary human B cells or on CD19 positive tumor cell lines (WSU-DLCL2 cells, DSMZ No. ACC 575). Briefly, fresh peripheral blood mononuclear cells (PBMCs) were purified from buffy coats from healthy donors. Cells resuspended in DPBS (Gibco by Life Technologies, Cat. No. 14190 326) were added to each well of a round-bottom suspension cell 96-well plates (greiner bio-one, cellstar, Cat. No. 650185). Cells were washed once with 200 µL DPBS. Cells were resuspended in 100 µL/well of 4° C. cold DPBS buffer containing 1:5000 diluted Fixable Viability Dye eFluor 660 (eBioscience, Cat. No. 65-0864-18) and plates were incubated for 30 minutes at 4° C. Cells were washed once with 200 µL/well 4° C. cold DPBS buffer and resuspended in 50 µL/well of 4° C. cold FACS buffer (DPBS supplied with 2% FBS, 5 mM EDTA pH8 (Amresco, Cat. No. E177) and 7.5 mM Sodium azide (Sigma-Aldrich S2002)) containing constructs (mono CD19(018)-4-1BBL, bi CD19(018)-4-1BBL, mono CD19(2B11)-4-1BBL, mono untargeted 4-1BBL and/or bi untargeted 4-1BBL) at a series of concentrations, followed by incubation for 1 hour at 4° C.

After extensive washing, cells were further stained with 50 µL/well of 4° C. cold FACS buffer containing 5 µg/mL PE-conjugated AffiniPure anti-human IgG F(ab') 2-fragment-specific goat F(ab')$_2$ fragment (Jackson ImmunoResearch, Cat. No. 109 116 098), and with an APC-H7-conjugated CD20 Antibody (BD, Cat. No. 560734), and an APC-conjugated anti-CD3 Antibody (Biolegend, Cat. No. 300312), and/or a FITC-conjugated anti-CD19 Antibody (BD) for 30 minutes at 4° C. Cells were washed twice with 200 µL/well 4° C. FACS buffer and cells were fixed in 50 DPBS containing 1% Formaldehyde (Sigma, HT501320-9.5L). Cells were resuspended in 100 µL/well FACS-buffer and acquired using the FACS LSR II (BD Biosciences). Data were analyzed using FlowJo V10 (FlowJo, LLC) and GraphPad Prism 6.04 (GraphPad Software, Inc).

Figure 2A:
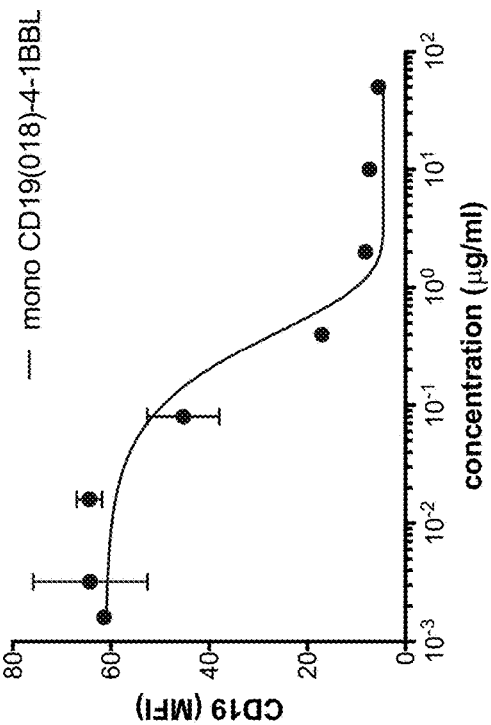
In FIG. 2A the binding of mono CD19 (018)-4-1BBL to CD19$^+$ human B cells is shown, as detected by a secondary antibody against human Fc. In comparison to the untargeted construct mono CD19 (018)-4-1BBL exhibits strong binding to CD19$^+$ human B cells in a dose dependent manner. The decrease of CD19 expression on B cells after binding by mono CD19(018)-4-1BBL is illustrated in FIG. 2B, indicating that binding is CD19 specific.
Figure 2B:
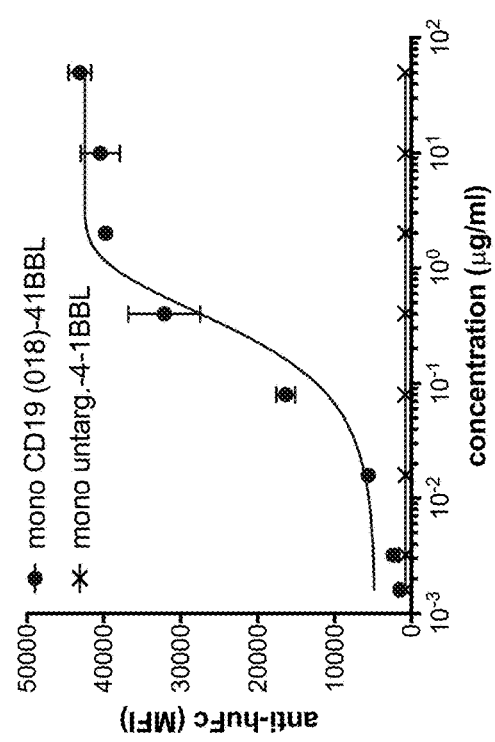
FIG. 2C shows the binding of different CD19-4-1BBL constructs to CD19$^+$ WSU-DLCL2 cell lines, detected by the secondary antibody against human Fc. It shows that the monovalent CD19-4-1BBL constructs demonstrated better binding to the cells than the bivalent CD19-4-1BBL construct.
Figure 2C:
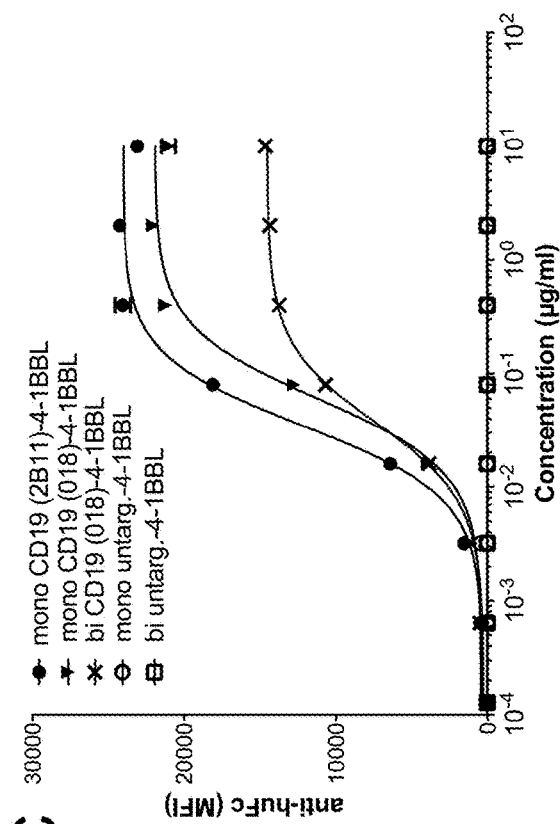

Cells were gated on CD3-CD20$^+$ living populations, and geo means of fluorescence intensity of PE-conjugated AffiniPure anti-human IgG IgG Fcγ-fragment-specific goat F(ab')2 fragment were plotted against the titrated concentration of constructs. As shown in FIG. 2A, CD19-4-1BBL binds to human B cells in a dose-dependent manner, while untargeted 4-1BBL did not bind to B cells in human PBMCs. FIG. 2B shows how the CD19 expression on B cells decreases after the binding of CD19-4-1BBL, indicating that CD19-4-1BBL binds to CD19 specifically. Similarly, CD19-4-1BBL constructs bind to CD19$^+$ WSU tumor cells, and binding affinity is much higher in the monovalent constructs than the bivalent one (FIG. 2C).

b) CD19-4-1BBL Binds to 4-1BB on Activated T Cells

To check the binding of 4-1BBL to 4-1BB expressing T cells, human PBMCs were pre-activated by TCR stimulation for the upregulation of 4-1BB on T cells for 48 hours. Purified PBMCs were diluted into a concentration of $2.8 \times 10^6$/ml and resuspended in RPMI medium (Gibco, Cat No. 72400-054)+10% FBS (Gibco, Cat No. 20012-068) and 1% penicillin-Streptomycin (Gibco, Cat No. 15070-063) and 50 µM of 2-Mercaptoethanol (Gibco, Cat No. 31350-010). 90 µl of cells were added to each well of round-bottom 96-well plates (greiner bio-one, cellstar, Cat. No. 650185). Then, additional 50 µl anti-CD3 and anti-CD28 microbeads (Life Technologies, Cat No. 11131D) at $8 \times 10^5$ beads/ml were added to the wells. Two days later, cells were washed with cold PBS (Gibco, 20012-068) one time, and resuspended with 90 µl of cold PBS, and incubated with 10 µl of solutions containing constructs (monovalent CD19(018)-4-1BBL, bivalent CD19(018)-4-1BBL, and monovalent untargeted 4-1BBL) for 1 hour at 4° C. After extensive washing, cells were further stained with 50 µL/well of cold FACS buffer containing 5 µg/mL PE-conjugated AffiniPure anti-human IgG F(ab')$_2$-fragment-specific goat F(ab')2 fragment (Jackson ImmunoResearch, Cat. No. 109 116 098), and additionally with anti-human CD3 (Biolegend, Cat No. 300312), CD4 (Biolegend, Cat No. 317434) and CD8 (Biolegend, Cat No. 344710) Antibody for 30 minutes at 4° C. Cells were washed twice with 200 µL/well 4° C. FACS buffer and cells were fixed in 50 µL/well DPBS containing 1% Formaldehyde (Sigma, HT501320-9.5L). Cells were resuspended in 100 µL/well FACS-buffer and acquired using the FACS LSR II (BD Biosciences). Data was analyzed using FlowJo V10 (FlowJo, LLC) and GraphPad Prism 6.04 (GraphPad Software, Inc).

Figure 3A:
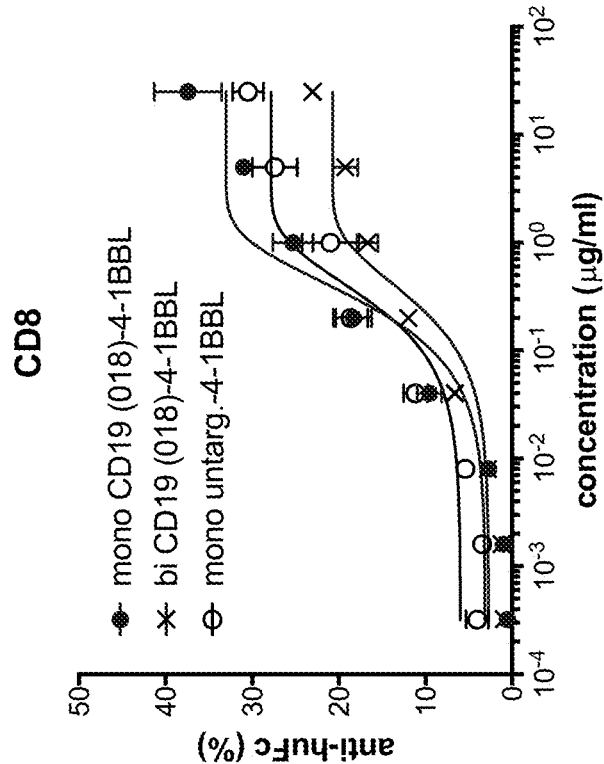
FIGS. 3A and 3B show the binding of mono and bi CD19 (018)-4-1BBL to 4-1BBL to activated CD4 T cells (FIG. 3A) or activated CD8 T cells (FIG. 3B). Total human PBMCs were pre-activated by anti-CD3 and anti-CD28 microbeads to engage with TCR on T cells (CD4 and CD8). Activated T cells did upregulate 4-1BB. Two days later, cells were harvested and co-incubated on ice with a titrated concentration of CD19-4-1BBL for binding to 4-1BB on T cells. Specific binding was detected by the secondary antibody against human IgG Fc.
Figure 3B:
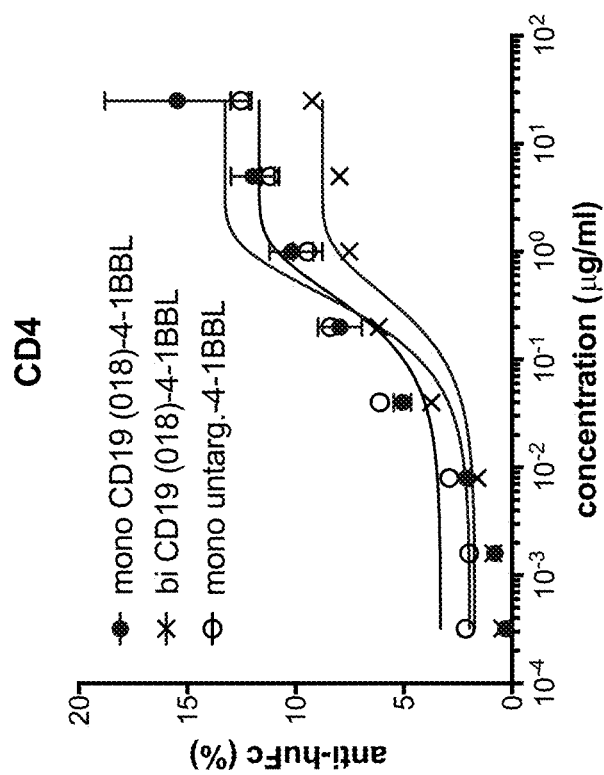

The specific binding was gated on pure population of activated CD4 and CD8 cells. All constructs showed similar binding properties to 4-1BB expressing CD4 or CD8 T cells in a dose dependent manner (FIGS. 3A and 3B).

c) CD19-4-1BBL Shows Biological Activity

Figure 4:
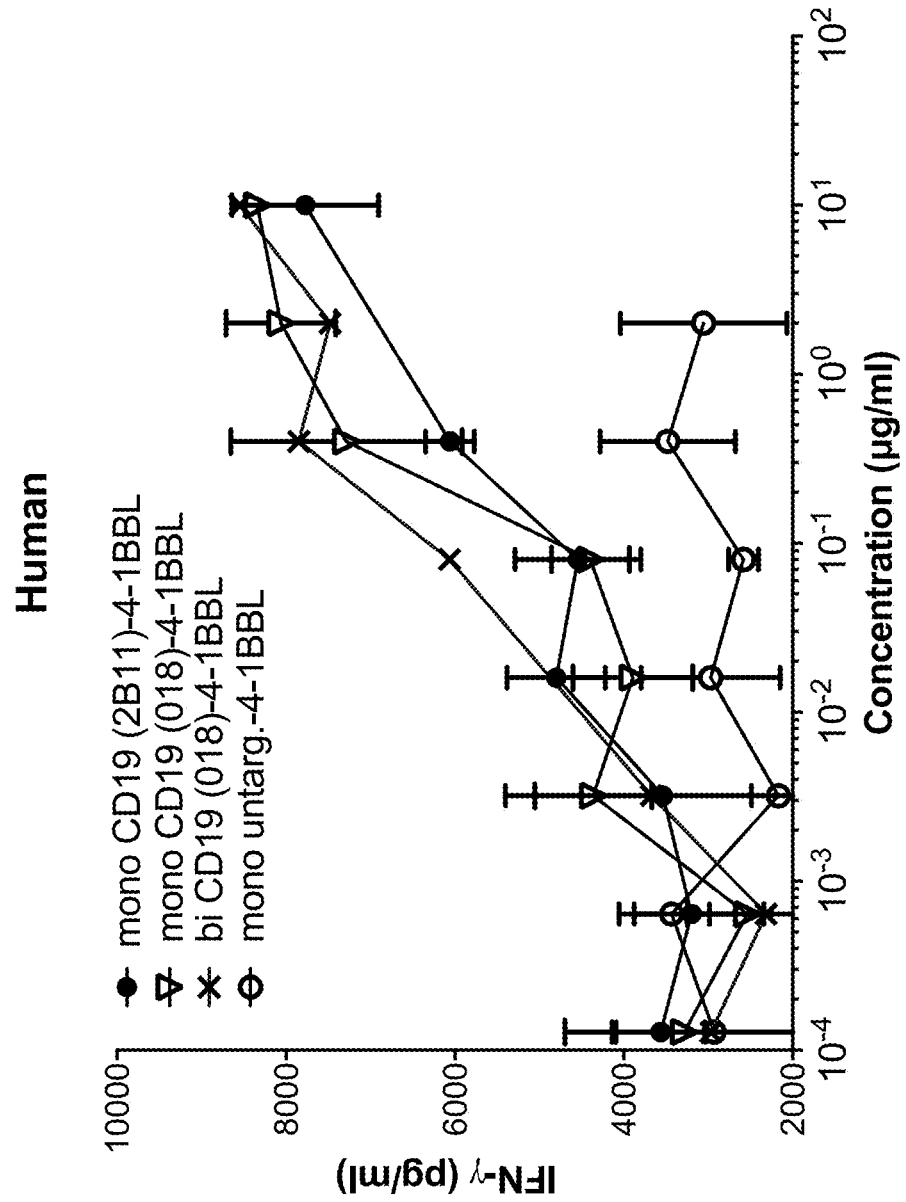
In FIG. 4 is shown the IFN-γ release by activated PBMCs caused by mono or bi CD19 (018)-4-1BBL. Total human PBMCs were incubated with anti-CD3 and anti-CD28 microbeads and with a titrated concentration of CD19-4-1BBL. Two days later the supernatants were collected for the measurement of IFN-γ by ELISA.

To measure the biological activities in physiological settings, we used activated human PBMCs to check the release of effector function molecule IFN-γ by costimluating T cells and NK cells. Briefly, purified PBMCs co-cultured with constructs (monovalent CD19(018)-4-1BBL, bivalent CD19 (018)-4-1BBL, monovalent CD19(2B11)-4-1BBL, and monovalent untargeted 4-1BBL) were added to the wells at a series of concentrations, and 50 µl anti-CD3 and anti-CD28 microbeads were added (Life Technologies, Cat No. 11131D) at $8 \times 10^5$ beads/ml. After 48 hours of incubation, the supernatants were collected for the measurement of IFN-γ by ELISA (DuoSet Human IFN-γ ELISA kit, R&D Systems, Cat No. DY285). FIG. 4 shows that both monovalent and bivalent constructs stimulate PBMCs to produce a similar amount of IFN-γ, whereas the negative untargeted 4-1BBL constructs did not activate T cells or NK cells due to the lack of cross-linking.

Example 4

Mechanisms of Combination Therapy of CD19-4-1BBL and CD20 TCB In Vitro a) CD20 TCB Mediates Redistribution of CD19-4-1BBL on T Cells Our hypothesis for the combination therapy of CD19-4-1BBL and CD20 TCB was based on the assumption that CD20 TCB would trigger initial T cell activation through the binding of tumor antigen CD20, leading to upregulation of 4-1BB on activated T cells, therefore allowing CD19-4-1BBL to co-stimulate 4-1BB and thereby boosting T cell effector function. To understand and confirm such modes of actions of this combination therapy, we took advantage of time-lapse confocal microscopy to monitor the immunological synapse formation on activated T cells. WSU-DLCL2 cells were stained with Blue CMAC dye (Molecular Probes, Life Technologies) and plated overnight on 8 well "ibiTreat" slides (ibidi) at 37° C. to adhere. Cells were washed after 24 hours and replaced with media before adding activated CD8-positive T cells stained with CMFDA (Molecular Probes, Life Technologies). CD19-41BBL labeled with Alexa F647 (10 µg/ml) and CD20 CD3 TCB (5 ng/ml or 500 ng/ml) were additionally added directly into the growth media. Imaging slides were then transferred to the confocal microscope (inverted LSM 700, Zeiss) with a temperature and $CO_2$ controlled stage and allowed within 15 minutes to equilibrate to the temperature inside the microscope incubator before live acquisition with a 60× oil objective. Movies were collected using the Zen software (Zeiss) coupled to the microscope, while analysis of CD19-41BBL intensity at the site of interaction was performed with Imaris (Bitplane; Oxford Instruments). Quantification was performed using the IMARIS surface-surface contact area algorithm. The algorithm creates a one voxel thick surface object on the primary surface (tumor cell) in the area covered by the secondary surface (T cell). Total intensity of the CD19-41BBL signal is then measured inside the resulting contact surface and quantified over time.

Figure 5B:
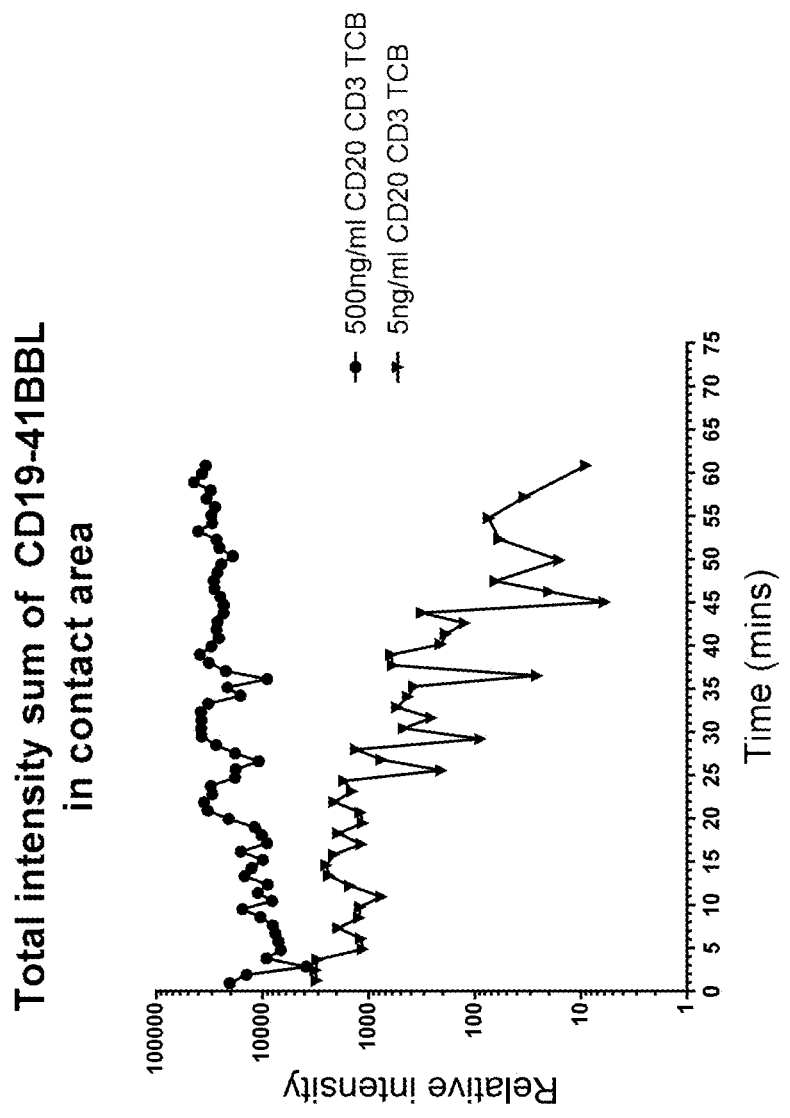

FIG. 5A shows the dynamic localization of CD19-41BBL during CD20 CD3 TCB-mediated T- and tumor cell cross-linking, which was concentrated at sites of interaction in a CD20 CD3 TCB dose-dependent manner. The interaction is first initiated by the crosslinking of CD20 CD3 TCB, followed by the redistribution of CD19-41BBL to the immunological synapse possibly mediated by lipid rafts attracted by the binding to CD20 (the binder originates from the type II anti-body, obinutuzumab). The polarization of CD19-41BBL at the T- and tumor cell synapse suggest a possible combinatorial mode-of-action by which a threshold of CD20 CD3 TCB concentration (FIG. 5B) is able to localize and sustain 41BB co-stimulatory signals, which synergizes with the early CD3 activation signals. This synergism might trigger the 41BB cascade signals for preventing T cell activation induced cell death, resulting in a more robust T cell population in the tumor microenvironment as observed by histological analysis in the in vivo efficacy experiment.

b) CD19-4-1BBL is not Internalized by CD19 on B Cells

Figure 6:
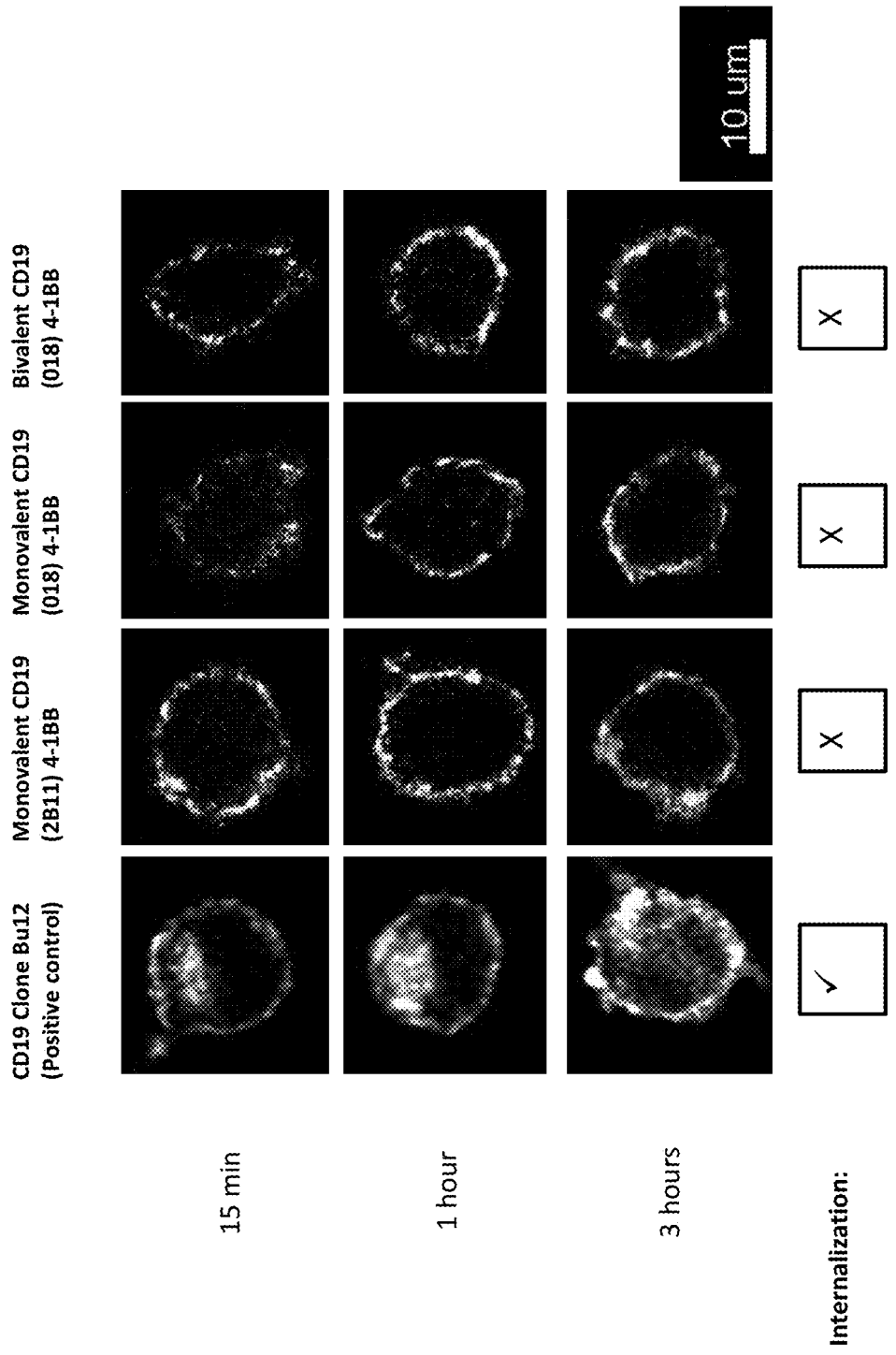
FIG. 6 relates to the internalization of CD19-4-1BBL constructs by WSU tumor cells. A CD19 antibody clone BU12 was quickly internalized in the tumor cell whereas the CD19-4-1BBL were not internalized into the tumor cells and thus maintain their ability to interact with tumor microenvironment.

The sub-cellular localization of CD19-4-1BBL molecule is a critical parameter for its functionality and for its synergy with CD20 TCB bispecific antibody. Not only the CD19-4-1BBL molecule should target the CD19 expressing tumor cells but it should not be internalized as 4-1BB agonism via 4-1BBL needs antibody cross-linking on CD19. It has been reported that many CD19 antibodies can be rapidly internalized by B cells including non-Hodgkin lymphoma (NHL) cells (Ingle et al, 2008). Therefore we tested our constructs by confocal microscope to see whether they can be internalized by NHL cell line WSU DLCL2 cells. To do so, CD19-4-1BBL constructs were first labeled with Alexa-647 prior to incubation with WSU cells at 37° C., and then the interaction was fixed at different time-points (at 15 minutes, 1 and 3 hours) and the localization (intracellular or membrane located) of CD19-4-1BBL was assessed by confocal microscopy. By looking at the central Z stack of the image, it is possible to observe that the CD19-4-1BBL-Alexa-647 molecule is mostly located to the membrane for all the 3 hours (FIG. 6). In contrast the positive control of an anti-CD19 antibody (clone Bu12) is quickly internalized, reducing its exposure on the surface of the tumor cells.

Example 5

Potent Anti-Tumor Effect by Combination Therapy of CD19-4-1BBL and CD20 TCB In Vivo a) SDPK of CD19-4-1BBL Constructs in Immunodeficient NOD/Shi-Scid/IL-2Rγnull (NOG) Mice Prior to the in vivo efficacy studies, we first performed a single dose pharmacodynamics (SDPK) study. Female NOD/Shi-scid/IL-2Rγnull (NOG) mice, in the age of 6-7 weeks at start of the experiment (bred at Taconic, Denmark) were maintained under specific-pathogen-free condition with daily cycles of 12 h light/12 h darkness according to committed guidelines (GV-Solas; Felasa; TierschG). The experimental study protocol was reviewed and approved by local government (ZH193/2014). After arrival, animals were maintained for one week to get accustomed to the new environment and for observation. Continuous health monitoring was carried out on a regular basis.

Figure 7:
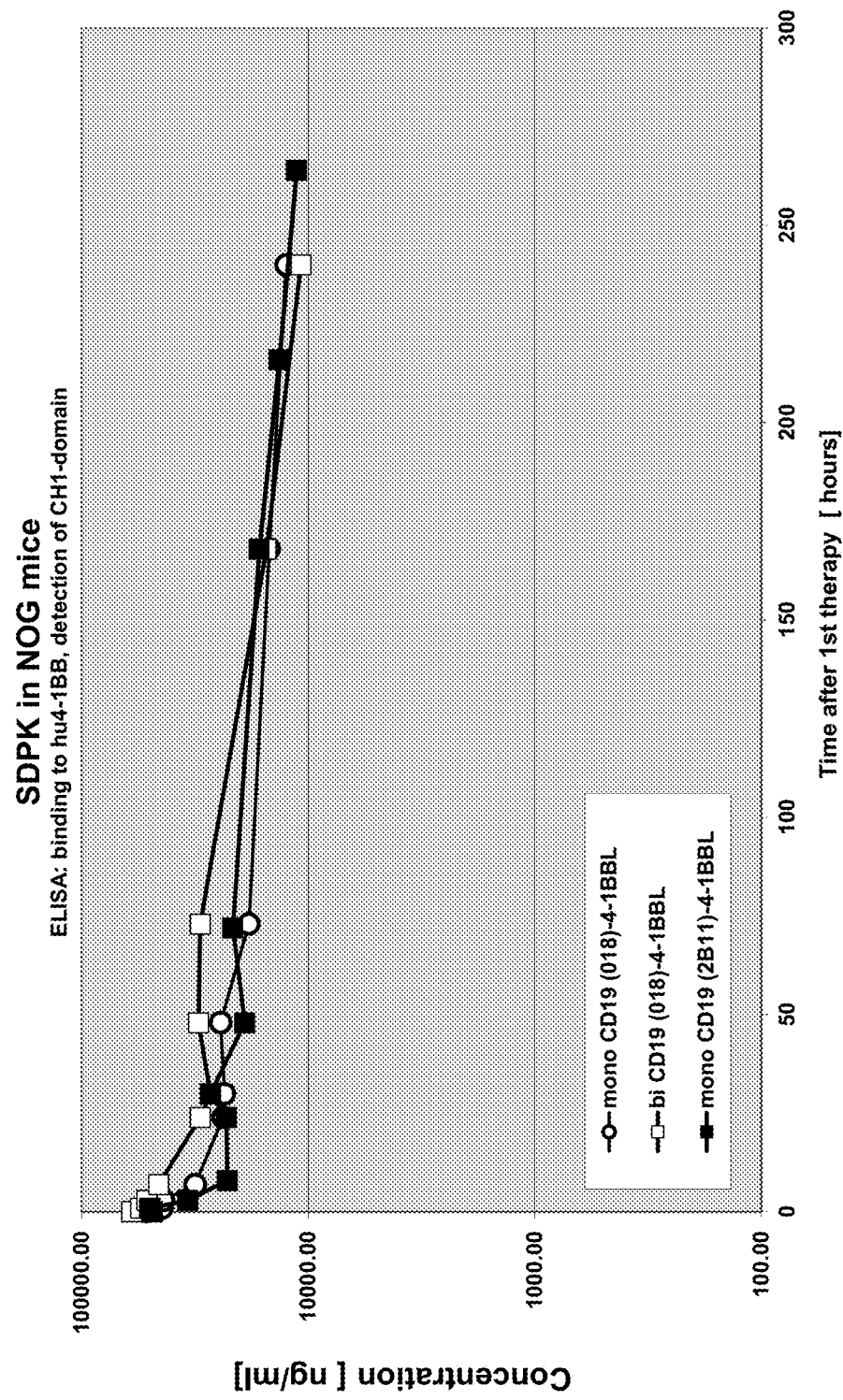
FIG. 7 shows the single dose pharmacokinetic profile (SDPK) of mono and bi CD19 (018)-4-1BBL and mono CD19 (2B11)-4-1BBL in immunodeficient NOD/Shi-scid/IL-2Rγnull (NOG) mice. As can be seen from the graphs all molecules revealed a stable and IgG-like PK-profile.

Mice were injected i.v. with 50 µg/mouse (2.5 mg/kg) of the three different 4-1-BBL constructs (see compositions in Table 3) whereas 3 mice were bled per group and time point. All mice were injected with a total volume of 200 µl of the appropriate solution. To obtain the proper amount of the constructs per 200 µl, the stock solutions were diluted with PBS when necessary. Serum samples were collected 10 min, 1 h, 3 h, 8 h, 24 h, 48 h, 72 h, 96 h and 168 h after therapy injection. As seen in FIG. 7, all molecules reveal a stable and IgG-like PK-profile.

TABLE 3

Compositions used in the in vivo experiments

| Compound | Dose | Formulation buffer | Concentration (mg/mL) |
|---|---|---|---|
| mono CD19 (018)-4-1BBL | 2.5 mg/kg | 20 mM Histidine, 140 mM NaCl, pH 6.0 | 5.40 (=stock solution) |
| bi CD19 (018)-4-1BBL | 2.5 mg/kg | 20 mM Histidine, 140 mM NaCl, pH 6.0 | 3.78 (=stock solution) |
| mono CD19 (2B11)-4-1BBL | 2.5 mg/kg | 20 mM Histidine, 140 mM NaCl, pH 6.0 | 4.61 (=stock solution) | b) Superior Anti-Tumor Activity of Monovalent CD19-4-1BBL Construct in Combination with CD20 TCB as Compared to Bivalent Construct The first proof on concept for the combination of CD20 TCB and CD19-4-1BBL was aimed to select the best format (mono vs. bi-valent binding for CD19, clone 018) of the CD19-4-1BBL constructs in terms of tumor regression in fully humanized NOG mice.

WSU-DLCL2 cells (human diffuse large B cell lymphoma) were originally obtained from ECACC (European Collection of Cell Culture) and after expansion deposited in the Roche Glycart internal cell bank. Cells were cultured in RPMI containing 10% FCS and 1× Glutamax. The cells were cultured at 37° C. in a water-saturated atmosphere at 5% $CO_2$. $1.5 \times 10^6$ cells (in vitro passage 18) per animal were injected s.c. into the right flank of the animals in RPMI cell culture medium (Gibco) and GFR matrigel (1:1, total volume of 100 ul) at a viability of >95.0%.

Female NOD/Shi-scid/IL-2Rγnull (NOG) mice, in the age of 4-5 weeks at the start of the experiment (bred at Taconic, Denmark) were maintained under specific-pathogen-free condition with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis.

According to the protocol (FIG. 8), female NOG mice were injected i.p. with 15 mg/kg of Busulfan followed one day later by an i.v. injection of $1 \times 10^5$ human hematopoietic stem cells isolated from cord blood. At week 14-16 after stem cell injection, mice were bled sublingual and blood was analyzed by flow cytometry for successful humanization. Efficiently engrafted mice were randomized according to their human T cell frequencies into the different treatment groups (FIG. 8, n=10/group). At that time, mice were injected with tumor cells s.c. as described above and treated once weekly with the compounds or PBS (Vehicle) when tumor size reached appr. 450 mm³. All mice were injected i.v. with 200 µl of the appropriate solution. To obtain the proper amount of compounds per 200 µl, the stock solutions (Table 4) were diluted with PBS when necessary.

TABLE 4

Compositions used in this experiment

| Compound | Formulation buffer | Concentration (mg/mL) |
|---|---|---|
| mono CD19 (018)-4-1BBL | 20 mM Histidine, 140 mM NaCl, pH 6.0 | 5.12 (=stock solution) |
| bi CD19 (018)-4-1BBL | 20 mM Histidine, 140 mM NaCl, pH 6.0 | 3.32 (=stock solution) |
| mono untarg.-4-1BBL | 20 mM Histidine, 140 mM NaCl, pH 6.0 | 1.06 (=stock solution) |
| CD20 TCB | 20 mM Histidine, 140 mM NaCl, pH 6.0 | 4.12 (=stock solution) |

For combination therapies (Animal groups E to I, see Table in FIG. 8) with CD20 TCB, the CD19-4-1BBL constructs were injected concomitant. Tumor growth was measured twice weekly using a caliper and tumor volume was calculated as followed:

$T_v := (W^2/2) \times L$ ($W$: Width, $L$: Length)

Figure 9B:
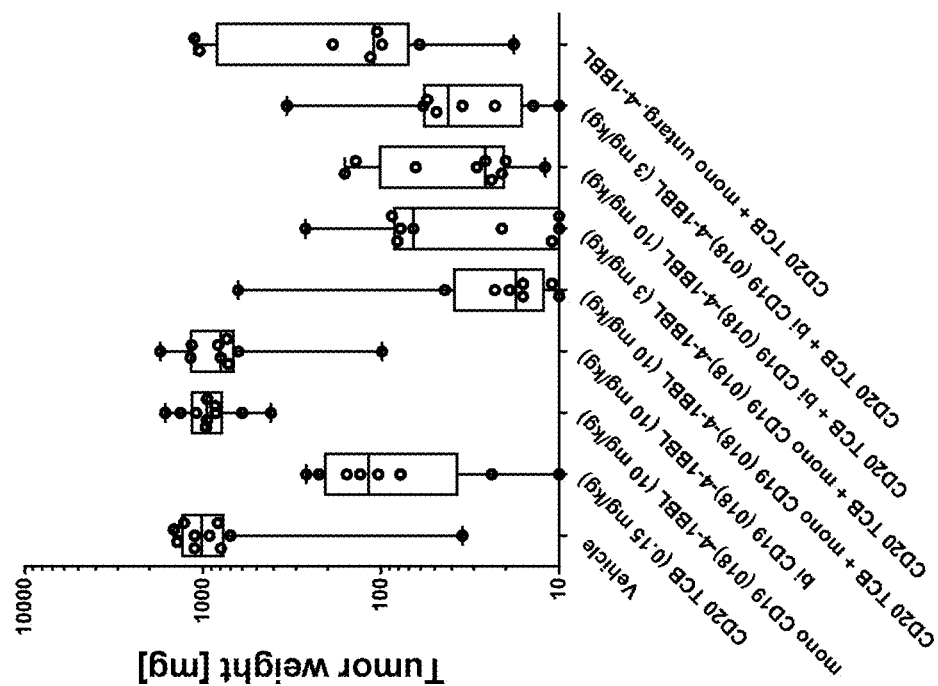
As shown in FIG. 9B, the tumor weights at study termination confirmed these findings; however, the striking differences in terms of tumor growth inhibition is seen in the kinetics of tumor growth, especially at earlier time points (FIG. 9A). This data suggest the monovalent binding to CD19 (mono CD19 (018)-4-1BBL) to be superior to the bivalent one in terms of tumor growth inhibition when combined with CD20 TCB.
Figure 9A:
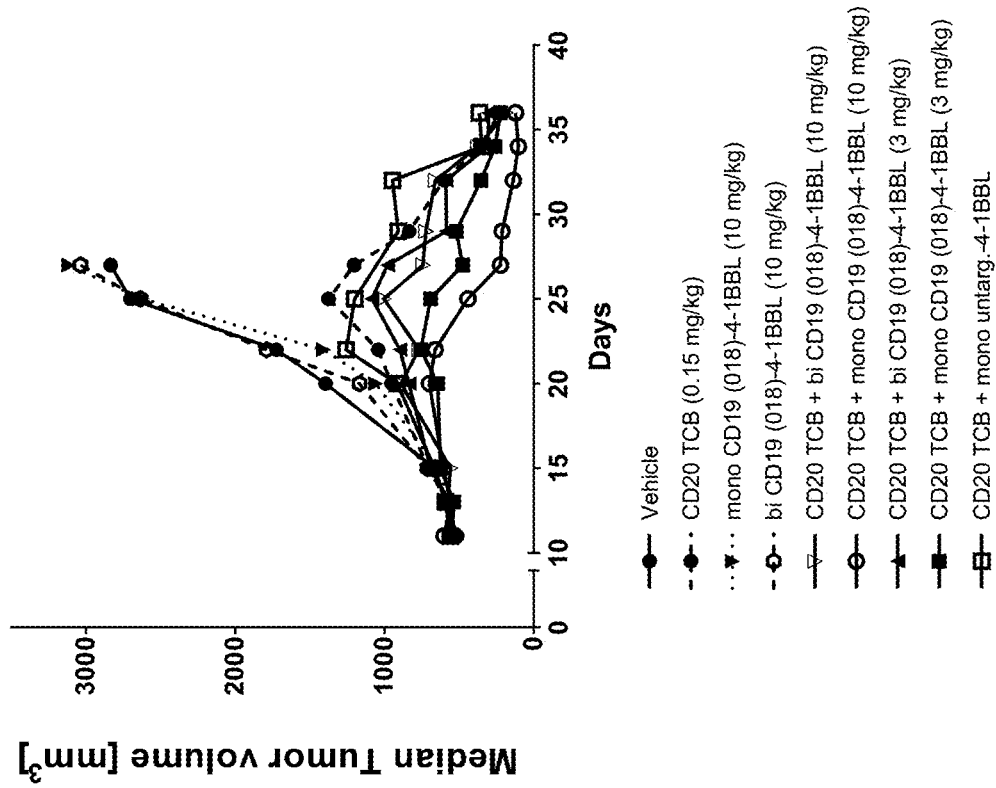
Figure 10:
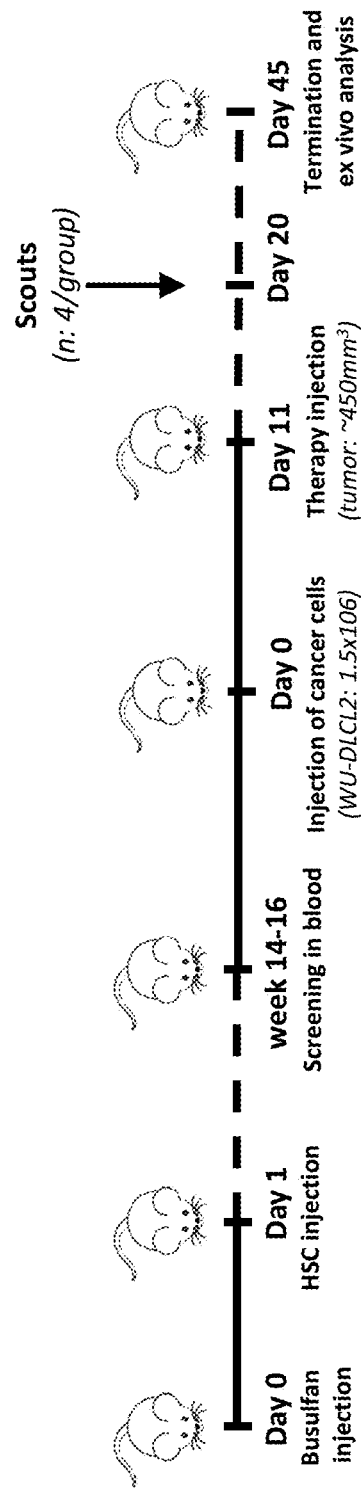
In FIG. 10 is shown the comparison of in vivo efficacy of mono CD19 (018)-4-1BBL vs. mono CD19 (2B11)-4-1BBL constructs in combination with CD20 TCB in WSU-DLCL2-bearing fully humanized NOG mice. Shown is the protocol of this study and in the table below the subgroups of mice receiving different combinations are defined. The results of this study are illustrated in FIGS. 11A and 11B. Both, the combination of mono CD19 (018)-4-1BBL or mono CD19 (2B11)-4-1BBL in combination with CD20 TCB induced enhanced and faster tumor growth inhibition as compared to monotherapy of CD20 TCB. However, no difference was observed between the two clones of CD19 binder. Both molecules are comparable in boosting CD20 TCB-mediated tumor growth inhibition.

The study was terminated and all mice were sacrificed after four injections of the compounds (day 37 after tumor cell injection) and tumors were explanted and weighted. FIG. 9A shows the tumor growth kinetics (Median) in all treatment groups as well as the tumor weights at study termination. Both, the monotherapies of mono and bi CD19 (018)-4-1BBL did not reveal any tumor growth inhibition whereas CD20 TCB as a single agent induced strong tumor growth inhibition. However, the combination of mono CD19 (018)-4-1BBL with CD20 TCB did not only induce stronger and faster tumor growth inhibition as compared to monotherapy of CD20 TCB, but was also superior to the combination of bivalent CD19 (018)-4-1BBL or monovalent untargeted 4-1BBL and CD20 TCB in all doses tested. As shown as well in FIG. 9B, the tumor weights at study termination confirmed these findings; however, the striking differences in terms of tumor growth inhibition is seen in the kinetics of tumor growth, especially at earlier time points (FIG. 9A). This data suggest the monovalent binding to CD19 (mono CD19 (018)-4-1BBL) to be superior in terms of tumor growth inhibition when combined with CD20 TCB.

c) Combinations of CD19-4-1BBL and CD20 TCB Synergize in Inducing Massive T Cell Infiltration into the Tumor To understand the modes of action of the combination of CD19-4-1BBL and CD20 TCB, a new study was performed to study the pharmacodynamics of immune response in these mice. The experiment was designed in a similar way as described in the above study (FIG. 10). We have included two clones of CD19 binders in this study (clone 018 vs clone 2B11) (Table 5).

TABLE 5

Compositions used in this experiment

| Compound | Formulation buffer | Concentration (mg/mL) |
|---|---|---|
| mono CD19 (018)-4-1BBL | 20 mM Histidine, 140 mM NaCl, pH 6.0 | 5.12 (=stock solution) |
| mono CD19 (2B11)-4-1BBL | 20 mM Histidine, 140 mM NaCl, pH 6.0 | 4.61 (=stock solution) |
| CD20 TCB | 20 mM Histidine, 140 mM NaCl, pH 6.0 | 4.12 (=stock solution) |

Figure 11B:
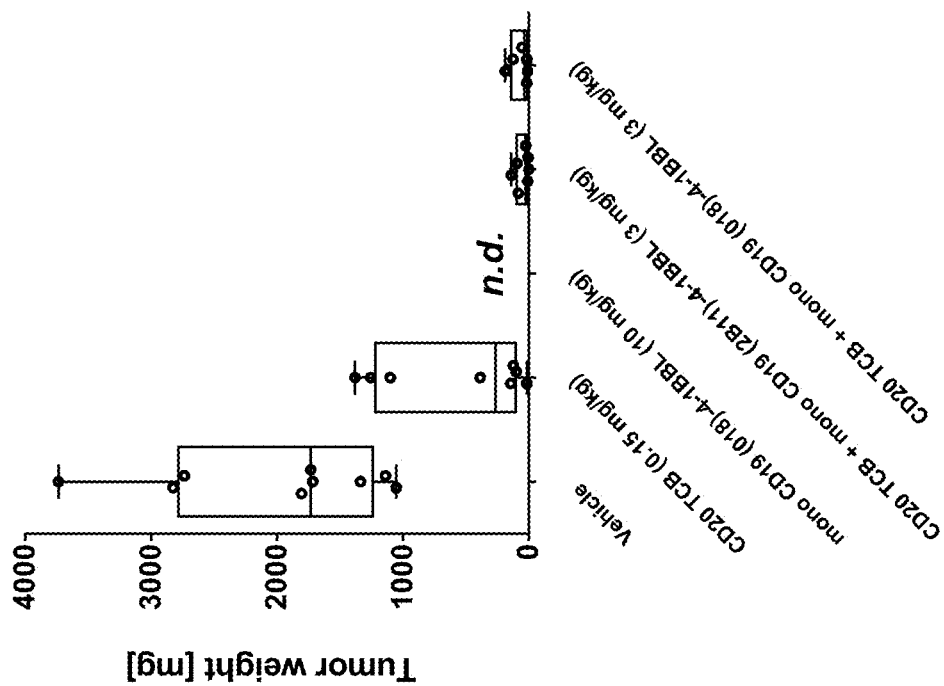
Figure 11A:
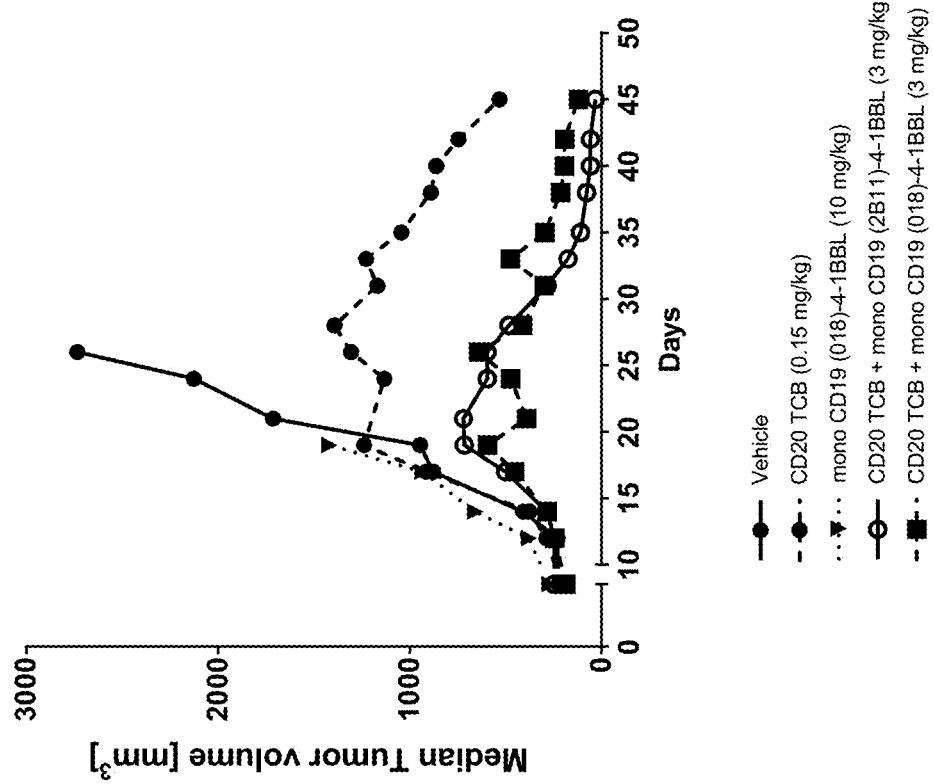

FIG. 11A shows the tumor growth kinetics (Median) in all treatment groups as well as the tumor weights at study termination. As shown in the earlier study (FIG. 9A), CD20 TCB as a single agent induced strong tumor growth inhibition. Combination of mono CD19 (018)-4-1BBL or mono CD19 (2B11)-4-1BBL in combination with CD20 TCB induced enhanced and faster tumor growth inhibition as compared to monotherapy of CD20 TCB. However, both molecules are comparable in boosting CD20 TCB-mediated tumor growth inhibition. As shown as well in FIG. 11B, the tumor weights at study termination confirmed these findings.

Analysis of tumors from animals sacrificed at study day 20 revealed an enhanced intra-tumoral human T-cell infiltration (FIG. 12A) and a shift of CD8/CD4 and CD8/Treg ratios towards CD8 cells in both combination groups as compared to CD20 TCB alone or vehicle treatment (FIGS. 12B and 12C). Therefore, we confirmed a novel combination therapy by which CD19-4-1BBL and CD20 TCB synergize to eradicate tumors by empowering T cells in the tumors.

REFERENCES

Bartkowiak, T., and Curran, M. A. (2015). 4-1BB Agonists: Multi-Potent Potentiators of Tumor Immunity. Front Oncol 5, 117.

Diehl, L., van Mierlo, G. J., den Boer, A. T., van der Voort, E., Fransen, M., van Bostelen, L., Krimpenfort, P., Melief, C. J., Mittler, R., Toes, R. E., and Offringa, R. (2002). In vivo triggering through 4-1BB enables Th-independent priming of CTL in the presence of an intact CD28 costimulatory pathway. J Immunol 168, 3755-3762.

Dubrot, J., Milheiro, F., Alfaro, C., Palazon, A., Martinez-Forero, I., Perez-Gracia, J. L., Morales-Kastresana, A., Romero-Trevejo, J. L., Ochoa, M. C., Hervas-Stubbs, S., et al. (2010). Treatment with anti-CD137 mAbs causes intense accumulations of liver T cells without selective antitumor immunotherapeutic effects in this organ. Cancer Immunol Immunother 59, 1223-1233.

Goodwin, R. G., Din, W. S., Davis-Smith, T., Anderson, D. M., Gimpel, S. D., Sato, T. A., Maliszewski, C. R., Brannan, C. I., Copeland, N. G., Jenkins, N. A., and et al. (1993). Molecular cloning of a ligand for the inducible T cell gene 4-1BB: a member of an emerging family of cytokines with homology to tumor necrosis factor. Eur J Immunol 23, 2631-2641.

Hornig, N., Kermer, V., Frey, K., Diebolder, P., Kontermann, R. E., and Muller, D. (2012). Combination of a bispecific antibody and costimulatory antibody-ligand fusion proteins for targeted cancer immunotherapy. J Immunother 35, 418-429.

Ingle, G. S., Chan, P., Elliott, J. M., Chang, W. S., Koeppen, H., Stephan, J. P., and Scales, S. J. (2008). High CD21 expression inhibits internalization of anti-CD19 antibodies and cytotoxicity of an anti-CD19-drug conjugate. Br J Haematol 140, 46-58.

Kwon, B. S., and Weissman, S. M. (1989). cDNA sequences of two inducible T-cell genes. Proc Natl Acad Sci USA 86, 1963-1967.

Li, F., and Ravetch, J. V. (2011). Inhibitory Fcgamma receptor engagement drives adjuvant and anti-tumor activities of agonistic CD40 antibodies. Science 333, 1030-1034.

Melero, I., Shuford, W. W., Newby, S. A., Aruffo, A., Ledbetter, J. A., Hellstrom, K. E., Mittler, R. S., and Chen, L. (1997). Monoclonal antibodies against the 4-1BB T-cell activation molecule eradicate established tumors. Nat Med 3, 682-685.

Muller, D., Frey, K., and Kontermann, R. E. (2008). A novel antibody-4-1BBL fusion protein for targeted costimulation in cancer immunotherapy. J Immunother 31, 714-722.

Shao, Z., and Schwarz, H. (2011). CD137 ligand, a member of the tumor necrosis factor family, regulates immune responses via reverse signal transduction. J Leukoc Biol 89, 21-29.

Simeone, E., and Ascierto, P. A. (2012). Immunomodulating antibodies in the treatment of metastatic melanoma: the experience with anti-CTLA-4, anti-CD137, and anti-PD1. J Immunotoxicol 9, 241-247.

Snell, L. M., Lin, G. H., McPherson, A. J., Moraes, T. J., and Watts, T. H. (2011). T-cell intrinsic effects of GITR and 4-1BB during viral infection and cancer immunotherapy. Immunol Rev 244, 197-217.

Vinay, D. S., and Kwon, B. S. (2011). 4-1BB signaling beyond T cells. Cell Mol Immunol 8, 281-284.

Zhang, N., Sadun, R. E., Arias, R. S., Flanagan, M. L., Sachsman, S. M., Nien, Y. C., Khawli, L. A., Hu, P., and Epstein, A. L. (2007). Targeted and untargeted CD137L fusion proteins for the immunotherapy of experimental solid tumors. Clin Cancer Res 13, 2758-2767.

Zhang, X., Voskens, C. J., Sallin, M., Maniar, A., Montes, C. L., Zhang, Y., Lin, W., Li, G., Burch, E., Tan, M., et al. (2010). CD137 promotes proliferation and survival of human B cells. J Immunol 184, 787-795.

---

The invention claimed is:

1. A method for treating or delaying progression of a proliferative disease that expresses CD20 and CD19 in a subject, wherein the method comprises administering to the subject an effective amount of an anti-CD20/anti-CD3 bispecific antibody and a 4-1BB agonist, wherein the anti-CD20/anti-CD3 bispecific antibody comprises: (a) a first antigen binding domain comprising a heavy chain variable region (V$_H$CD3) comprising CDR-H1 sequence of SEQ ID NO:56, CDR-H2 sequency of SEQ ID NO:57, and CDR-H3 sequence of SEQ ID NO:58; and a light chain variable region (V$_L$CD3) comprising CDR-L1 sequence of SEQ ID NO:59, CDR-L2 sequence of SEQ ID NO:60, and CDR-L3 sequence of SEQ ID NO:61; and (b) a second antigen binding domain comprising a heavy chain variable region (V$_H$CD20) comprising CDR-H1 sequence of SEQ ID NO:64, CDR-H2 sequence of SEQ ID NO:65, and CDR-H3 sequence of SEQ ID NO:66; and a light chain variable region (V$_L$CD20) comprising CDR-L1 sequence of SEQ ID NO:67, CDR-L2 sequence of SEQ ID NO:68, and CDR-L3 sequence of SEQ ID NO:69; and wherein the 4-1BB agonist comprises: (c) three ectodomains of 4-1BBL that independently comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7, and SEQ ID NO:8; and (d) a CD19 heavy chain variable region (V$_H$CD19) comprising (i) CDR-H1 comprising the amino acid sequence of SEQ ID NO: 15, (ii) CDR-H2 comprising the amino acid sequence of SEQ ID NO: 16, and (iii) CDR-H3 comprising the amino acid sequence of SEQ ID NO: 17; and a CD19 light chain variable region (V$_L$CD19) comprising (iv) CDR-L1 comprising the amino acid sequence of SEQ ID NO: 18, (v) CDR-L2 comprising the amino acid sequence of SEQ ID NO: 19, and (vi) CDR-L3 comprising the amino acid sequence of SEQ ID NO:20; or a CD19 heavy chain variable region (V$_H$CD19) comprising (i) CDR-H1 comprising the amino acid sequence of SEQ ID NO:9, (ii) CDR-H2 comprising the amino acid sequence of SEQ ID NO: 10, and (iii) CDR-H3 comprising the amino acid sequence of SEQ ID NO: 11; and a CD19 light chain variable region (V$_L$CD19) comprising (iv) CDR-L1 comprising the amino acid sequence of SEQ ID NO: 12, (v) CDR-L2 comprising the amino acid sequence of SEQ ID NO: 13, and (vi) CDR-L3 comprising the amino acid sequence of SEQ ID NO:14.

2. The method of claim 1, wherein the anti-CD20/anti-CD3 bispecific antibody and the 4-1BB agonist are administered together in a single composition or administered separately in two or more different compositions.

3. The method of claim 1, wherein the anti-CD20/anti-CD3 bispecific antibody and the 4-1BB agonist are administered intravenously or subcutaneously.

4. The method of claim 1, wherein the anti-CD20/anti-CD3 bispecific antibody is administered concurrently with, prior to, or subsequently to the 4-1BB agonist.

5. The method of claim 1, wherein the proliferative disease is cancer.

6. The method of claim 1, wherein the proliferative disease is a B cell proliferative disorder.

7. The method of claim 6, wherein the B cell proliferative disorder is selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM), and Hodgkin lymphoma (HL).

8. The method of claim 1, wherein each of the three ectodomains of 4-1BBL or fragments thereof independently comprises an amino acid sequence of SEQ ID NO:1 or SEQ ID NO:5.

9. The method of claim 1, wherein the 4-1BB agonist comprises at least one antigen binding domain and an IgG Fc domain.

10. The method of claim 9, wherein the IgG Fc domain is an IgG1 Fc domain or an IgG4 Fc domain.

11. The method of claim 9, wherein the 4-1BB agonist comprises at least one antigen binding domain and an Fc domain comprising one or more amino acid substitutions that reduce binding to an Fc receptor and/or effector function.

12. The method of claim 1, wherein the 4-1BB agonist comprises a first polypeptide and a second polypeptide that are linked to each other by a disulfide bond, wherein the first polypeptide comprises two ectodomains of 4-1BBL or fragments thereof that are connected to each other by a peptide linker and the second polypeptide comprises one ectodomain of 4-1BBL or a fragment thereof.

13. The method of claim 1, wherein the 4-1BB agonist comprises a polypeptide comprising three ectodomains of 4-1BBL or fragments thereof that are connected to each other by peptide linkers.

14. The method of claim 1, wherein the 4-1BB agonist comprises:
    (a) at least one antigen binding domain,
    (b) a polypeptide comprising three ectodomains of 4-1BBL or fragments thereof that are connected to each other by peptide linkers, and
    (c) an Fc domain composed of a first subunit and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain.

15. The method of claim 14, wherein the polypeptide comprising the three ectodomains of 4-1BBL or fragments thereof that are connected to each other by peptide linkers is fused to the N- or C-terminal amino acid of one of the two subunits of the Fc domain through a peptide linker.

16. The method of claim 1, wherein the first antigen binding domain comprises a CD3 heavy chain variable region ($V_H$CD3) comprising the amino acid sequence of SEQ ID NO:62 and/or a CD3 light chain variable region ($V_L$CD3) comprising the amino acid sequence of SEQ ID NO:63.

17. The method of claim 1, wherein the second antigen binding domain comprises a CD20 heavy chain variable region ($V_H$CD20) comprising the amino acid sequence of SEQ ID NO:70 and/or a CD20 light chain variable region ($V_L$CD20) comprising the amino acid sequence of SEQ ID NO:71.

18. The method of claim 1, wherein the anti-CD20/anti-CD3 bispecific antibody comprises a third antigen binding domain that binds to CD20.

19. The method of claim 1, wherein the anti-CD20/anti-CD3 bispecific antibody comprises an Fc domain comprising one or more amino acid substitutions that reduce binding to an Fc receptor and/or effector function.

20. The method of claim 1, wherein the anti-CD20/anti-CD3 bispecific antibody and the 4-1BB agonist are administered at intervals from about one week to three weeks.

21. The method of claim 1, wherein the subject is pretreated with a Type II anti-CD20 antibody prior to administration of the anti-CD20/anti-CD3 bispecific antibody and the 4-1BB agonist, and wherein the period of time between the pretreatment and the administration of the anti-CD20/anti-CD3 bispecific antibody and the 4-1BB agonist is sufficient for the reduction of B-cells in the individual in response to the Type II anti-CD20 antibody.

22. The method of claim 21, wherein the Type II anti-CD20 antibody is obinutuzumab.

23. The method of claim 1, wherein the anti-CD20/anti-CD3 bispecific antibody and the 4-1BB agonist are administered in combination with an agent blocking PD-L1/PD-1 interaction.

24. The method of claim 23, wherein the agent blocking PD-L1/PD-1 interaction is an anti-PD-L1 antibody or an anti-PD1 antibody.

25. The method of claim 24, wherein the agent blocking PD-L1/PD-1 interaction is an anti-PD-L1 antibody, wherein the anti-PD-L1 antibody is atezolizumab.

26. The method of claim 1, wherein the 4-1BB agonist is not internalized by CD19-expressing B cells.

27. The method of claim 1, wherein the 4-1BB agonist comprises: (a) at least one Fab domain capable of specific binding to CD19 comprising a CD19 heavy chain variable region ($V_H$CD19) comprising the amino acid sequence of SEQ ID NO:21 and a CD19 light chain variable region ($V_L$CD19) comprising the amino acid sequence of SEQ ID NO:22 or a CD19 heavy chain variable region ($V_H$CD19) comprising the amino acid sequence of SEQ ID NO:23 and a CD19 light chain variable region ($V_L$CD19) comprising the amino acid sequence of SEQ ID NO:24, and (b) a first polypeptide and a second polypeptide that are linked to each other by a disulfide bond, wherein the first polypeptide comprises an amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31, and SEQ ID NO:32 and the second polypeptide comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:8.

28. The method of claim 1, wherein the 4-1BB agonist is selected from the group consisting of:
    a) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:35, and a second light chain comprising the amino acid sequence of SEQ ID NO:36;
    b) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:37, and a second light chain comprising the amino acid sequence of SEQ ID NO:38;
    c) a molecule comprising two light chains comprising the amino acid sequence of SEQ ID NO:34, a first heavy chain comprising the amino acid sequence of SEQ ID NO:39, and a second heavy chain comprising the amino acid sequence of SEQ ID NO:40;
    d) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:41, and a second light chain comprising the amino acid sequence of SEQ ID NO:42;
    e) a molecule comprising a first heavy chain comprising the amino acid sequence of SEQ ID NO:33, a first light chain comprising the amino acid sequence of SEQ ID NO:34, a second heavy chain comprising the amino acid sequence of SEQ ID NO:43, and a second light chain comprising the amino acid sequence of SEQ ID NO:44;
    f) a molecule comprising two light chains comprising the amino acid sequence of SEQ ID NO:34, a first heavy chain comprising the amino acid sequence of SEQ ID NO:45, and a second heavy chain comprising the amino acid sequence of SEQ ID NO:46;
    g) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:35, and a second light chain comprising the amino acid sequence of SEQ ID NO:36;

h) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:37, and a second light chain comprising the amino acid sequence of SEQ ID NO:38;

i) a molecule comprising two light chains comprising the amino acid sequence of SEQ ID NO:48, a first heavy chain comprising the amino acid sequence of SEQ ID NO:49, and a second heavy chain comprising the amino acid sequence of SEQ ID NO:50;

j) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:41, and a second light chain comprising the amino acid sequence of SEQ ID NO:42;

k) a molecule comprising a first heavy chain comprising the amino acid sequence of SEQ ID NO:47, a first light chain comprising the amino acid sequence of SEQ ID NO:48, a second heavy chain comprising the amino acid sequence of SEQ ID NO:43, and a second light chain comprising the amino acid sequence of SEQ ID NO:44; and l) a molecule comprising two light chains comprising the amino acid sequence of SEQ ID NO:48, a first heavy chain comprising the amino acid sequence of SEQ ID NO:51, and a second heavy chain comprising the amino acid sequence of SEQ ID NO:52.

29. The method of claim 1, wherein the anti-CD20/anti-CD3 bispecific antibody comprises a first heavy chain comprising an amino acid sequence of SEQ ID NO:76, a second heavy chain comprising an amino acid sequence of SEQ ID NO:77, a first light chain comprising an amino acid sequence of SEQ ID NO:78, and a second light chain comprising an amino acid sequence of SEQ ID NO:79.

30. The method of claim 29, wherein the anti-CD20/anti-CD3 bispecific antibody comprises a third light chain comprising an amino acid sequence of SEQ ID NO:78.

31. The method of claim 8, wherein each of the three ectodomains of 4-1BBL or fragments thereof comprise an amino acid sequence of SEQ ID NO:5.

32. The method of claim 12, wherein the two ectodomains of 4-1BBL are connected by a GGGGSGGGGS (SEQ ID NO: 92) peptide linker.

* * * * *

SEQUENCE LISTING

```
<160> NUMBER OF SEQ ID NOS: 115

<210> SEQ ID NO 1
<211> LENGTH: 184
<212> TYPE: PRT
<213> ORGANISM: Homo sapiens

<400> SEQUENCE: 1

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
```

```
            115                 120                 125
Phe Gln Gly Arg Leu Leu His Leu Ser Ala Gly Gln Arg Leu Gly Val
        130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180

<210> SEQ ID NO 2
<211> LENGTH: 170
<212> TYPE: PRT
<213> ORGANISM: Homo sapiens

<400> SEQUENCE: 2

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170

<210> SEQ ID NO 3
<211> LENGTH: 175
<212> TYPE: PRT
<213> ORGANISM: Homo sapiens

<400> SEQUENCE: 3

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
```

```
                             85                  90                  95
Ala Ala Ala Leu Ala Leu Thr Val Asp Leu Pro Pro Ala Ser Ser Glu
                100                 105                 110

Ala Arg Asn Ser Ala Phe Gly Phe Gln Gly Arg Leu Leu His Leu Ser
                115                 120                 125

Ala Gly Gln Arg Leu Gly Val His Leu His Thr Glu Ala Arg Ala Arg
                130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175

<210> SEQ ID NO 4
<211> LENGTH: 203
<212> TYPE: PRT
<213> ORGANISM: Homo sapiens

<400> SEQUENCE: 4

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
                20                  25                  30

Leu Leu Asp Leu Arg Gln Gly Met Phe Ala Gln Leu Val Ala Gln Asn
                35                  40                  45

Val Leu Leu Ile Asp Gly Pro Leu Ser Trp Tyr Ser Asp Pro Gly Leu
            50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
                100                 105                 110

Ala Leu His Leu Gln Pro Leu Arg Ser Ala Ala Gly Ala Ala Ala Leu
                115                 120                 125

Ala Leu Thr Val Asp Leu Pro Pro Ala Ser Ser Glu Ala Arg Asn Ser
                130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
                180                 185                 190

Ile Pro Ala Gly Leu Pro Ser Pro Arg Ser Glu
                195                 200

<210> SEQ ID NO 5
<211> LENGTH: 178
<212> TYPE: PRT
<213> ORGANISM: Homo sapiens

<400> SEQUENCE: 5

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
                20                  25                  30

Ile Asp Gly Pro Leu Ser Trp Tyr Ser Asp Pro Gly Leu Ala Gly Val
```

```
                35                  40                  45
Ser Leu Thr Gly Gly Leu Ser Tyr Lys Glu Asp Thr Lys Glu Leu Val
 50                  55                  60
Val Ala Lys Ala Gly Val Tyr Tyr Val Phe Phe Gln Leu Glu Leu Arg
 65                  70                  75                  80
Arg Val Val Ala Gly Glu Gly Ser Gly Ser Val Ser Leu Ala Leu His
                 85                  90                  95
Leu Gln Pro Leu Arg Ser Ala Ala Gly Ala Ala Leu Ala Leu Thr
            100                 105                 110
Val Asp Leu Pro Pro Ala Ser Ser Glu Ala Arg Asn Ser Ala Phe Gly
            115                 120                 125
Phe Gln Gly Arg Leu Leu His Leu Ser Ala Gly Gln Arg Leu Gly Val
            130                 135                 140
His Leu His Thr Glu Ala Arg Ala Arg His Ala Trp Gln Leu Thr Gln
145                 150                 155                 160
Gly Ala Thr Val Leu Gly Leu Phe Arg Val Thr Pro Glu Ile Pro Ala
                165                 170                 175
Gly Leu

<210> SEQ ID NO 6
<211> LENGTH: 164
<212> TYPE: PRT
<213> ORGANISM: Homo sapiens

<400> SEQUENCE: 6

Leu Asp Leu Arg Gln Gly Met Phe Ala Gln Leu Val Ala Gln Asn Val
 1               5                  10                  15
Leu Leu Ile Asp Gly Pro Leu Ser Trp Tyr Ser Asp Pro Gly Leu Ala
                20                  25                  30
Gly Val Ser Leu Thr Gly Gly Leu Ser Tyr Lys Glu Asp Thr Lys Glu
             35                  40                  45
Leu Val Val Ala Lys Ala Gly Val Tyr Tyr Val Phe Phe Gln Leu Glu
         50                  55                  60
Leu Arg Arg Val Val Ala Gly Glu Gly Ser Gly Ser Val Ser Leu Ala
 65                  70                  75                  80
Leu His Leu Gln Pro Leu Arg Ser Ala Ala Gly Ala Ala Leu Ala Leu
                 85                  90                  95
Leu Thr Val Asp Leu Pro Pro Ala Ser Ser Glu Ala Arg Asn Ser Ala
            100                 105                 110
Phe Gly Phe Gln Gly Arg Leu Leu His Leu Ser Ala Gly Gln Arg Leu
            115                 120                 125
Gly Val His Leu His Thr Glu Ala Arg Ala Arg His Ala Trp Gln Leu
            130                 135                 140
Thr Gln Gly Ala Thr Val Leu Gly Leu Phe Arg Val Thr Pro Glu Ile
145                 150                 155                 160
Pro Ala Gly Leu

<210> SEQ ID NO 7
<211> LENGTH: 169
<212> TYPE: PRT
<213> ORGANISM: Homo sapiens

<400> SEQUENCE: 7

Asp Pro Ala Gly Leu Leu Asp Leu Arg Gln Gly Met Phe Ala Gln Leu
 1               5                  10                  15
```

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu
                165

<210> SEQ ID NO 8
<211> LENGTH: 197
<212> TYPE: PRT
<213> ORGANISM: Homo sapiens

<400> SEQUENCE: 8

Pro Trp Ala Val Ser Gly Ala Arg Ala Ser Pro Gly Ser Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu
        195

<210> SEQ ID NO 9

```
<211> LENGTH: 5
<212> TYPE: PRT
<213> ORGANISM: Artificial Sequence
<220> FEATURE:
<223> OTHER INFORMATION: CD19 (8B8-018) CDR-H1

<400> SEQUENCE: 9

Asp Tyr Ile Met His
1               5

<210> SEQ ID NO 10
<211> LENGTH: 17
<212> TYPE: PRT
<213> ORGANISM: Artificial Sequence
<220> FEATURE:
<223> OTHER INFORMATION: CD19 (8B8-018) CDR-H2

<400> SEQUENCE: 10

Tyr Ile Asn Pro Tyr Asn Asp Gly Ser Lys Tyr Thr Glu Lys Phe Gln
1               5                   10                  15

Gly

<210> SEQ ID NO 11
<211> LENGTH: 12
<212> TYPE: PRT
<213> ORGANISM: Artificial Sequence
<220> FEATURE:
<223> OTHER INFORMATION: CD19 (8B8-018) CDR-H3

<400> SEQUENCE: 11

Gly Thr Tyr Tyr Tyr Gly Ser Ala Leu Phe Asp Tyr
1               5                   10

<210> SEQ ID NO 12
<211> LENGTH: 16
<212> TYPE: PRT
<213> ORGANISM: Artificial Sequence
<220> FEATURE:
<223> OTHER INFORMATION: CD19 (8B8-018) CDR-L1

<400> SEQUENCE: 12

Lys Ser Ser Gln Ser Leu Glu Asn Pro Asn Gly Asn Thr Tyr Leu Asn
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: CD19 (8B8-018) CDR-L2

<400> SEQUENCE: 13

Arg Val Ser Lys Arg Phe Ser
1               5

<210> SEQ ID NO 14
<211> LENGTH: 9
<212> TYPE: PRT
<213> ORGANISM: Artificial Sequence
<220> FEATURE:
<223> OTHER INFORMATION: CD19 (8B8-018) CDR-L3

<400> SEQUENCE: 14

Leu Gln Leu Thr His Val Pro Tyr Thr
1               5
```

```
<210> SEQ ID NO 15
<211> LENGTH: 5
<212> TYPE: PRT
<213> ORGANISM: Artificial Sequence
<220> FEATURE:
<223> OTHER INFORMATION: CD19 (8B8-2B11) CDR-H1

<400> SEQUENCE: 15

Asp Tyr Ile Met His
1               5

<210> SEQ ID NO 16
<211> LENGTH: 17
<212> TYPE: PRT
<213> ORGANISM: Artificial Sequence
<220> FEATURE:
<223> OTHER INFORMATION: CD19 (8B8-2B11) CDR-H2

<400> SEQUENCE: 16

Tyr Ile Asn Pro Tyr Asn Asp Gly Ser Lys Tyr Thr Glu Lys Phe Gln
1               5                   10                  15

Gly

<210> SEQ ID NO 17
<211> LENGTH: 12
<212> TYPE: PRT
<213> ORGANISM: Artificial Sequence
<220> FEATURE:
<223> OTHER INFORMATION: CD19 (8B8-2B11) CDR-H3

<400> SEQUENCE: 17

Gly Thr Tyr Tyr Tyr Gly Pro Gln Leu Phe Asp Tyr
1               5                   10

<210> SEQ ID NO 18
<211> LENGTH: 16
<212> TYPE: PRT
<213> ORGANISM: Artificial Sequence
<220> FEATURE:
<223> OTHER INFORMATION: CD19 (8B8-2B11) CDR-L1

<400> SEQUENCE: 18

Lys Ser Ser Gln Ser Leu Glu Thr Ser Thr Gly Thr Thr Tyr Leu Asn
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: RVSKRFS

<400> SEQUENCE: 19

Arg Val Ser Lys Arg Phe Ser
1               5

<210> SEQ ID NO 20
<211> LENGTH: 9
<212> TYPE: PRT
<213> ORGANISM: Artificial Sequence
<220> FEATURE:
<223> OTHER INFORMATION: CD19 (8B8-2B11) CDR-L3

<400> SEQUENCE: 20

Leu Gln Leu Leu Glu Asp Pro Tyr Thr
1               5
```

<210> SEQ ID NO 21
<211> LENGTH: 121
<212> TYPE: PRT
<213> ORGANISM: Artificial Sequence
<220> FEATURE:
<223> OTHER INFORMATION: CD19 (8B8-018) VH

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Ser Ala Leu Phe Asp Tyr Trp Gly
            100                 105                 110

Gln Gly Thr Thr Val Thr Val Ser Ser
        115                 120

<210> SEQ ID NO 22
<211> LENGTH: 112
<212> TYPE: PRT
<213> ORGANISM: Artificial Sequence
<220> FEATURE:
<223> OTHER INFORMATION: CD19 (8B8-018) VL

<400> SEQUENCE: 22

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Pro
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110

<210> SEQ ID NO 23
<211> LENGTH: 121
<212> TYPE: PRT
<213> ORGANISM: Artificial Sequence
<220> FEATURE:
<223> OTHER INFORMATION: CD19 (8B8-2B11) VH

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

```
                     20                  25                  30
Ile Met His Trp Val Arg Gln Ala Pro Gly Gln Gly Leu Glu Trp Met
                 35                  40                  45

Gly Tyr Ile Asn Pro Tyr Asn Asp Gly Ser Lys Tyr Thr Glu Lys Phe
             50                  55                  60

Gln Gly Arg Val Thr Met Thr Ser Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Thr Tyr Tyr Tyr Gly Pro Gln Leu Phe Asp Tyr Trp Gly
                100                 105                 110

Gln Gly Thr Thr Val Thr Val Ser Ser
            115                 120

<210> SEQ ID NO 24
<211> LENGTH: 112
<212> TYPE: PRT
<213> ORGANISM: Artificial Sequence
<220> FEATURE:
<223> OTHER INFORMATION: CD19 (8B8-2B11) VL

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
                 20                  25                  30

Thr Gly Thr Thr Tyr Leu Asn Trp Tyr Leu Gln Lys Pro Gly Gln Ser
             35                  40                  45

Pro Gln Leu Leu Ile Tyr Arg Val Ser Lys Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Leu
                 85                  90                  95

Leu Glu Asp Pro Tyr Thr Phe Gly Gln Gly Thr Lys Leu Glu Ile Lys
                100                 105                 110

<210> SEQ ID NO 25
<211> LENGTH: 378
<212> TYPE: PRT
<213> ORGANISM: Artificial Sequence
<220> FEATURE:
<223> OTHER INFORMATION: dimeric hu 4-1BBL (71-254) connected by (G4S)2
      linker

<400> SEQUENCE: 25

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
                 20                  25                  30

Ile Asp Gly Pro Leu Ser Trp Tyr Ser Asp Pro Gly Leu Ala Gly Val
             35                  40                  45

Ser Leu Thr Gly Gly Leu Ser Tyr Lys Glu Asp Thr Lys Glu Leu Val
         50                  55                  60

Val Ala Lys Ala Gly Val Tyr Tyr Val Phe Phe Gln Leu Glu Leu Arg
 65                  70                  75                  80

Arg Val Val Ala Gly Glu Gly Ser Gly Ser Val Ser Leu Ala Leu His
                 85                  90                  95
```

```
Leu Gln Pro Leu Arg Ser Ala Ala Gly Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Arg Glu Gly Pro Glu Leu Ser Pro Asp Asp Pro Ala Gly Leu
        195                 200                 205

Leu Asp Leu Arg Gln Gly Met Phe Ala Gln Leu Val Ala Gln Asn Val
    210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Leu Ala
    290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
        355                 360                 365

Pro Ala Gly Leu Pro Ser Pro Arg Ser Glu
    370                 375

<210> SEQ ID NO 26
<211> LENGTH: 350
<212> TYPE: PRT
<213> ORGANISM: Artificial Sequence
<220> FEATURE:
<223> OTHER INFORMATION: dimeric hu 4-1BBL (85-254) connected by (G4S)2
      linker

<400> SEQUENCE: 26

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
```

```
                65                  70                  75                  80
Leu His Leu Gln Pro Leu Arg Ser Ala Ala Gly Ala Ala Ala Leu Ala
                    85                  90                  95
Leu Thr Val Asp Leu Pro Pro Ala Ser Ser Glu Ala Arg Asn Ser Ala
                    100                 105                 110
Phe Gly Phe Gln Gly Arg Leu Leu His Leu Ser Ala Gly Gln Arg Leu
                    115                 120                 125
Gly Val His Leu His Thr Glu Ala Arg Ala Arg His Ala Trp Gln Leu
                    130                 135                 140
Thr Gln Gly Ala Thr Val Leu Gly Leu Phe Arg Val Thr Pro Glu Ile
145                 150                 155                 160
Pro Ala Gly Leu Pro Ser Pro Arg Ser Glu Gly Gly Gly Ser Gly
                    165                 170                 175
Gly Gly Gly Ser Leu Asp Leu Arg Gln Gly Met Phe Ala Gln Leu Val
                    180                 185                 190
Ala Gln Asn Val Leu Leu Ile Asp Gly Pro Leu Ser Trp Tyr Ser Asp
                    195                 200                 205
Pro Gly Leu Ala Gly Val Ser Leu Thr Gly Gly Leu Ser Tyr Lys Glu
                    210                 215                 220
Asp Thr Lys Glu Leu Val Val Ala Lys Ala Gly Val Tyr Tyr Val Phe
225                 230                 235                 240
Phe Gln Leu Glu Leu Arg Arg Val Val Ala Gly Glu Gly Ser Gly Ser
                    245                 250                 255
Val Ser Leu Ala Leu His Leu Gln Pro Leu Arg Ser Ala Ala Gly Ala
                    260                 265                 270
Ala Ala Leu Ala Leu Thr Val Asp Leu Pro Pro Ala Ser Ser Glu Ala
                    275                 280                 285
Arg Asn Ser Ala Phe Gly Phe Gln Gly Arg Leu Leu His Leu Ser Ala
                    290                 295                 300
Gly Gln Arg Leu Gly Val His Leu His Thr Glu Ala Arg Ala Arg His
305                 310                 315                 320
Ala Trp Gln Leu Thr Gln Gly Ala Thr Val Leu Gly Leu Phe Arg Val
                    325                 330                 335
Thr Pro Glu Ile Pro Ala Gly Leu Pro Ser Pro Arg Ser Glu
                    340                 345                 350

<210> SEQ ID NO 27
<211> LENGTH: 360
<212> TYPE: PRT
<213> ORGANISM: Artificial Sequence
<220> FEATURE:
<223> OTHER INFORMATION: dimeric hu 4-1BBL (80-254) connected by (G4S)2
      linker

<400> SEQUENCE: 27

Asp Pro Ala Gly Leu Leu Asp Leu Arg Gln Gly Met Phe Ala Gln Leu
1               5                   10                  15
Val Ala Gln Asn Val Leu Leu Ile Asp Gly Pro Leu Ser Trp Tyr Ser
                    20                  25                  30
Asp Pro Gly Leu Ala Gly Val Ser Leu Thr Gly Gly Leu Ser Tyr Lys
                    35                  40                  45
Glu Asp Thr Lys Glu Leu Val Val Ala Lys Ala Gly Val Tyr Tyr Val
                    50                  55                  60
Phe Phe Gln Leu Glu Leu Arg Arg Val Val Ala Gly Glu Gly Ser Gly
65                  70                  75                  80
```

```
Ser Val Ser Leu Ala Leu His Leu Gln Pro Leu Arg Ser Ala Ala Gly
             85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
            130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu Gly
                165                 170                 175

Gly Gly Gly Ser Gly Gly Gly Ser Asp Pro Ala Gly Leu Leu Asp
                180                 185                 190

Leu Arg Gln Gly Met Phe Ala Gln Leu Val Ala Gln Asn Val Leu Leu
            195                 200                 205

Ile Asp Gly Pro Leu Ser Trp Tyr Ser Asp Pro Gly Leu Ala Gly Val
            210                 215                 220

Ser Leu Thr Gly Gly Leu Ser Tyr Lys Glu Asp Thr Lys Glu Leu Val
225                 230                 235                 240

Val Ala Lys Ala Gly Val Tyr Tyr Val Phe Phe Gln Leu Glu Leu Arg
                245                 250                 255

Arg Val Val Ala Gly Glu Gly Ser Gly Ser Val Ser Leu Ala Leu His
                260                 265                 270

Leu Gln Pro Leu Arg Ser Ala Ala Gly Ala Ala Ala Leu Ala Leu Thr
            275                 280                 285

Val Asp Leu Pro Pro Ala Ser Ser Glu Ala Arg Asn Ser Ala Phe Gly
290                 295                 300

Phe Gln Gly Arg Leu Leu His Leu Ser Ala Gly Gln Arg Leu Gly Val
305                 310                 315                 320

His Leu His Thr Glu Ala Arg Ala Arg His Ala Trp Gln Leu Thr Gln
                325                 330                 335

Gly Ala Thr Val Leu Gly Leu Phe Arg Val Thr Pro Glu Ile Pro Ala
                340                 345                 350

Gly Leu Pro Ser Pro Arg Ser Glu
            355                 360

<210> SEQ ID NO 28
<211> LENGTH: 416
<212> TYPE: PRT
<213> ORGANISM: Artificial Sequence
<220> FEATURE:
<223> OTHER INFORMATION: dimeric hu 4-1BBL (52-254) connected by (G4S)2
      linker

<400> SEQUENCE: 28

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
                20                  25                  30

Leu Leu Asp Leu Arg Gln Gly Met Phe Ala Gln Leu Val Ala Gln Asn
            35                  40                  45

Val Leu Leu Ile Asp Gly Pro Leu Ser Trp Tyr Ser Asp Pro Gly Leu
            50                  55                  60

Ala Gly Val Ser Leu Thr Gly Gly Leu Ser Tyr Lys Glu Asp Thr Lys
65                  70                  75                  80
```

Glu Leu Val Val Ala Lys Ala Gly Val Tyr Tyr Val Phe Gln Leu
                    85                  90                  95

Glu Leu Arg Arg Val Val Ala Gly Glu Gly Ser Gly Ser Val Ser Leu
                100                 105                 110

Ala Leu His Leu Gln Pro Leu Arg Ser Ala Ala Gly Ala Ala Ala Leu
            115                 120                 125

Ala Leu Thr Val Asp Leu Pro Pro Ala Ser Ser Glu Ala Arg Asn Ser
        130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
                180                 185                 190

Ile Pro Ala Gly Leu Pro Ser Pro Arg Ser Glu Gly Gly Gly Gly Ser
                195                 200                 205

Gly Gly Gly Gly Ser Pro Trp Ala Val Ser Gly Ala Arg Ala Ser Pro
210                 215                 220

Gly Ser Ala Ala Ser Pro Arg Leu Arg Glu Gly Pro Glu Leu Ser Pro
225                 230                 235                 240

Asp Asp Pro Ala Gly Leu Leu Asp Leu Arg Gln Gly Met Phe Ala Gln
                245                 250                 255

Leu Val Ala Gln Asn Val Leu Leu Ile Asp Gly Pro Leu Ser Trp Tyr
                260                 265                 270

Ser Asp Pro Gly Leu Ala Gly Val Ser Leu Thr Gly Gly Leu Ser Tyr
                275                 280                 285

Lys Glu Asp Thr Lys Glu Leu Val Val Ala Lys Ala Gly Val Tyr Tyr
                290                 295                 300

Val Phe Phe Gln Leu Glu Leu Arg Arg Val Val Ala Gly Glu Gly Ser
305                 310                 315                 320

Gly Ser Val Ser Leu Ala Leu His Leu Gln Pro Leu Arg Ser Ala Ala
                325                 330                 335

Gly Ala Ala Ala Leu Ala Leu Thr Val Asp Leu Pro Pro Ala Ser Ser
                340                 345                 350

Glu Ala Arg Asn Ser Ala Phe Gly Phe Gln Gly Arg Leu Leu His Leu
                355                 360                 365

Ser Ala Gly Gln Arg Leu Gly Val His Leu His Thr Glu Ala Arg Ala
        370                 375                 380

Arg His Ala Trp Gln Leu Thr Gln Gly Ala Thr Val Leu Gly Leu Phe
385                 390                 395                 400

Arg Val Thr Pro Glu Ile Pro Ala Gly Leu Pro Ser Pro Arg Ser Glu
                405                 410                 415

<210> SEQ ID NO 29
<211> LENGTH: 366
<212> TYPE: PRT
<213> ORGANISM: Artificial Sequence
<220> FEATURE:
<223> OTHER INFORMATION: dimeric hu 4-1BBL (71-248) connected by (G4S)2
      linker

<400> SEQUENCE: 29

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu

-continued

```
                20                  25                  30
Ile Asp Gly Pro Leu Ser Trp Tyr Ser Asp Pro Gly Leu Ala Gly Val
            35                  40                  45
Ser Leu Thr Gly Gly Leu Ser Tyr Lys Glu Asp Thr Lys Glu Leu Val
        50                  55                  60
Val Ala Lys Ala Gly Val Tyr Tyr Val Phe Phe Gln Leu Glu Leu Arg
65                  70                  75                  80
Arg Val Val Ala Gly Glu Gly Ser Gly Ser Val Ser Leu Ala Leu His
                85                  90                  95
Leu Gln Pro Leu Arg Ser Ala Ala Gly Ala Ala Ala Leu Ala Leu Thr
            100                 105                 110
Val Asp Leu Pro Pro Ala Ser Ser Glu Ala Arg Asn Ser Ala Phe Gly
        115                 120                 125
Phe Gln Gly Arg Leu Leu His Leu Ser Ala Gly Gln Arg Leu Gly Val
    130                 135                 140
His Leu His Thr Glu Ala Arg Ala Arg His Ala Trp Gln Leu Thr Gln
145                 150                 155                 160
Gly Ala Thr Val Leu Gly Leu Phe Arg Val Thr Pro Glu Ile Pro Ala
                165                 170                 175
Gly Leu Gly Gly Gly Gly Ser Gly Gly Gly Gly Ser Arg Glu Gly Pro
            180                 185                 190
Glu Leu Ser Pro Asp Asp Pro Ala Gly Leu Leu Asp Leu Arg Gln Gly
        195                 200                 205
Met Phe Ala Gln Leu Val Ala Gln Asn Val Leu Leu Ile Asp Gly Pro
    210                 215                 220
Leu Ser Trp Tyr Ser Asp Pro Gly Leu Ala Gly Val Ser Leu Thr Gly
225                 230                 235                 240
Gly Leu Ser Tyr Lys Glu Asp Thr Lys Glu Leu Val Val Ala Lys Ala
                245                 250                 255
Gly Val Tyr Tyr Val Phe Phe Gln Leu Glu Leu Arg Arg Val Val Ala
            260                 265                 270
Gly Glu Gly Ser Gly Ser Val Ser Leu Ala Leu His Leu Gln Pro Leu
        275                 280                 285
Arg Ser Ala Ala Gly Ala Ala Ala Leu Ala Leu Thr Val Asp Leu Pro
    290                 295                 300
Pro Ala Ser Ser Glu Ala Arg Asn Ser Ala Phe Gly Phe Gln Gly Arg
305                 310                 315                 320
Leu Leu His Leu Ser Ala Gly Gln Arg Leu Gly Val His Leu His Thr
                325                 330                 335
Glu Ala Arg Ala Arg His Ala Trp Gln Leu Thr Gln Gly Ala Thr Val
            340                 345                 350
Leu Gly Leu Phe Arg Val Thr Pro Glu Ile Pro Ala Gly Leu
        355                 360                 365

<210> SEQ ID NO 30
<211> LENGTH: 338
<212> TYPE: PRT
<213> ORGANISM: Artificial Sequence
<220> FEATURE:
<223> OTHER INFORMATION: dimeric hu 4-1BBL (85-248) connected by (G4S)2
      linker

<400> SEQUENCE: 30

Leu Asp Leu Arg Gln Gly Met Phe Ala Gln Leu Val Ala Gln Asn Val
1               5                   10                  15
```

```
Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu Gly Gly Gly Ser Gly Gly Gly Ser Leu Asp
                165                 170                 175

Leu Arg Gln Gly Met Phe Ala Gln Leu Val Ala Gln Asn Val Leu Leu
                180                 185                 190

Ile Asp Gly Pro Leu Ser Trp Tyr Ser Asp Pro Gly Leu Ala Gly Val
            195                 200                 205

Ser Leu Thr Gly Gly Leu Ser Tyr Lys Glu Asp Thr Lys Glu Leu Val
210                 215                 220

Val Ala Lys Ala Gly Val Tyr Tyr Val Phe Phe Gln Leu Glu Leu Arg
225                 230                 235                 240

Arg Val Val Ala Gly Glu Gly Ser Gly Ser Val Ser Leu Ala Leu His
                245                 250                 255

Leu Gln Pro Leu Arg Ser Ala Ala Gly Ala Ala Ala Leu Ala Leu Thr
            260                 265                 270

Val Asp Leu Pro Pro Ala Ser Ser Glu Ala Arg Asn Ser Ala Phe Gly
        275                 280                 285

Phe Gln Gly Arg Leu Leu His Leu Ser Ala Gly Gln Arg Leu Gly Val
290                 295                 300

His Leu His Thr Glu Ala Arg Ala Arg His Ala Trp Gln Leu Thr Gln
305                 310                 315                 320

Gly Ala Thr Val Leu Gly Leu Phe Arg Val Thr Pro Glu Ile Pro Ala
                325                 330                 335

Gly Leu

<210> SEQ ID NO 31
<211> LENGTH: 348
<212> TYPE: PRT
<213> ORGANISM: Artificial Sequence
<220> FEATURE:
<223> OTHER INFORMATION: dimeric hu 4-1BBL (80-248) connected by (G4S)2
      linker

<400> SEQUENCE: 31

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30
```

```
Asp Pro Gly Leu Ala Gly Val Ser Leu Thr Gly Gly Leu Ser Tyr Lys
         35                  40                  45

Glu Asp Thr Lys Glu Leu Val Val Ala Lys Ala Gly Val Tyr Tyr Val
 50                  55                  60

Phe Phe Gln Leu Glu Leu Arg Arg Val Val Ala Gly Glu Gly Ser Gly
 65                  70                  75                  80

Ser Val Ser Leu Ala Leu His Leu Gln Pro Leu Arg Ser Ala Ala Gly
                 85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Gly Gly Gly Ser Gly Gly Gly
                165                 170                 175

Gly Gly Ser Asp Pro Ala Gly Leu Leu Asp Leu Arg Gln Gly Met Phe
            180                 185                 190

Ala Gln Leu Val Ala Gln Asn Val Leu Leu Ile Asp Gly Pro Leu Ser
        195                 200                 205

Trp Tyr Ser Asp Pro Gly Leu Ala Gly Val Ser Leu Thr Gly Gly Leu
    210                 215                 220

Ser Tyr Lys Glu Asp Thr Lys Glu Leu Val Val Ala Lys Ala Gly Val
225                 230                 235                 240

Tyr Tyr Val Phe Phe Gln Leu Glu Leu Arg Arg Val Val Ala Gly Glu
                245                 250                 255

Gly Ser Gly Ser Val Ser Leu Ala Leu His Leu Gln Pro Leu Arg Ser
            260                 265                 270

Ala Ala Gly Ala Ala Ala Leu Ala Leu Thr Val Asp Leu Pro Pro Ala
        275                 280                 285

Ser Ser Glu Ala Arg Asn Ser Ala Phe Gly Phe Gln Gly Arg Leu Leu
    290                 295                 300

His Leu Ser Ala Gly Gln Arg Leu Gly Val His Leu His Thr Glu Ala
305                 310                 315                 320

Arg Ala Arg His Ala Trp Gln Leu Thr Gln Gly Ala Thr Val Leu Gly
                325                 330                 335

Leu Phe Arg Val Thr Pro Glu Ile Pro Ala Gly Leu
            340                 345

<210> SEQ ID NO 32
<211> LENGTH: 404
<212> TYPE: PRT
<213> ORGANISM: Artificial Sequence
<220> FEATURE:
<223> OTHER INFORMATION: dimeric hu 4-1BBL (52-248) connected by (G4S)2
      linker

<400> SEQUENCE: 32

Pro Trp Ala Val Ser Gly Ala Arg Ala Ser Pro Gly Ser Ala Ala Ser
 1               5                  10                  15

Pro Arg Leu Arg Glu Gly Pro Glu Leu Ser Pro Asp Asp Pro Ala Gly
                20                  25                  30

Leu Leu Asp Leu Arg Gln Gly Met Phe Ala Gln Leu Val Ala Gln Asn
            35                  40                  45
```

Val Leu Leu Ile Asp Gly Pro Leu Ser Trp Tyr Ser Asp Pro Gly Leu
 50                  55                  60

Ala Gly Val Ser Leu Thr Gly Gly Leu Ser Tyr Lys Glu Asp Thr Lys
 65                  70                  75                  80

Glu Leu Val Val Ala Lys Ala Gly Val Tyr Tyr Val Phe Phe Gln Leu
                 85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
            115                 120                 125

Ala Leu Thr Val Asp Leu Pro Pro Ala Ser Ser Glu Ala Arg Asn Ser
        130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Gly Gly Gly Ser Gly Gly Gly Ser Pro
            195                 200                 205

Trp Ala Val Ser Gly Ala Arg Ala Ser Pro Gly Ser Ala Ala Ser Pro
210                 215                 220

Arg Leu Arg Glu Gly Pro Glu Leu Ser Pro Asp Asp Pro Ala Gly Leu
225                 230                 235                 240

Leu Asp Leu Arg Gln Gly Met Phe Ala Gln Leu Val Ala Gln Asn Val
                245                 250                 255

Leu Leu Ile Asp Gly Pro Leu Ser Trp Tyr Ser Asp Pro Gly Leu Ala
                260                 265                 270

Gly Val Ser Leu Thr Gly Gly Leu Ser Tyr Lys Glu Asp Thr Lys Glu
            275                 280                 285

Leu Val Val Ala Lys Ala Gly Val Tyr Tyr Val Phe Phe Gln Leu Glu
        290                 295                 300

Leu Arg Arg Val Val Ala Gly Glu Gly Ser Gly Ser Val Ser Leu Ala
305                 310                 315                 320

Leu His Leu Gln Pro Leu Arg Ser Ala Ala Gly Ala Ala Ala Leu Ala
                325                 330                 335

Leu Thr Val Asp Leu Pro Pro Ala Ser Ser Glu Ala Arg Asn Ser Ala
            340                 345                 350

Phe Gly Phe Gln Gly Arg Leu Leu His Leu Ser Ala Gly Gln Arg Leu
        355                 360                 365

Gly Val His Leu His Thr Glu Ala Arg Ala Arg His Ala Trp Gln Leu
    370                 375                 380

Thr Gln Gly Ala Thr Val Leu Gly Leu Phe Arg Val Thr Pro Glu Ile
385                 390                 395                 400

Pro Ala Gly Leu

<210> SEQ ID NO 33
<211> LENGTH: 451
<212> TYPE: PRT
<213> ORGANISM: Artificial Sequence
<220> FEATURE:
<223> OTHER INFORMATION: anti-CD19(8B8-018) Fc hole chain

<400> SEQUENCE: 33

-continued

```
Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asp Tyr
             20                  25                  30
Ile Met His Trp Val Arg Gln Ala Pro Gly Gln Gly Leu Glu Trp Met
         35                  40                  45
Gly Tyr Ile Asn Pro Tyr Asn Asp Gly Ser Lys Tyr Thr Glu Lys Phe
     50                  55                  60
Gln Gly Arg Val Thr Met Thr Ser Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Gly Thr Tyr Tyr Gly Ser Ala Leu Phe Asp Tyr Trp Gly
            100                 105                 110
Gln Gly Thr Thr Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
            340                 345                 350
Cys Thr Leu Pro Pro Ser Arg Asp Glu Leu Thr Lys Asn Gln Val Ser
    355                 360                 365
Leu Ser Cys Ala Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
```

-continued

```
                420                 425                 430

His Glu Ala Leu His Asn His Tyr Thr Gln Lys Ser Leu Ser Leu Ser
        435                 440                 445

Pro Gly Lys
    450

<210> SEQ ID NO 34
<211> LENGTH: 219
<212> TYPE: PRT
<213> ORGANISM: Artificial Sequence
<220> FEATURE:
<223> OTHER INFORMATION: anti-CD19(8B8-018) light chain

<400> SEQUENCE: 34

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Pro
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 35
<211> LENGTH: 722
<212> TYPE: PRT
<213> ORGANISM: Artificial Sequence
<220> FEATURE:
<223> OTHER INFORMATION: dimeric hu 4-1BBL (71-254)-CL* Fc knob chain

<400> SEQUENCE: 35

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45
```

```
Ser Leu Thr Gly Gly Leu Ser Tyr Lys Glu Asp Thr Lys Glu Leu Val
 50                  55                  60
Val Ala Lys Ala Gly Val Tyr Tyr Val Phe Phe Gln Leu Glu Leu Arg
 65                  70                  75                  80
Arg Val Val Ala Gly Glu Gly Ser Gly Ser Val Ser Leu Ala Leu His
                     85                  90                  95
Leu Gln Pro Leu Arg Ser Ala Ala Gly Ala Ala Leu Ala Leu Thr
                100                 105                 110
Val Asp Leu Pro Pro Ala Ser Ser Glu Ala Arg Asn Ser Ala Phe Gly
                115                 120                 125
Phe Gln Gly Arg Leu Leu His Leu Ser Ala Gly Gln Arg Leu Gly Val
130                 135                 140
His Leu His Thr Glu Ala Arg Ala Arg His Ala Trp Gln Leu Thr Gln
145                 150                 155                 160
Gly Ala Thr Val Leu Gly Leu Phe Arg Val Thr Pro Glu Ile Pro Ala
                    165                 170                 175
Gly Leu Pro Ser Pro Arg Ser Glu Gly Gly Gly Ser Gly Gly Gly
                180                 185                 190
Gly Ser Arg Glu Gly Pro Glu Leu Ser Pro Asp Asp Pro Ala Gly Leu
                195                 200                 205
Leu Asp Leu Arg Gln Gly Met Phe Ala Gln Leu Val Ala Gln Asn Val
                210                 215                 220
Leu Leu Ile Asp Gly Pro Leu Ser Trp Tyr Ser Asp Pro Gly Leu Ala
225                 230                 235                 240
Gly Val Ser Leu Thr Gly Gly Leu Ser Tyr Lys Glu Asp Thr Lys Glu
                    245                 250                 255
Leu Val Val Ala Lys Ala Gly Val Tyr Tyr Val Phe Phe Gln Leu Glu
                260                 265                 270
Leu Arg Arg Val Val Ala Gly Glu Gly Ser Gly Ser Val Ser Leu Ala
                275                 280                 285
Leu His Leu Gln Pro Leu Arg Ser Ala Ala Gly Ala Ala Leu Ala
                290                 295                 300
Leu Thr Val Asp Leu Pro Pro Ala Ser Ser Glu Ala Arg Asn Ser Ala
305                 310                 315                 320
Phe Gly Phe Gln Gly Arg Leu Leu His Leu Ser Ala Gly Gln Arg Leu
                    325                 330                 335
Gly Val His Leu His Thr Glu Ala Arg Ala Arg His Ala Trp Gln Leu
                340                 345                 350
Thr Gln Gly Ala Thr Val Leu Gly Leu Phe Arg Val Thr Pro Glu Ile
                355                 360                 365
Pro Ala Gly Leu Pro Ser Pro Arg Ser Glu Gly Gly Gly Ser Gly
370                 375                 380
Gly Gly Gly Ser Arg Thr Val Ala Ala Pro Ser Val Phe Ile Phe Pro
385                 390                 395                 400
Pro Ser Asp Arg Lys Leu Lys Ser Gly Thr Ala Ser Val Val Cys Leu
                405                 410                 415
Leu Asn Asn Phe Tyr Pro Arg Glu Ala Lys Val Gln Trp Lys Val Asp
                420                 425                 430
Asn Ala Leu Gln Ser Gly Asn Ser Gln Glu Ser Val Thr Glu Gln Asp
                435                 440                 445
Ser Lys Asp Ser Thr Tyr Ser Leu Ser Ser Thr Leu Thr Leu Ser Lys
                450                 455                 460
Ala Asp Tyr Glu Lys His Lys Val Tyr Ala Cys Glu Val Thr His Gln
```

```
465                 470                 475                 480
Gly Leu Ser Ser Pro Val Thr Lys Ser Phe Asn Arg Gly Glu Cys Asp
                    485                 490                 495

Lys Thr His Thr Cys Pro Pro Cys Pro Ala Pro Glu Ala Ala Gly Gly
                500                 505                 510

Pro Ser Val Phe Leu Phe Pro Lys Pro Lys Asp Thr Leu Met Ile
            515                 520                 525

Ser Arg Thr Pro Glu Val Thr Cys Val Val Val Asp Val Ser His Glu
530                 535                 540

Asp Pro Glu Val Lys Phe Asn Trp Tyr Val Asp Gly Val Glu Val His
545                 550                 555                 560

Asn Ala Lys Thr Lys Pro Arg Glu Glu Gln Tyr Asn Ser Thr Tyr Arg
                565                 570                 575

Val Val Ser Val Leu Thr Val Leu His Gln Asp Trp Leu Asn Gly Lys
            580                 585                 590

Glu Tyr Lys Cys Lys Val Ser Asn Lys Ala Leu Gly Ala Pro Ile Glu
        595                 600                 605

Lys Thr Ile Ser Lys Ala Lys Gly Gln Pro Arg Glu Pro Gln Val Tyr
    610                 615                 620

Thr Leu Pro Pro Cys Arg Asp Glu Leu Thr Lys Asn Gln Val Ser Leu
625                 630                 635                 640

Trp Cys Leu Val Lys Gly Phe Tyr Pro Ser Asp Ile Ala Val Glu Trp
                645                 650                 655

Glu Ser Asn Gly Gln Pro Glu Asn Asn Tyr Lys Thr Thr Pro Pro Val
            660                 665                 670

Leu Asp Ser Asp Gly Ser Phe Phe Leu Tyr Ser Lys Leu Thr Val Asp
        675                 680                 685

Lys Ser Arg Trp Gln Gln Gly Asn Val Phe Ser Cys Ser Val Met His
    690                 695                 700

Glu Ala Leu His Asn His Tyr Thr Gln Lys Ser Leu Ser Leu Ser Pro
705                 710                 715                 720

Gly Lys

<210> SEQ ID NO 36
<211> LENGTH: 297
<212> TYPE: PRT
<213> ORGANISM: Artificial Sequence
<220> FEATURE:
<223> OTHER INFORMATION: monomeric hu 4-1BBL (71-254)-CH1*

<400> SEQUENCE: 36

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
                20                  25                  30

Ile Asp Gly Pro Leu Ser Trp Tyr Ser Asp Pro Gly Leu Ala Gly Val
            35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110
```

Val Asp Leu Pro Pro Ala Ser Ser Glu Ala Arg Asn Ser Ala Phe Gly
          115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Ala Ser Thr Lys Gly Pro Ser Val Phe Pro Leu Ala Pro Ser
            195                 200                 205

Ser Lys Ser Thr Ser Gly Gly Thr Ala Ala Leu Gly Cys Leu Val Glu
    210                 215                 220

Asp Tyr Phe Pro Glu Pro Val Thr Val Ser Trp Asn Ser Gly Ala Leu
225                 230                 235                 240

Thr Ser Gly Val His Thr Phe Pro Ala Val Leu Gln Ser Ser Gly Leu
                245                 250                 255

Tyr Ser Leu Ser Ser Val Val Thr Val Pro Ser Ser Ser Leu Gly Thr
            260                 265                 270

Gln Thr Tyr Ile Cys Asn Val Asn His Lys Pro Ser Asn Thr Lys Val
        275                 280                 285

Asp Glu Lys Val Glu Pro Lys Ser Cys
290                 295

<210> SEQ ID NO 37
<211> LENGTH: 722
<212> TYPE: PRT
<213> ORGANISM: Artificial Sequence
<220> FEATURE:
<223> OTHER INFORMATION: dimeric hu 4-1BBL (71-254)-CL Fc knob chain

<400> SEQUENCE: 37

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

```
Gly Leu Pro Ser Pro Arg Ser Glu Gly Gly Gly Ser Gly Gly Gly
            180                 185                 190

Gly Ser Arg Glu Gly Pro Glu Leu Ser Pro Asp Pro Ala Gly Leu
        195                 200                 205

Leu Asp Leu Arg Gln Gly Met Phe Ala Gln Leu Val Ala Gln Asn Val
210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Ala Leu Ala
    290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
        355                 360                 365

Pro Ala Gly Leu Pro Ser Pro Arg Ser Glu Gly Gly Gly Ser Gly
370                 375                 380

Gly Gly Gly Ser Arg Thr Val Ala Ala Pro Ser Val Phe Ile Phe Pro
385                 390                 395                 400

Pro Ser Asp Glu Gln Leu Lys Ser Gly Thr Ala Ser Val Val Cys Leu
                405                 410                 415

Leu Asn Asn Phe Tyr Pro Arg Glu Ala Lys Val Gln Trp Lys Val Asp
            420                 425                 430

Asn Ala Leu Gln Ser Gly Asn Ser Gln Glu Ser Val Thr Glu Gln Asp
        435                 440                 445

Ser Lys Asp Ser Thr Tyr Ser Leu Ser Ser Thr Leu Thr Leu Ser Lys
    450                 455                 460

Ala Asp Tyr Glu Lys His Lys Val Tyr Ala Cys Glu Val Thr His Gln
465                 470                 475                 480

Gly Leu Ser Ser Pro Val Thr Lys Ser Phe Asn Arg Gly Glu Cys Asp
                485                 490                 495

Lys Thr His Thr Cys Pro Pro Cys Pro Ala Pro Glu Ala Ala Gly Gly
            500                 505                 510

Pro Ser Val Phe Leu Phe Pro Pro Lys Pro Lys Asp Thr Leu Met Ile
        515                 520                 525

Ser Arg Thr Pro Glu Val Thr Cys Val Val Val Asp Val Ser His Glu
    530                 535                 540

Asp Pro Glu Val Lys Phe Asn Trp Tyr Val Asp Gly Val Glu Val His
545                 550                 555                 560

Asn Ala Lys Thr Lys Pro Arg Glu Glu Gln Tyr Asn Ser Thr Tyr Arg
                565                 570                 575

Val Val Ser Val Leu Thr Val Leu His Gln Asp Trp Leu Asn Gly Lys
            580                 585                 590
```

```
Glu Tyr Lys Cys Lys Val Ser Asn Lys Ala Leu Gly Ala Pro Ile Glu
            595                 600                 605

Lys Thr Ile Ser Lys Ala Lys Gly Gln Pro Arg Glu Pro Gln Val Tyr
610                 615                 620

Thr Leu Pro Pro Cys Arg Asp Glu Leu Thr Lys Asn Gln Val Ser Leu
625                 630                 635                 640

Trp Cys Leu Val Lys Gly Phe Tyr Pro Ser Asp Ile Ala Val Glu Trp
                645                 650                 655

Glu Ser Asn Gly Gln Pro Glu Asn Asn Tyr Lys Thr Thr Pro Pro Val
            660                 665                 670

Leu Asp Ser Asp Gly Ser Phe Phe Leu Tyr Ser Lys Leu Thr Val Asp
        675                 680                 685

Lys Ser Arg Trp Gln Gln Gly Asn Val Phe Ser Cys Ser Val Met His
690                 695                 700

Glu Ala Leu His Asn His Tyr Thr Gln Lys Ser Leu Ser Leu Ser Pro
705                 710                 715                 720

Gly Lys

<210> SEQ ID NO 38
<211> LENGTH: 297
<212> TYPE: PRT
<213> ORGANISM: Artificial Sequence
<220> FEATURE:
<223> OTHER INFORMATION: monomeric hu 4-1BBL (71-254)-CH1

<400> SEQUENCE: 38

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Ala Ser Thr Lys Gly Pro Ser Val Phe Pro Leu Ala Pro Ser
        195                 200                 205

Ser Lys Ser Thr Ser Gly Gly Thr Ala Ala Leu Gly Cys Leu Val Lys
    210                 215                 220

Asp Tyr Phe Pro Glu Pro Val Thr Val Ser Trp Asn Ser Gly Ala Leu
```

```
                    225                 230                 235                 240
Thr Ser Gly Val His Thr Phe Pro Ala Val Leu Gln Ser Ser Gly Leu
                245                 250                 255

Tyr Ser Leu Ser Ser Val Val Thr Val Pro Ser Ser Ser Leu Gly Thr
                260                 265                 270

Gln Thr Tyr Ile Cys Asn Val Asn His Lys Pro Ser Asn Thr Lys Val
                275                 280                 285

Asp Lys Lys Val Glu Pro Lys Ser Cys
                290                 295

<210> SEQ ID NO 39
<211> LENGTH: 838
<212> TYPE: PRT
<213> ORGANISM: Artificial Sequence
<220> FEATURE:
<223> OTHER INFORMATION: anti-CD19(8B8-018) Fc hole dimeric ligand chain

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Ser Ala Leu Phe Asp Tyr Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
```

-continued

```
              290                 295                 300
Arg Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
                340                 345                 350

Cys Thr Leu Pro Pro Ser Arg Asp Glu Leu Thr Lys Asn Gln Val Ser
                355                 360                 365

Leu Ser Cys Ala Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Gly Gly Gly Ser Gly Gly Gly Gly Ser Arg Glu Gly Pro
450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                485                 490                 495

Leu Ser Trp Tyr Ser Asp Pro Gly Leu Ala Gly Val Ser Leu Thr Gly
                500                 505                 510

Gly Leu Ser Tyr Lys Glu Asp Thr Lys Glu Leu Val Val Ala Lys Ala
                515                 520                 525

Gly Val Tyr Tyr Val Phe Phe Gln Leu Glu Leu Arg Arg Val Val Ala
            530                 535                 540

Gly Glu Gly Ser Gly Ser Val Ser Leu Ala Leu His Leu Gln Pro Leu
545                 550                 555                 560

Arg Ser Ala Ala Gly Ala Ala Leu Ala Leu Thr Val Asp Leu Pro
                565                 570                 575

Pro Ala Ser Ser Glu Ala Arg Asn Ser Ala Phe Gly Phe Gln Gly Arg
                580                 585                 590

Leu Leu His Leu Ser Ala Gly Gln Arg Leu Gly Val His Leu His Thr
            595                 600                 605

Glu Ala Arg Ala Arg His Ala Trp Gln Leu Thr Gln Gly Ala Thr Val
610                 615                 620

Leu Gly Leu Phe Arg Val Thr Pro Glu Ile Pro Ala Gly Leu Pro Ser
625                 630                 635                 640

Pro Arg Ser Glu Gly Gly Gly Ser Gly Gly Gly Gly Ser Arg Glu
                645                 650                 655

Gly Pro Glu Leu Ser Pro Asp Asp Pro Ala Gly Leu Leu Asp Leu Arg
                660                 665                 670

Gln Gly Met Phe Ala Gln Leu Val Ala Gln Asn Val Leu Leu Ile Asp
            675                 680                 685

Gly Pro Leu Ser Trp Tyr Ser Asp Pro Gly Leu Ala Gly Val Ser Leu
            690                 695                 700

Thr Gly Gly Leu Ser Tyr Lys Glu Asp Thr Lys Glu Leu Val Val Ala
705                 710                 715                 720
```

-continued

```
Lys Ala Gly Val Tyr Tyr Val Phe Phe Gln Leu Glu Leu Arg Arg Val
            725                 730                 735

Val Ala Gly Glu Gly Ser Gly Ser Val Ser Leu Ala Leu His Leu Gln
            740                 745                 750

Pro Leu Arg Ser Ala Ala Gly Ala Ala Ala Leu Ala Leu Thr Val Asp
            755                 760                 765

Leu Pro Pro Ala Ser Ser Glu Ala Arg Asn Ser Ala Phe Gly Phe Gln
            770                 775                 780

Gly Arg Leu Leu His Leu Ser Ala Gly Gln Arg Leu Gly Val His Leu
785                 790                 795                 800

His Thr Glu Ala Arg Ala Arg His Ala Trp Gln Leu Thr Gln Gly Ala
            805                 810                 815

Thr Val Leu Gly Leu Phe Arg Val Thr Pro Glu Ile Pro Ala Gly Leu
            820                 825                 830

Pro Ser Pro Arg Ser Glu
            835

<210> SEQ ID NO 40
<211> LENGTH: 644
<212> TYPE: PRT
<213> ORGANISM: Artificial Sequence
<220> FEATURE:
<223> OTHER INFORMATION: anti-CD19(8B8-018) Fc knob monomeric ligand

<400> SEQUENCE: 40

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Ser Ala Leu Phe Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240
```

```
Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
            355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Gly Gly Gly Ser Gly Gly Gly Ser Arg Glu Gly Pro
    450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
            485                 490                 495

Leu Ser Trp Tyr Ser Asp Pro Gly Leu Ala Gly Val Ser Leu Thr Gly
            500                 505                 510

Gly Leu Ser Tyr Lys Glu Asp Thr Lys Glu Leu Val Val Ala Lys Ala
            515                 520                 525

Gly Val Tyr Tyr Val Phe Phe Gln Leu Glu Leu Arg Arg Val Val Ala
            530                 535                 540

Gly Glu Gly Ser Gly Ser Val Ser Leu Ala Leu His Leu Gln Pro Leu
545                 550                 555                 560

Arg Ser Ala Ala Gly Ala Ala Ala Leu Ala Leu Thr Val Asp Leu Pro
                565                 570                 575

Pro Ala Ser Ser Glu Ala Arg Asn Ser Ala Phe Gly Phe Gln Gly Arg
            580                 585                 590

Leu Leu His Leu Ser Ala Gly Gln Arg Leu Gly Val His Leu His Thr
            595                 600                 605

Glu Ala Arg Ala Arg His Ala Trp Gln Leu Thr Gln Gly Ala Thr Val
            610                 615                 620

Leu Gly Leu Phe Arg Val Thr Pro Glu Ile Pro Ala Gly Leu Pro Ser
625                 630                 635                 640

Pro Arg Ser Glu
```

```
<210> SEQ ID NO 41
<211> LENGTH: 710
<212> TYPE: PRT
<213> ORGANISM: Artificial Sequence
<220> FEATURE:
<223> OTHER INFORMATION: dimeric hu 4-1BBL (71-248)-CL* Fc knob chain

<400> SEQUENCE: 41
```

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Gly Ser Gly Gly Gly Ser Arg Glu Gly Pro
            180                 185                 190

Glu Leu Ser Pro Asp Asp Pro Ala Gly Leu Leu Asp Leu Arg Gln Gly
        195                 200                 205

Met Phe Ala Gln Leu Val Ala Gln Asn Val Leu Leu Ile Asp Gly Pro
210                 215                 220

Leu Ser Trp Tyr Ser Asp Pro Gly Leu Ala Gly Val Ser Leu Thr Gly
225                 230                 235                 240

Gly Leu Ser Tyr Lys Glu Asp Thr Lys Glu Leu Val Val Ala Lys Ala
                245                 250                 255

Gly Val Tyr Tyr Val Phe Phe Gln Leu Glu Leu Arg Arg Val Val Ala
            260                 265                 270

Gly Glu Gly Ser Gly Ser Val Ser Leu Ala Leu His Leu Gln Pro Leu
        275                 280                 285

Arg Ser Ala Ala Gly Ala Ala Ala Leu Ala Leu Thr Val Asp Leu Pro
290                 295                 300

Pro Ala Ser Ser Glu Ala Arg Asn Ser Ala Phe Gly Phe Gln Gly Arg
305                 310                 315                 320

Leu Leu His Leu Ser Ala Gly Gln Arg Leu Gly Val His Leu His Thr
                325                 330                 335

Glu Ala Arg Ala Arg His Ala Trp Gln Leu Thr Gln Gly Ala Thr Val
            340                 345                 350

Leu Gly Leu Phe Arg Val Thr Pro Glu Ile Pro Ala Gly Leu Gly Gly
        355                 360                 365

Gly Gly Ser Gly Gly Gly Gly Ser Arg Thr Val Ala Ala Pro Ser Val

```
                370                 375                 380
Phe Ile Phe Pro Pro Ser Asp Arg Lys Leu Lys Ser Gly Thr Ala Ser
385                 390                 395                 400

Val Val Cys Leu Leu Asn Asn Phe Tyr Pro Arg Glu Ala Lys Val Gln
                405                 410                 415

Trp Lys Val Asp Asn Ala Leu Gln Ser Gly Asn Ser Gln Glu Ser Val
            420                 425                 430

Thr Glu Gln Asp Ser Lys Asp Ser Thr Tyr Ser Leu Ser Ser Thr Leu
        435                 440                 445

Thr Leu Ser Lys Ala Asp Tyr Glu Lys His Lys Val Tyr Ala Cys Glu
    450                 455                 460

Val Thr His Gln Gly Leu Ser Ser Pro Val Thr Lys Ser Phe Asn Arg
465                 470                 475                 480

Gly Glu Cys Asp Lys Thr His Thr Cys Pro Pro Cys Pro Ala Pro Glu
                485                 490                 495

Ala Ala Gly Gly Pro Ser Val Phe Leu Phe Pro Pro Lys Pro Lys Asp
            500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Gly
            580                 585                 590

Ala Pro Ile Glu Lys Thr Ile Ser Lys Ala Lys Gly Gln Pro Arg Glu
        595                 600                 605

Pro Gln Val Tyr Thr Leu Pro Pro Cys Arg Asp Glu Leu Thr Lys Asn
    610                 615                 620

Gln Val Ser Leu Trp Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
    690                 695                 700

Ser Leu Ser Pro Gly Lys
705                 710

<210> SEQ ID NO 42
<211> LENGTH: 291
<212> TYPE: PRT
<213> ORGANISM: Artificial Sequence
<220> FEATURE:
<223> OTHER INFORMATION: monomeric hu 4-1BBL (71-248)-CH1*

<400> SEQUENCE: 42

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
```

```
            20                  25                  30
Ile Asp Gly Pro Leu Ser Trp Tyr Ser Asp Pro Gly Leu Ala Gly Val
        35                  40                  45
Ser Leu Thr Gly Gly Leu Ser Tyr Lys Glu Asp Thr Lys Glu Leu Val
    50                  55                  60
Val Ala Lys Ala Gly Val Tyr Tyr Val Phe Phe Gln Leu Glu Leu Arg
65                  70                  75                  80
Arg Val Val Ala Gly Glu Gly Ser Gly Ser Val Ser Leu Ala Leu His
                85                  90                  95
Leu Gln Pro Leu Arg Ser Ala Gly Ala Ala Leu Ala Leu Thr
            100                 105                 110
Val Asp Leu Pro Pro Ala Ser Ser Glu Ala Arg Asn Ser Ala Phe Gly
            115                 120                 125
Phe Gln Gly Arg Leu Leu His Leu Ser Ala Gly Gln Arg Leu Gly Val
        130                 135                 140
His Leu His Thr Glu Ala Arg Ala Arg His Ala Trp Gln Leu Thr Gln
145                 150                 155                 160
Gly Ala Thr Val Leu Gly Leu Phe Arg Val Thr Pro Glu Ile Pro Ala
                165                 170                 175
Gly Leu Gly Gly Gly Gly Ser Gly Gly Gly Ser Ala Ser Thr Lys
            180                 185                 190
Gly Pro Ser Val Phe Pro Leu Ala Pro Ser Ser Lys Ser Thr Ser Gly
        195                 200                 205
Gly Thr Ala Ala Leu Gly Cys Leu Val Glu Asp Tyr Phe Pro Glu Pro
    210                 215                 220
Val Thr Val Ser Trp Asn Ser Gly Ala Leu Thr Ser Gly Val His Thr
225                 230                 235                 240
Phe Pro Ala Val Leu Gln Ser Ser Gly Leu Tyr Ser Leu Ser Ser Val
                245                 250                 255
Val Thr Val Pro Ser Ser Ser Leu Gly Thr Gln Thr Tyr Ile Cys Asn
            260                 265                 270
Val Asn His Lys Pro Ser Asn Thr Lys Val Asp Glu Lys Val Glu Pro
        275                 280                 285
Lys Ser Cys
    290

<210> SEQ ID NO 43
<211> LENGTH: 710
<212> TYPE: PRT
<213> ORGANISM: Artificial Sequence
<220> FEATURE:
<223> OTHER INFORMATION: dimeric hu 4-1BBL (71-248) - CL Fc knob chain

<400> SEQUENCE: 43

Arg Glu Gly Pro Glu Leu Ser Pro Asp Asp Pro Ala Gly Leu Leu Asp
1               5                   10                  15
Leu Arg Gln Gly Met Phe Ala Gln Leu Val Ala Gln Asn Val Leu Leu
            20                  25                  30
Ile Asp Gly Pro Leu Ser Trp Tyr Ser Asp Pro Gly Leu Ala Gly Val
        35                  40                  45
Ser Leu Thr Gly Gly Leu Ser Tyr Lys Glu Asp Thr Lys Glu Leu Val
    50                  55                  60
Val Ala Lys Ala Gly Val Tyr Tyr Val Phe Phe Gln Leu Glu Leu Arg
65                  70                  75                  80
Arg Val Val Ala Gly Glu Gly Ser Gly Ser Val Ser Leu Ala Leu His
```

-continued

```
                85                  90                  95
Leu Gln Pro Leu Arg Ser Ala Gly Ala Ala Leu Ala Leu Thr
            100                 105                 110
Val Asp Leu Pro Pro Ala Ser Ser Glu Ala Arg Asn Ser Ala Phe Gly
            115                 120                 125
Phe Gln Gly Arg Leu Leu His Leu Ser Ala Gly Gln Arg Leu Gly Val
    130                 135                 140
His Leu His Thr Glu Ala Arg Ala Arg His Ala Trp Gln Leu Thr Gln
145                 150                 155                 160
Gly Ala Thr Val Leu Gly Leu Phe Arg Val Thr Pro Glu Ile Pro Ala
                165                 170                 175
Gly Leu Gly Gly Gly Ser Gly Gly Gly Ser Arg Glu Gly Pro
            180                 185                 190
Glu Leu Ser Pro Asp Asp Pro Ala Gly Leu Leu Asp Leu Arg Gln Gly
            195                 200                 205
Met Phe Ala Gln Leu Val Ala Gln Asn Val Leu Leu Ile Asp Gly Pro
    210                 215                 220
Leu Ser Trp Tyr Ser Asp Pro Gly Leu Ala Gly Val Ser Leu Thr Gly
225                 230                 235                 240
Gly Leu Ser Tyr Lys Glu Asp Thr Lys Glu Leu Val Val Ala Lys Ala
                245                 250                 255
Gly Val Tyr Tyr Val Phe Phe Gln Leu Glu Leu Arg Arg Val Val Ala
            260                 265                 270
Gly Glu Gly Ser Gly Ser Val Ser Leu Ala Leu His Leu Gln Pro Leu
            275                 280                 285
Arg Ser Ala Ala Gly Ala Ala Ala Leu Ala Leu Thr Val Asp Leu Pro
    290                 295                 300
Pro Ala Ser Ser Glu Ala Arg Asn Ser Ala Phe Gly Phe Gln Gly Arg
305                 310                 315                 320
Leu Leu His Leu Ser Ala Gly Gln Arg Leu Gly Val His Leu His Thr
                325                 330                 335
Glu Ala Arg Ala Arg His Ala Trp Gln Leu Thr Gln Gly Ala Thr Val
            340                 345                 350
Leu Gly Leu Phe Arg Val Thr Pro Glu Ile Pro Ala Gly Leu Gly Gly
            355                 360                 365
Gly Gly Ser Gly Gly Gly Ser Arg Thr Val Ala Ala Pro Ser Val
    370                 375                 380
Phe Ile Phe Pro Pro Ser Asp Glu Gln Leu Lys Ser Gly Thr Ala Ser
385                 390                 395                 400
Val Val Cys Leu Leu Asn Asn Phe Tyr Pro Arg Glu Ala Lys Val Gln
                405                 410                 415
Trp Lys Val Asp Asn Ala Leu Gln Ser Gly Asn Ser Gln Glu Ser Val
            420                 425                 430
Thr Glu Gln Asp Ser Lys Asp Ser Thr Tyr Ser Leu Ser Ser Thr Leu
            435                 440                 445
Thr Leu Ser Lys Ala Asp Tyr Glu Lys His Lys Val Tyr Ala Cys Glu
    450                 455                 460
Val Thr His Gln Gly Leu Ser Ser Pro Val Thr Lys Ser Phe Asn Arg
465                 470                 475                 480
Gly Glu Cys Asp Lys Thr His Thr Cys Pro Pro Cys Pro Ala Pro Glu
                485                 490                 495
Ala Ala Gly Gly Pro Ser Val Phe Leu Phe Pro Pro Lys Pro Lys Asp
            500                 505                 510
```

```
Thr Leu Met Ile Ser Arg Thr Pro Glu Val Thr Cys Val Val Asp
            515                 520                 525

Val Ser His Glu Asp Pro Glu Val Lys Phe Asn Trp Tyr Val Asp Gly
        530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Gly
            580                 585                 590

Ala Pro Ile Glu Lys Thr Ile Ser Lys Ala Lys Gly Gln Pro Arg Glu
            595                 600                 605

Pro Gln Val Tyr Thr Leu Pro Pro Cys Arg Asp Glu Leu Thr Lys Asn
            610                 615                 620

Gln Val Ser Leu Trp Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
            675                 680                 685

Ser Val Met His Glu Ala Leu His Asn His Tyr Thr Gln Lys Ser Leu
            690                 695                 700

Ser Leu Ser Pro Gly Lys
705                 710

<210> SEQ ID NO 44
<211> LENGTH: 291
<212> TYPE: PRT
<213> ORGANISM: Artificial Sequence
<220> FEATURE:
<223> OTHER INFORMATION: Monomeric hu 4-1BBL (71-248) - CH1

<400> SEQUENCE: 44

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
        130                 135                 140

His Leu His Thr Glu Ala Arg Ala Arg His Ala Trp Gln Leu Thr Gln
145                 150                 155                 160
```

```
Gly Ala Thr Val Leu Gly Leu Phe Arg Val Thr Pro Glu Ile Pro Ala
                165                 170                 175

Gly Leu Gly Gly Gly Ser Gly Gly Gly Ser Ala Ser Thr Lys
            180                 185                 190

Gly Pro Ser Val Phe Pro Leu Ala Pro Ser Ser Lys Ser Thr Ser Gly
            195                 200                 205

Gly Thr Ala Ala Leu Gly Cys Leu Val Lys Asp Tyr Phe Pro Glu Pro
    210                 215                 220

Val Thr Val Ser Trp Asn Ser Gly Ala Leu Thr Ser Gly Val His Thr
225                 230                 235                 240

Phe Pro Ala Val Leu Gln Ser Ser Gly Leu Tyr Ser Leu Ser Ser Val
                245                 250                 255

Val Thr Val Pro Ser Ser Ser Leu Gly Thr Gln Thr Tyr Ile Cys Asn
            260                 265                 270

Val Asn His Lys Pro Ser Asn Thr Lys Val Asp Lys Lys Val Glu Pro
        275                 280                 285

Lys Ser Cys
    290
```

<210> SEQ ID NO 45
<211> LENGTH: 826
<212> TYPE: PRT
<213> ORGANISM: Artificial Sequence
<220> FEATURE:
<223> OTHER INFORMATION: anti-CD19(8B8-018) Fc hole dimeric ligand
      (71-248) chain

<400> SEQUENCE: 45

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Ser Ala Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

-continued

```
            210                 215                 220
Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
                340                 345                 350

Cys Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Gly Gly Gly Ser Gly Gly Gly Ser Arg Glu Gly Pro
450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                485                 490                 495

Leu Ser Trp Tyr Ser Asp Pro Gly Leu Ala Gly Val Ser Leu Thr Gly
            500                 505                 510

Gly Leu Ser Tyr Lys Glu Asp Thr Lys Glu Leu Val Val Ala Lys Ala
            515                 520                 525

Gly Val Tyr Tyr Val Phe Phe Gln Leu Glu Leu Arg Arg Val Val Ala
530                 535                 540

Gly Glu Gly Ser Gly Ser Val Ser Leu Ala Leu His Leu Gln Pro Leu
545                 550                 555                 560

Arg Ser Ala Ala Gly Ala Ala Ala Leu Ala Leu Thr Val Asp Leu Pro
                565                 570                 575

Pro Ala Ser Ser Glu Ala Arg Asn Ser Ala Phe Gly Phe Gln Gly Arg
            580                 585                 590

Leu Leu His Leu Ser Ala Gly Gln Arg Leu Gly Val His Leu His Thr
            595                 600                 605

Glu Ala Arg Ala Arg His Ala Trp Gln Leu Thr Gln Gly Ala Thr Val
            610                 615                 620

Leu Gly Leu Phe Arg Val Thr Pro Glu Ile Pro Ala Gly Leu Gly Gly
625                 630                 635                 640
```

Gly Gly Ser Gly Gly Gly Ser Arg Glu Gly Pro Glu Leu Ser Pro
                645                 650                 655

Asp Asp Pro Ala Gly Leu Leu Asp Leu Arg Gln Gly Met Phe Ala Gln
            660                 665                 670

Leu Val Ala Gln Asn Val Leu Leu Ile Asp Gly Pro Leu Ser Trp Tyr
            675                 680                 685

Ser Asp Pro Gly Leu Ala Gly Val Ser Leu Thr Gly Gly Leu Ser Tyr
690                 695                 700

Lys Glu Asp Thr Lys Glu Leu Val Val Ala Lys Ala Gly Val Tyr Tyr
705                 710                 715                 720

Val Phe Phe Gln Leu Glu Leu Arg Arg Val Val Ala Gly Glu Gly Ser
                725                 730                 735

Gly Ser Val Ser Leu Ala Leu His Leu Gln Pro Leu Arg Ser Ala Ala
            740                 745                 750

Gly Ala Ala Ala Leu Ala Leu Thr Val Asp Leu Pro Pro Ala Ser Ser
            755                 760                 765

Glu Ala Arg Asn Ser Ala Phe Gly Phe Gln Gly Arg Leu Leu His Leu
770                 775                 780

Ser Ala Gly Gln Arg Leu Gly Val His Leu His Thr Glu Ala Arg Ala
785                 790                 795                 800

Arg His Ala Trp Gln Leu Thr Gln Gly Ala Thr Val Leu Gly Leu Phe
                805                 810                 815

Arg Val Thr Pro Glu Ile Pro Ala Gly Leu
                820                 825

<210> SEQ ID NO 46
<211> LENGTH: 638
<212> TYPE: PRT
<213> ORGANISM: Artificial Sequence
<220> FEATURE:
<223> OTHER INFORMATION: anti-CD19(8B8-018) Fc knob monomeric (71-248)
      ligand

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Ser Ala Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala

```
                    165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Val Glu Pro Lys Ser Cys
        210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Cys Arg Asp Glu Leu Thr Lys Asn Gln Val Ser
        355                 360                 365
Leu Trp Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Gly Gly Gly Ser Gly Gly Gly Ser Arg Glu Gly Pro
    450                 455                 460
Glu Leu Ser Pro Asp Asp Pro Ala Gly Leu Leu Asp Leu Arg Gln Gly
465                 470                 475                 480
Met Phe Ala Gln Leu Val Ala Gln Asn Val Leu Leu Ile Asp Gly Pro
                485                 490                 495
Leu Ser Trp Tyr Ser Asp Pro Gly Leu Ala Gly Val Ser Leu Thr Gly
            500                 505                 510
Gly Leu Ser Tyr Lys Glu Asp Thr Lys Glu Leu Val Val Ala Lys Ala
        515                 520                 525
Gly Val Tyr Tyr Val Phe Phe Gln Leu Glu Leu Arg Arg Val Val Ala
    530                 535                 540
Gly Glu Gly Ser Gly Ser Val Ser Leu Ala Leu His Leu Gln Pro Leu
545                 550                 555                 560
Arg Ser Ala Ala Gly Ala Ala Ala Leu Ala Leu Thr Val Asp Leu Pro
                565                 570                 575
Pro Ala Ser Ser Glu Ala Arg Asn Ser Ala Phe Gly Phe Gln Gly Arg
            580                 585                 590
```

```
Leu Leu His Leu Ser Ala Gly Gln Arg Leu Gly Val His Leu His Thr
            595                 600                 605

Glu Ala Arg Ala Arg His Ala Trp Gln Leu Thr Gln Gly Ala Thr Val
    610                 615                 620

Leu Gly Leu Phe Arg Val Thr Pro Glu Ile Pro Ala Gly Leu
625                 630                 635

<210> SEQ ID NO 47
<211> LENGTH: 451
<212> TYPE: PRT
<213> ORGANISM: Artificial Sequence
<220> FEATURE:
<223> OTHER INFORMATION: anti-CD19(8B8-2B11) Fc hole chain

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 48
<211> LENGTH: 219
<212> TYPE: PRT
<213> ORGANISM: Artificial Sequence
<220> FEATURE:
<223> OTHER INFORMATION: CD19 (8B8-2B11) light chain

<400> SEQUENCE: 48

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

-continued

```
<210> SEQ ID NO 49
<211> LENGTH: 838
<212> TYPE: PRT
<213> ORGANISM: Artificial Sequence
<220> FEATURE:
<223> OTHER INFORMATION: anti-CD19(8B8-2B11) Fc hole dimeric ligand
      (71-254) chain

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
```

```
            355                 360                 365
Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Gly Gly Gly Ser Gly Gly Gly Ser Arg Glu Gly Pro
        450                 455                 460

Glu Leu Ser Pro Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                485                 490                 495

Leu Ser Trp Tyr Ser Asp Pro Gly Leu Ala Gly Val Ser Leu Thr Gly
            500                 505                 510

Gly Leu Ser Tyr Lys Glu Asp Thr Lys Glu Leu Val Val Ala Lys Ala
        515                 520                 525

Gly Val Tyr Tyr Val Phe Phe Gln Leu Glu Leu Arg Arg Val Val Ala
    530                 535                 540

Gly Glu Gly Ser Gly Ser Val Ser Leu Ala Leu His Leu Gln Pro Leu
545                 550                 555                 560

Arg Ser Ala Ala Gly Ala Ala Ala Leu Ala Leu Thr Val Asp Leu Pro
                565                 570                 575

Pro Ala Ser Ser Glu Ala Arg Asn Ser Ala Phe Gly Phe Gln Gly Arg
            580                 585                 590

Leu Leu His Leu Ser Ala Gly Gln Arg Leu Gly Val His Leu His Thr
        595                 600                 605

Glu Ala Arg Ala Arg His Ala Trp Gln Leu Thr Gln Gly Ala Thr Val
610                 615                 620

Leu Gly Leu Phe Arg Val Thr Pro Glu Ile Pro Ala Gly Leu Pro Ser
625                 630                 635                 640

Pro Arg Ser Glu Gly Gly Gly Ser Gly Gly Gly Ser Arg Glu
                645                 650                 655

Gly Pro Glu Leu Ser Pro Asp Asp Pro Ala Gly Leu Leu Asp Leu Arg
        660                 665                 670

Gln Gly Met Phe Ala Gln Leu Val Ala Gln Asn Val Leu Leu Ile Asp
    675                 680                 685

Gly Pro Leu Ser Trp Tyr Ser Asp Pro Gly Leu Ala Gly Val Ser Leu
        690                 695                 700

Thr Gly Gly Leu Ser Tyr Lys Glu Asp Thr Lys Glu Leu Val Val Ala
705                 710                 715                 720

Lys Ala Gly Val Tyr Tyr Val Phe Phe Gln Leu Glu Leu Arg Arg Val
                725                 730                 735

Val Ala Gly Glu Gly Ser Gly Ser Val Ser Leu Ala Leu His Leu Gln
            740                 745                 750

Pro Leu Arg Ser Ala Ala Gly Ala Ala Ala Leu Ala Leu Thr Val Asp
        755                 760                 765

Leu Pro Pro Ala Ser Ser Glu Ala Arg Asn Ser Ala Phe Gly Phe Gln
770                 775                 780
```

```
Gly Arg Leu Leu His Leu Ser Ala Gly Gln Arg Leu Gly Val His Leu
785                 790                 795                 800

His Thr Glu Ala Arg Ala Arg His Ala Trp Gln Leu Thr Gln Gly Ala
                805                 810                 815

Thr Val Leu Gly Leu Phe Arg Val Thr Pro Glu Ile Pro Ala Gly Leu
            820                 825                 830

Pro Ser Pro Arg Ser Glu
        835

<210> SEQ ID NO 50
<211> LENGTH: 644
<212> TYPE: PRT
<213> ORGANISM: Artificial Sequence
<220> FEATURE:
<223> OTHER INFORMATION: anti-CD19(8B8-2B11) Fc knob monomeric (71-254)
      ligand

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                290                 295                 300
Arg Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Cys Arg Asp Glu Leu Thr Lys Asn Gln Val Ser
                355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Gly Gly Gly Ser Gly Gly Gly Ser Arg Glu Gly Pro
450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                485                 490                 495

Leu Ser Trp Tyr Ser Asp Pro Gly Leu Ala Gly Val Ser Leu Thr Gly
                500                 505                 510

Gly Leu Ser Tyr Lys Glu Asp Thr Lys Glu Leu Val Val Ala Lys Ala
                515                 520                 525

Gly Val Tyr Tyr Val Phe Phe Gln Leu Glu Leu Arg Arg Val Val Ala
                530                 535                 540

Gly Glu Gly Ser Gly Ser Val Ser Leu Ala Leu His Leu Gln Pro Leu
545                 550                 555                 560

Arg Ser Ala Ala Gly Ala Ala Ala Leu Ala Leu Thr Val Asp Leu Pro
                565                 570                 575

Pro Ala Ser Ser Glu Ala Arg Asn Ser Ala Phe Gly Phe Gln Gly Arg
                580                 585                 590

Leu Leu His Leu Ser Ala Gly Gln Arg Leu Gly Val His Leu His Thr
                595                 600                 605

Glu Ala Arg Ala Arg His Ala Trp Gln Leu Thr Gln Gly Ala Thr Val
610                 615                 620

Leu Gly Leu Phe Arg Val Thr Pro Glu Ile Pro Ala Gly Leu Pro Ser
625                 630                 635                 640

Pro Arg Ser Glu
```

<210> SEQ ID NO 51
<211> LENGTH: 826
<212> TYPE: PRT
<213> ORGANISM: Artificial Sequence
<220> FEATURE:
<223> OTHER INFORMATION: anti-CD19(8B8-2B11) Fc hole dimeric ligand
      (71-248) chain

<400> SEQUENCE: 51

Gln Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Thr Phe Thr Asp Tyr
                    20                  25                  30

Ile Met His Trp Val Arg Gln Ala Pro Gly Gln Gly Leu Glu Trp Met
                    35                  40                  45

Gly Tyr Ile Asn Pro Tyr Asn Asp Gly Ser Lys Tyr Thr Glu Lys Phe
        50                  55                  60

Gln Gly Arg Val Thr Met Thr Ser Asp Thr Ser Ile Ser Thr Ala Tyr
65                      70                  75                  80

Met Glu Leu Ser Arg Leu Arg Ser Asp Asp Thr Ala Val Tyr Tyr Cys
                    85                  90                  95

Ala Arg Gly Thr Tyr Tyr Gly Pro Gln Leu Phe Asp Tyr Trp Gly
                    100                 105                 110             Gly

Gln Gly Thr Thr Val Thr Val Ser Ser Ala Ser Thr Lys Gly Pro Ser
                    115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                     150                 155                 160

Ser Trp Asn Ser Gly Ala Leu Thr Ser Gly Val His Thr Phe Pro Ala
                    165                 170                 175

Val Leu Gln Ser Ser Gly Leu Tyr Ser Leu Ser Ser Val Val Thr Val
                    180                 185                 190

Pro Ser Ser Ser Leu Gly Thr Gln Thr Tyr Ile Cys Asn Val Asn His
                    195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Ala Ala Gly
225                     230                 235                 240

Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                    260                 265                 270

Glu Asp Pro Glu Val Lys Phe Asn Trp Tyr Val Asp Gly Val Glu Val
                    275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                     310                 315                 320

Lys Glu Tyr Lys Cys Lys Val Ser Asn Lys Ala Leu Gly Ala Pro Ile
                    325                 330                 335

Glu Lys Thr Ile Ser Lys Ala Lys Gly Gln Pro Arg Glu Pro Gln Val
                    340                 345                 350

Cys Thr Leu Pro Pro Ser Arg Asp Glu Leu Thr Lys Asn Gln Val Ser
                    355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Tyr Lys Thr Thr Pro Pro
385                     390                 395                 400

Val Leu Asp Ser Asp Gly Ser Phe Phe Leu Val Ser Lys Leu Thr Val
                    405                 410                 415

Asp Lys Ser Arg Trp Gln Gln Gly Asn Val Phe Ser Cys Ser Val Met
                    420                 425                 430
```

```
His Glu Ala Leu His Asn His Tyr Thr Gln Lys Ser Leu Ser Leu Ser
            435                 440                 445

Pro Gly Gly Gly Gly Ser Gly Gly Gly Ser Arg Glu Gly Pro
450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                485                 490                 495

Leu Ser Trp Tyr Ser Asp Pro Gly Leu Ala Gly Val Ser Leu Thr Gly
                500                 505                 510

Gly Leu Ser Tyr Lys Glu Asp Thr Lys Glu Leu Val Ala Lys Ala
            515                 520                 525

Gly Val Tyr Tyr Val Phe Phe Gln Leu Glu Leu Arg Arg Val Val Ala
            530                 535                 540

Gly Glu Gly Ser Gly Ser Val Ser Leu Ala Leu His Leu Gln Pro Leu
545                 550                 555                 560

Arg Ser Ala Ala Gly Ala Ala Leu Ala Leu Thr Val Asp Leu Pro
                565                 570                 575

Pro Ala Ser Ser Glu Ala Arg Asn Ser Ala Phe Gly Phe Gln Gly Arg
                580                 585                 590

Leu Leu His Leu Ser Ala Gly Gln Arg Leu Gly Val His Leu His Thr
            595                 600                 605

Glu Ala Arg Ala Arg His Ala Trp Gln Leu Thr Gln Gly Ala Thr Val
610                 615                 620

Leu Gly Leu Phe Arg Val Thr Pro Glu Ile Pro Ala Gly Leu Gly Gly
625                 630                 635                 640

Gly Gly Ser Gly Gly Gly Gly Ser Arg Glu Gly Pro Glu Leu Ser Pro
                645                 650                 655

Asp Asp Pro Ala Gly Leu Leu Asp Leu Arg Gln Gly Met Phe Ala Gln
                660                 665                 670

Leu Val Ala Gln Asn Val Leu Leu Ile Asp Gly Pro Leu Ser Trp Tyr
            675                 680                 685

Ser Asp Pro Gly Leu Ala Gly Val Ser Leu Thr Gly Gly Leu Ser Tyr
            690                 695                 700

Lys Glu Asp Thr Lys Glu Leu Val Val Ala Lys Ala Gly Val Tyr Tyr
705                 710                 715                 720

Val Phe Phe Gln Leu Glu Leu Arg Arg Val Val Ala Gly Glu Gly Ser
                725                 730                 735

Gly Ser Val Ser Leu Ala Leu His Leu Gln Pro Leu Arg Ser Ala Ala
            740                 745                 750

Gly Ala Ala Ala Leu Ala Leu Thr Val Asp Leu Pro Pro Ala Ser Ser
            755                 760                 765

Glu Ala Arg Asn Ser Ala Phe Gly Phe Gln Gly Arg Leu Leu His Leu
770                 775                 780

Ser Ala Gly Gln Arg Leu Gly Val His Leu His Thr Glu Ala Arg Ala
785                 790                 795                 800

Arg His Ala Trp Gln Leu Thr Gln Gly Ala Thr Val Leu Gly Leu Phe
                805                 810                 815

Arg Val Thr Pro Glu Ile Pro Ala Gly Leu
                820                 825

<210> SEQ ID NO 52
<211> LENGTH: 638
```

<212> TYPE: PRT
<213> ORGANISM: Artificial Sequence
<220> FEATURE:
<223> OTHER INFORMATION: anti-CD19(8B8-2B11) Fc knob monomeric (71-248) ligand

<400> SEQUENCE: 52

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Ser Arg Glu Gly Pro
450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                485                 490                 495

Leu Ser Trp Tyr Ser Asp Pro Gly Leu Ala Gly Val Ser Leu Thr Gly
                500                 505                 510

Gly Leu Ser Tyr Lys Glu Asp Thr Lys Glu Leu Val Val Ala Lys Ala
            515                 520                 525

Gly Val Tyr Tyr Val Phe Phe Gln Leu Glu Leu Arg Arg Val Val Ala
530                 535                 540

Gly Glu Gly Ser Gly Ser Val Ser Leu Ala Leu His Leu Gln Pro Leu
545                 550                 555                 560

Arg Ser Ala Ala Gly Ala Ala Ala Leu Ala Leu Thr Val Asp Leu Pro
                565                 570                 575

Pro Ala Ser Ser Glu Ala Arg Asn Ser Ala Phe Gly Phe Gln Gly Arg
                580                 585                 590

Leu Leu His Leu Ser Ala Gly Gln Arg Leu Gly Val His Leu His Thr
            595                 600                 605

Glu Ala Arg Ala Arg His Ala Trp Gln Leu Thr Gln Gly Ala Thr Val
        610                 615                 620

Leu Gly Leu Phe Arg Val Thr Pro Glu Ile Pro Ala Gly Leu
625                 630                 635
```

<210> SEQ ID NO 53
<211> LENGTH: 809
<212> TYPE: PRT
<213> ORGANISM: Artificial Sequence
<220> FEATURE:
<223> OTHER INFORMATION: trimeric hu 4-1BBL (71-254) Fc knob chain

<400> SEQUENCE: 53

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110
```

```
Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
        130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Arg Glu Gly Pro Glu Leu Ser Pro Asp Pro Ala Gly Leu
        195                 200                 205

Leu Asp Leu Arg Gln Gly Met Phe Ala Gln Leu Val Ala Gln Asn Val
    210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Ala Leu Ala
    290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
        355                 360                 365

Pro Ala Gly Leu Pro Ser Pro Arg Ser Glu Gly Gly Gly Ser Gly
    370                 375                 380

Gly Gly Ser Arg Glu Gly Pro Glu Leu Ser Pro Asp Pro Ala
385                 390                 395                 400

Gly Leu Leu Asp Leu Arg Gln Gly Met Phe Ala Gln Leu Val Ala Gln
                405                 410                 415

Asn Val Leu Leu Ile Asp Gly Pro Leu Ser Trp Tyr Ser Asp Pro Gly
            420                 425                 430

Leu Ala Gly Val Ser Leu Thr Gly Gly Leu Ser Tyr Lys Glu Asp Thr
        435                 440                 445

Lys Glu Leu Val Val Ala Lys Ala Gly Val Tyr Tyr Val Phe Phe Gln
    450                 455                 460

Leu Glu Leu Arg Arg Val Val Ala Gly Glu Gly Ser Gly Ser Val Ser
465                 470                 475                 480

Leu Ala Leu His Leu Gln Pro Leu Arg Ser Ala Ala Gly Ala Ala Ala
                485                 490                 495

Leu Ala Leu Thr Val Asp Leu Pro Pro Ala Ser Ser Glu Ala Arg Asn
            500                 505                 510

Ser Ala Phe Gly Phe Gln Gly Arg Leu Leu His Leu Ser Ala Gly Gln
        515                 520                 525
```

```
Arg Leu Gly Val His Leu His Thr Glu Ala Arg Ala Arg His Ala Trp
530                 535                 540
Gln Leu Thr Gln Gly Ala Thr Val Leu Gly Leu Phe Arg Val Thr Pro
545                 550                 555                 560
Glu Ile Pro Ala Gly Leu Pro Ser Pro Arg Ser Glu Gly Ser Pro Gly
                565                 570                 575
Ser Ser Ser Ser Gly Ser Asp Lys Thr His Thr Cys Pro Pro Cys Pro
            580                 585                 590
Ala Pro Glu Ala Ala Gly Gly Pro Ser Val Phe Leu Phe Pro Pro Lys
        595                 600                 605
Pro Lys Asp Thr Leu Met Ile Ser Arg Thr Pro Glu Val Thr Cys Val
    610                 615                 620
Val Val Asp Val Ser His Glu Asp Pro Glu Val Lys Phe Asn Trp Tyr
625                 630                 635                 640
Val Asp Gly Val Glu Val His Asn Ala Lys Thr Lys Pro Arg Glu Glu
                645                 650                 655
Gln Tyr Asn Ser Thr Tyr Arg Val Val Ser Val Leu Thr Val Leu His
            660                 665                 670
Gln Asp Trp Leu Asn Gly Lys Glu Tyr Lys Cys Lys Val Ser Asn Lys
        675                 680                 685
Ala Leu Gly Ala Pro Ile Glu Lys Thr Ile Ser Lys Ala Lys Gly Gln
    690                 695                 700
Pro Arg Glu Pro Gln Val Tyr Thr Leu Pro Pro Cys Arg Asp Glu Leu
705                 710                 715                 720
Thr Lys Asn Gln Val Ser Leu Trp Cys Leu Val Lys Gly Phe Tyr Pro
                725                 730                 735
Ser Asp Ile Ala Val Glu Trp Glu Ser Asn Gly Gln Pro Glu Asn Asn
            740                 745                 750
Tyr Lys Thr Thr Pro Pro Val Leu Asp Ser Asp Gly Ser Phe Phe Leu
        755                 760                 765
Tyr Ser Lys Leu Thr Val Asp Lys Ser Arg Trp Gln Gln Gly Asn Val
    770                 775                 780
Phe Ser Cys Ser Val Met His Glu Ala Leu His Asn His Tyr Thr Gln
785                 790                 795                 800
Lys Ser Leu Ser Leu Ser Pro Gly Lys
                805

<210> SEQ ID NO 54
<211> LENGTH: 1032
<212> TYPE: PRT
<213> ORGANISM: Artificial Sequence
<220> FEATURE:
<223> OTHER INFORMATION: anti- CD19(8B8-018) Fc knob chain fused to
      trimeric hu 4-1BBL (71-254)

<400> SEQUENCE: 54

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
                20                  25                  30
Ile Met His Trp Val Arg Gln Ala Pro Gly Gln Gly Leu Glu Trp Met
            35                  40                  45
Gly Tyr Ile Asn Pro Tyr Asn Asp Gly Ser Lys Tyr Thr Glu Lys Phe
        50                  55                  60
Gln Gly Arg Val Thr Met Thr Ser Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                85                  90                  95

Ala Arg Gly Thr Tyr Tyr Tyr Gly Ser Ala Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Ser Arg Glu Gly Pro
    450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                485                 490                 495
```

```
Leu Ser Trp Tyr Ser Asp Pro Gly Leu Ala Gly Val Ser Leu Thr Gly
            500                 505                 510
Gly Leu Ser Tyr Lys Glu Asp Thr Lys Glu Leu Val Val Ala Lys Ala
        515                 520                 525
Gly Val Tyr Tyr Val Phe Phe Gln Leu Glu Leu Arg Arg Val Val Ala
        530                 535                 540
Gly Glu Gly Ser Gly Ser Val Ser Leu Ala Leu His Leu Gln Pro Leu
545                 550                 555                 560
Arg Ser Ala Ala Gly Ala Ala Leu Ala Leu Thr Val Asp Leu Pro
                565                 570                 575
Pro Ala Ser Ser Glu Ala Arg Asn Ser Ala Phe Gly Phe Gln Gly Arg
        580                 585                 590
Leu Leu His Leu Ser Ala Gly Gln Arg Leu Gly Val His Leu His Thr
            595                 600                 605
Glu Ala Arg Ala Arg His Ala Trp Gln Leu Thr Gln Gly Ala Thr Val
610                 615                 620
Leu Gly Leu Phe Arg Val Thr Pro Glu Ile Pro Ala Gly Leu Pro Ser
625                 630                 635                 640
Pro Arg Ser Glu Gly Gly Gly Ser Gly Gly Gly Ser Arg Glu
                645                 650                 655
Gly Pro Glu Leu Ser Pro Asp Pro Ala Gly Leu Leu Asp Leu Arg
            660                 665                 670
Gln Gly Met Phe Ala Gln Leu Val Ala Gln Asn Val Leu Leu Ile Asp
            675                 680                 685
Gly Pro Leu Ser Trp Tyr Ser Asp Pro Gly Leu Ala Gly Val Ser Leu
        690                 695                 700
Thr Gly Leu Ser Tyr Lys Glu Asp Thr Lys Glu Leu Val Val Ala
705                 710                 715                 720
Lys Ala Gly Val Tyr Tyr Val Phe Phe Gln Leu Glu Leu Arg Arg Val
                725                 730                 735
Val Ala Gly Glu Gly Ser Gly Ser Val Ser Leu Ala Leu His Leu Gln
            740                 745                 750
Pro Leu Arg Ser Ala Ala Gly Ala Ala Leu Ala Leu Thr Val Asp
        755                 760                 765
Leu Pro Pro Ala Ser Ser Glu Ala Arg Asn Ser Ala Phe Gly Phe Gln
770                 775                 780
Gly Arg Leu Leu His Leu Ser Ala Gly Gln Arg Leu Gly Val His Leu
785                 790                 795                 800
His Thr Glu Ala Arg Ala Arg His Ala Trp Gln Leu Thr Gln Gly Ala
                805                 810                 815
Thr Val Leu Gly Leu Phe Arg Val Thr Pro Glu Ile Pro Ala Gly Leu
            820                 825                 830
Pro Ser Pro Arg Ser Glu Gly Gly Gly Ser Gly Gly Gly Ser
        835                 840                 845
Arg Glu Gly Pro Glu Leu Ser Pro Asp Pro Ala Gly Leu Leu Asp
850                 855                 860
Leu Arg Gln Gly Met Phe Ala Gln Leu Val Ala Gln Asn Val Leu Leu
865                 870                 875                 880
Ile Asp Gly Pro Leu Ser Trp Tyr Ser Asp Pro Gly Leu Ala Gly Val
                885                 890                 895
Ser Leu Thr Gly Gly Leu Ser Tyr Lys Glu Asp Thr Lys Glu Leu Val
            900                 905                 910
Val Ala Lys Ala Gly Val Tyr Tyr Val Phe Phe Gln Leu Glu Leu Arg
```

```
              915                 920                 925
Arg Val Val Ala Gly Glu Gly Ser Gly Ser Val Ser Leu Ala Leu His
            930                 935                 940

Leu Gln Pro Leu Arg Ser Ala Ala Gly Ala Ala Ala Leu Ala Leu Thr
945                 950                 955                 960

Val Asp Leu Pro Pro Ala Ser Ser Glu Ala Arg Asn Ser Ala Phe Gly
                965                 970                 975

Phe Gln Gly Arg Leu Leu His Leu Ser Ala Gly Gln Arg Leu Gly Val
            980                 985                 990

His Leu His Thr Glu Ala Arg Ala Arg His Ala Trp Gln Leu Thr Gln
            995                1000                1005

Gly Ala Thr Val Leu Gly Leu Phe Arg Val Thr Pro Glu Ile Pro
       1010                1015                1020

Ala Gly Leu Pro Ser Pro Arg Ser Glu
       1025                1030

<210> SEQ ID NO 55
<211> LENGTH: 1032
<212> TYPE: PRT
<213> ORGANISM: Artificial Sequence
<220> FEATURE:
<223> OTHER INFORMATION: anti- CD19(8B8-2B11) Fc knob chain fused to
      trimeric hu 4-1BBL (71-254)

<400> SEQUENCE: 55

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
         35                  40                  45

Gly Tyr Ile Asn Pro Tyr Asn Asp Gly Ser Lys Tyr Thr Glu Lys Phe
 50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
            100                 105                 110

Gln Gly Thr Thr Val Thr Val Ser Ser Ala Ser Thr Lys Gly Pro Ser
         115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
         195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240
```

-continued

Gly Pro Ser Val Phe Leu Phe Pro Pro Lys Pro Asp Thr Leu Met
             245                 250                 255

Ile Ser Arg Thr Pro Glu Val Thr Cys Val Val Val Asp Val Ser His
             260                 265                 270

Glu Asp Pro Glu Val Lys Phe Asn Trp Tyr Val Asp Gly Val Glu Val
             275                 280                 285

His Asn Ala Lys Thr Lys Pro Arg Glu Glu Gln Tyr Asn Ser Thr Tyr
             290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                 325                 330                 335

Glu Lys Thr Ile Ser Lys Ala Lys Gly Gln Pro Arg Glu Pro Gln Val
             340                 345                 350

Tyr Thr Leu Pro Pro Cys Arg Asp Glu Leu Thr Lys Asn Gln Val Ser
             355                 360                 365

Leu Trp Cys Leu Val Lys Gly Phe Tyr Pro Ser Asp Ile Ala Val Glu
         370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                 405                 410                 415

Asp Lys Ser Arg Trp Gln Gln Gly Asn Val Phe Ser Cys Ser Val Met
                 420                 425                 430

His Glu Ala Leu His Asn His Tyr Thr Gln Lys Ser Leu Ser Leu Ser
             435                 440                 445

Pro Gly Gly Gly Gly Ser Gly Gly Gly Ser Arg Glu Gly Pro
         450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                 485                 490                 495

Leu Ser Trp Tyr Ser Asp Pro Gly Leu Ala Gly Val Ser Leu Thr Gly
             500                 505                 510

Gly Leu Ser Tyr Lys Glu Asp Thr Lys Glu Leu Val Val Ala Lys Ala
         515                 520                 525

Gly Val Tyr Tyr Val Phe Phe Gln Leu Glu Leu Arg Arg Val Val Ala
         530                 535                 540

Gly Glu Gly Ser Gly Ser Val Ser Leu Ala Leu His Leu Gln Pro Leu
545                 550                 555                 560

Arg Ser Ala Ala Gly Ala Ala Ala Leu Ala Leu Thr Val Asp Leu Pro
                 565                 570                 575

Pro Ala Ser Ser Glu Ala Arg Asn Ser Ala Phe Gly Phe Gln Gly Arg
             580                 585                 590

Leu Leu His Leu Ser Ala Gly Gln Arg Leu Gly Val His Leu His Thr
         595                 600                 605

Glu Ala Arg Ala Arg His Ala Trp Gln Leu Thr Gln Gly Ala Thr Val
         610                 615                 620

Leu Gly Leu Phe Arg Val Thr Pro Glu Ile Pro Ala Gly Leu Pro Ser
625                 630                 635                 640

Pro Arg Ser Glu Gly Gly Gly Ser Gly Gly Gly Ser Arg Glu
                 645                 650                 655

Gly Pro Glu Leu Ser Pro Asp Asp Pro Ala Gly Leu Leu Asp Leu Arg

```
                    660                 665                 670
Gln Gly Met Phe Ala Gln Leu Val Ala Gln Asn Val Leu Leu Ile Asp
            675                 680                 685

Gly Pro Leu Ser Trp Tyr Ser Asp Pro Gly Leu Ala Gly Val Ser Leu
        690                 695                 700

Thr Gly Gly Leu Ser Tyr Lys Glu Asp Thr Lys Glu Leu Val Val Ala
705                 710                 715                 720

Lys Ala Gly Val Tyr Tyr Val Phe Phe Gln Leu Glu Leu Arg Arg Val
                725                 730                 735

Val Ala Gly Glu Gly Ser Gly Ser Val Ser Leu Ala Leu His Leu Gln
            740                 745                 750

Pro Leu Arg Ser Ala Ala Gly Ala Ala Ala Leu Ala Leu Thr Val Asp
        755                 760                 765

Leu Pro Pro Ala Ser Ser Glu Ala Arg Asn Ser Ala Phe Gly Phe Gln
        770                 775                 780

Gly Arg Leu Leu His Leu Ser Ala Gly Gln Arg Leu Gly Val His Leu
785                 790                 795                 800

His Thr Glu Ala Arg Ala Arg His Ala Trp Gln Leu Thr Gln Gly Ala
                805                 810                 815

Thr Val Leu Gly Leu Phe Arg Val Thr Pro Glu Ile Pro Ala Gly Leu
            820                 825                 830

Pro Ser Pro Arg Ser Glu Gly Gly Gly Ser Gly Gly Gly Ser
        835                 840                 845

Arg Glu Gly Pro Glu Leu Ser Pro Asp Asp Pro Ala Gly Leu Leu Asp
850                 855                 860

Leu Arg Gln Gly Met Phe Ala Gln Leu Val Ala Gln Asn Val Leu Leu
865                 870                 875                 880

Ile Asp Gly Pro Leu Ser Trp Tyr Ser Asp Pro Gly Leu Ala Gly Val
                885                 890                 895

Ser Leu Thr Gly Gly Leu Ser Tyr Lys Glu Asp Thr Lys Glu Leu Val
            900                 905                 910

Val Ala Lys Ala Gly Val Tyr Tyr Val Phe Phe Gln Leu Glu Leu Arg
        915                 920                 925

Arg Val Val Ala Gly Glu Gly Ser Gly Ser Val Ser Leu Ala Leu His
    930                 935                 940

Leu Gln Pro Leu Arg Ser Ala Ala Gly Ala Ala Ala Leu Ala Leu Thr
945                 950                 955                 960

Val Asp Leu Pro Pro Ala Ser Ser Glu Ala Arg Asn Ser Ala Phe Gly
                965                 970                 975

Phe Gln Gly Arg Leu Leu His Leu Ser Ala Gly Gln Arg Leu Gly Val
            980                 985                 990

His Leu His Thr Glu Ala Arg Ala  Arg His Ala Trp Gln  Leu Thr Gln
        995                  1000                  1005

Gly Ala  Thr Val Leu Gly Leu  Phe Arg Val Thr Pro  Glu Ile Pro
    1010                  1015                  1020

Ala Gly  Leu Pro Ser Pro Arg  Ser Glu
    1025                  1030

<210> SEQ ID NO 56
<211> LENGTH: 5
<212> TYPE: PRT
<213> ORGANISM: Artificial Sequence
<220> FEATURE:
<223> OTHER INFORMATION: CD3-HCDR1
```

```
<400> SEQUENCE: 56

Thr Tyr Ala Met Asn
1               5

<210> SEQ ID NO 57
<211> LENGTH: 19
<212> TYPE: PRT
<213> ORGANISM: Artificial Sequence
<220> FEATURE:
<223> OTHER INFORMATION: CD3-HCDR2

<400> SEQUENCE: 57

Arg Ile Arg Ser Lys Tyr Asn Asn Tyr Ala Thr Tyr Tyr Ala Asp Ser
1               5                   10                  15

Val Lys Gly

<210> SEQ ID NO 58
<211> LENGTH: 14
<212> TYPE: PRT
<213> ORGANISM: Artificial Sequence
<220> FEATURE:
<223> OTHER INFORMATION: CD3-HCDR3

<400> SEQUENCE: 58

His Gly Asn Phe Gly Asn Ser Tyr Val Ser Trp Phe Ala Tyr
1               5                   10

<210> SEQ ID NO 59
<211> LENGTH: 14
<212> TYPE: PRT
<213> ORGANISM: Artificial Sequence
<220> FEATURE:
<223> OTHER INFORMATION: CD3-LCDR1

<400> SEQUENCE: 59

Gly Ser Ser Thr Gly Ala Val Thr Thr Ser Asn Tyr Ala Asn
1               5                   10

<210> SEQ ID NO 60
<211> LENGTH: 7
<212> TYPE: PRT
<213> ORGANISM: Artificial Sequence
<220> FEATURE:
<223> OTHER INFORMATION: CD3-LCDR2

<400> SEQUENCE: 60

Gly Thr Asn Lys Arg Ala Pro
1               5

<210> SEQ ID NO 61
<211> LENGTH: 9
<212> TYPE: PRT
<213> ORGANISM: Artificial Sequence
<220> FEATURE:
<223> OTHER INFORMATION: CD3-LCDR3

<400> SEQUENCE: 61

Ala Leu Trp Tyr Ser Asn Leu Trp Val
1               5

<210> SEQ ID NO 62
<211> LENGTH: 125
<212> TYPE: PRT
<213> ORGANISM: Artificial Sequence
<220> FEATURE:
<223> OTHER INFORMATION: CD3 VH
```

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120             125

<210> SEQ ID NO 63
<211> LENGTH: 109
<212> TYPE: PRT
<213> ORGANISM: Artificial Sequence
<220> FEATURE:
<223> OTHER INFORMATION: CD3 VL

<400> SEQUENCE: 63

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 64
<211> LENGTH: 5
<212> TYPE: PRT
<213> ORGANISM: Artificial Sequence
<220> FEATURE:
<223> OTHER INFORMATION: CD20-HCDR1

<400> SEQUENCE: 64

Tyr Ser Trp Ile Asn
1               5

<210> SEQ ID NO 65
<211> LENGTH: 16
<212> TYPE: PRT
<213> ORGANISM: Artificial Sequence
<220> FEATURE:
<223> OTHER INFORMATION: CD20-HCDR2

```
<400> SEQUENCE: 65

Arg Ile Phe Pro Gly Asp Gly Asp Thr Asp Tyr Asn Gly Lys Phe Lys
1               5                   10                  15

<210> SEQ ID NO 66
<211> LENGTH: 10
<212> TYPE: PRT
<213> ORGANISM: Artificial Sequence
<220> FEATURE:
<223> OTHER INFORMATION: CD20-HCDR3

<400> SEQUENCE: 66

Asn Val Phe Asp Gly Tyr Trp Leu Val Tyr
1               5                   10

<210> SEQ ID NO 67
<211> LENGTH: 16
<212> TYPE: PRT
<213> ORGANISM: Artificial Sequence
<220> FEATURE:
<223> OTHER INFORMATION: CD20-LCDR1

<400> SEQUENCE: 67

Arg Ser Ser Lys Ser Leu Leu His Ser Asn Gly Ile Thr Tyr Leu Tyr
1               5                   10                  15

<210> SEQ ID NO 68
<211> LENGTH: 7
<212> TYPE: PRT
<213> ORGANISM: Artificial Sequence
<220> FEATURE:
<223> OTHER INFORMATION: CD20-LCDR2

<400> SEQUENCE: 68

Gln Met Ser Asn Leu Val Ser
1               5

<210> SEQ ID NO 69
<211> LENGTH: 9
<212> TYPE: PRT
<213> ORGANISM: Artificial Sequence
<220> FEATURE:
<223> OTHER INFORMATION: CD20-LCDR3

<400> SEQUENCE: 69

Ala Gln Asn Leu Glu Leu Pro Tyr Thr
1               5

<210> SEQ ID NO 70
<211> LENGTH: 119
<212> TYPE: PRT
<213> ORGANISM: Artificial Sequence
<220> FEATURE:
<223> OTHER INFORMATION: CD20 VH

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60
```

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 71
<211> LENGTH: 115
<212> TYPE: PRT
<213> ORGANISM: Artificial Sequence
<220> FEATURE:
<223> OTHER INFORMATION: CD20 VL

<400> SEQUENCE: 71

Asp Ile Val Met Thr Gln Thr Pro Leu Ser Leu Pro Val Thr Pro Gly
  1               5                  10                  15

Glu Pro Ala Ser Ile Ser Cys Arg Ser Ser Lys Ser Leu Leu His Ser
                 20                  25                  30

Asn Gly Ile Thr Tyr Leu Tyr Trp Tyr Leu Gln Lys Pro Gly Gln Ser
             35                  40                  45

Pro Gln Leu Leu Ile Tyr Gln Met Ser Asn Leu Val Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Val Glu Ile Lys
            100                 105                 110

Arg Thr Val
        115

<210> SEQ ID NO 72
<211> LENGTH: 445
<212> TYPE: PRT
<213> ORGANISM: Artificial Sequence
<220> FEATURE:
<223> OTHER INFORMATION: DP47 Fc hole chain

<400> SEQUENCE: 72

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125
```

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
                340                 345                 350

Arg Asp Glu Leu Thr Lys Asn Gln Val Ser Leu Ser Cys Ala Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 73
<211> LENGTH: 215
<212> TYPE: PRT
<213> ORGANISM: Artificial Sequence
<220> FEATURE:
<223> OTHER INFORMATION: DP47 light chain

<400> SEQUENCE: 73

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 74
<211> LENGTH: 834
<212> TYPE: PRT
<213> ORGANISM: Artificial Sequence
<220> FEATURE:
<223> OTHER INFORMATION: DP47 Fc hole chain fused to dimeric hu 4-1BBL
      (71-254)

<400> SEQUENCE: 74

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ile Gly Ser Gly Ala Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser

-continued

```
                180                 185                 190
Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Arg Glu Gly Pro Glu Leu Ser Pro
    450                 455                 460

Asp Asp Pro Ala Gly Leu Leu Asp Leu Arg Gln Gly Met Phe Ala Gln
465                 470                 475                 480

Leu Val Ala Gln Asn Val Leu Leu Ile Asp Gly Pro Leu Ser Trp Tyr
                485                 490                 495

Ser Asp Pro Gly Leu Ala Gly Val Ser Leu Thr Gly Gly Leu Ser Tyr
            500                 505                 510

Lys Glu Asp Thr Lys Glu Leu Val Val Ala Lys Ala Gly Val Tyr Tyr
        515                 520                 525

Val Phe Phe Gln Leu Glu Leu Arg Arg Val Val Ala Gly Glu Gly Ser
    530                 535                 540

Gly Ser Val Ser Leu Ala Leu His Leu Gln Pro Leu Arg Ser Ala Ala
545                 550                 555                 560

Gly Ala Ala Ala Leu Ala Leu Thr Val Asp Leu Pro Pro Ala Ser Ser
                565                 570                 575

Glu Ala Arg Asn Ser Ala Phe Gly Phe Gln Gly Arg Leu Leu His Leu
            580                 585                 590

Ser Ala Gly Gln Arg Leu Gly Val His Leu His Thr Glu Ala Arg Ala
        595                 600                 605
```

-continued

Arg His Ala Trp Gln Leu Thr Gln Gly Ala Thr Val Leu Gly Leu Phe
610                 615                 620

Arg Val Thr Pro Glu Ile Pro Ala Gly Leu Pro Ser Pro Arg Ser Glu
625                 630                 635                 640

Gly Gly Gly Gly Ser Gly Gly Gly Ser Arg Glu Gly Pro Glu Leu
        645                 650                 655

Ser Pro Asp Asp Pro Ala Gly Leu Leu Asp Leu Arg Gln Gly Met Phe
        660                 665                 670

Ala Gln Leu Val Ala Gln Asn Val Leu Leu Ile Asp Gly Pro Leu Ser
        675                 680                 685

Trp Tyr Ser Asp Pro Gly Leu Ala Gly Val Ser Leu Thr Gly Gly Leu
    690                 695                 700

Ser Tyr Lys Glu Asp Thr Lys Glu Leu Val Val Ala Lys Ala Gly Val
705                 710                 715                 720

Tyr Tyr Val Phe Phe Gln Leu Glu Leu Arg Arg Val Val Ala Gly Glu
            725                 730                 735

Gly Ser Gly Ser Val Ser Leu Ala Leu His Leu Gln Pro Leu Arg Ser
        740                 745                 750

Ala Ala Gly Ala Ala Leu Ala Leu Thr Val Asp Leu Pro Pro Ala
        755                 760                 765

Ser Ser Glu Ala Arg Asn Ser Ala Phe Gly Phe Gln Gly Arg Leu Leu
770                 775                 780

His Leu Ser Ala Gly Gln Arg Leu Gly Val His Leu His Thr Glu Ala
785                 790                 795                 800

Arg Ala Arg His Ala Trp Gln Leu Thr Gln Gly Ala Thr Val Leu Gly
                805                 810                 815

Leu Phe Arg Val Thr Pro Glu Ile Pro Ala Gly Leu Pro Ser Pro Arg
            820                 825                 830

Ser Glu

<210> SEQ ID NO 75
<211> LENGTH: 640
<212> TYPE: PRT
<213> ORGANISM: Artificial Sequence
<220> FEATURE:
<223> OTHER INFORMATION: DP47 Fc knob chain fused to monomeric hu 4-1BBL
    (71-254)

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

-continued

```
Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Arg Glu Gly Pro Glu Leu Ser Pro
    450                 455                 460

Asp Asp Pro Ala Gly Leu Leu Asp Leu Arg Gln Gly Met Phe Ala Gln
465                 470                 475                 480

Leu Val Ala Gln Asn Val Leu Leu Ile Asp Gly Pro Leu Ser Trp Tyr
                485                 490                 495

Ser Asp Pro Gly Leu Ala Gly Val Ser Leu Thr Gly Gly Leu Ser Tyr
            500                 505                 510

Lys Glu Asp Thr Lys Glu Leu Val Val Ala Lys Ala Gly Val Tyr Tyr
        515                 520                 525

Val Phe Phe Gln Leu Glu Leu Arg Arg Val Val Ala Gly Glu Gly Ser
    530                 535                 540
```

```
Gly Ser Val Ser Leu Ala Leu His Leu Gln Pro Leu Arg Ser Ala Ala
545                 550                 555                 560

Gly Ala Ala Ala Leu Ala Leu Thr Val Asp Leu Pro Pro Ala Ser Ser
                565                 570                 575

Glu Ala Arg Asn Ser Ala Phe Gly Phe Gln Gly Arg Leu Leu His Leu
            580                 585                 590

Ser Ala Gly Gln Arg Leu Gly Val His Leu His Thr Glu Ala Arg Ala
        595                 600                 605

Arg His Ala Trp Gln Leu Thr Gln Gly Ala Thr Val Leu Gly Leu Phe
    610                 615                 620

Arg Val Thr Pro Glu Ile Pro Ala Gly Leu Pro Ser Pro Arg Ser Glu
625                 630                 635                 640

<210> SEQ ID NO 76
<211> LENGTH: 672
<212> TYPE: PRT
<213> ORGANISM: Artificial Sequence
<220> FEATURE:
<223> OTHER INFORMATION: CD20 VH-CH1(EE)-CD3 VL-CH1-Fc (knob, P329G
      LALA)CD20 VH-CH1(EE)-CD3 VL-CH1-Fc (knob, P329G LALA)

<400> SEQUENCE: 76

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Gly
    210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
            260                 265                 270
```

```
Glu Lys Pro Gly Gln Ala Phe Arg Gly Leu Ile Gly Gly Thr Asn Lys
            275                 280                 285
Arg Ala Pro Gly Thr Pro Ala Arg Phe Ser Gly Ser Leu Leu Gly Gly
        290                 295                 300
Lys Ala Ala Leu Thr Leu Ser Gly Ala Gln Pro Glu Asp Glu Ala Glu
305                 310                 315                 320
Tyr Tyr Cys Ala Leu Trp Tyr Ser Asn Leu Trp Val Phe Gly Gly Gly
                325                 330                 335
Thr Lys Leu Thr Val Leu Ser Ser Ala Ser Thr Lys Gly Pro Ser Val
            340                 345                 350
Phe Pro Leu Ala Pro Ser Ser Lys Ser Thr Ser Gly Gly Thr Ala Ala
        355                 360                 365
Leu Gly Cys Leu Val Lys Asp Tyr Phe Pro Glu Pro Val Thr Val Ser
    370                 375                 380
Trp Asn Ser Gly Ala Leu Thr Ser Gly Val His Thr Phe Pro Ala Val
385                 390                 395                 400
Leu Gln Ser Ser Gly Leu Tyr Ser Leu Ser Ser Val Val Thr Val Pro
                405                 410                 415
Ser Ser Ser Leu Gly Thr Gln Thr Tyr Ile Cys Asn Val Asn His Lys
            420                 425                 430
Pro Ser Asn Thr Lys Val Asp Lys Lys Val Glu Pro Lys Ser Cys Asp
        435                 440                 445
Lys Thr His Thr Cys Pro Pro Cys Pro Ala Pro Glu Ala Ala Gly Gly
    450                 455                 460
Pro Ser Val Phe Leu Phe Pro Pro Lys Pro Lys Asp Thr Leu Met Ile
465                 470                 475                 480
Ser Arg Thr Pro Glu Val Thr Cys Val Val Val Asp Val Ser His Glu
                485                 490                 495
Asp Pro Glu Val Lys Phe Asn Trp Tyr Val Asp Gly Val Glu Val His
            500                 505                 510
Asn Ala Lys Thr Lys Pro Arg Glu Glu Gln Tyr Asn Ser Thr Tyr Arg
        515                 520                 525
Val Val Ser Val Leu Thr Val Leu His Gln Asp Trp Leu Asn Gly Lys
    530                 535                 540
Glu Tyr Lys Cys Lys Val Ser Asn Lys Ala Leu Gly Ala Pro Ile Glu
545                 550                 555                 560
Lys Thr Ile Ser Lys Ala Lys Gly Gln Pro Arg Glu Pro Gln Val Tyr
                565                 570                 575
Thr Leu Pro Pro Cys Arg Asp Glu Leu Thr Lys Asn Gln Val Ser Leu
            580                 585                 590
Trp Cys Leu Val Lys Gly Phe Tyr Pro Ser Asp Ile Ala Val Glu Trp
        595                 600                 605
Glu Ser Asn Gly Gln Pro Glu Asn Asn Tyr Lys Thr Thr Pro Pro Val
    610                 615                 620
Leu Asp Ser Asp Gly Ser Phe Phe Leu Tyr Ser Lys Leu Thr Val Asp
625                 630                 635                 640
Lys Ser Arg Trp Gln Gln Gly Asn Val Phe Ser Cys Ser Val Met His
                645                 650                 655
Glu Ala Leu His Asn His Tyr Thr Gln Lys Ser Leu Ser Leu Ser Pro
            660                 665                 670

<210> SEQ ID NO 77
<211> LENGTH: 447
```

```
<212> TYPE: PRT
<213> ORGANISM: Artificial Sequence
<220> FEATURE:
<223> OTHER INFORMATION: CD20 VH-CH1(EE)-Fc (hole, P329G LALA)

<400> SEQUENCE: 77
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Tyr | Ala | Phe | Ser | Tyr | Ser |
| | | | 20 | | | | | 25 | | | | | 30 | | |
| Trp | Ile | Asn | Trp | Val | Arg | Gln | Ala | Pro | Gly | Gln | Gly | Leu | Glu | Trp | Met |
| | | | 35 | | | | | 40 | | | | | 45 | | |
| Gly | Arg | Ile | Phe | Pro | Gly | Asp | Gly | Asp | Thr | Asp | Tyr | Asn | Gly | Lys | Phe |
| | 50 | | | | | 55 | | | | | 60 | | | | |
| Lys | Gly | Arg | Val | Thr | Ile | Thr | Ala | Asp | Lys | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Asn | Val | Phe | Asp | Gly | Tyr | Trp | Leu | Val | Tyr | Trp | Gly | Gln | Gly |
| | | | 100 | | | | | 105 | | | | | 110 | | |
| Thr | Leu | Val | Thr | Val | Ser | Ser | Ala | Ser | Thr | Lys | Gly | Pro | Ser | Val | Phe |
| | | | 115 | | | | | 120 | | | | | 125 | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Glu | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Glu | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Ala | Ala | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | | 275 | | | | | 280 | | | | | 285 | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Gly | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Cys | Thr |
| | | | 340 | | | | | 345 | | | | | 350 | | |
| Leu | Pro | Pro | Ser | Arg | Asp | Glu | Leu | Thr | Lys | Asn | Gln | Val | Ser | Leu | Ser |
| | | | 355 | | | | | 360 | | | | | 365 | | |
| Cys | Ala | Val | Lys | Gly | Phe | Tyr | Pro | Ser | Asp | Ile | Ala | Val | Glu | Trp | Glu |
| | 370 | | | | | 375 | | | | | 380 | | | | |

Ser Asn Gly Gln Pro Glu Asn Asn Tyr Lys Thr Thr Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 78
<211> LENGTH: 219
<212> TYPE: PRT
<213> ORGANISM: Artificial Sequence
<220> FEATURE:
<223> OTHER INFORMATION: CD20 VL-CL(RK)

<400> SEQUENCE: 78

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 79
<211> LENGTH: 232
<212> TYPE: PRT
<213> ORGANISM: Artificial Sequence
<220> FEATURE:
<223> OTHER INFORMATION: CD3 VH-CL

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
                35                  40                  45

Ser Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Val
                115                 120                 125

Ala Ala Pro Ser Val Phe Ile Phe Pro Pro Ser Asp Glu Gln Leu Lys
                130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
                180                 185                 190

Leu Ser Ser Thr Leu Thr Leu Ser Lys Ala Asp Tyr Glu Lys His Lys
                195                 200                 205

Val Tyr Ala Cys Glu Val Thr His Gln Gly Leu Ser Ser Pro Val Thr
                210                 215                 220

Lys Ser Phe Asn Arg Gly Glu Cys
225                 230

<210> SEQ ID NO 80
<211> LENGTH: 556
<212> TYPE: PRT
<213> ORGANISM: Homo sapiens

<400> SEQUENCE: 80

Met Pro Pro Pro Arg Leu Leu Phe Phe Leu Leu Phe Leu Thr Pro Met
 1                   5                  10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
                35                  40                  45

Gln Leu Thr Trp Ser Arg Glu Ser Pro Leu Lys Pro Phe Leu Lys Leu
 50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
                115                 120                 125

Leu Gly Gly Leu Gly Cys Gly Leu Lys Asn Arg Ser Ser Glu Gly Pro
                130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro

```
                165                 170                 175
Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555

<210> SEQ ID NO 81
<211> LENGTH: 297
<212> TYPE: PRT
<213> ORGANISM: Homo sapiens
```

<400> SEQUENCE: 81

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 82
<211> LENGTH: 112
<212> TYPE: PRT
<213> ORGANISM: Artificial Sequence
<220> FEATURE:
<223> OTHER INFORMATION: murine anti-CD20 B-Ly1 VH

<400> SEQUENCE: 82

Gly Pro Glu Leu Val Lys Pro Gly Ala Ser Val Lys Ile Ser Cys Lys
1               5                   10                  15

Ala Ser Gly Tyr Ala Phe Ser Tyr Ser Trp Met Asn Trp Val Lys Leu
            20                  25                  30

Arg Pro Gly Gln Gly Leu Glu Trp Ile Gly Arg Ile Phe Pro Gly Asp
        35                  40                  45

```
Gly Asp Thr Asp Tyr Asn Gly Lys Phe Lys Gly Lys Ala Thr Leu Thr
    50                  55                  60

Ala Asp Lys Ser Ser Asn Thr Ala Tyr Met Gln Leu Thr Ser Leu Thr
 65                  70                  75                  80

Ser Val Asp Ser Ala Val Tyr Leu Cys Ala Arg Asn Val Phe Asp Gly
                85                  90                  95

Tyr Trp Leu Val Tyr Trp Gly Gln Gly Thr Leu Val Thr Val Ser Ala
                100                 105                 110
```

<210> SEQ ID NO 83
<211> LENGTH: 103
<212> TYPE: PRT
<213> ORGANISM: Artificial Sequence
<220> FEATURE:
<223> OTHER INFORMATION: murine anti-CD20 B-Ly1 VL

<400> SEQUENCE: 83

```
Asn Pro Val Thr Leu Gly Thr Ser Ala Ser Ile Ser Cys Arg Ser Ser
 1               5                  10                  15

Lys Ser Leu Leu His Ser Asn Gly Ile Thr Tyr Leu Tyr Trp Tyr Leu
                20                  25                  30

Gln Lys Pro Gly Gln Ser Pro Gln Leu Leu Ile Tyr Gln Met Ser Asn
                35                  40                  45

Leu Val Ser Gly Val Pro Asp Arg Phe Ser Ser Gly Ser Gly Thr
 50                  55                  60

Asp Phe Thr Leu Arg Ile Ser Arg Val Glu Ala Glu Asp Val Gly Val
 65                  70                  75                  80

Tyr Tyr Cys Ala Gln Asn Leu Glu Leu Pro Tyr Thr Phe Gly Gly Gly
                85                  90                  95

Thr Lys Leu Glu Ile Lys Arg
                100
```

<210> SEQ ID NO 84
<211> LENGTH: 207
<212> TYPE: PRT
<213> ORGANISM: Homo sapiens

<400> SEQUENCE: 84

```
Met Gln Ser Gly Thr His Trp Arg Val Leu Gly Leu Cys Leu Leu Ser
 1               5                  10                  15

Val Gly Val Trp Gly Gln Asp Gly Asn Glu Met Gly Gly Ile Thr
                20                  25                  30

Gln Thr Pro Tyr Lys Val Ser Ile Ser Gly Thr Thr Val Ile Leu Thr
                35                  40                  45

Cys Pro Gln Tyr Pro Gly Ser Glu Ile Leu Trp Gln His Asn Asp Lys
 50                  55                  60

Asn Ile Gly Gly Asp Glu Asp Lys Asn Ile Gly Ser Asp Glu Asp
 65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
                115                 120                 125

Ser Val Ala Thr Ile Val Ile Val Asp Ile Cys Ile Thr Gly Gly Leu
                130                 135                 140

Leu Leu Leu Val Tyr Tyr Trp Ser Lys Asn Arg Lys Ala Lys Ala Lys
```

```
                145                 150                 155                 160
Pro Val Thr Arg Gly Ala Gly Gly Arg Gln Arg Gly Gln Asn
                    165                 170                 175
Lys Glu Arg Pro Pro Val Pro Asn Pro Asp Tyr Glu Pro Ile Arg
                    180                 185                 190
Lys Gly Gln Arg Asp Leu Tyr Ser Gly Leu Asn Gln Arg Ile
                    195                 200                 205

<210> SEQ ID NO 85
<211> LENGTH: 198
<212> TYPE: PRT
<213> ORGANISM: Cynomolgus

<400> SEQUENCE: 85

Met Gln Ser Gly Thr Arg Trp Arg Val Leu Gly Leu Cys Leu Leu Ser
1               5                   10                  15
Ile Gly Val Trp Gly Gln Asp Gly Asn Glu Glu Met Gly Ser Ile Thr
                20                  25                  30
Gln Thr Pro Tyr Gln Val Ser Ile Ser Gly Thr Thr Val Ile Leu Thr
            35                  40                  45
Cys Ser Gln His Leu Gly Ser Glu Ala Gln Trp Gln His Asn Gly Lys
        50                  55                  60
Asn Lys Glu Asp Ser Gly Asp Arg Leu Phe Leu Pro Glu Phe Ser Glu
65                  70                  75                  80
Met Glu Gln Ser Gly Tyr Tyr Val Cys Tyr Pro Arg Gly Ser Asn Pro
                85                  90                  95
Glu Asp Ala Ser His His Leu Tyr Leu Lys Ala Arg Val Cys Glu Asn
            100                 105                 110
Cys Met Glu Met Asp Val Met Ala Val Ala Thr Ile Val Ile Val Asp
        115                 120                 125
Ile Cys Ile Thr Leu Gly Leu Leu Leu Val Tyr Tyr Trp Ser Lys
        130                 135                 140
Asn Arg Lys Ala Lys Ala Lys Pro Val Thr Arg Gly Ala Gly Ala Gly
145                 150                 155                 160
Gly Arg Gln Arg Gly Gln Asn Lys Glu Arg Pro Pro Val Pro Asn
                165                 170                 175
Pro Asp Tyr Glu Pro Ile Arg Lys Gly Gln Gln Asp Leu Tyr Ser Gly
                180                 185                 190
Leu Asn Gln Arg Arg Ile
            195

<210> SEQ ID NO 86
<211> LENGTH: 254
<212> TYPE: PRT
<213> ORGANISM: Homo sapiens

<400> SEQUENCE: 86

Met Glu Tyr Ala Ser Asp Ala Ser Leu Asp Pro Glu Ala Pro Trp Pro
1               5                   10                  15
Pro Ala Pro Arg Ala Arg Ala Cys Arg Val Leu Pro Trp Ala Leu Val
                20                  25                  30
Ala Gly Leu Leu Leu Leu Leu Leu Ala Ala Ala Cys Ala Val Phe
            35                  40                  45
Leu Ala Cys Pro Trp Ala Val Ser Gly Ala Arg Ala Ser Pro Gly Ser
        50                  55                  60
Ala Ala Ser Pro Arg Leu Arg Glu Gly Pro Glu Leu Ser Pro Asp Asp
```

```
                65                  70                  75                  80
Pro Ala Gly Leu Leu Asp Leu Arg Gln Gly Met Phe Ala Gln Leu Val
                    85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
                115                 120                 125

Asp Thr Lys Glu Leu Val Val Ala Lys Ala Gly Val Tyr Tyr Val Phe
                130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
                210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 87
<211> LENGTH: 205
<212> TYPE: PRT
<213> ORGANISM: Homo sapiens

<400> SEQUENCE: 87

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
                20                  25                  30

Ala Gly Leu Leu Asp Leu Arg Gln Gly Met Phe Ala Gln Leu Val Ala
                35                  40                  45

Gln Asn Val Leu Leu Ile Asp Gly Pro Leu Ser Trp Tyr Ser Asp Pro
                50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
                100                 105                 110

Ser Leu Ala Leu His Leu Gln Pro Leu Arg Ser Ala Ala Gly Ala Ala
                115                 120                 125

Ala Leu Ala Leu Thr Val Asp Leu Pro Pro Ala Ser Ser Glu Ala Arg
                130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
                180                 185                 190
```

```
Pro Glu Ile Pro Ala Gly Leu Pro Ser Pro Arg Ser Glu
        195                 200                 205
```

<210> SEQ ID NO 88
<211> LENGTH: 163
<212> TYPE: PRT
<213> ORGANISM: Homo sapiens

<400> SEQUENCE: 88

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln
```

<210> SEQ ID NO 89
<211> LENGTH: 256
<212> TYPE: PRT
<213> ORGANISM: Mus musculus

<400> SEQUENCE: 89

```
Met Gly Asn Asn Cys Tyr Asn Val Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
```

```
145                 150                 155                 160
Pro Val Val Ser Phe Ser Pro Ser Thr Thr Ile Ser Val Thr Pro Glu
                165                 170                 175
Gly Gly Pro Gly Gly His Ser Leu Gln Val Leu Thr Leu Phe Leu Ala
                180                 185                 190
Leu Thr Ser Ala Leu Leu Leu Ala Leu Ile Phe Ile Thr Leu Leu Phe
                195                 200                 205
Ser Val Leu Lys Trp Ile Arg Lys Lys Phe Pro His Ile Phe Lys Gln
            210                 215                 220
Pro Phe Lys Lys Thr Thr Gly Ala Ala Gln Glu Glu Asp Ala Cys Ser
225                 230                 235                 240
Cys Arg Cys Pro Gln Glu Glu Glu Gly Gly Gly Gly Tyr Glu Leu
                245                 250                 255
```

<210> SEQ ID NO 90
<211> LENGTH: 254
<212> TYPE: PRT
<213> ORGANISM: cynomolgus

<400> SEQUENCE: 90

```
Met Gly Asn Ser Cys Tyr Asn Ile Val Ala Thr Leu Leu Leu Val Leu
1               5                   10                  15
Asn Phe Glu Arg Thr Arg Ser Leu Gln Asp Leu Cys Ser Asn Cys Pro
                20                  25                  30
Ala Gly Thr Phe Cys Asp Asn Asn Arg Ser Gln Ile Cys Ser Pro Cys
                35                  40                  45
Pro Pro Asn Ser Phe Ser Ser Ala Gly Gly Gln Arg Thr Cys Asp Ile
            50                  55                  60
Cys Arg Gln Cys Lys Gly Val Phe Lys Thr Arg Lys Glu Cys Ser Ser
65                  70                  75                  80
Thr Ser Asn Ala Glu Cys Asp Cys Ile Ser Gly Tyr His Cys Leu Gly
                85                  90                  95
Ala Glu Cys Ser Met Cys Glu Gln Asp Cys Lys Gln Gly Gln Glu Leu
                100                 105                 110
Thr Lys Lys Gly Cys Lys Asp Cys Cys Phe Gly Thr Phe Asn Asp Gln
            115                 120                 125
Lys Arg Gly Ile Cys Arg Pro Trp Thr Asn Cys Ser Leu Asp Gly Lys
130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Ala Thr Pro Pro Ala
                165                 170                 175
Pro Ala Arg Glu Pro Gly His Ser Pro Gln Ile Ile Phe Phe Leu Ala
                180                 185                 190
Leu Thr Ser Thr Val Val Leu Phe Leu Leu Phe Phe Leu Val Leu Arg
            195                 200                 205
Phe Ser Val Val Lys Arg Ser Arg Lys Lys Leu Leu Tyr Ile Phe Lys
210                 215                 220
Gln Pro Phe Met Arg Pro Val Gln Thr Thr Gln Glu Glu Asp Gly Cys
225                 230                 235                 240
Ser Cys Arg Phe Pro Glu Glu Glu Glu Gly Gly Cys Glu Leu
                245                 250
```

<210> SEQ ID NO 91
<211> LENGTH: 5

```
<212> TYPE: PRT
<213> ORGANISM: Artificial Sequence
<220> FEATURE:
<223> OTHER INFORMATION: G4S peptide linker

<400> SEQUENCE: 91

Gly Gly Gly Gly Ser
1               5

<210> SEQ ID NO 92
<211> LENGTH: 10
<212> TYPE: PRT
<213> ORGANISM: Artificial Sequence
<220> FEATURE:
<223> OTHER INFORMATION: (G4S)2

<400> SEQUENCE: 92

Gly Gly Gly Gly Ser Gly Gly Gly Gly Ser
1               5                   10

<210> SEQ ID NO 93
<211> LENGTH: 10
<212> TYPE: PRT
<213> ORGANISM: Artificial Sequence
<220> FEATURE:
<223> OTHER INFORMATION: (SG4)2

<400> SEQUENCE: 93

Ser Gly Gly Gly Gly Ser Gly Gly Gly Gly
1               5                   10

<210> SEQ ID NO 94
<211> LENGTH: 14
<212> TYPE: PRT
<213> ORGANISM: Artificial Sequence
<220> FEATURE:
<223> OTHER INFORMATION: peptide linker

<400> SEQUENCE: 94

Gly Gly Gly Gly Ser Gly Gly Gly Ser Gly Gly Gly Gly
1               5                   10

<210> SEQ ID NO 95
<211> LENGTH: 10
<212> TYPE: PRT
<213> ORGANISM: Artificial Sequence
<220> FEATURE:
<223> OTHER INFORMATION: peptide linker

<400> SEQUENCE: 95

Gly Ser Pro Gly Ser Ser Ser Ser Gly Ser
1               5                   10

<210> SEQ ID NO 96
<211> LENGTH: 15
<212> TYPE: PRT
<213> ORGANISM: Artificial Sequence
<220> FEATURE:
<223> OTHER INFORMATION: peptide linker 2

<400> SEQUENCE: 96

Gly Gly Gly Gly Ser Gly Gly Gly Gly Ser Gly Gly Gly Gly Ser
1               5                   10                  15

<210> SEQ ID NO 97
<211> LENGTH: 20
<212> TYPE: PRT
```

```
<213> ORGANISM: Artificial Sequence
<220> FEATURE:
<223> OTHER INFORMATION: peptide linker 3

<400> SEQUENCE: 97

Gly Gly Gly Gly Ser Gly Gly Gly Ser Gly Gly Gly Gly Ser Gly
1               5                   10                  15

Gly Gly Gly Ser
            20

<210> SEQ ID NO 98
<211> LENGTH: 8
<212> TYPE: PRT
<213> ORGANISM: Artificial Sequence
<220> FEATURE:
<223> OTHER INFORMATION: peptide linker 4

<400> SEQUENCE: 98

Gly Ser Gly Ser Gly Ser Gly Ser
1               5

<210> SEQ ID NO 99
<211> LENGTH: 8
<212> TYPE: PRT
<213> ORGANISM: Artificial Sequence
<220> FEATURE:
<223> OTHER INFORMATION: peptide linker 5

<400> SEQUENCE: 99

Gly Ser Gly Ser Gly Asn Gly Ser
1               5

<210> SEQ ID NO 100
<211> LENGTH: 8
<212> TYPE: PRT
<213> ORGANISM: Artificial Sequence
<220> FEATURE:
<223> OTHER INFORMATION: peptide linker 6

<400> SEQUENCE: 100

Gly Gly Ser Gly Ser Gly Ser Gly
1               5

<210> SEQ ID NO 101
<211> LENGTH: 6
<212> TYPE: PRT
<213> ORGANISM: Artificial Sequence
<220> FEATURE:
<223> OTHER INFORMATION: peptide linker 7

<400> SEQUENCE: 101

Gly Gly Ser Gly Ser Gly
1               5

<210> SEQ ID NO 102
<211> LENGTH: 4
<212> TYPE: PRT
<213> ORGANISM: Artificial Sequence
<220> FEATURE:
<223> OTHER INFORMATION: peptide linker 8

<400> SEQUENCE: 102

Gly Gly Ser Gly
1

<210> SEQ ID NO 103
```

```
<211> LENGTH: 8
<212> TYPE: PRT
<213> ORGANISM: Artificial Sequence
<220> FEATURE:
<223> OTHER INFORMATION: peptide linker 9

<400> SEQUENCE: 103

Gly Gly Ser Gly Asn Gly Ser Gly
1               5

<210> SEQ ID NO 104
<211> LENGTH: 8
<212> TYPE: PRT
<213> ORGANISM: Artificial Sequence
<220> FEATURE:
<223> OTHER INFORMATION: peptide linker 10

<400> SEQUENCE: 104

Gly Gly Asn Gly Ser Gly Ser Gly
1               5

<210> SEQ ID NO 105
<211> LENGTH: 6
<212> TYPE: PRT
<213> ORGANISM: Artificial Sequence
<220> FEATURE:
<223> OTHER INFORMATION: peptide linker 11

<400> SEQUENCE: 105

Gly Gly Asn Gly Ser Gly
1               5

<210> SEQ ID NO 106
<211> LENGTH: 290
<212> TYPE: PRT
<213> ORGANISM: Homo sapiens

<400> SEQUENCE: 106

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
```

```
              180                 185                 190
Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 107
<211> LENGTH: 288
<212> TYPE: PRT
<213> ORGANISM: Homo sapiens

<400> SEQUENCE: 107

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255
```

```
Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 108
<211> LENGTH: 118
<212> TYPE: PRT
<213> ORGANISM: Artificial Sequence
<220> FEATURE:
<223> OTHER INFORMATION: VH (PD-L1)

<400> SEQUENCE: 108

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115
```

<210> SEQ ID NO 109
<211> LENGTH: 107
<212> TYPE: PRT
<213> ORGANISM: Artificial Sequence
<220> FEATURE:
<223> OTHER INFORMATION: VL (PD-L1)

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105
```

<210> SEQ ID NO 110
<211> LENGTH: 121
<212> TYPE: PRT
<213> ORGANISM: Artificial Sequence
<220> FEATURE:
<223> OTHER INFORMATION: VH (PD-L1) 2

```
<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 111
<211> LENGTH: 108
<212> TYPE: PRT
<213> ORGANISM: Artificial Sequence
<220> FEATURE:
<223> OTHER INFORMATION: VL (PD-L1) 2

<400> SEQUENCE: 111

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 112
<211> LENGTH: 120
<212> TYPE: PRT
<213> ORGANISM: Artificial Sequence
<220> FEATURE:
<223> OTHER INFORMATION: VH (PD-1)

<400> SEQUENCE: 112

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
50                  55                  60
```

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 113
<211> LENGTH: 111
<212> TYPE: PRT
<213> ORGANISM: Artificial Sequence
<220> FEATURE:
<223> OTHER INFORMATION: VL (PD-1)

<400> SEQUENCE: 113

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 114
<211> LENGTH: 113
<212> TYPE: PRT
<213> ORGANISM: Artificial Sequence
<220> FEATURE:
<223> OTHER INFORMATION: VH (PD-1) 2

<400> SEQUENCE: 114

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 115
<211> LENGTH: 107

```
<212> TYPE: PRT
<213> ORGANISM: Artificial Sequence
<220> FEATURE:
<223> OTHER INFORMATION: VL (PD-1) 2

<400> SEQUENCE: 115

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
                100                 105
```